United States Patent
Cohen et al.

(10) Patent No.: US 10,596,180 B2
(45) Date of Patent: *Mar. 24, 2020

(54) SALTS AND SOLID FORMS OF (S)-3-(4-((4-(MORPHOLINOMETHYL) BENZYL)OXY)-1-OXOISOINDOLIN-2-YL)PIPERIDINE-2,6-DIONE AND COMPOSITIONS COMPRISING AND METHODS OF USING THE SAME

(71) Applicant: Celgene Corporation, Summit, NJ (US)

(72) Inventors: Benjamin M. Cohen, Cranford, NJ (US); John F. Traverse, Lebanon, NJ (US); Jean Xu, Warren, NJ (US); Ying Li, Millburn, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/443,161

(22) Filed: Jun. 17, 2019

(65) Prior Publication Data

US 2019/0365772 A1 Dec. 5, 2019

Related U.S. Application Data

(63) Continuation of application No. 15/856,845, filed on Dec. 28, 2017, now Pat. No. 10,463,672, which is a continuation of application No. 15/445,070, filed on Feb. 28, 2017, now Pat. No. 9,884,062, which is a continuation of application No. 14/945,147, filed on Nov. 18, 2015, now Pat. No. 9,629,849, which is a continuation of application No. 13/962,745, filed on Aug. 8, 2013, now Pat. No. 9,221,788.

(60) Provisional application No. 61/681,484, filed on Aug. 9, 2012.

(51) Int. Cl.
| | | |
|---|---|---|
| *A61K 31/5377* | (2006.01) | |
| *A61K 31/4035* | (2006.01) | |
| *A61K 31/4412* | (2006.01) | |
| *C07D 401/04* | (2006.01) | |

(52) U.S. Cl.
CPC ........ *A61K 31/5377* (2013.01); *C07D 401/04* (2013.01); *A61K 31/4035* (2013.01); *A61K 31/4412* (2013.01)

(58) Field of Classification Search
CPC ............ A61K 31/5377; A61K 31/4035; A61K 31/4412
USPC ...................................... 514/235.2, 414, 419
See application file for complete search history.

(56) References Cited

U.S. PATENT DOCUMENTS

| | | | |
|---|---|---|---|
| 9,221,788 B2 | 12/2015 | Cohen et al. | |
| 2011/0196150 A1* | 8/2011 | Man .................... | C07D 491/107 540/544 |

FOREIGN PATENT DOCUMENTS

WO    WO 2011/100380 A1    8/2011

OTHER PUBLICATIONS

Brittain, "Polymorphism in Pharmaceutical Solids", 2nd Edition, 2009, pp. 1-3 and 318.
Kumar et al., "Salt selection in drug development", Pharmaceutical Technology, Aovanstar Communications, vol. 32, No. 3, Mar. 1, 2008, pp. 128-146.
Gould, Philip L., "Salt selection for basic drugs", International Journal of Pharmaceutics, 1986, vol. 33, pp. 201-217.
C.G. Wermuth, Nagase, Hiroshi ed., Saishin Souyaku Kagaku, Gekan (The Practice of Medicinal Chemistry, Second Volume), Technomics, Inc, 1999, pp. 347-365.
Hirayama, Noriaki, Yuki Kagoubutsu Kessyo Sakusei Handbook (Organic Crystal Creating Handbook), JP, Maruzen Publishing Co., Ltd., 2008, pp. 17-12, 37-40, 45-51, 57-65.
Berge et al., "Pharmaceutical Salts," J. Pharm. Sci. 66(1):1-19 (1977).
Stahl, "Preparation of Water-Soluble Compounds Through Salt Formation", The Practice of Medicinal Chemistry, 2003, pp. 601-615.

* cited by examiner

*Primary Examiner* — Amanda L Aguirre
*Assistant Examiner* — Sagar Patel
(74) *Attorney, Agent, or Firm* — Jones Day

(57) ABSTRACT

Salts and solid forms of 3-(4-((4-(morpholinomethyl)benzyl)oxy)-1-oxoisoindolin-2-yl)piperidine-2,6-dione, or a stereoisomer thereof, are disclosed. Compositions comprising and methods of using the salts and solid forms are also disclosed.

14 Claims, 107 Drawing Sheets

Figure 1:
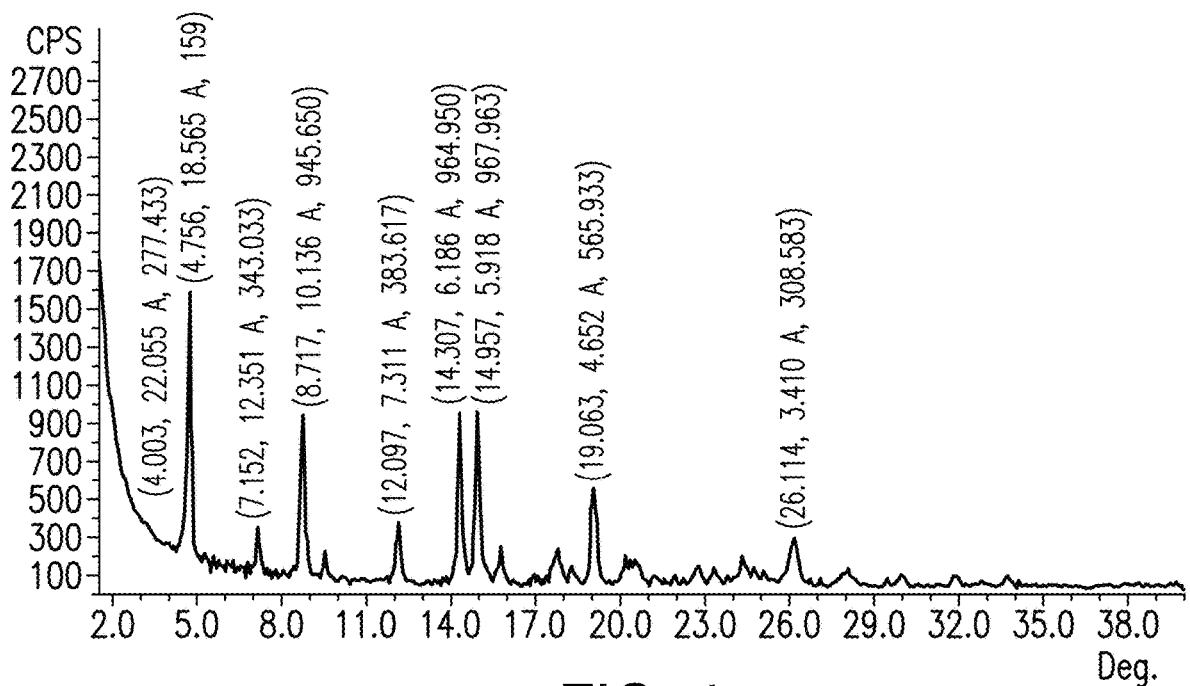

Crystal Habit of Form C of HCl Salt of Compound (I-S)

SALTS AND SOLID FORMS OF (S)-3-(4-((4-(MORPHOLINOMETHYL) BENZYL) OXY)-1-OXOISOINDOLIN-2-YL)PIPERIDINE-2,6-DIONE AND COMPOSITIONS COMPRISING AND METHODS OF USING THE SAME

The present application is a continuation application of U.S. patent application Ser. No. 15/856,845, filed Dec. 28, 2017, which is a continuation application of U.S. patent application Ser. No. 15/445,070, filed Feb. 28, 2017, now U.S. Pat. No. 9,884,062, which is a continuation application of U.S. patent application Ser. No. 14/945,147, filed Nov. 18, 2015, now U.S. Pat. No. 9,629,849, which is a continuation application of U.S. patent application Ser. No. 13/962,745, filed on Aug. 8, 2013, now U.S. Pat. No. 9,221,788, which claims priority to U.S. Provisional Patent Application No. 61/681,484, filed Aug. 9, 2012, the entirety of each of which is incorporated herein by reference.

1. FIELD

Provided herein are salts and solid forms of the compound of formula (I) or a stereoisomer thereof, solid forms of the salts, and methods of synthesizing the salts and solid forms.

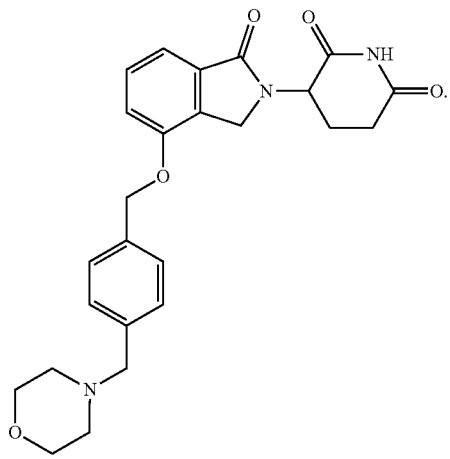

(I)

Also provided herein are pharmaceutical compositions comprising the salts and solid forms and methods for treating, preventing, and managing various disorders using the compositions, salts, and solid forms.

2. BACKGROUND (a) Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties, including tumor necrosis factor α (TNF-α). A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: diabetic retinopathy; retinopathy of prematurity; corneal graft rejection; neovascular glaucoma; retrolental fibroplasia; arthritis; and proliferative vitreoretinopathy.

Accordingly, compounds that can control angiogenesis or inhibit the production of certain cytokines, including TNF-α, may be useful in the treatment and prevention of various diseases and conditions.

(b) Methods of Treating Cancer

Current cancer therapy may involve surgery, chemotherapy, hormonal therapy and/or radiation treatment to eradicate neoplastic cells in a patient (see, e.g., Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health or age of a patient or may be unacceptable to the patient.

Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., Goodman and Gilman's: *The Pharmacological Basis of Therapeutics*, Tenth Ed. (McGraw Hill, N.Y.).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443.

Still, there is a significant need for safe and effective methods of treating, preventing and managing cancer and other diseases and conditions, including for diseases that are refractory to standard treatments, such as surgery, radiation therapy, chemotherapy and hormonal therapy, while reducing or avoiding the toxicities and/or side effects associated with the conventional therapies.

(c) Salts and Solid Forms

Compounds having a basic moiety can form various salts with acids. Different salts of a given compound may have different properties that affect the compound's stability, processability, in vivo performance as a pharmaceutical. The physical properties of certain salts of a given compound may also allow for or facilitate the isolation of optically or stereomerically pure forms of the compound.

Compounds may also exist in different solid forms. The selection of a solid form of a pharmaceutical compound may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., Adv. Drug. Deliv. Rev., (2001) 48:3-26; L. Yu, *Adv. Drug. Deliv. Rev.*, (2001) 48:27-42).

Whether crystalline or amorphous, potential solid forms of a pharmaceutical compound may include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette).

Additional diversity among the potential solid forms of a pharmaceutical compound may arise from the possibility of multiple-component solids. Crystalline solids comprising two or more ionic species are termed salts (see, e.g., *Handbook of Pharmaceutical Salts: Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., *Solid State Chemistry of Drugs*, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

3. SUMMARY

Provided herein are salts and solid forms of the compound of formula (I) or a stereoisomer thereof, solid forms of the salts, and methods of synthesizing the salts and solid forms.

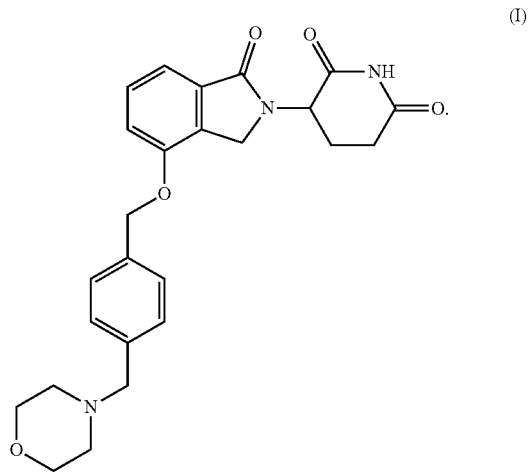 [SMILES: O=C1CCC(N2Cc3c(OCc4ccc(CN5CCOCC5)cc4)cccc3C2=O)C(=O)N1]

(I)

In one embodiment, provided herein are salts and solid forms of the racemic compound of formula (I), solid forms of the salts, and methods of synthesizing the salts and solid forms. In one embodiment, provided herein are solid forms comprising the racemic Compound of formula (I) and a significant quantity of one or more additional species, such as ions and/or molecules.

In one embodiment, provided herein are salts and solid forms of the compound of formula (I-S), solid forms of the salts, and methods of synthesizing the salts and solid forms. In one embodiment, provided herein are solid forms comprising the Compound of formula (I-S) and a significant quantity of one or more additional species, such as ions and/or molecules.

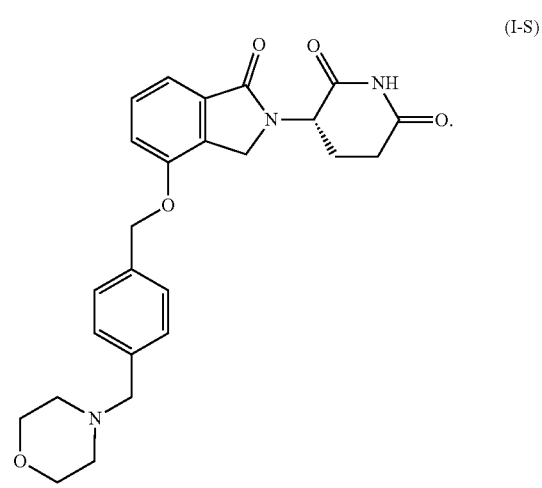 [SMILES: O=C1CC[C@H](N2Cc3c(OCc4ccc(CN5CCOCC5)cc4)cccc3C2=O)C(=O)N1]

(I-S)

The solids forms provided herein include, but are not limited to, hydrates, anhydrates, solvates, as well as crystal and amorphous forms. The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, a multiple-component crystal form, a single-component amorphous form and/or a multiple-component amorphous form comprising the compound of formula (I) or a stereoisomer thereof and a pharmaceutically acceptable diluent, excipient or carrier.

Provided herein are also pharmaceutical compositions, single unit dosage forms, dosing regimens and kits comprising the salts and solid forms.

Provided herein are also methods for treating, preventing, and managing various disorders using the compositions, salts, and solid forms. The methods comprise administering to a patient in need of such treatment or management a therapeutically effective amount of a salt or solid form provided herein. Further provided are methods of preventing various diseases and disorders, which comprise administering to a patient in need of such prevention a prophylactically effective amount of a salt or solid form provided herein.

4. BRIEF DESCRIPTION OF THE DRAWINGS

FIG. 1 provides a representative XRPD pattern of an anhydrate of Compound (I-S).

Figure 2:
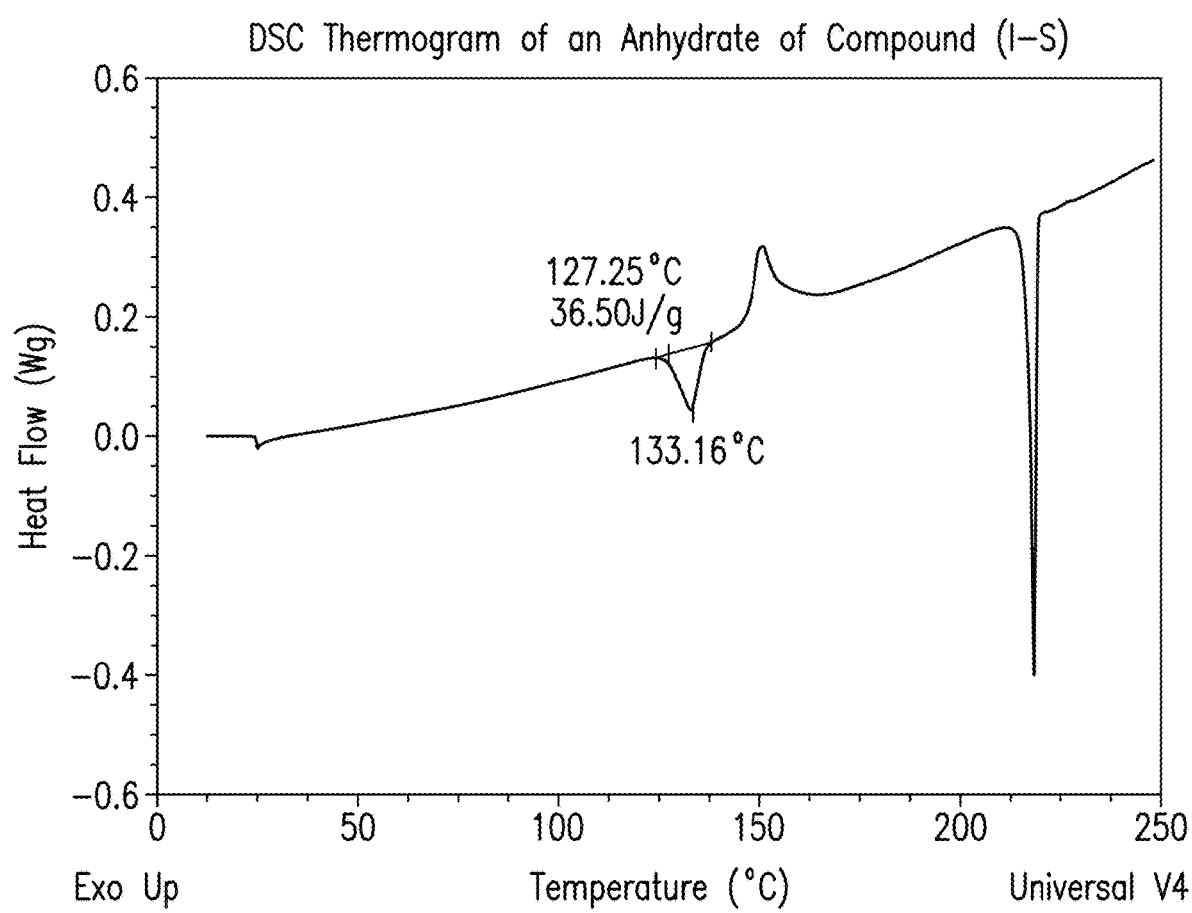

FIG. 2 provides a representative DSC thermogram of an anhydrate of Compound (I-S).

Figure 3:
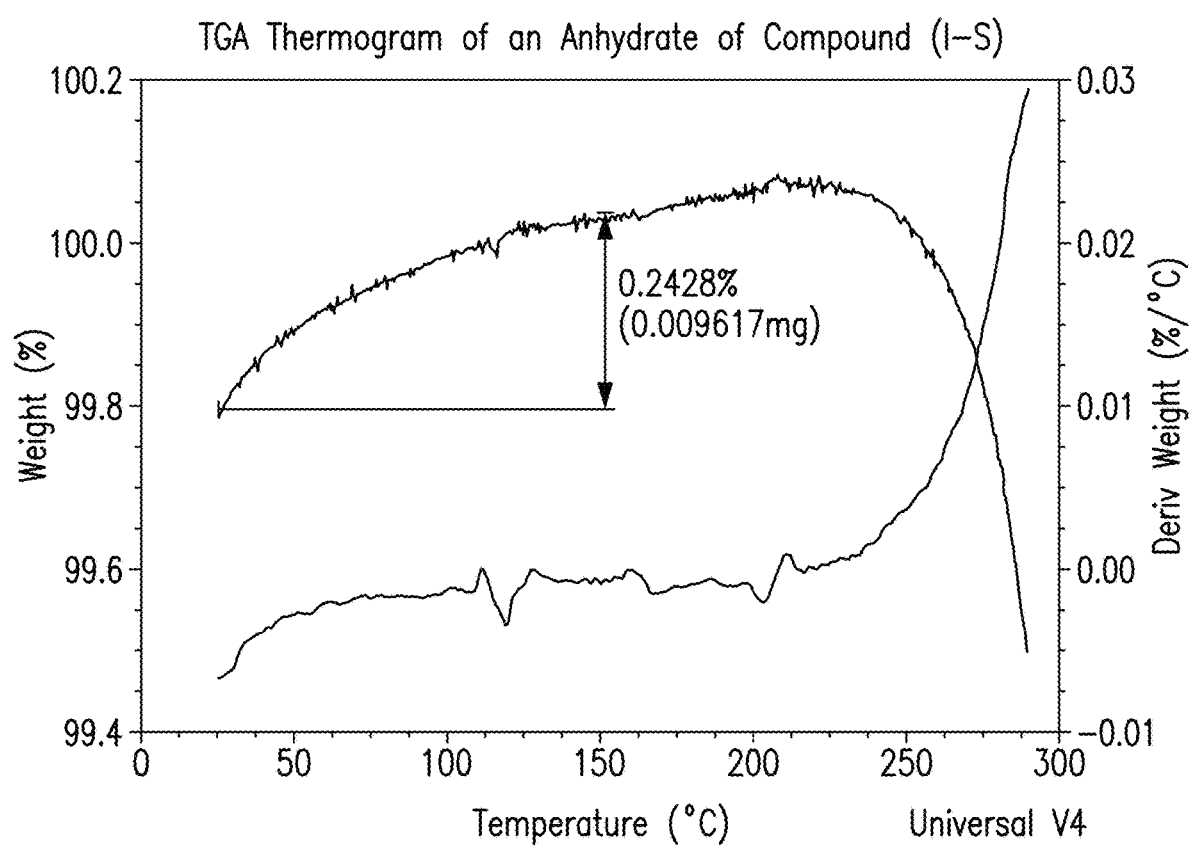

FIG. 3 provides a representative TGA thermogram of an anhydrate of Compound (I-S).

Figure 4:
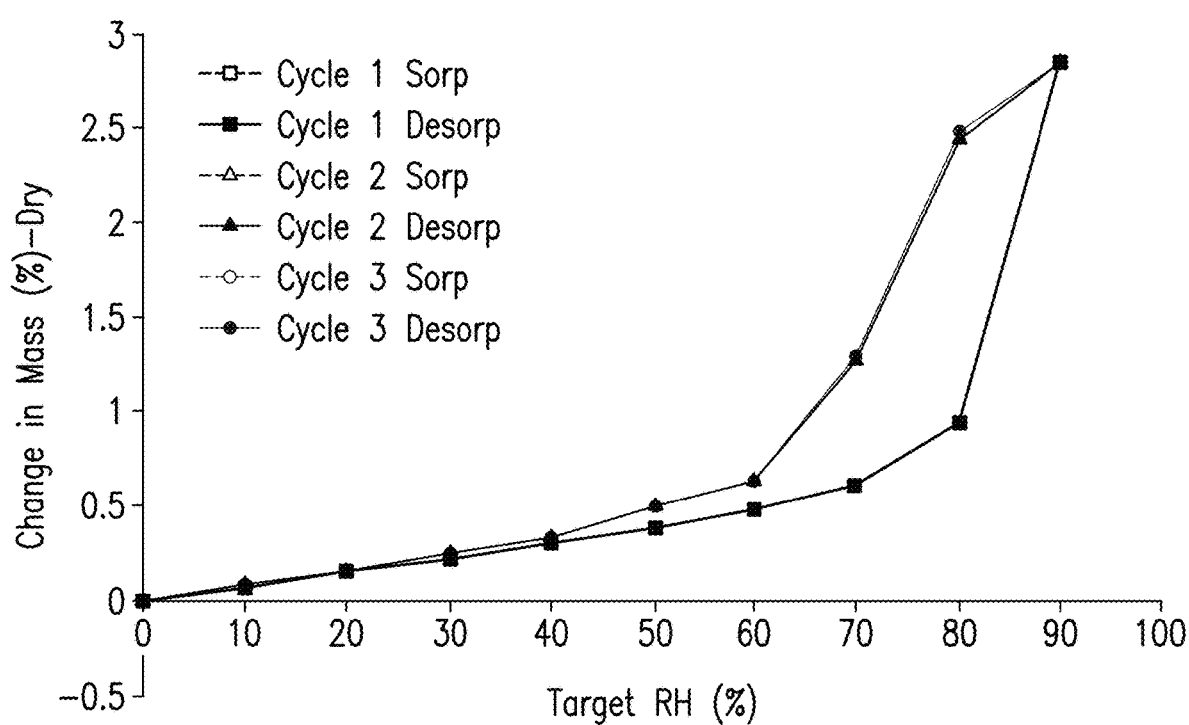

FIG. 4 provides a representative DVS plot of an anhydrate of Compound (I-S).

Figure 5:
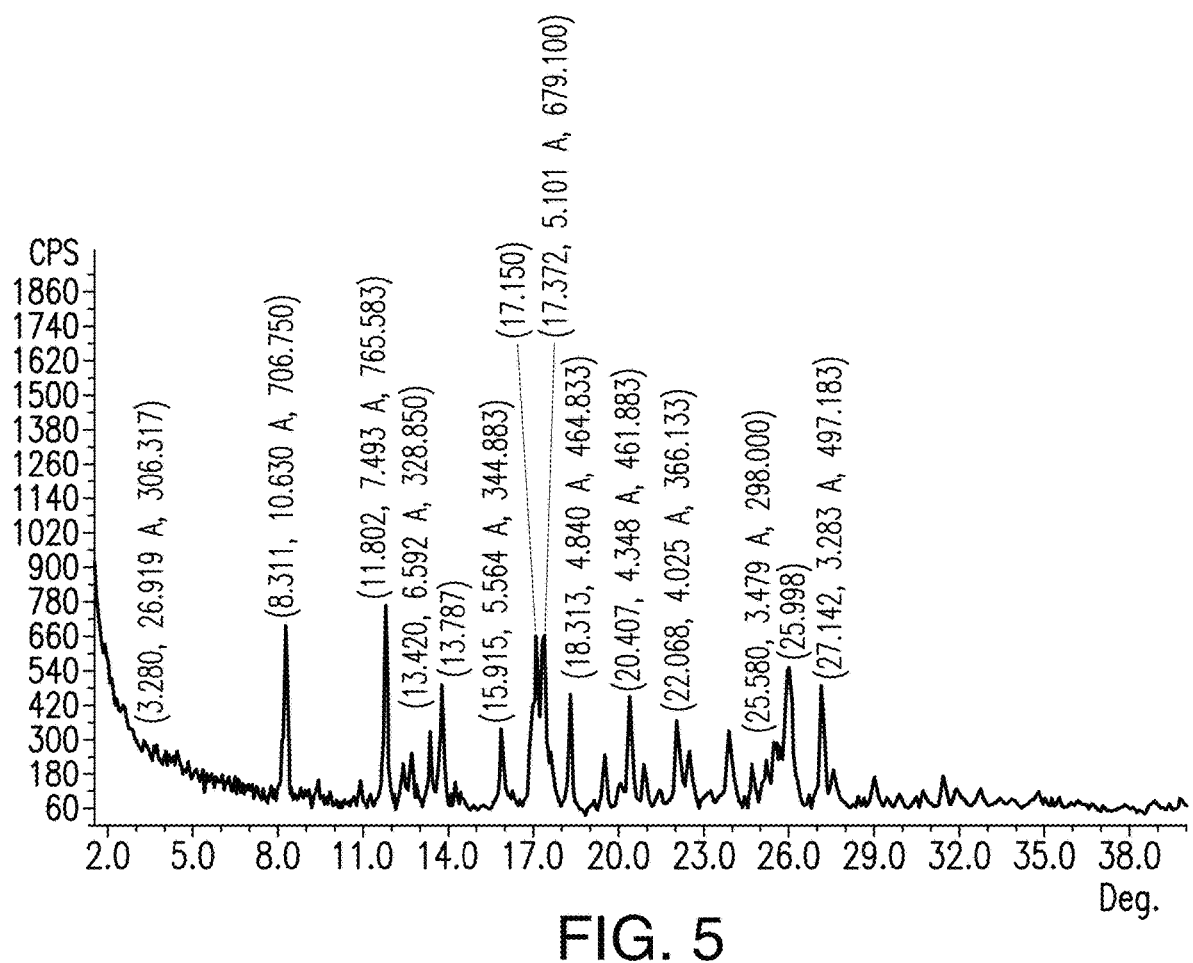

FIG. 5 provides a representative XRPD pattern of a hydrate of Compound (I-S).

Figure 6:
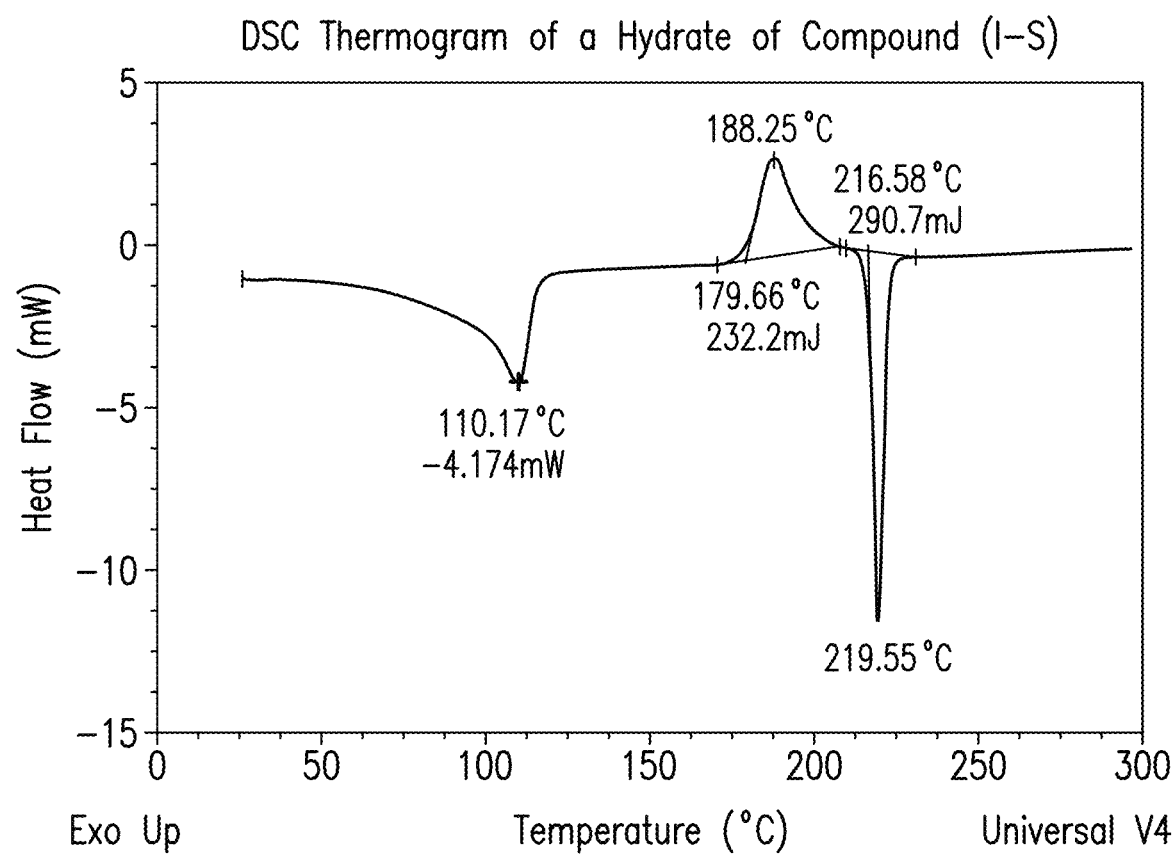

FIG. 6 provides a representative DSC thermogram of a hydrate of Compound (I-S).

Figure 7:
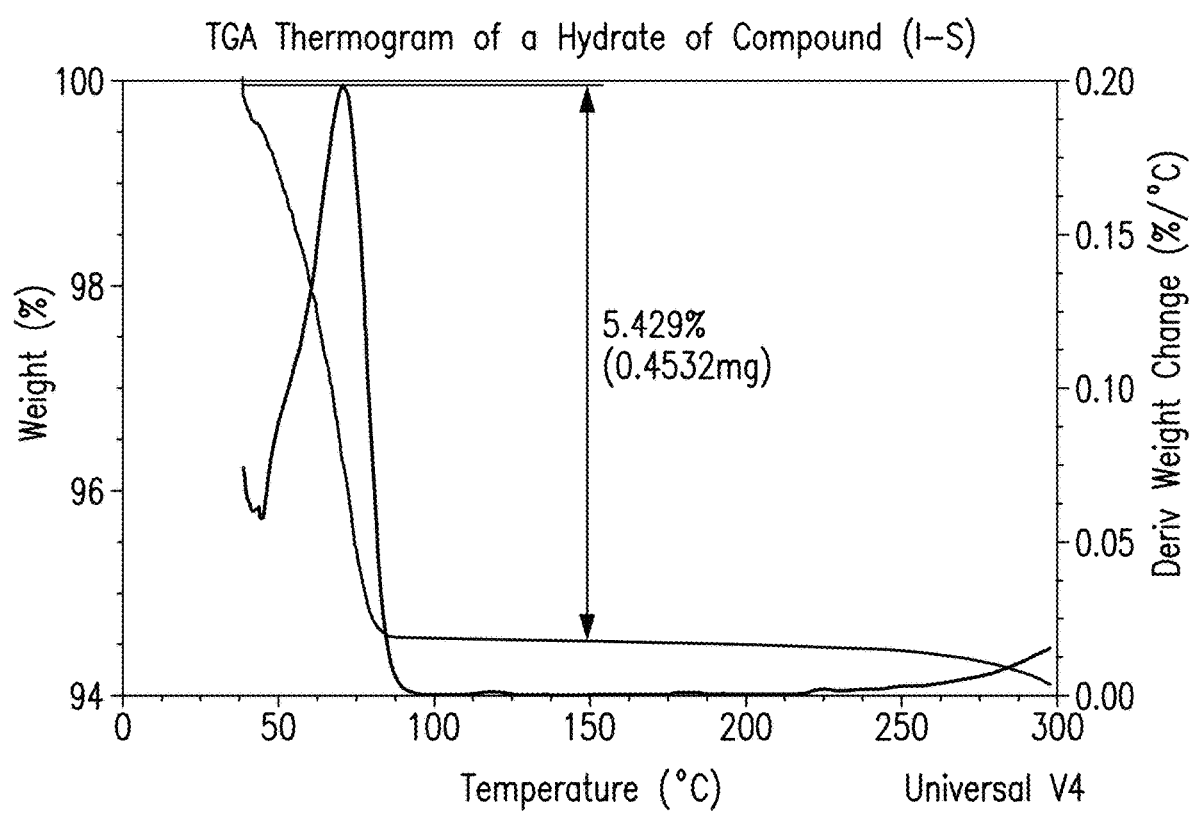

FIG. 7 provides a representative TGA thermogram of a hydrate of Compound (I-S).

Figure 8:
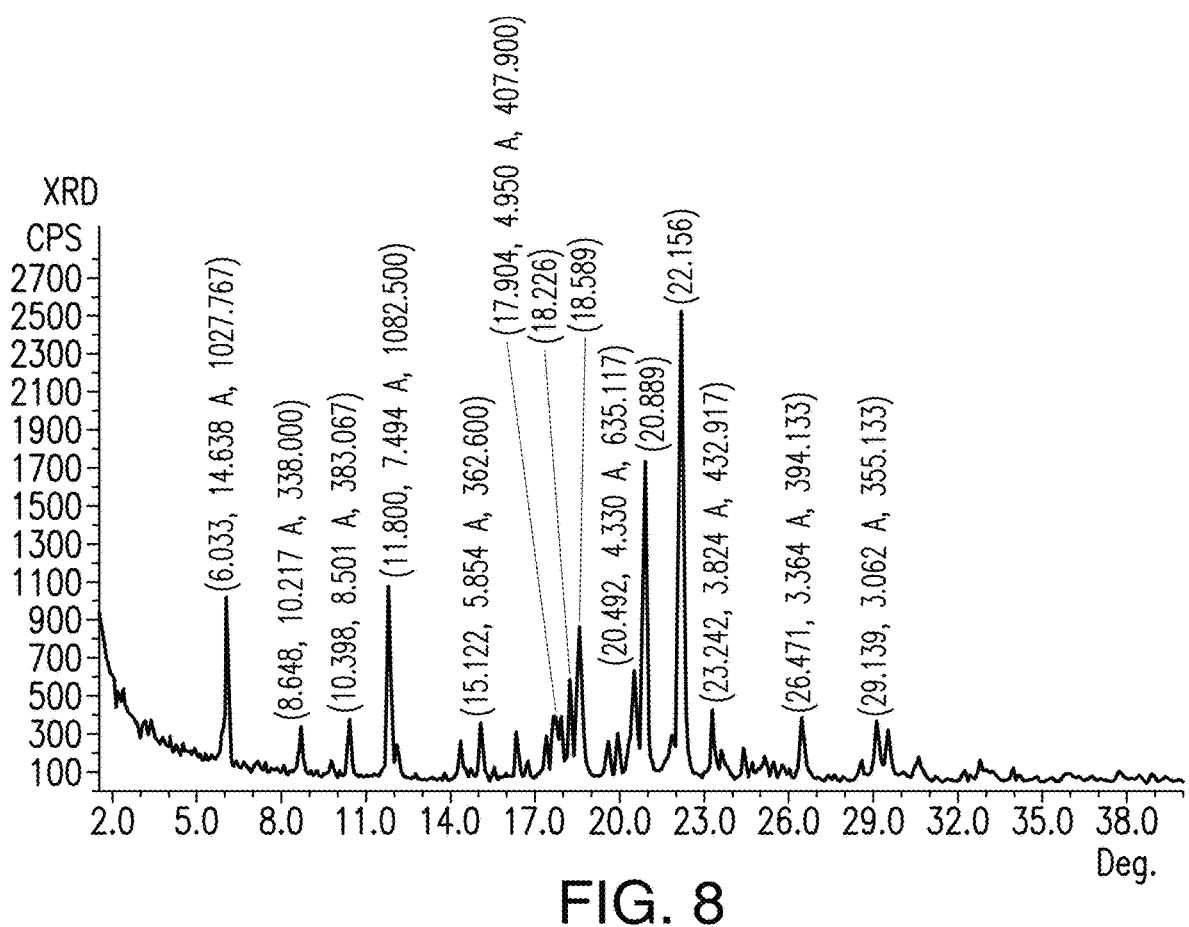

FIG. 8 provides a representative XRPD pattern of a THF solvate of Compound (I-S).

Figure 9:
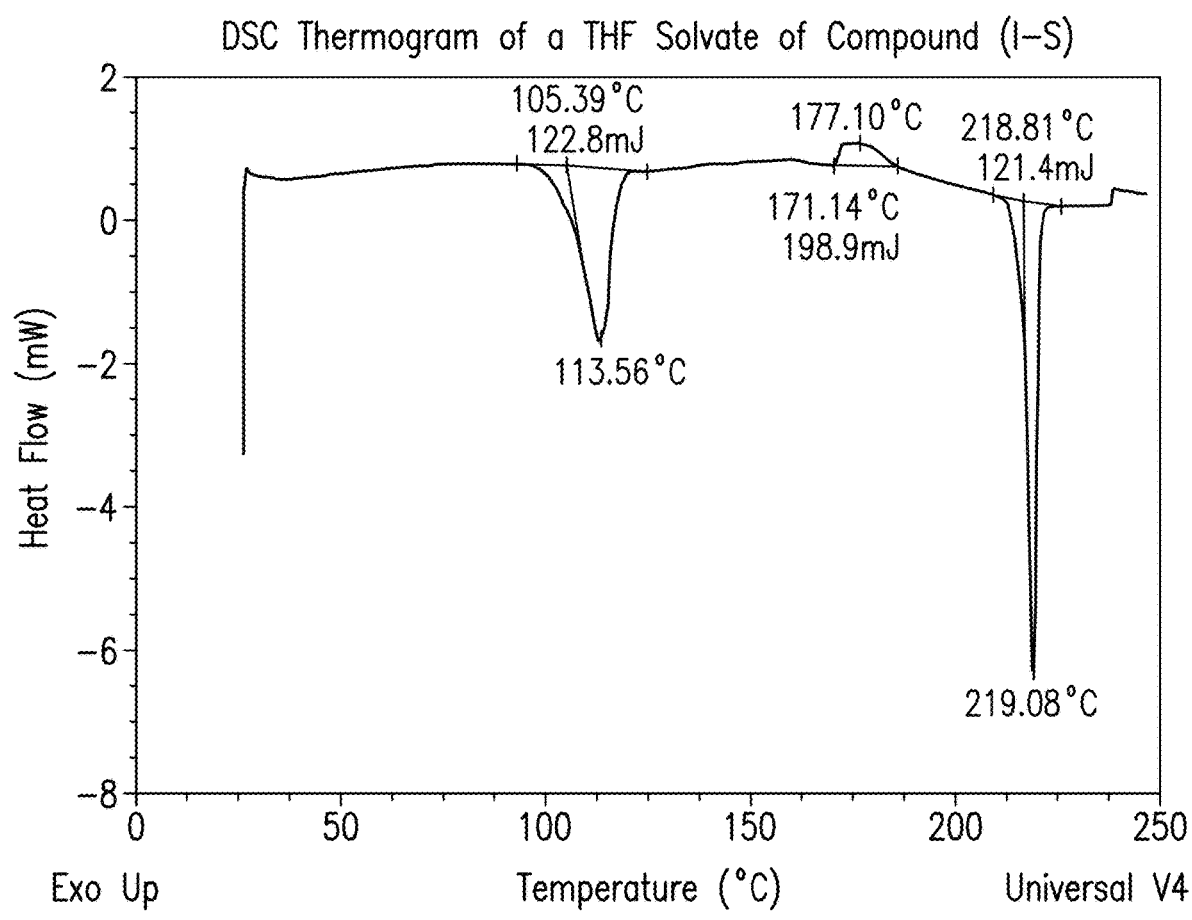

FIG. 9 provides a representative DSC thermogram of a THF solvate of Compound (I-S).

Figure 10:
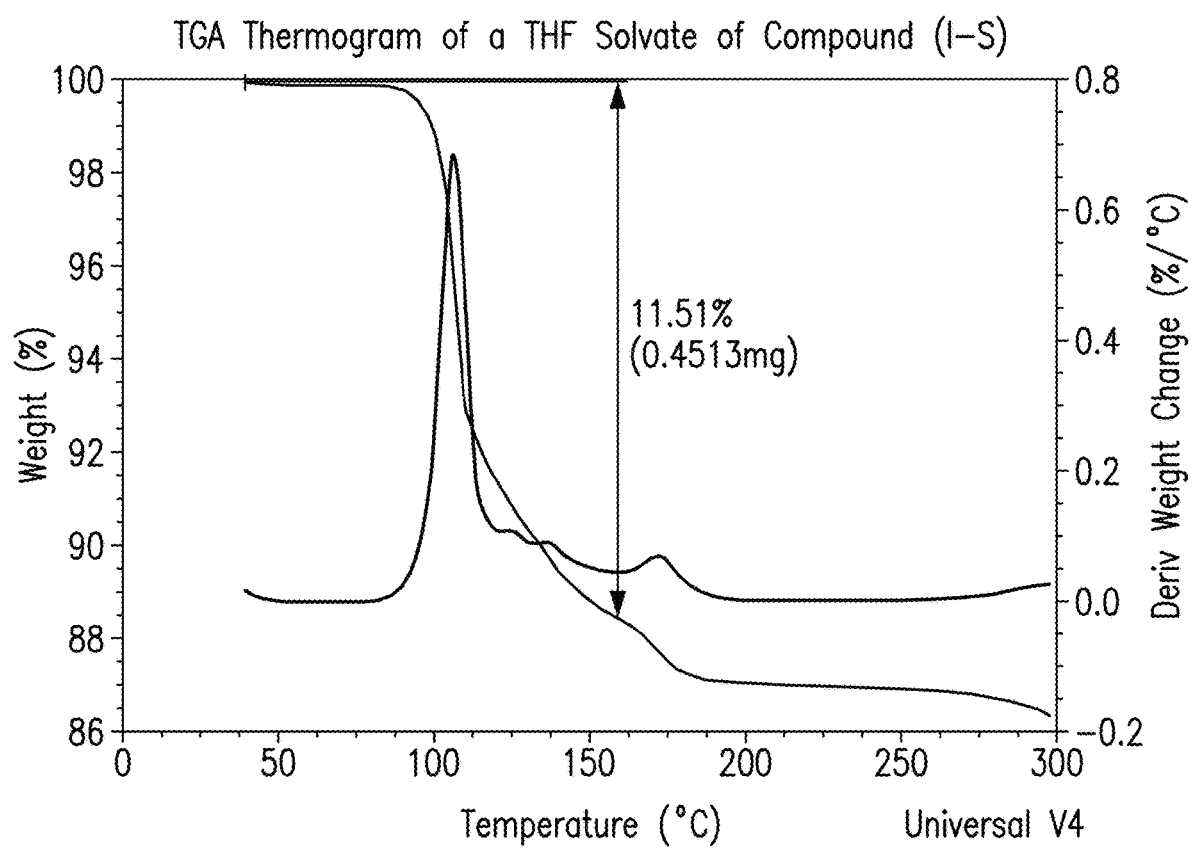

FIG. 10 provides a representative TGA thermogram of a THF solvate of Compound (I-S).

Figure 11:
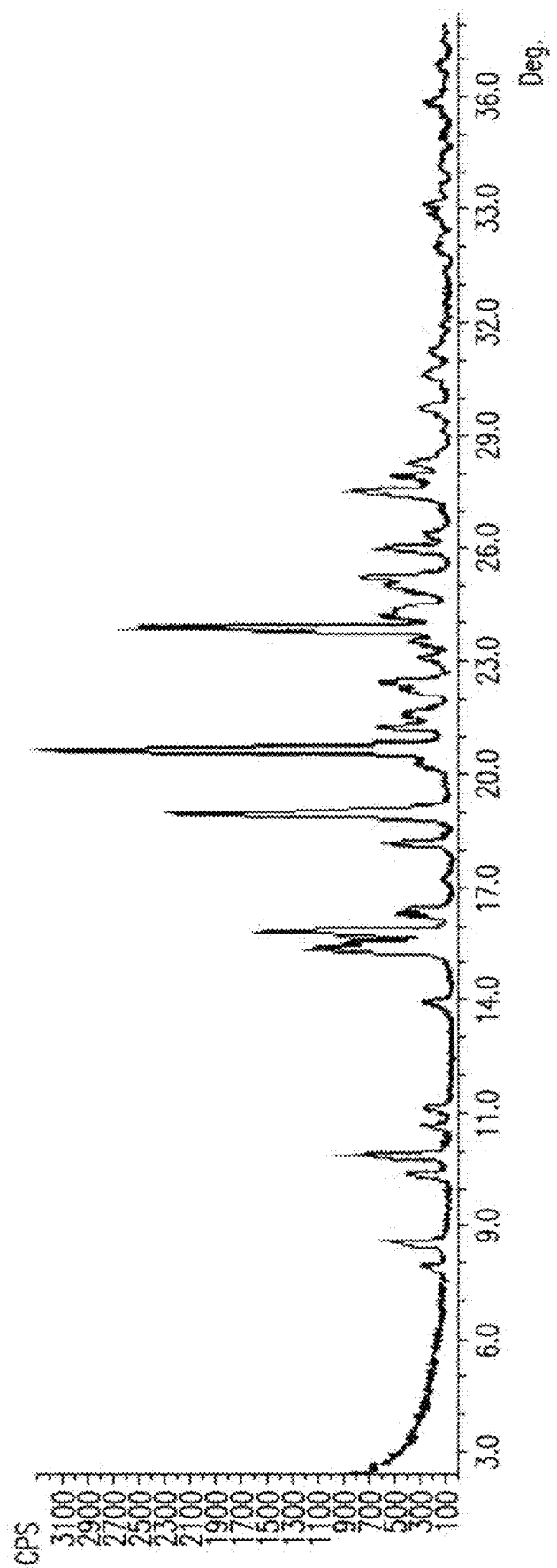

FIG. 11 provides a representative XRPD pattern of a besylate salt of Compound (I-S).

Figure 12:
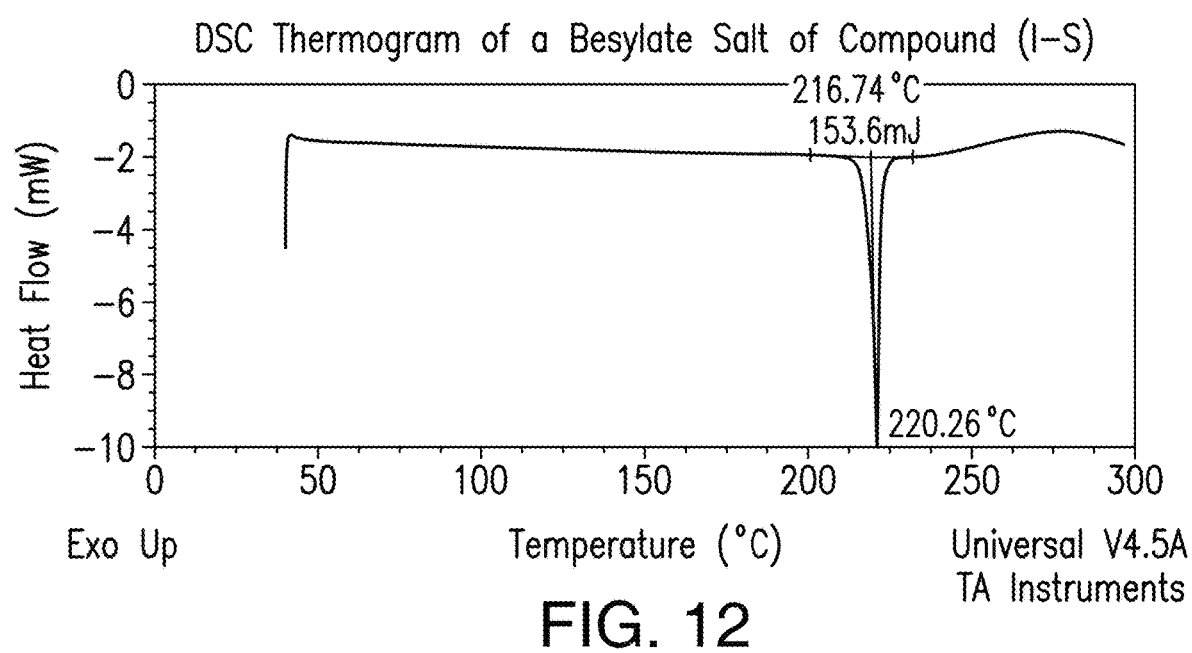

FIG. 12 provides a representative DSC thermogram of a besylate salt of Compound (I-S).

Figure 13:
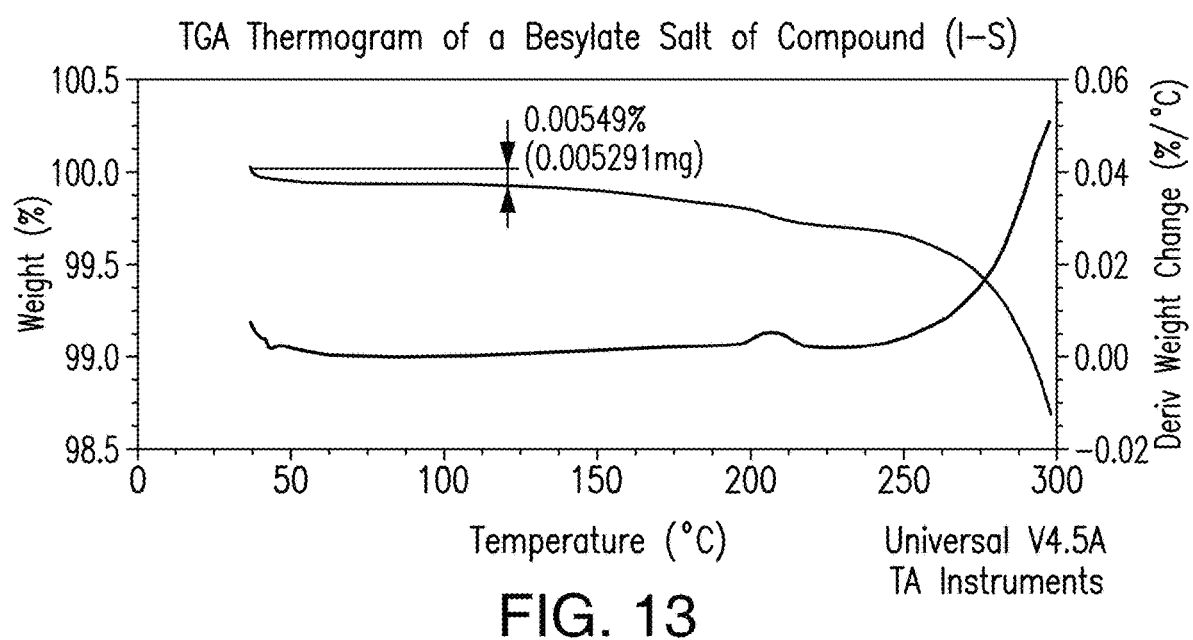

FIG. 13 provides a representative TGA thermogram of a besylate salt of Compound (I-S).

Figure 14:
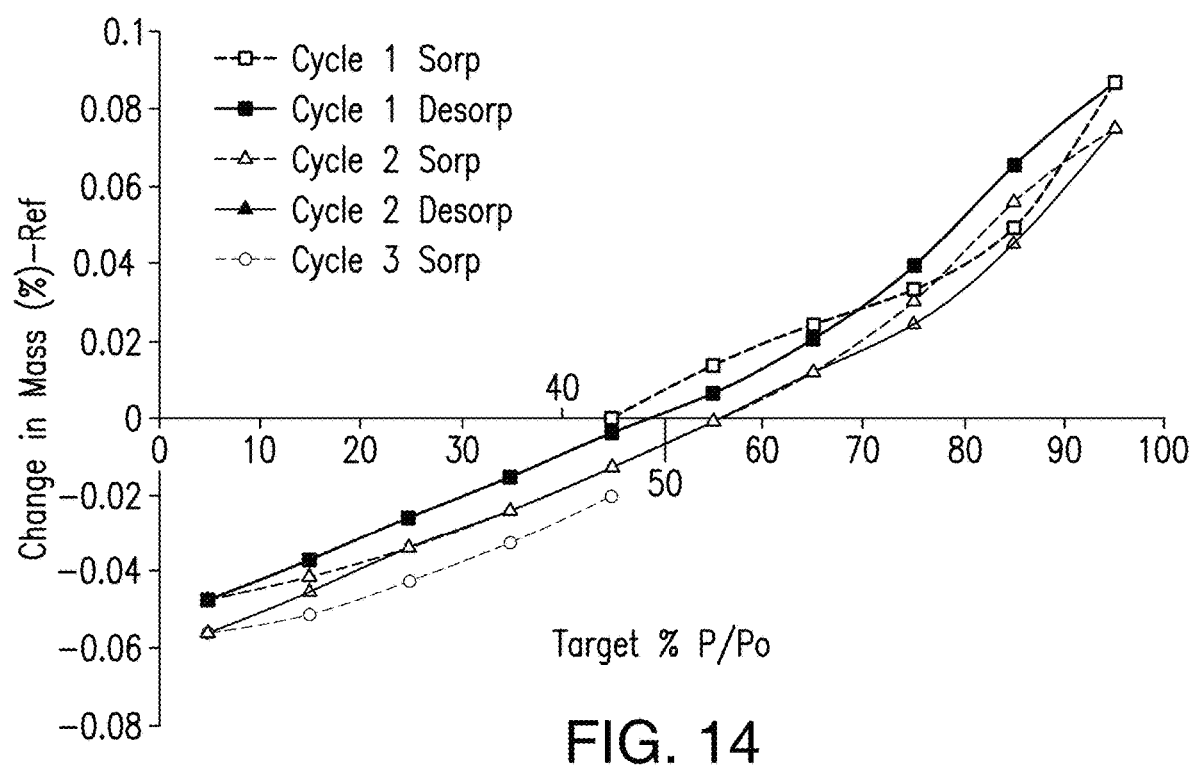

FIG. 14 provides a representative DVS plot of a besylate salt of Compound (I-S).

Figure 15:
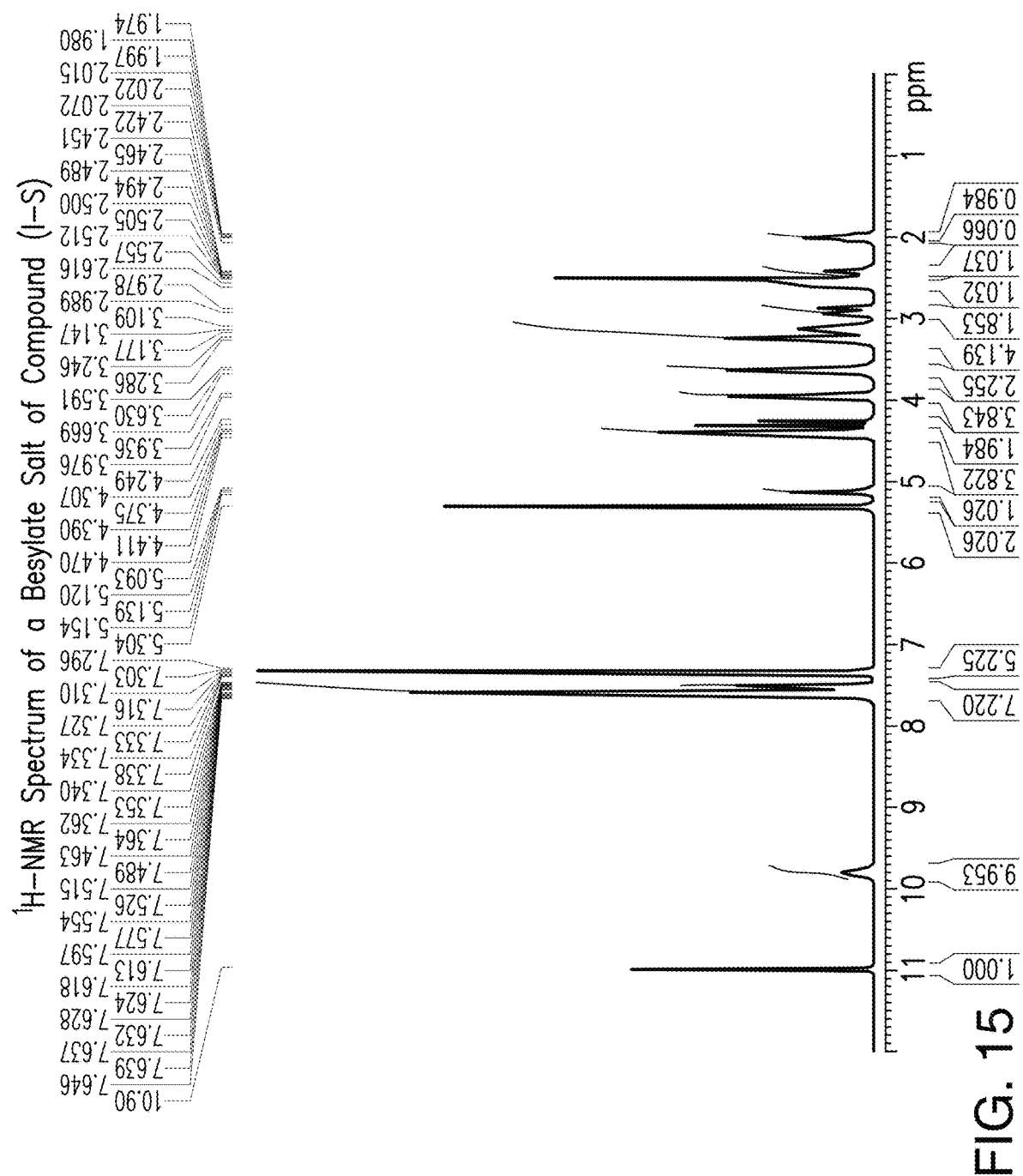

FIG. 15 provides a representative $^1$H-NMR spectrum of a besylate salt of Compound (I-S).

Figure 16:
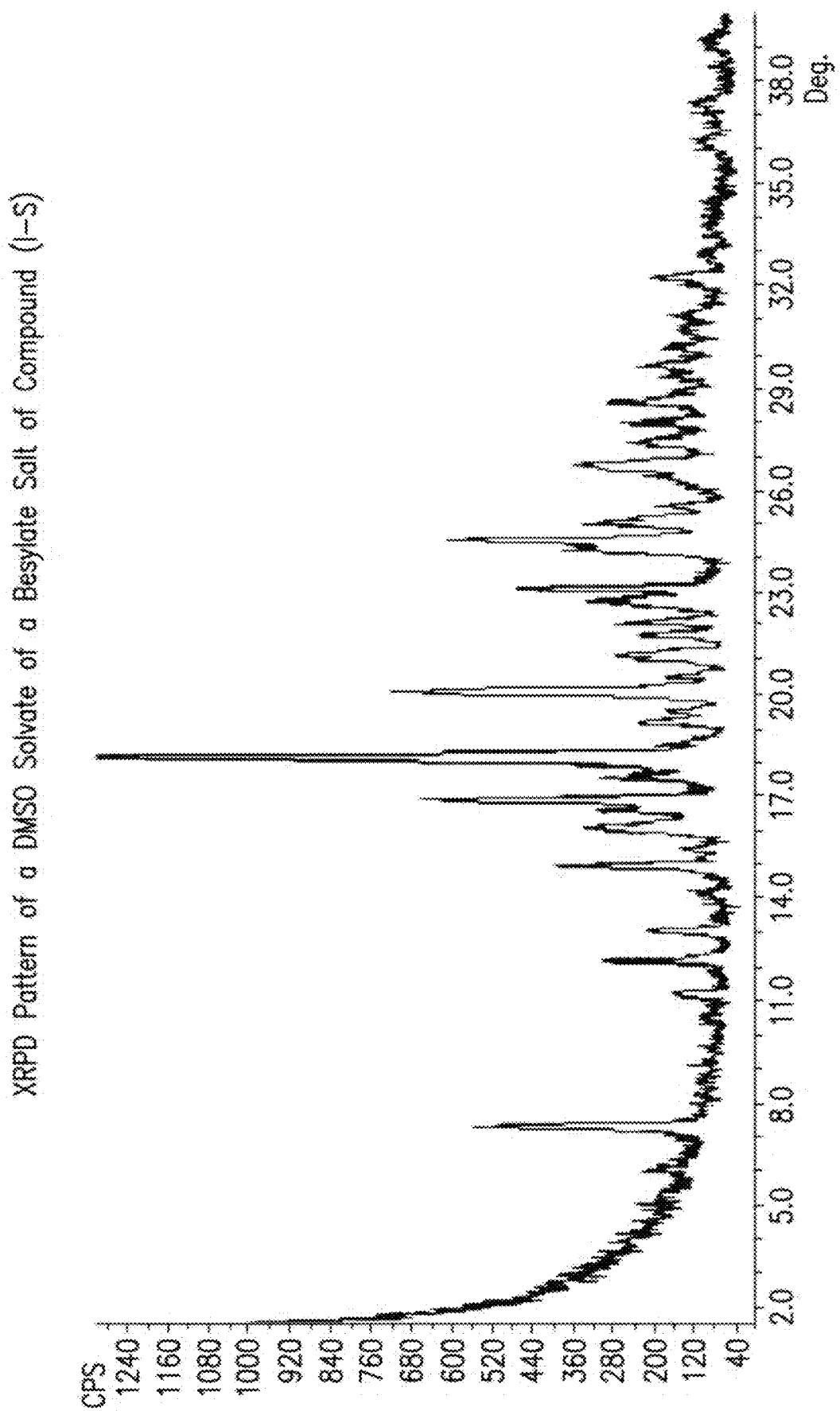

FIG. 16 provides a representative XRPD pattern of a DMSO solvate of a besylate salt of Compound (I-S).

Figure 17:
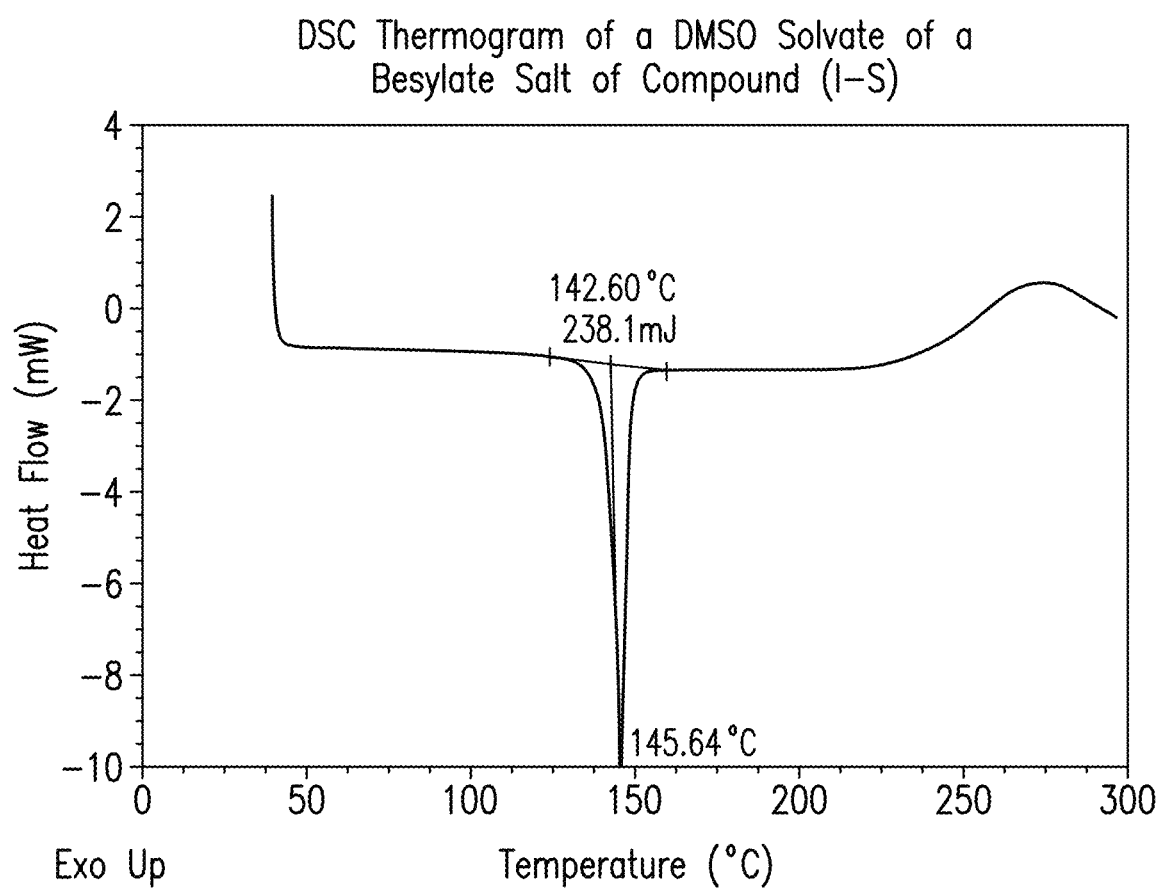

FIG. 17 provides a representative DSC thermogram of a DMSO solvate of a besylate salt of Compound (I-S).

Figure 18:
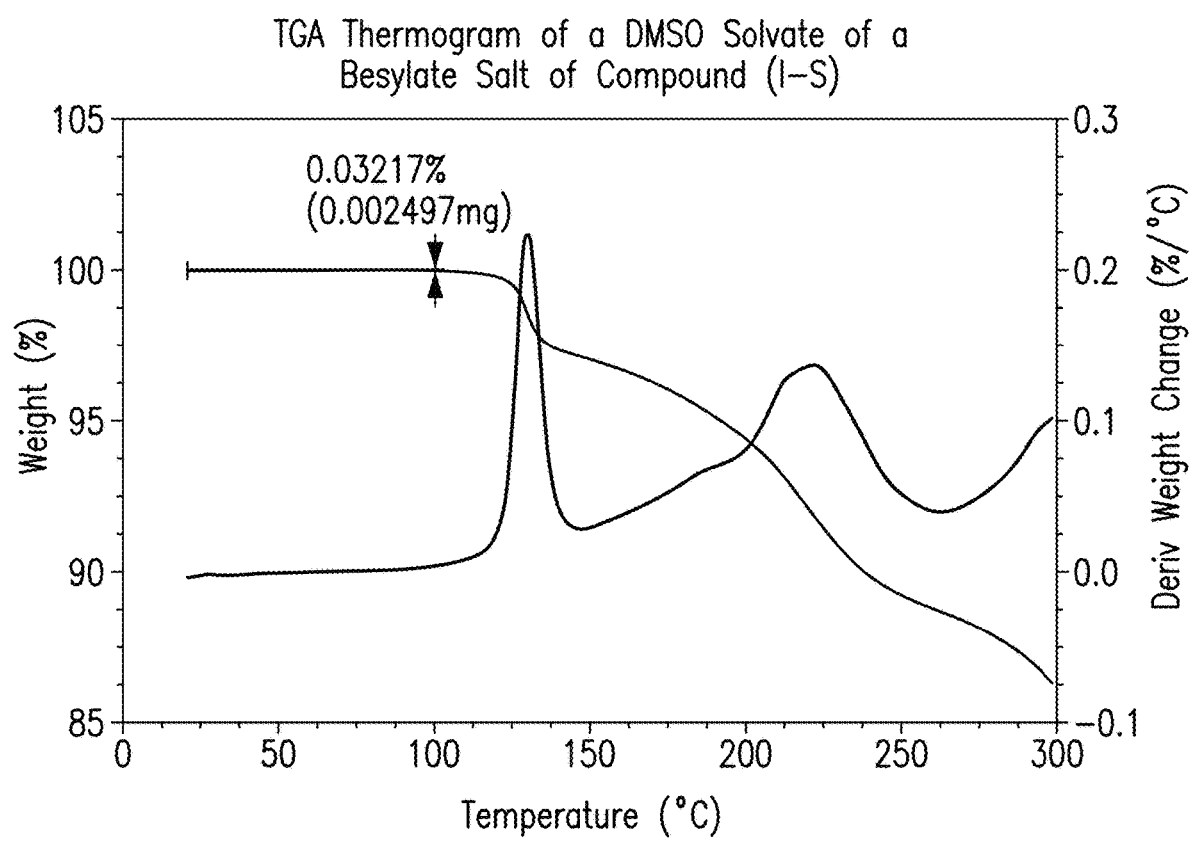

FIG. 18 provides a representative TGA thermogram of a DMSO solvate of a besylate salt of Compound (I-S).

Figure 19:
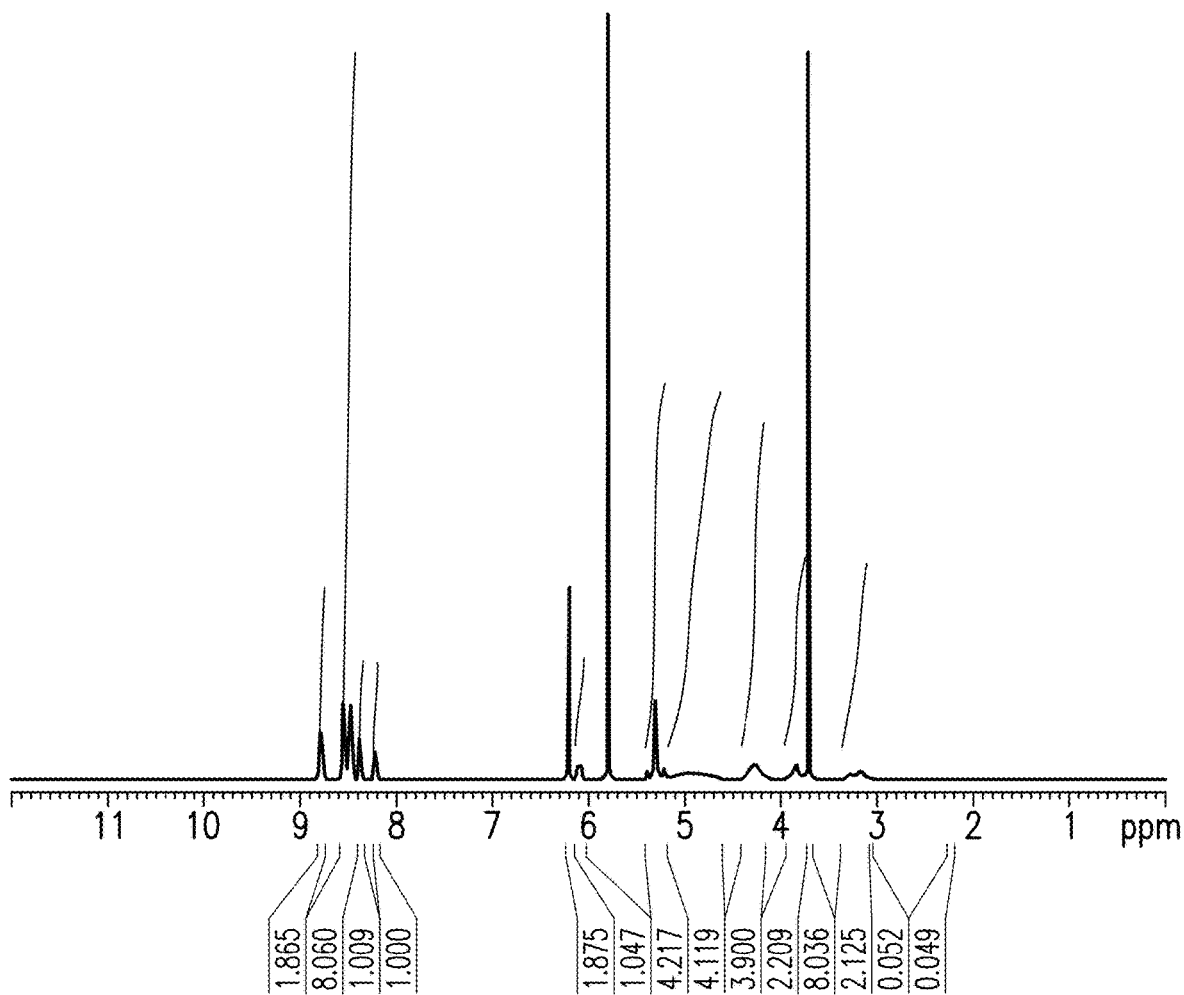

FIG. 19 provides a representative $^1$H-NMR spectrum of a DMSO solvate of a besylate salt of Compound (I-S).

Figure 20:
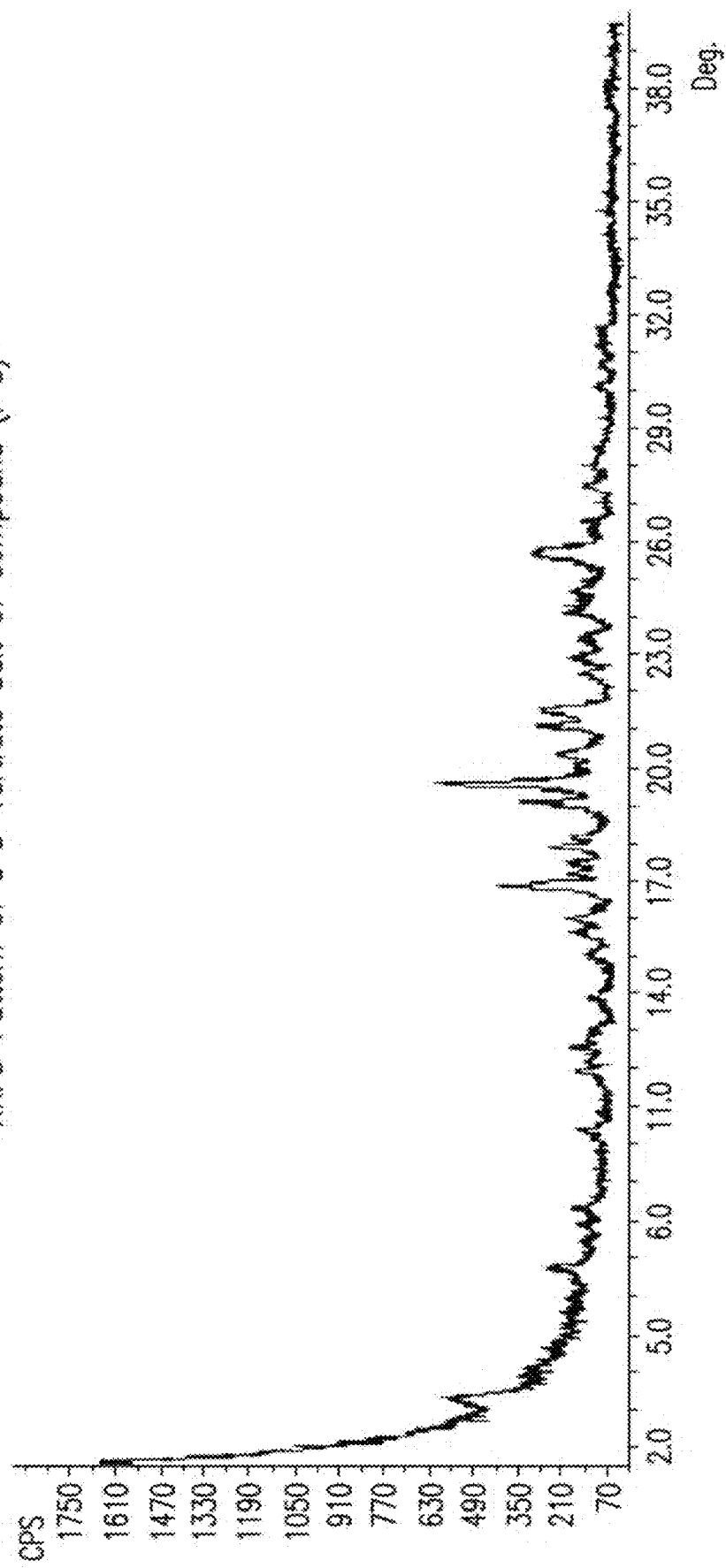

FIG. 20 provides a representative XRPD pattern of a D-tartrate salt of Compound (I-S).

Figure 21A:
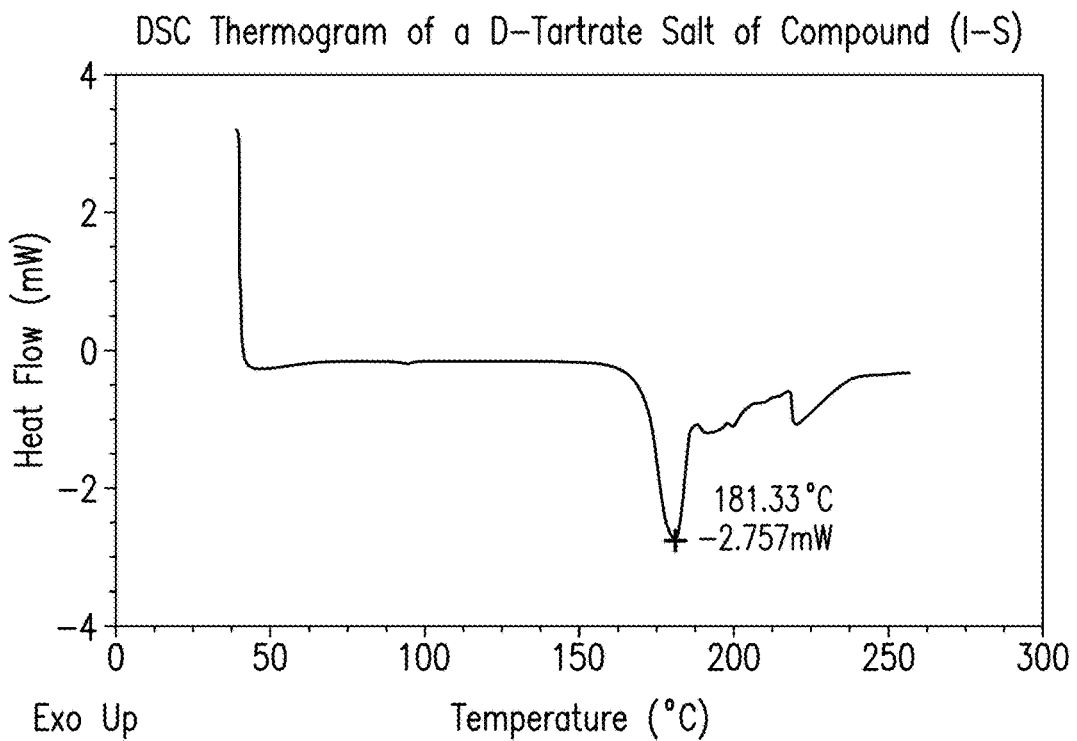

FIG. 21A provides a representative DSC thermogram of a D-tartrate salt of Compound (I-S).

Figure 21B:
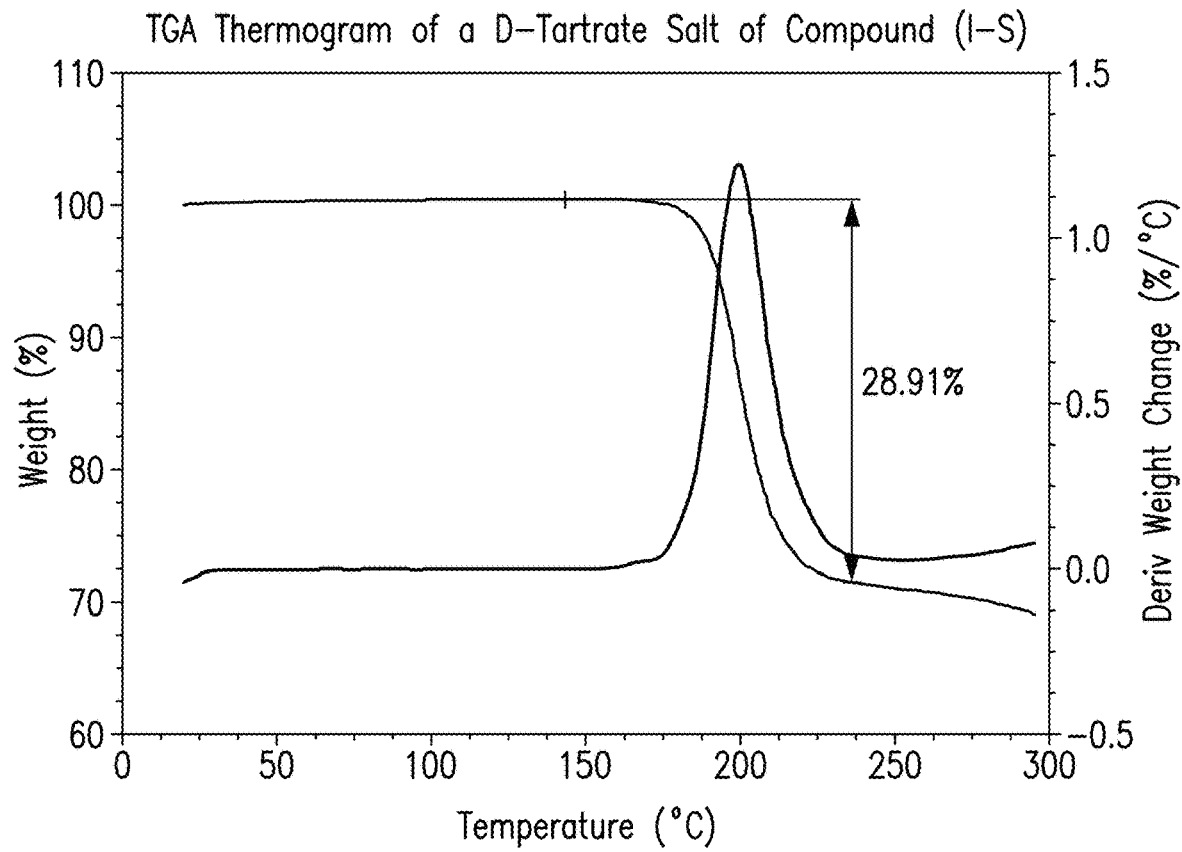

FIG. 21B provides a representative TGA thermogram of a D-tartrate salt of Compound (I-S).

Figure 22:
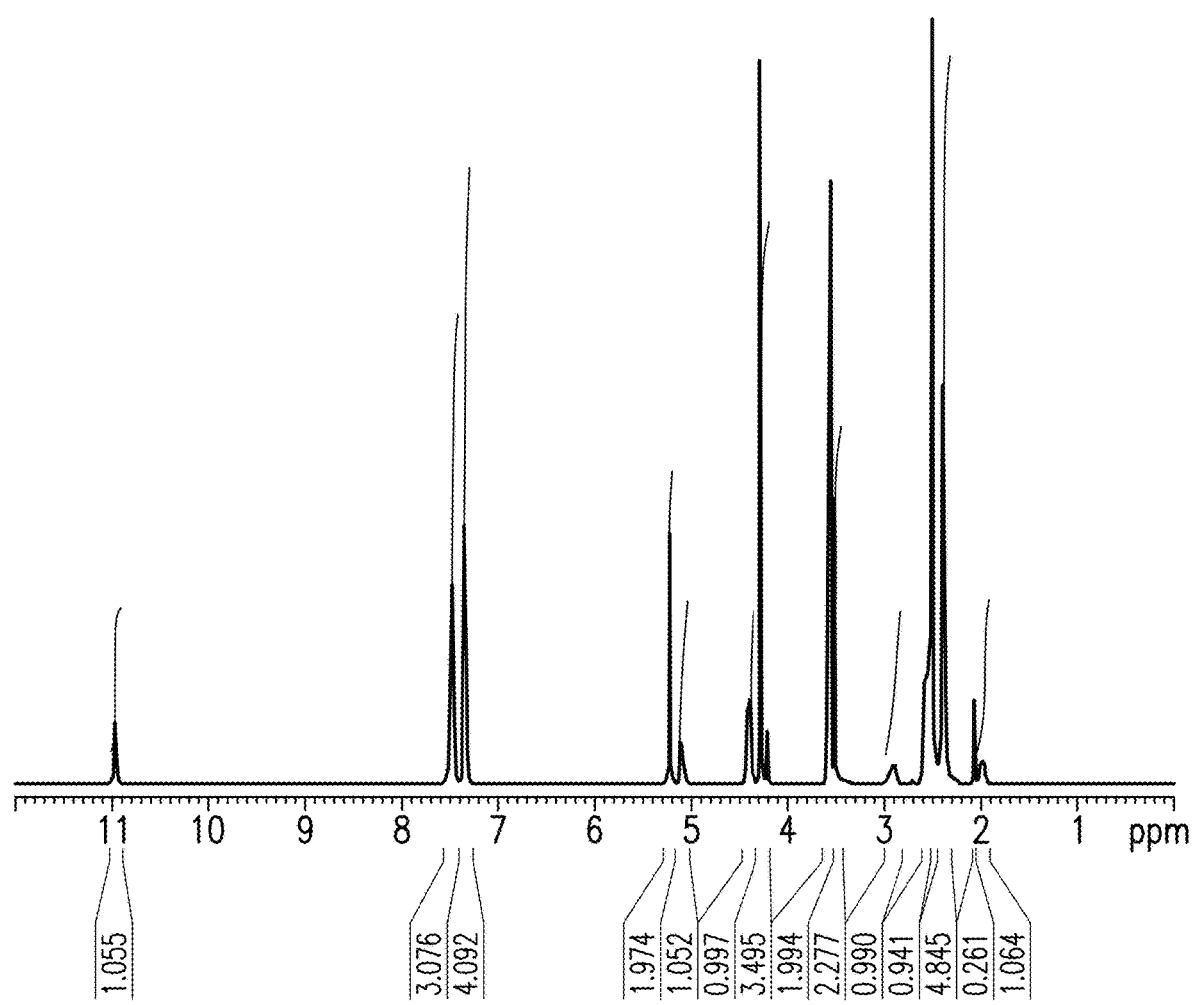

FIG. 22 provides a representative $^1$H-NMR spectrum of a D-tartrate salt of Compound (I-S).

Figure 23:
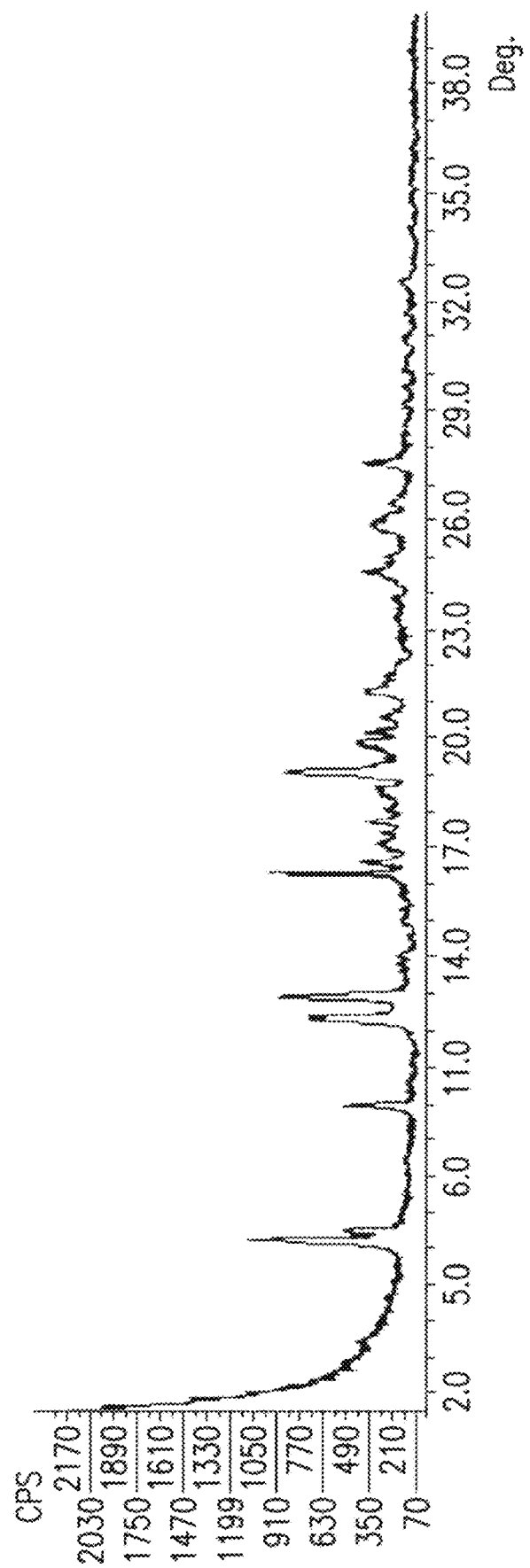

FIG. 23 provides a representative XRPD pattern of a hemi D-tartrate salt of Compound (I-S).

Figure 24A:
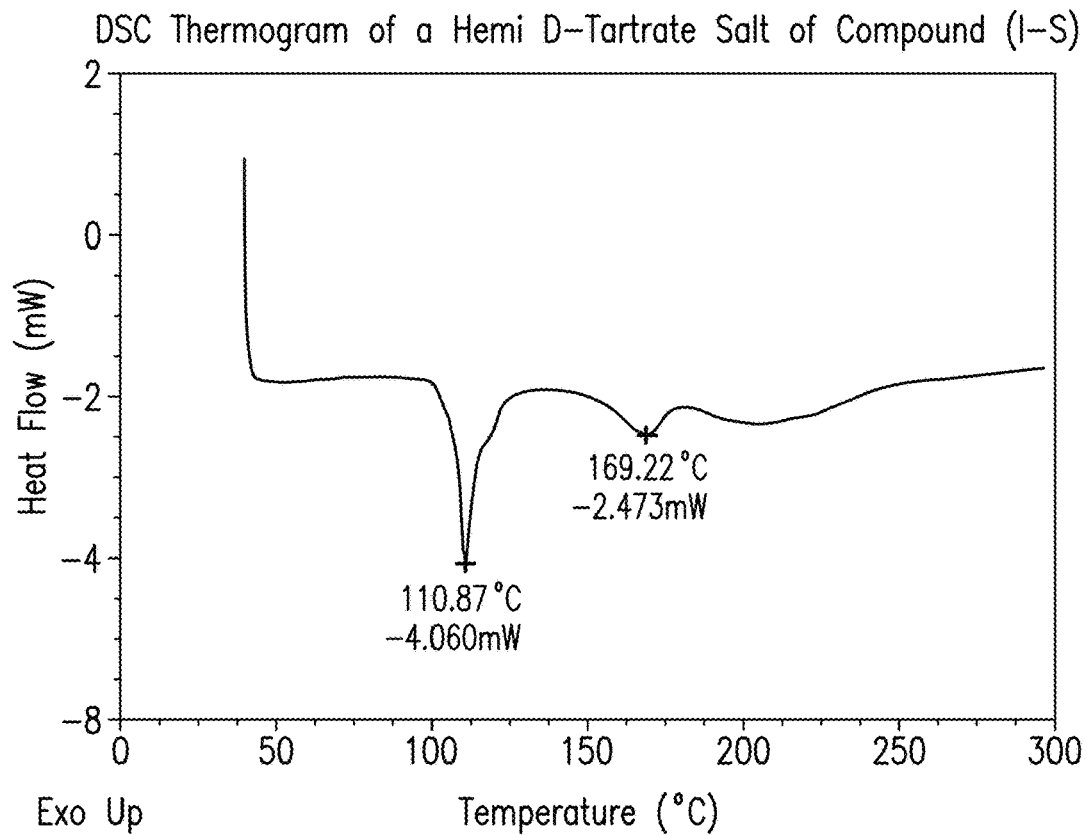

FIG. 24A provides a representative DSC thermogram of a hemi D-tartrate salt of Compound (I-S).

Figure 24B:
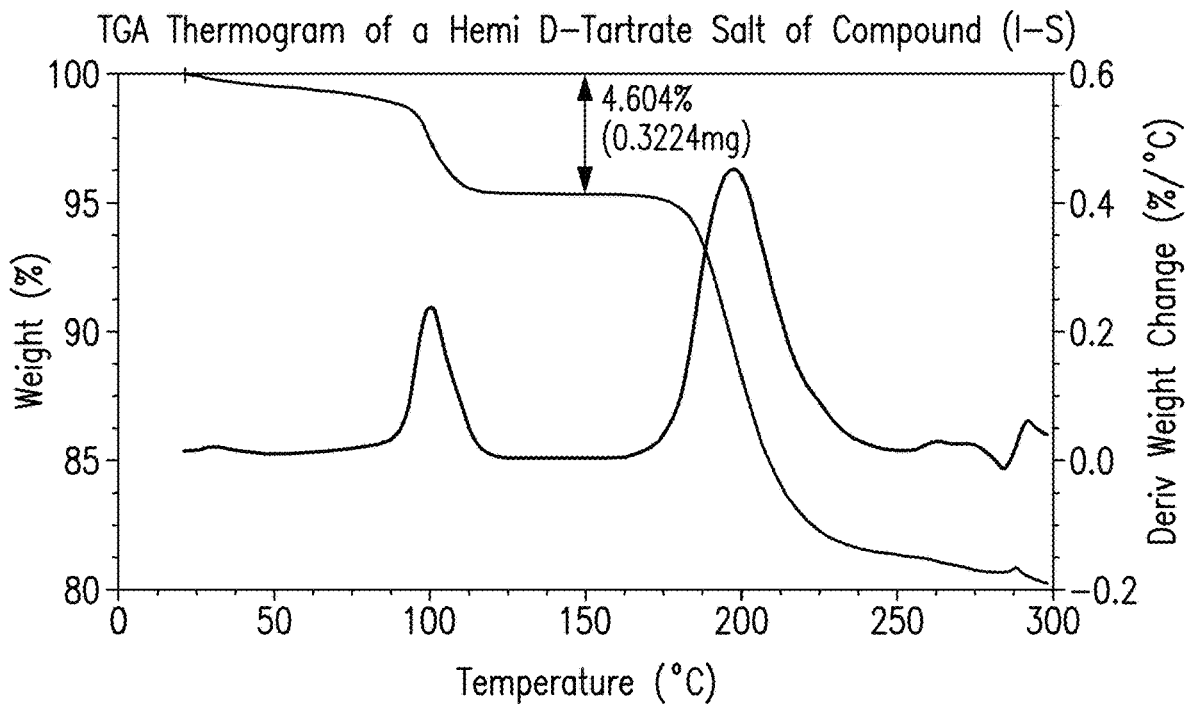

FIG. 24B provides a representative TGA thermogram of a hemi D-tartrate salt of Compound (I-S).

Figure 25:
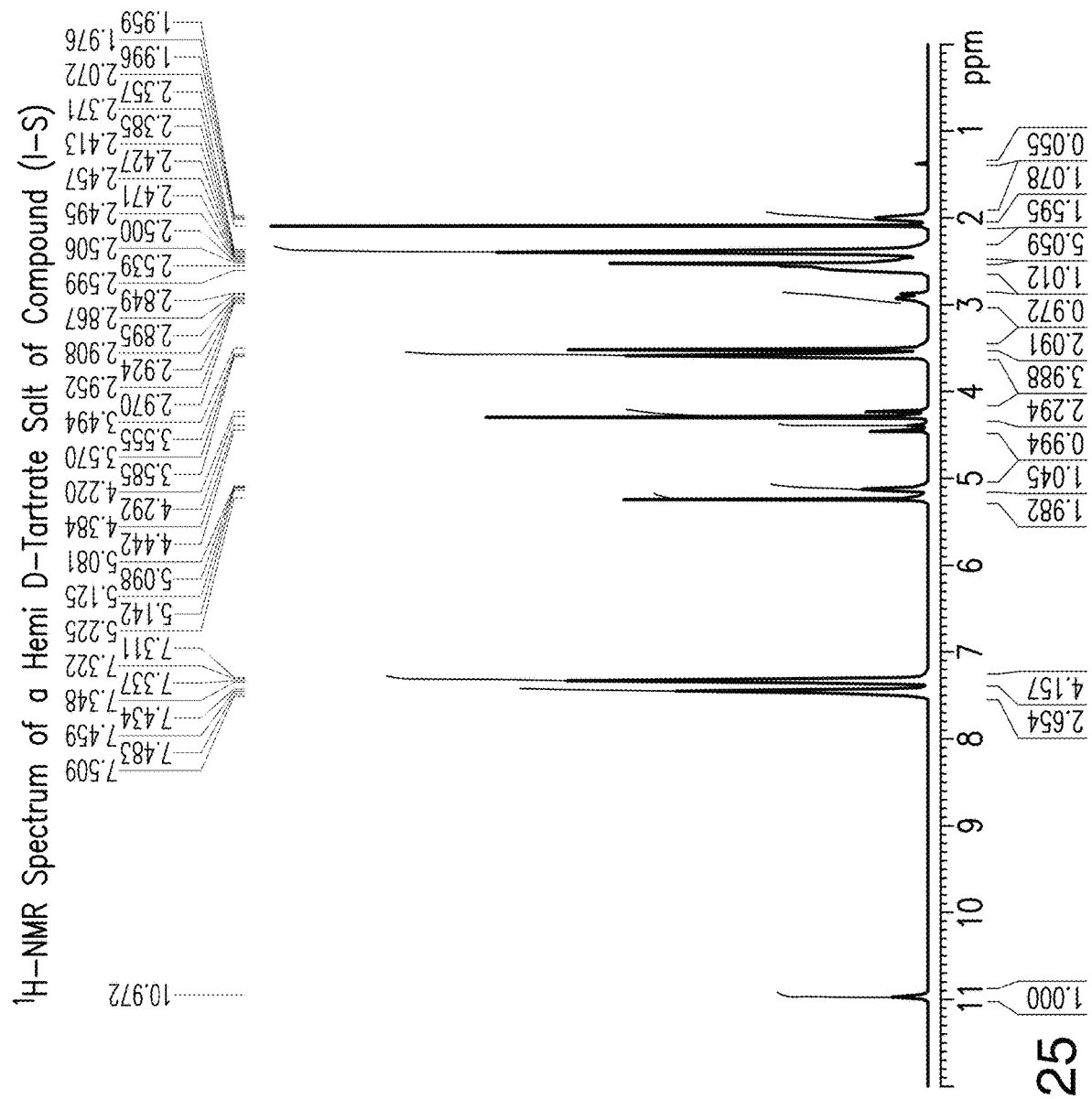

FIG. 25 provides a representative $^1$H-NMR spectrum of a hemi D-tartrate salt of Compound (I-S).

Figure 26:
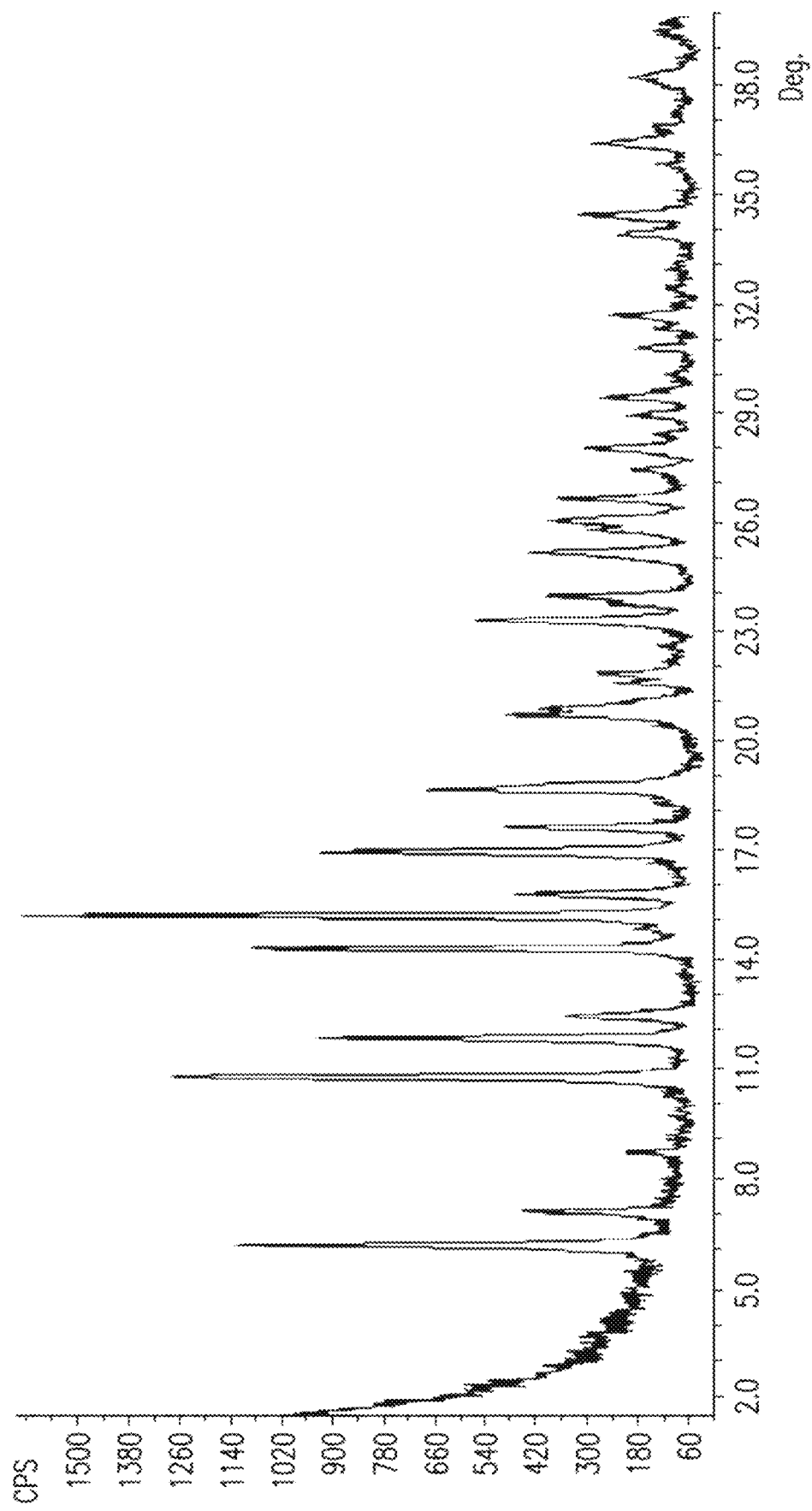

FIG. 26 provides a representative XRPD pattern of a L-tartrate salt of Compound (I-S).

Figure 27A:
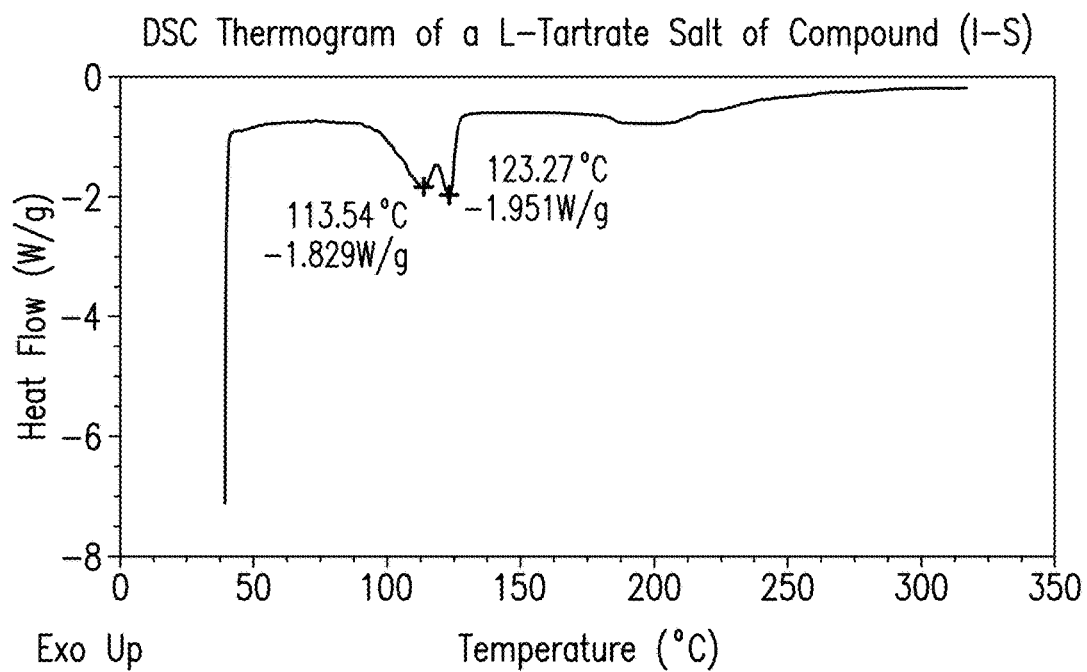

FIG. 27A provides a representative DSC thermogram of a L-tartrate salt of Compound (I-S).

Figure 27B:
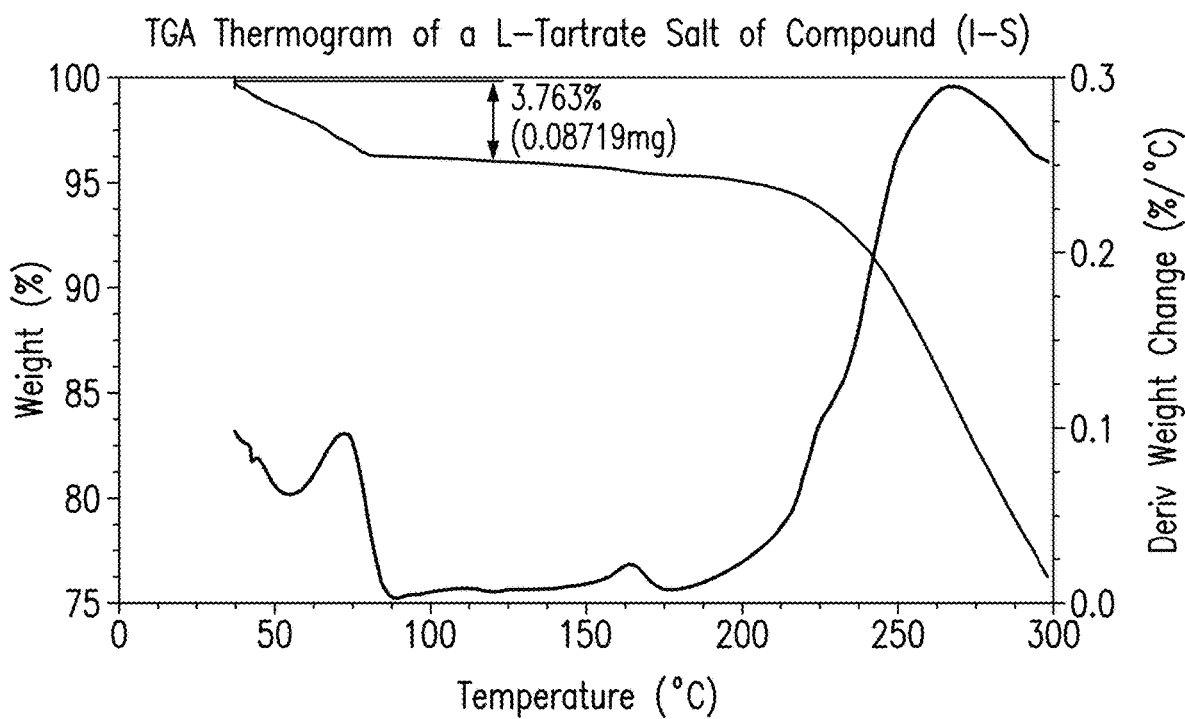

FIG. 27B provides a representative TGA thermogram of a L-tartrate salt of Compound (I-S).

Figure 28:
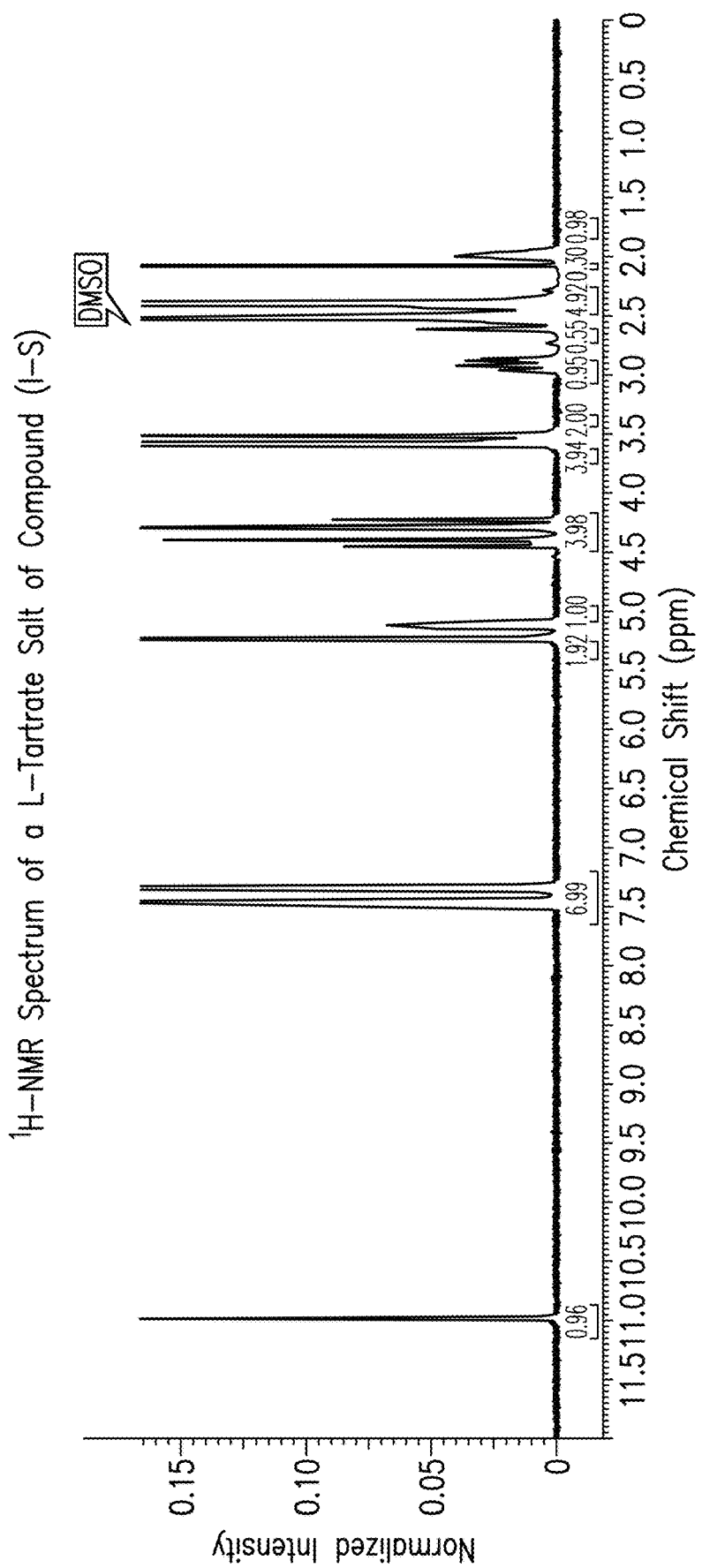

FIG. 28 provides a representative $^1$H-NMR spectrum of a L-tartrate salt of Compound (I-S).

Figure 29:
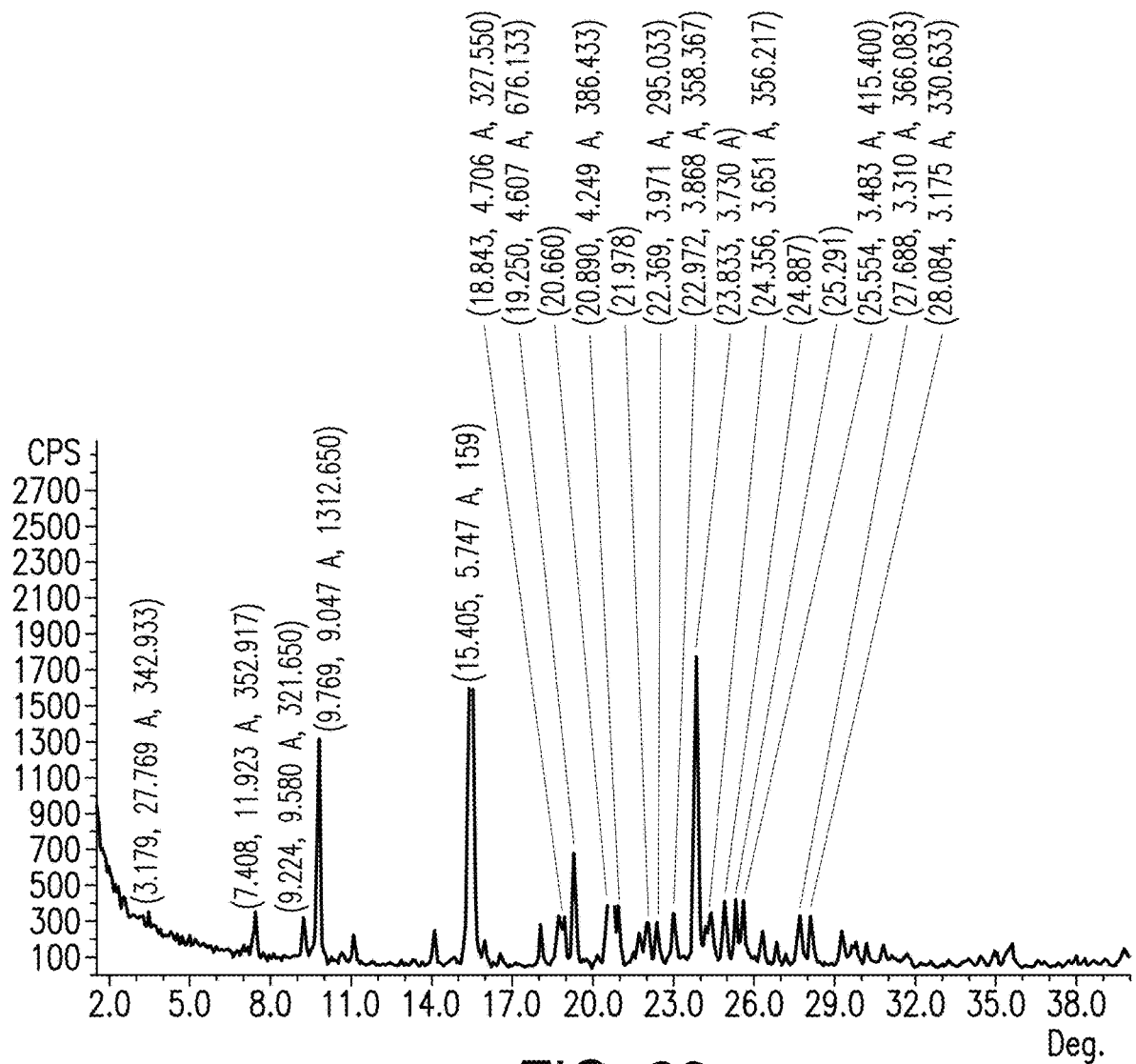

FIG. 29 provides a representative XRPD pattern of a tosylate salt of Compound (I-S).

Figure 30A:
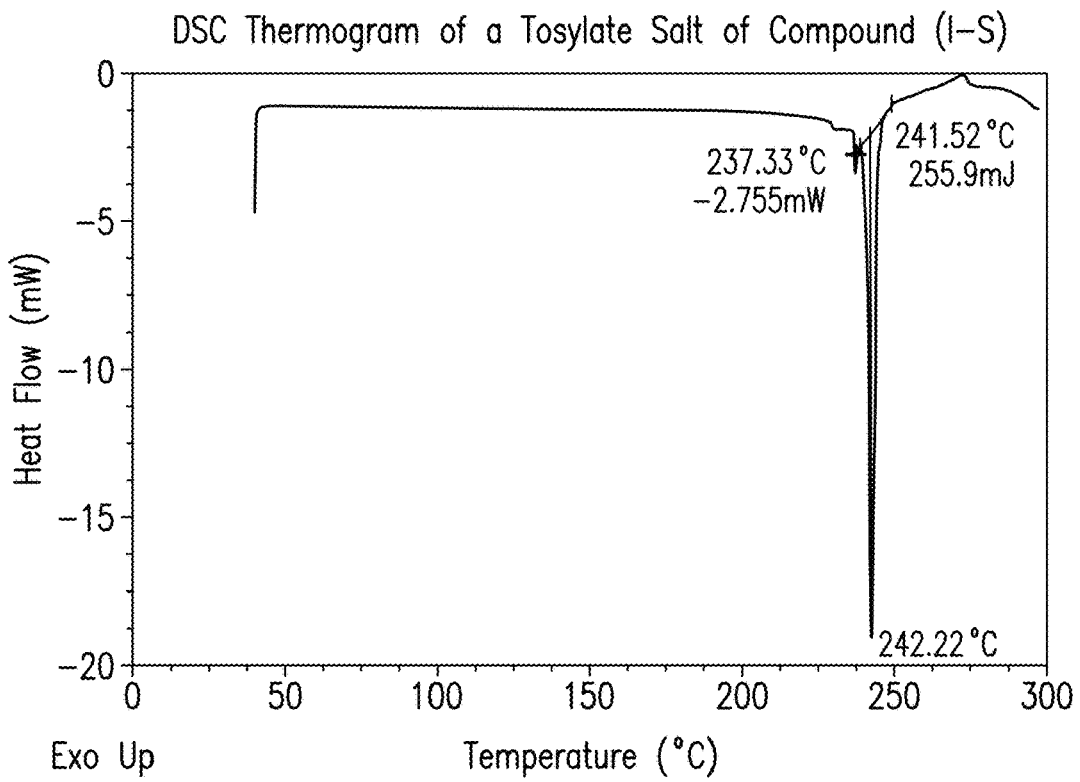

FIG. 30A provides a representative DSC thermogram of a tosylate salt of Compound (I-S).

Figure 30B:
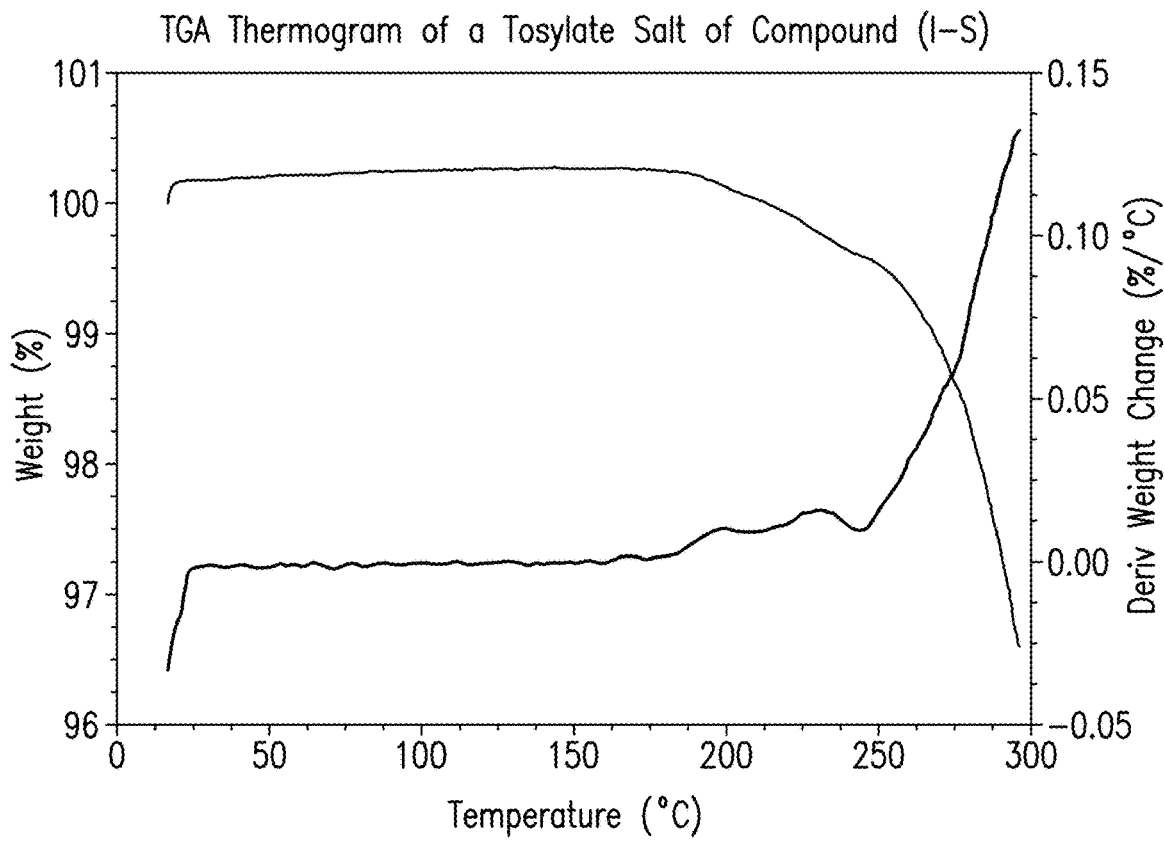

FIG. 30B provides a representative TGA thermogram of a tosylate salt of Compound (I-S).

Figure 31:
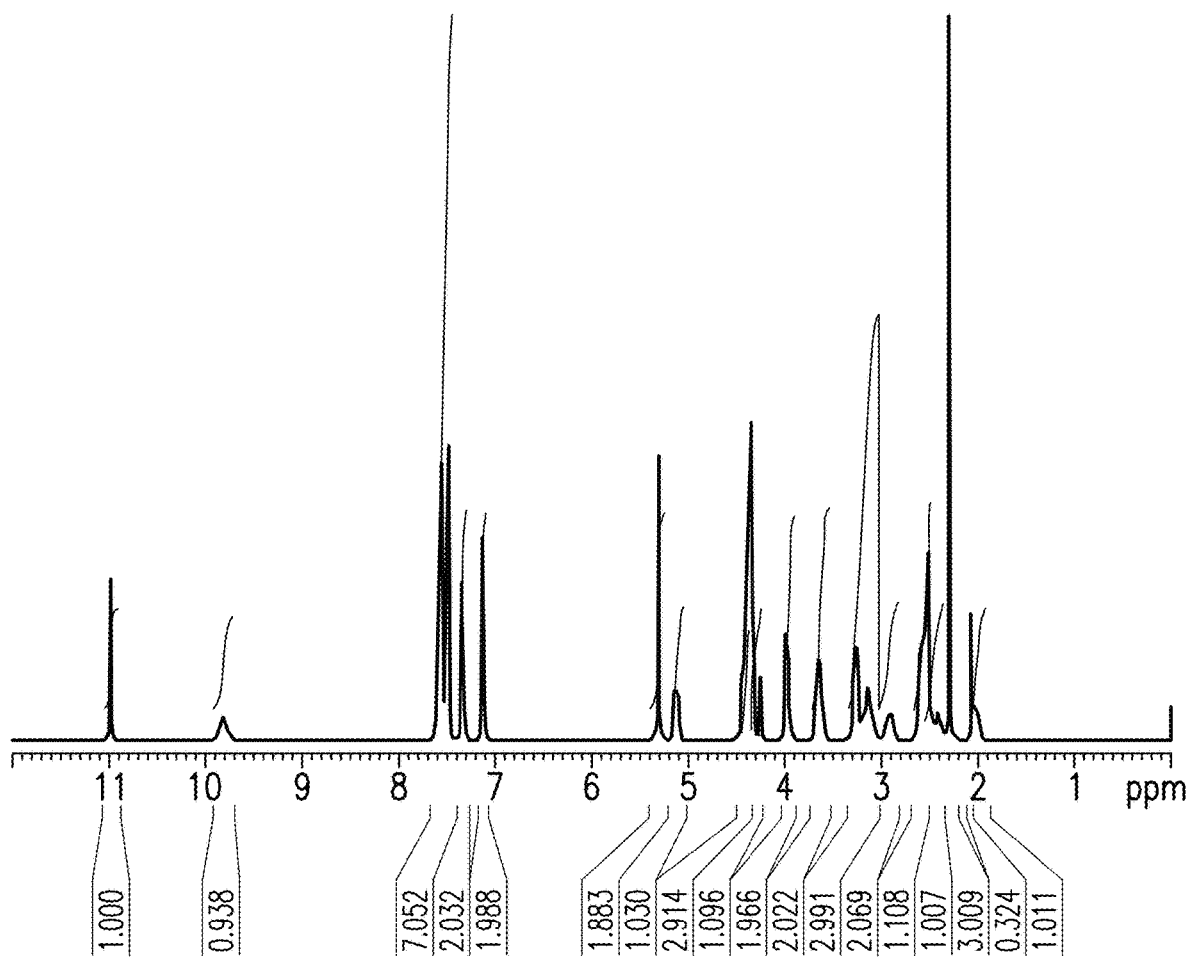

FIG. 31 provides a representative $^1$H-NMR spectrum of a tosylate salt of Compound (I-S).

Figure 32:
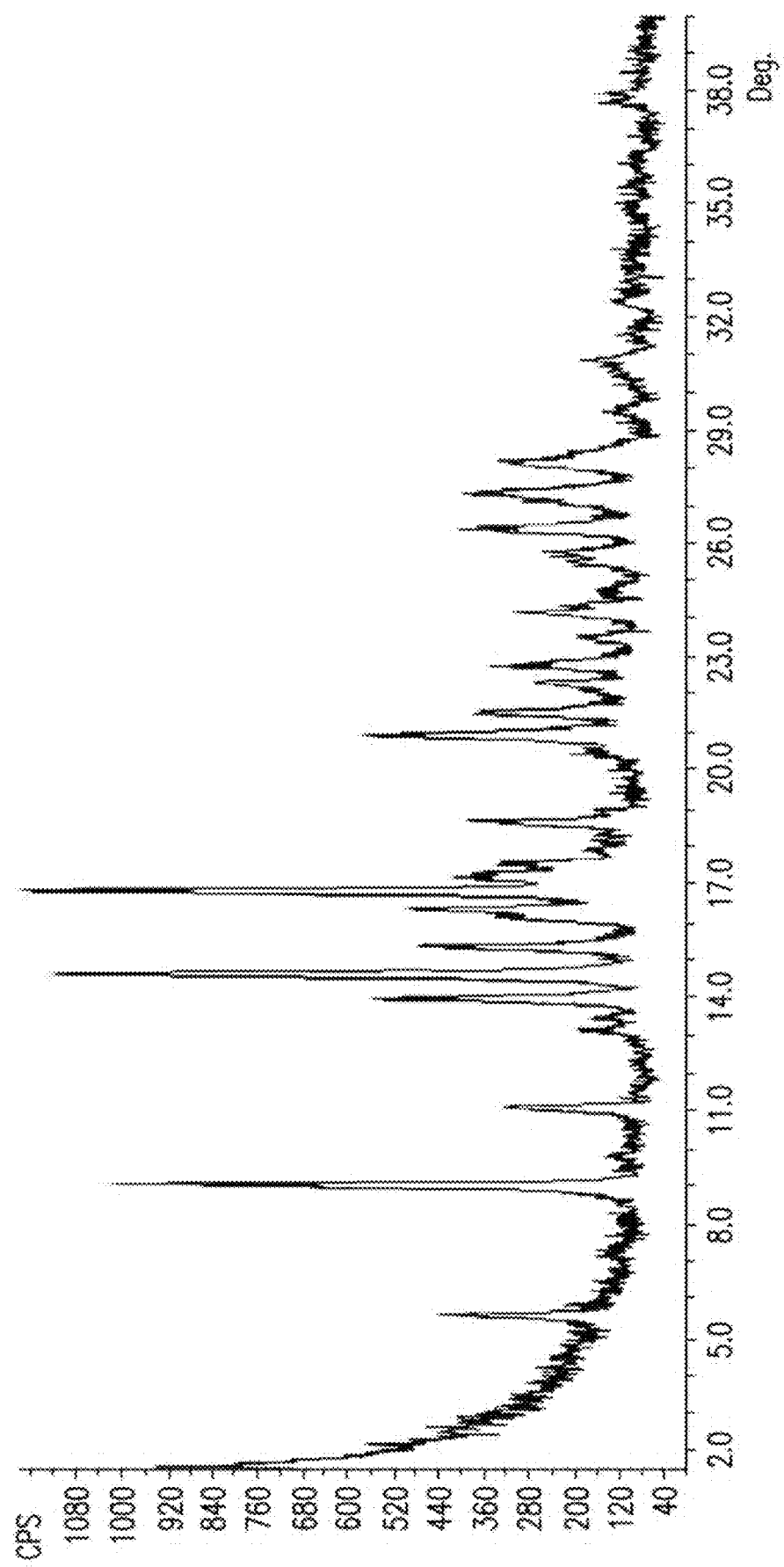

FIG. 32 provides a representative XRPD pattern of a (+) camphorsulfonic acid salt of Compound (I-S).

Figure 33:
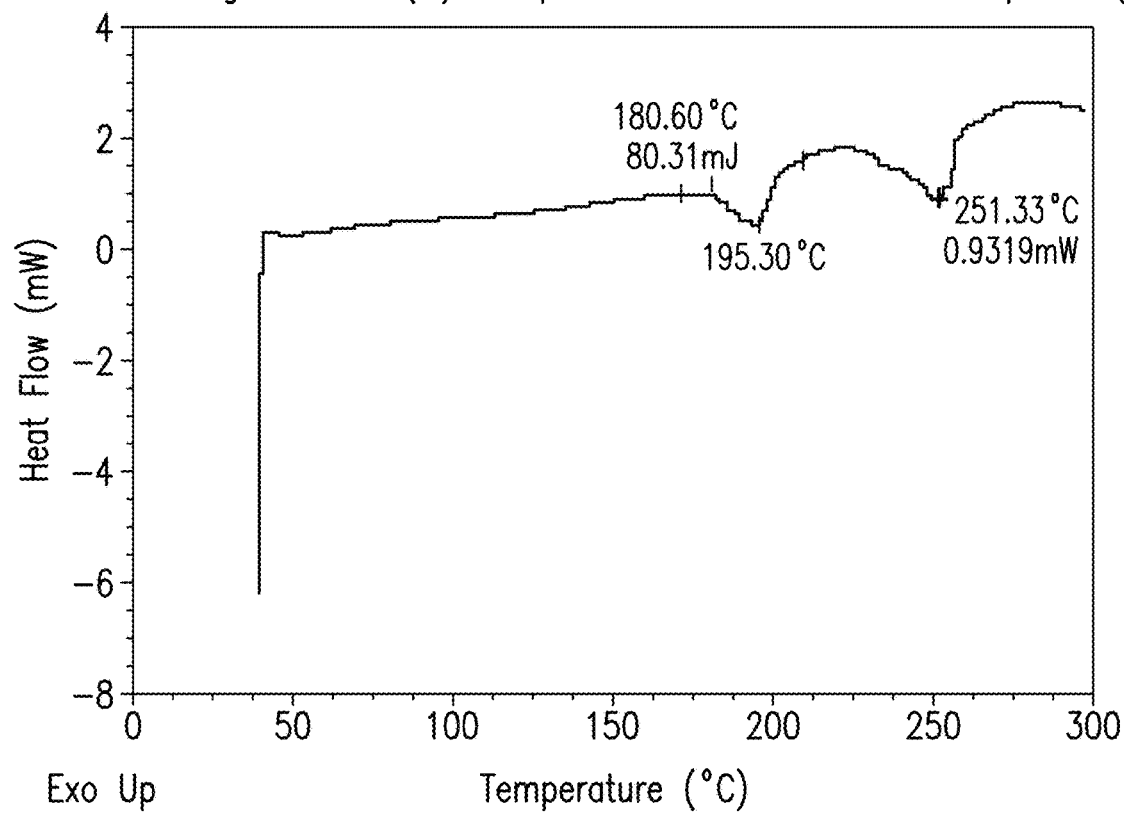

FIG. 33 provides a representative DSC thermogram of a (+) camphorsulfonic acid salt of Compound (I-S).

Figure 34:
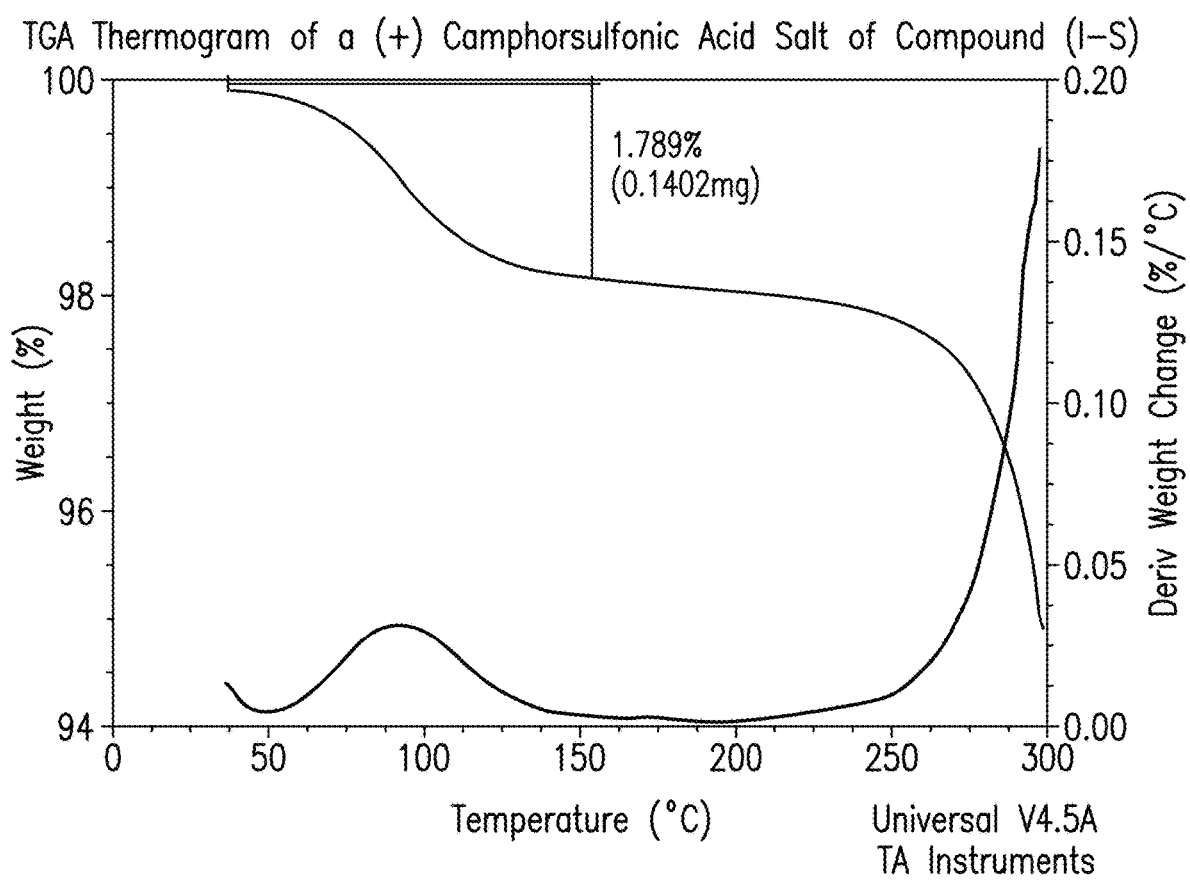

FIG. 34 provides a representative TGA thermogram of a (+) camphorsulfonic acid salt of Compound (I-S).

Figure 35:
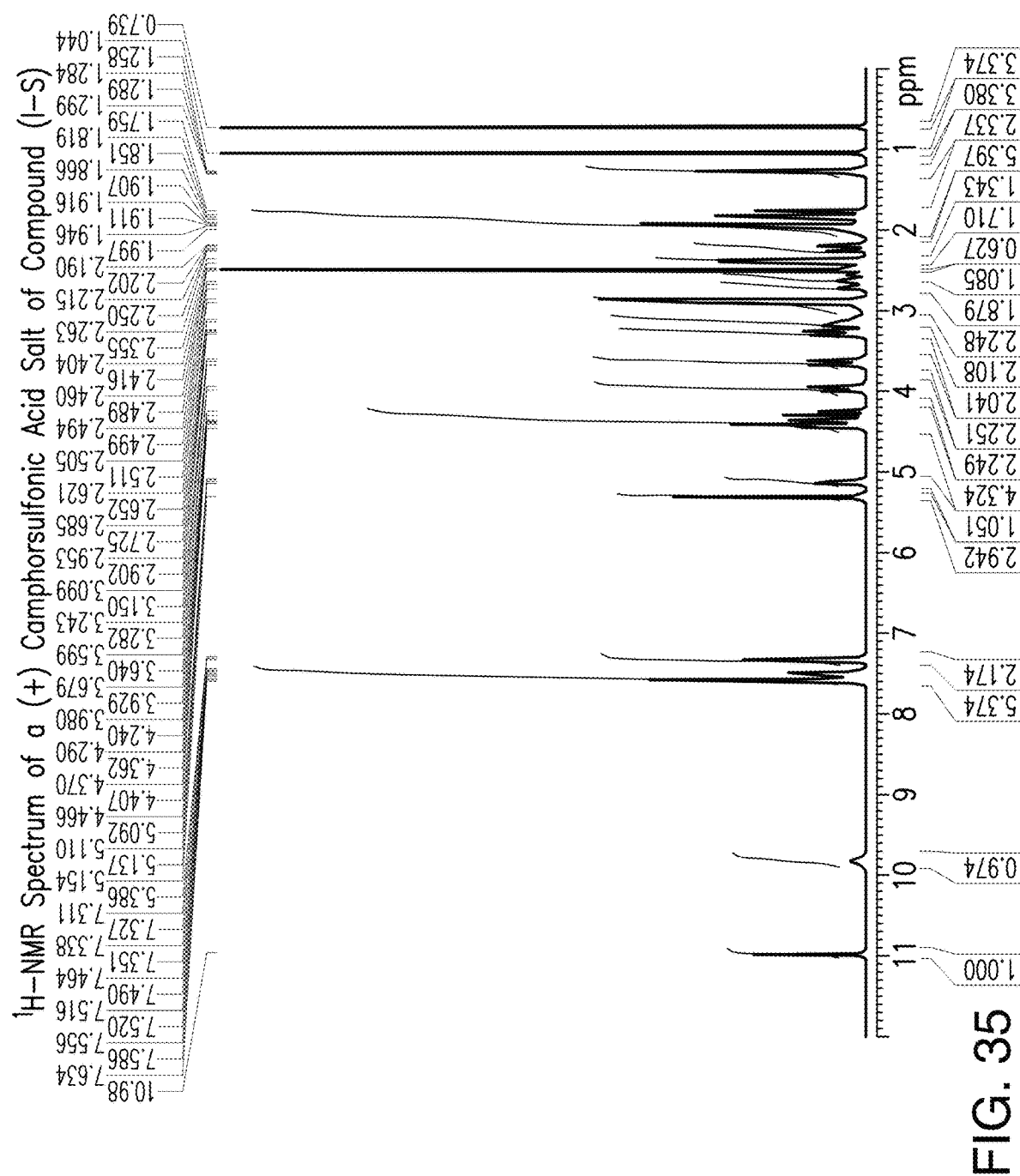

FIG. 35 provides a representative $^1$H-NMR spectrum of a (+) camphorsulfonic acid salt of Compound (I-S).

Figure 36:
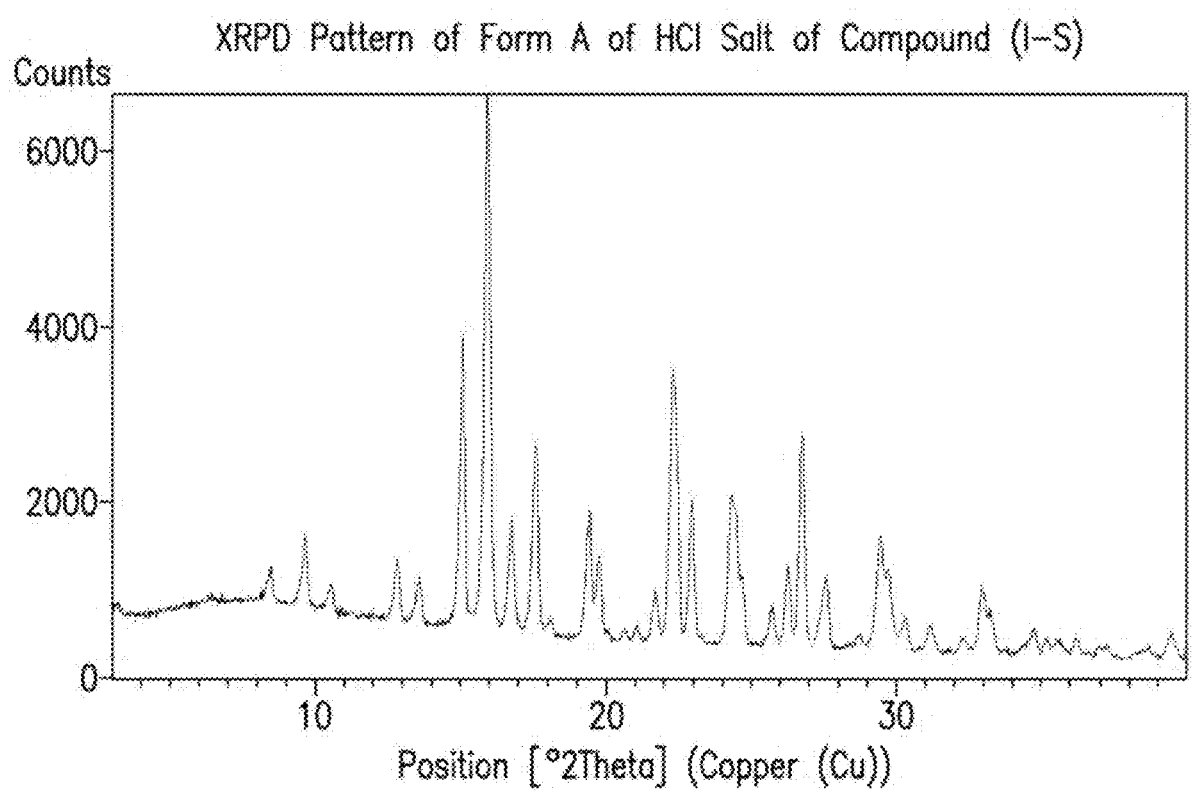

FIG. 36 provides a representative XRPD pattern of Form A of HCl salt of Compound (I-S).

Figure 37:
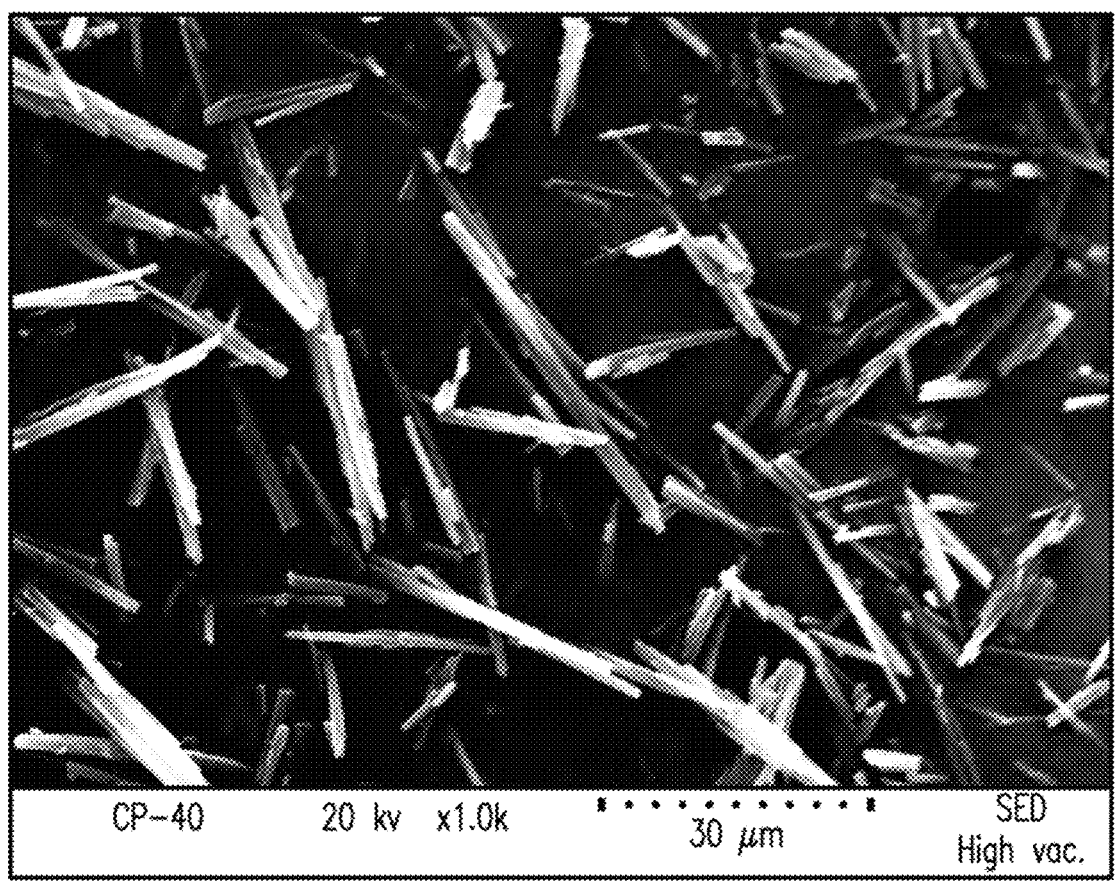

FIG. 37 provides a representative crystal habit of Form A of HCl salt of Compound (I-S).

Figure 38:
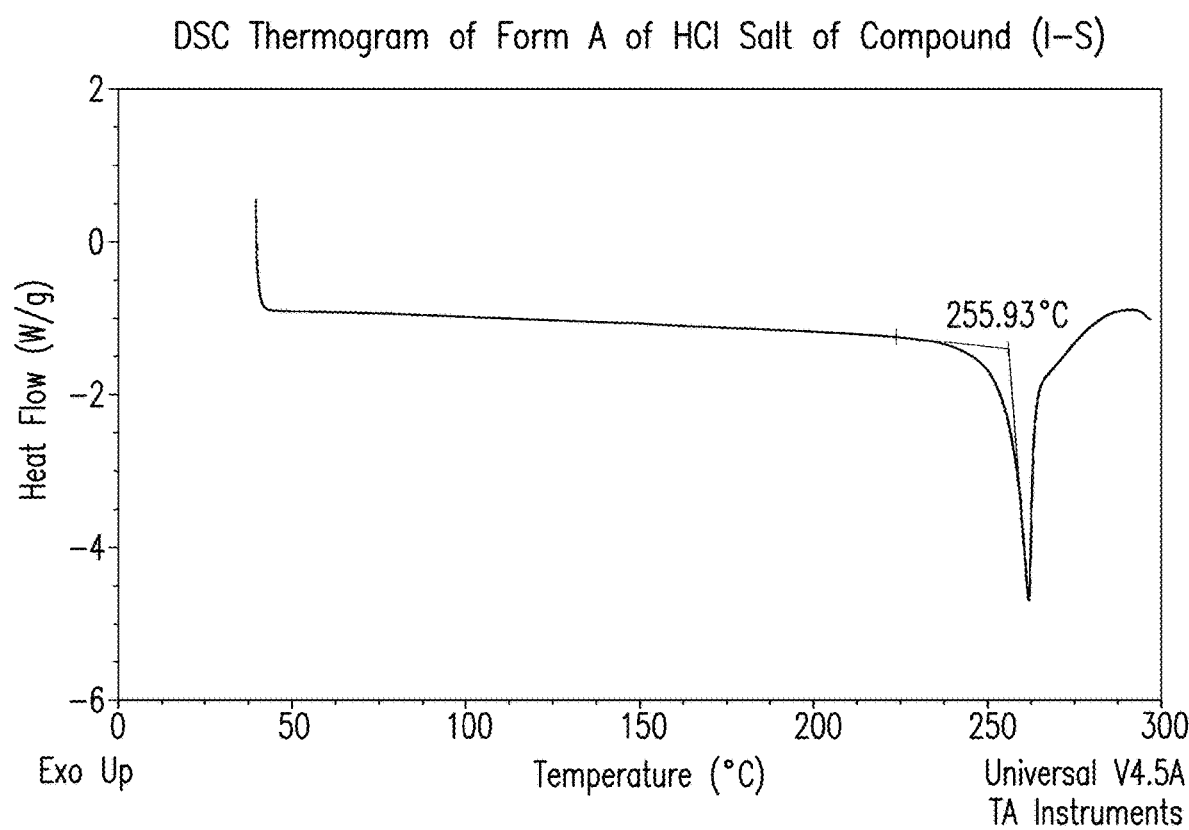

FIG. 38 provides a representative DSC thermogram of Form A of HCl salt of Compound (I-S).

Figure 39:
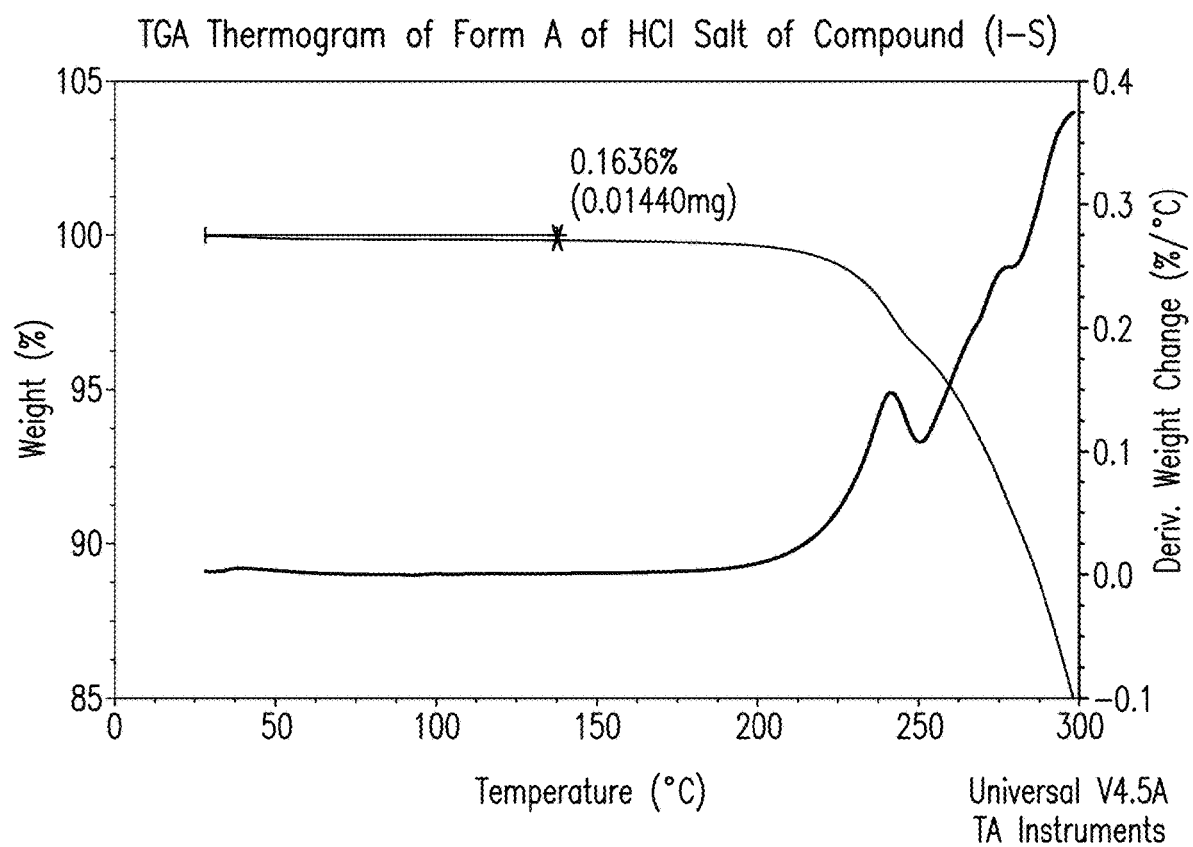

FIG. 39 provides a representative TGA thermogram of Form A of HCl salt of Compound (I-S).

Figure 40:
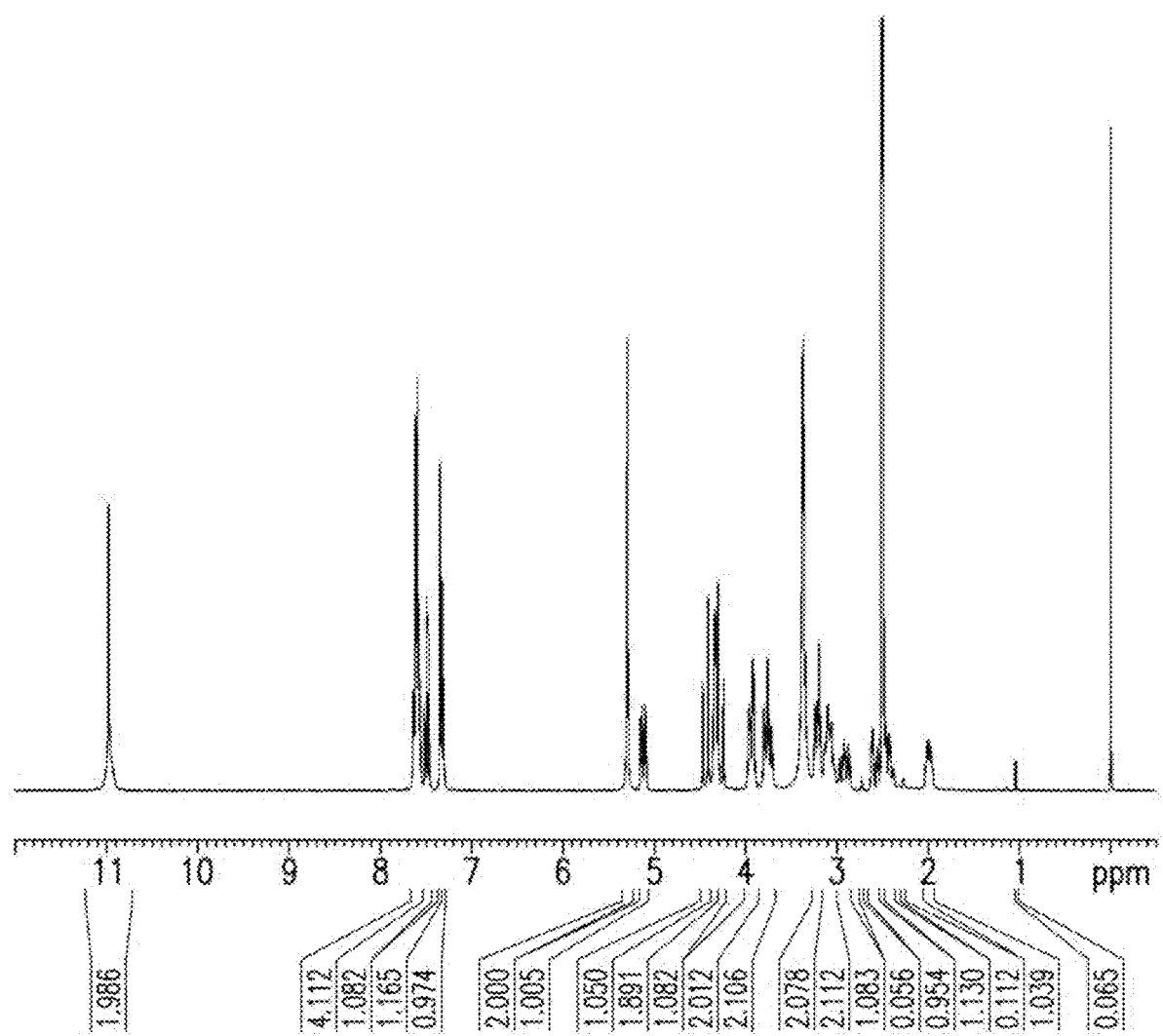

FIG. 40 provides a representative $^1$H-NMR spectrum of Form A of HCl salt of Compound (I-S).

Figure 41:
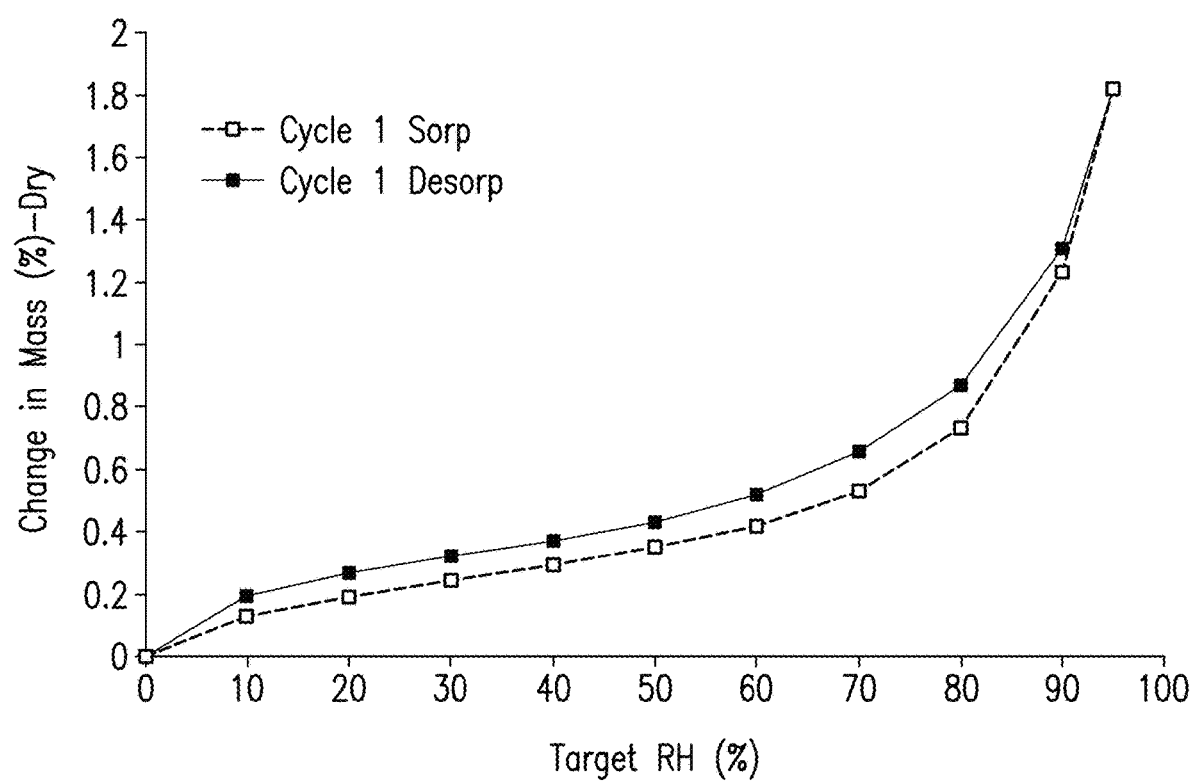

FIG. 41 provides a representative DVS plot of Form A of HCl salt of Compound (I-S).

Figure 42:
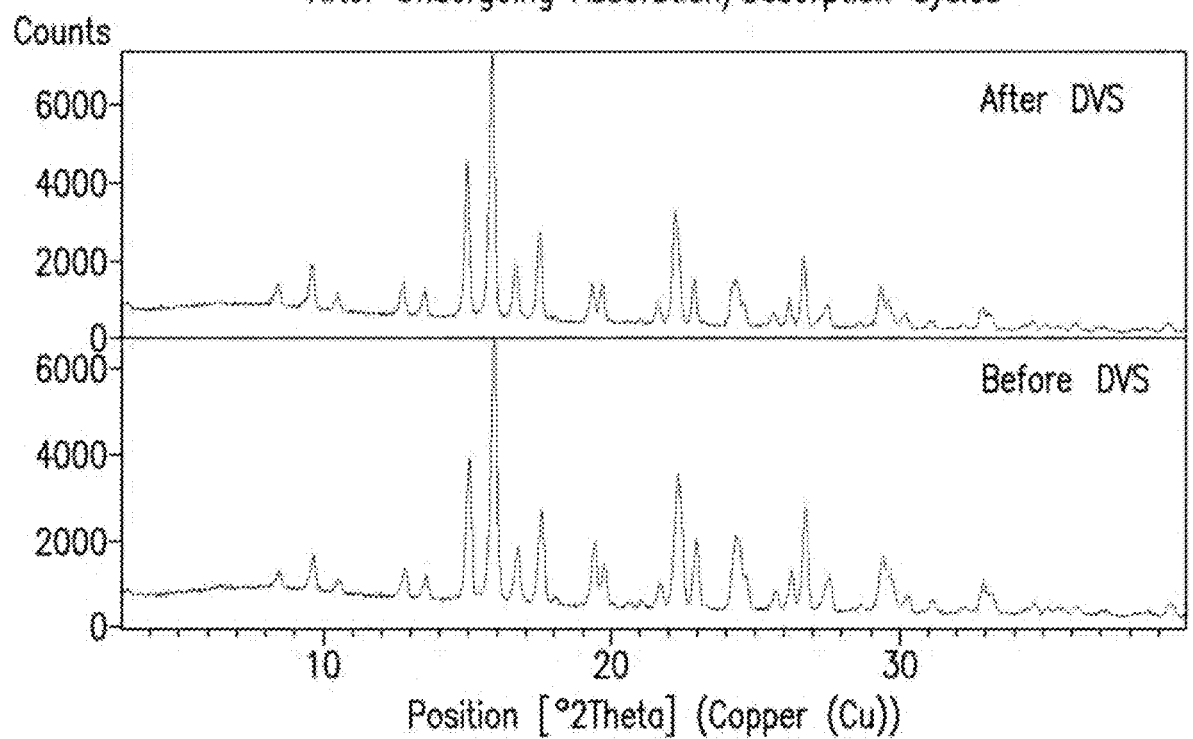

FIG. 42 provides representative XRPD patterns of Form A of HCl salt of Compound (I-S) before and after undergoing absorption/desorption cycles.

Figure 43:
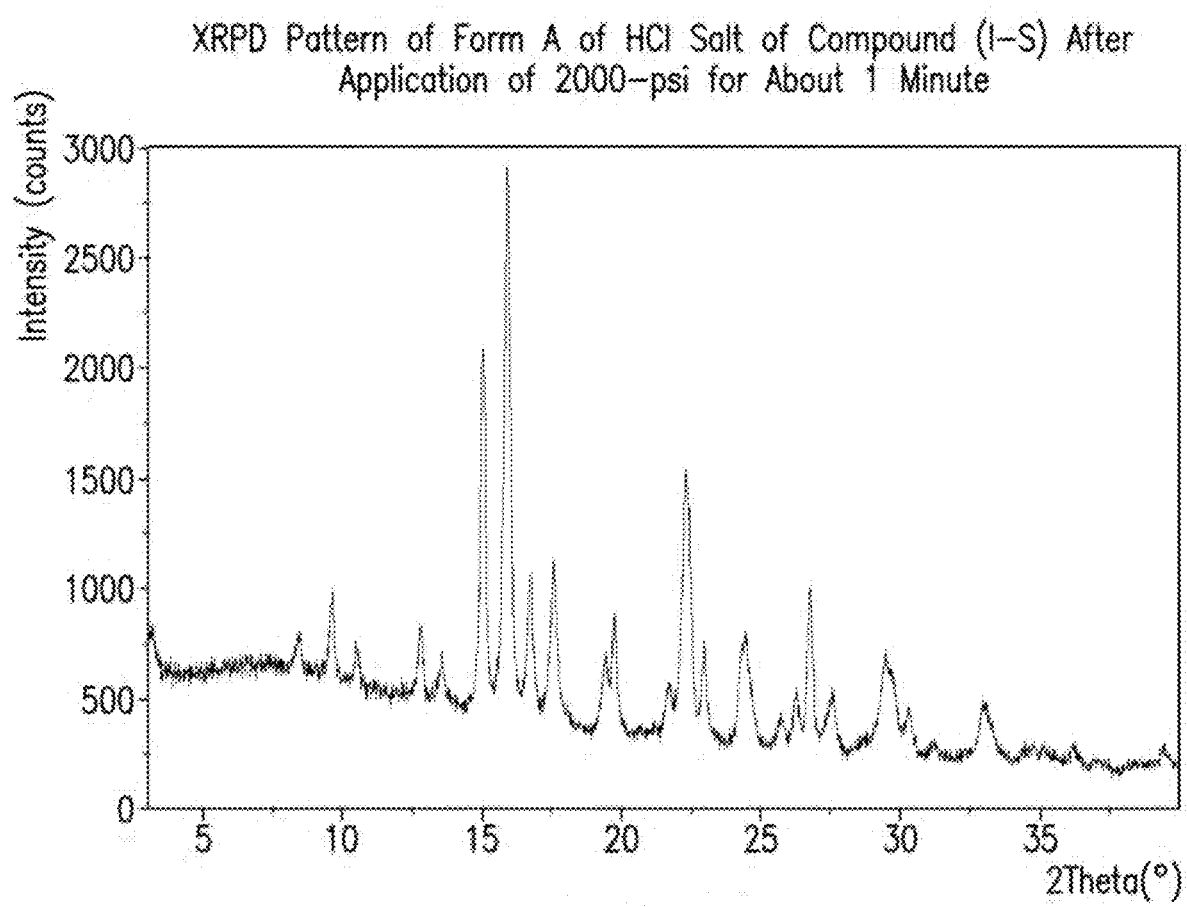

FIG. 43 provides a representative XRPD pattern of Form A of HCl salt of Compound (I-S) after application of 2000-psi for about 1 minute.

Figure 44:
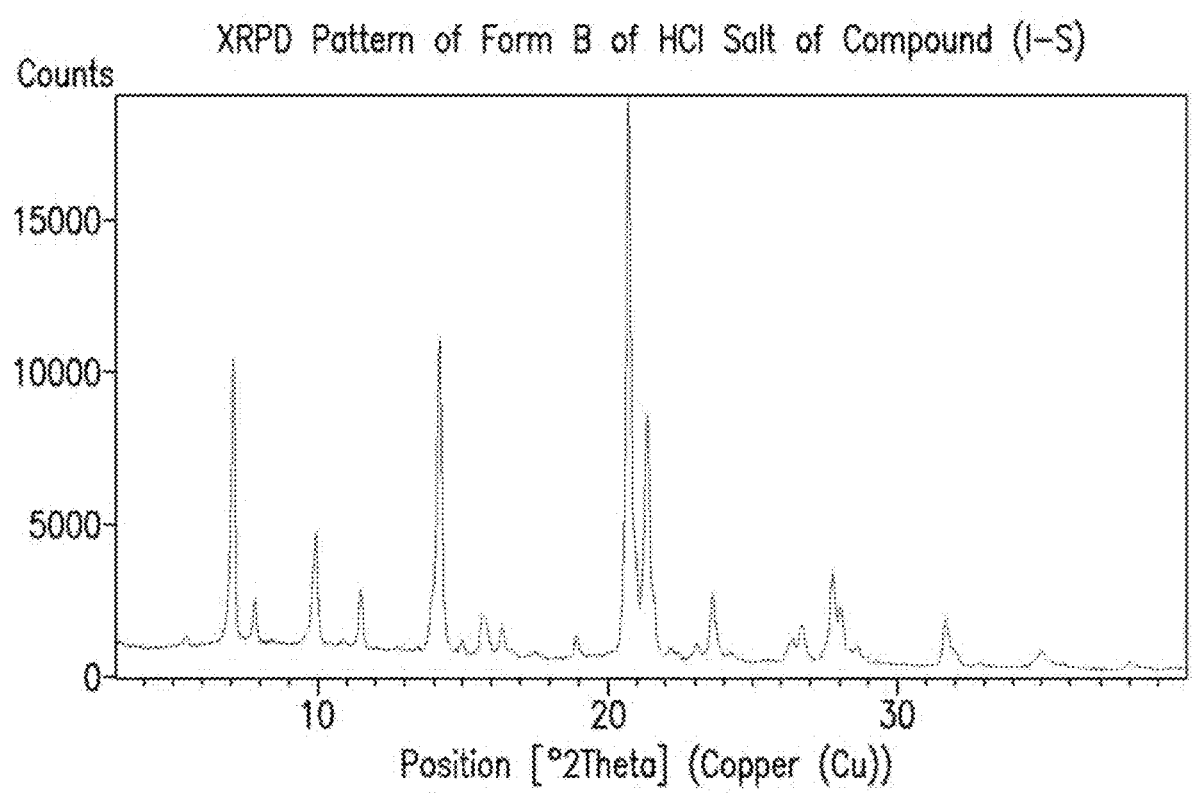

FIG. 44 provides a representative XRPD pattern of Form B of HCl salt of Compound (I-S).

Figure 45:
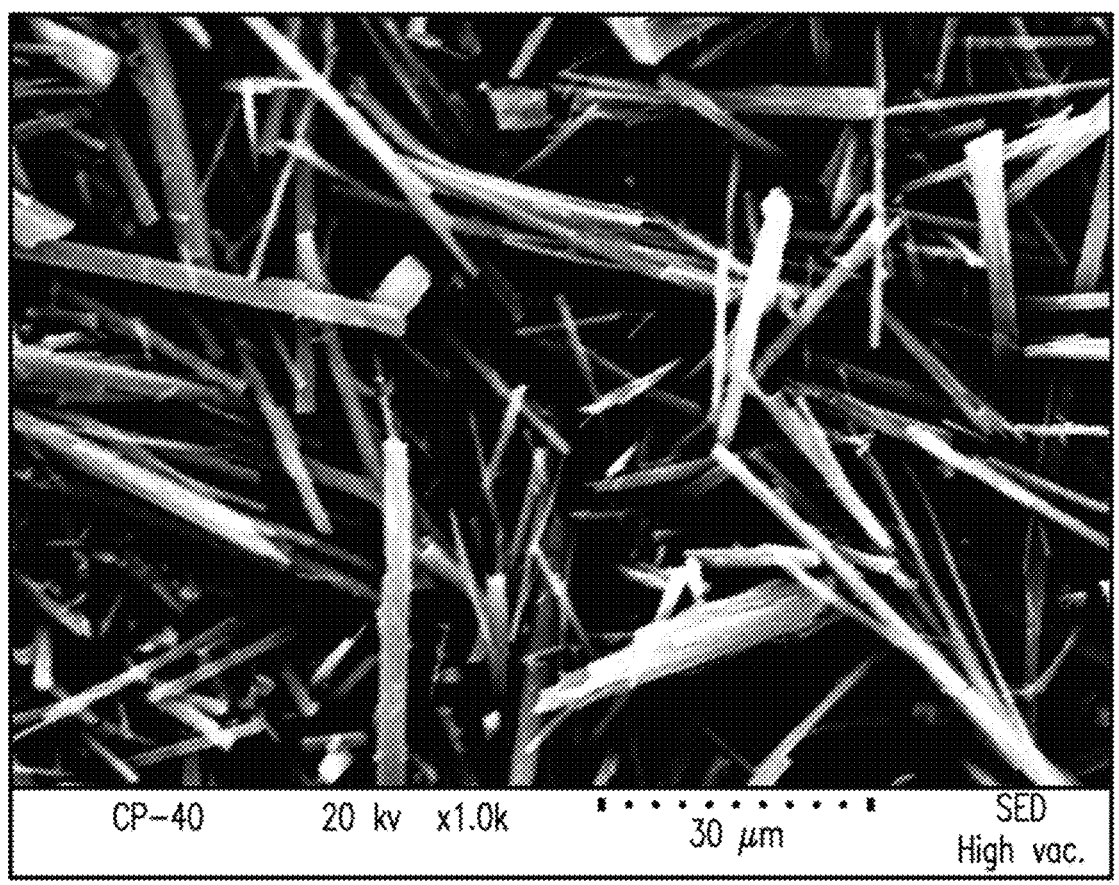

FIG. 45 provides a representative crystal habit of Form B of HCl salt of Compound (I-S).

Figure 46:
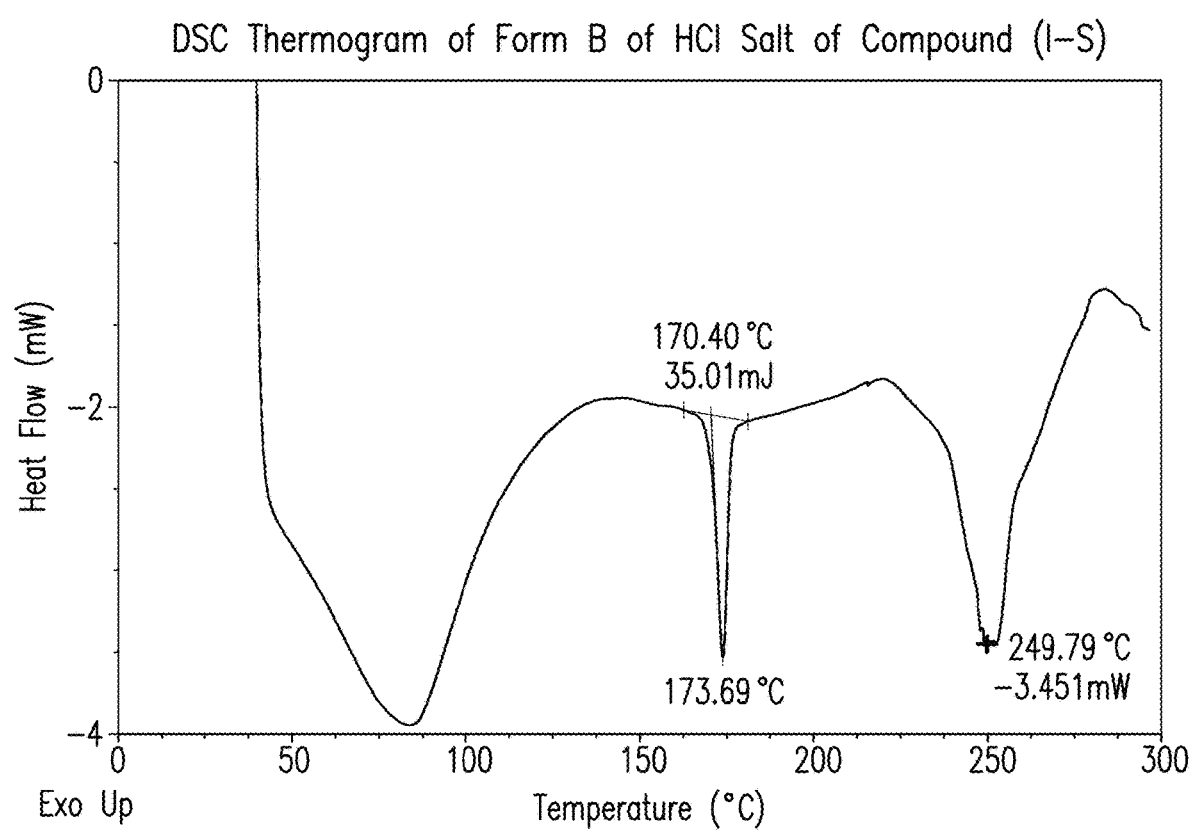

FIG. 46 provides a representative DSC thermogram of Form B of HCl salt of Compound (I-S).

Figure 47:
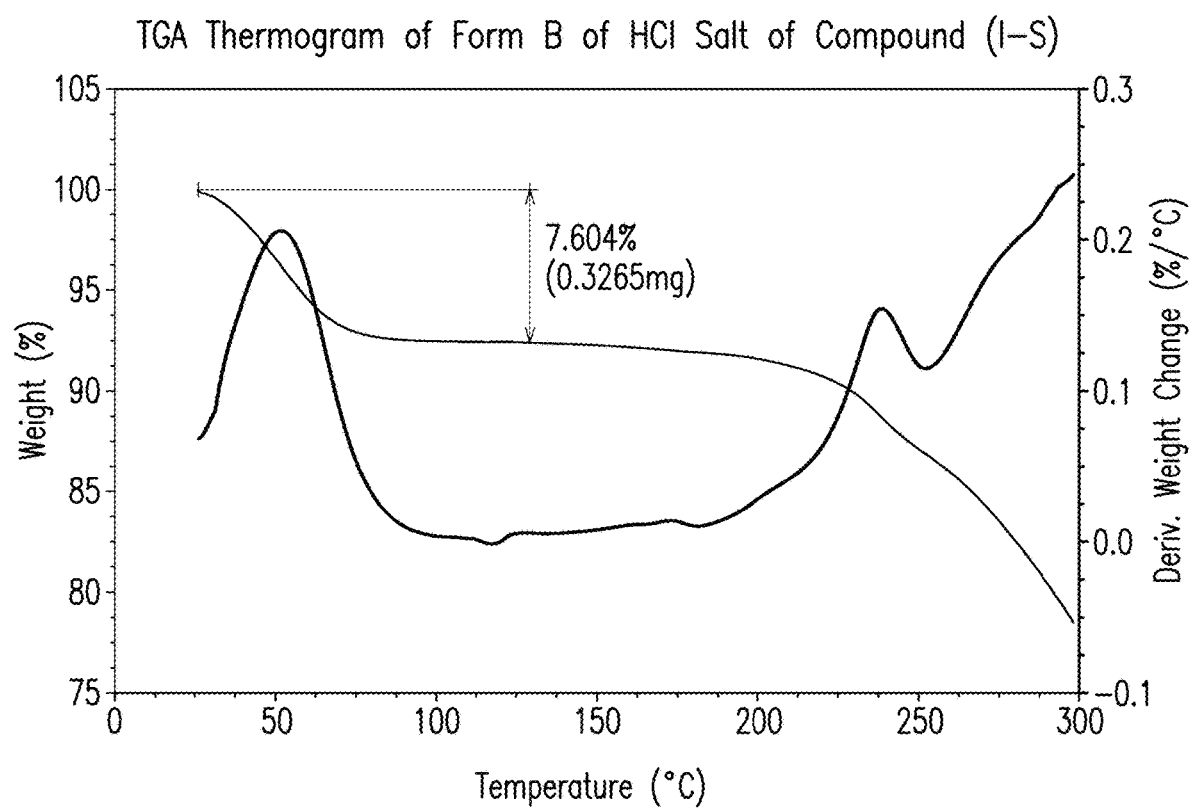

FIG. 47 provides a representative TGA thermogram of Form B of HCl salt of Compound (I-S).

Figure 48:
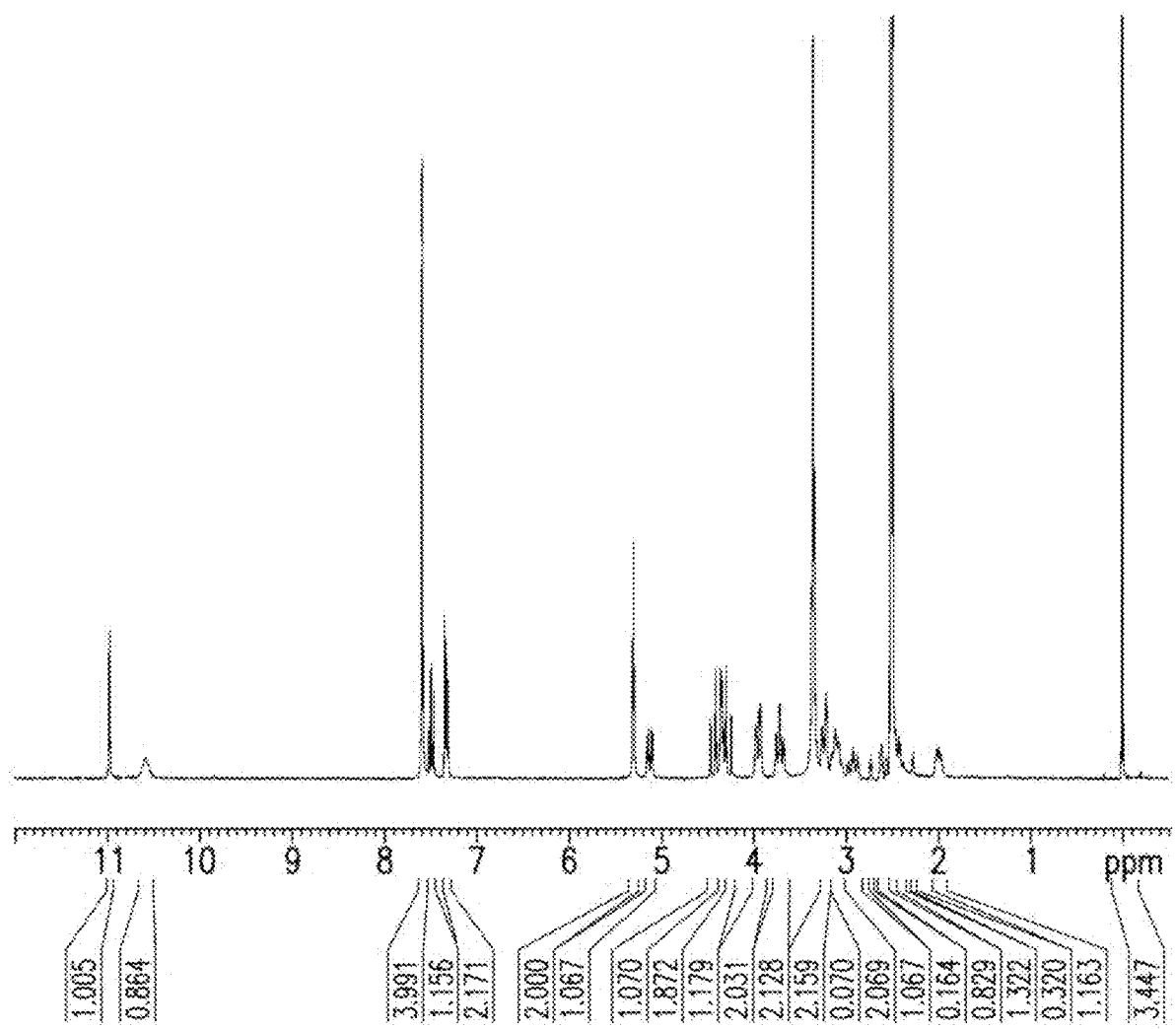

FIG. 48 provides a representative $^1$H-NMR spectrum of Form B of HCl salt of Compound (I-S).

Figure 49:
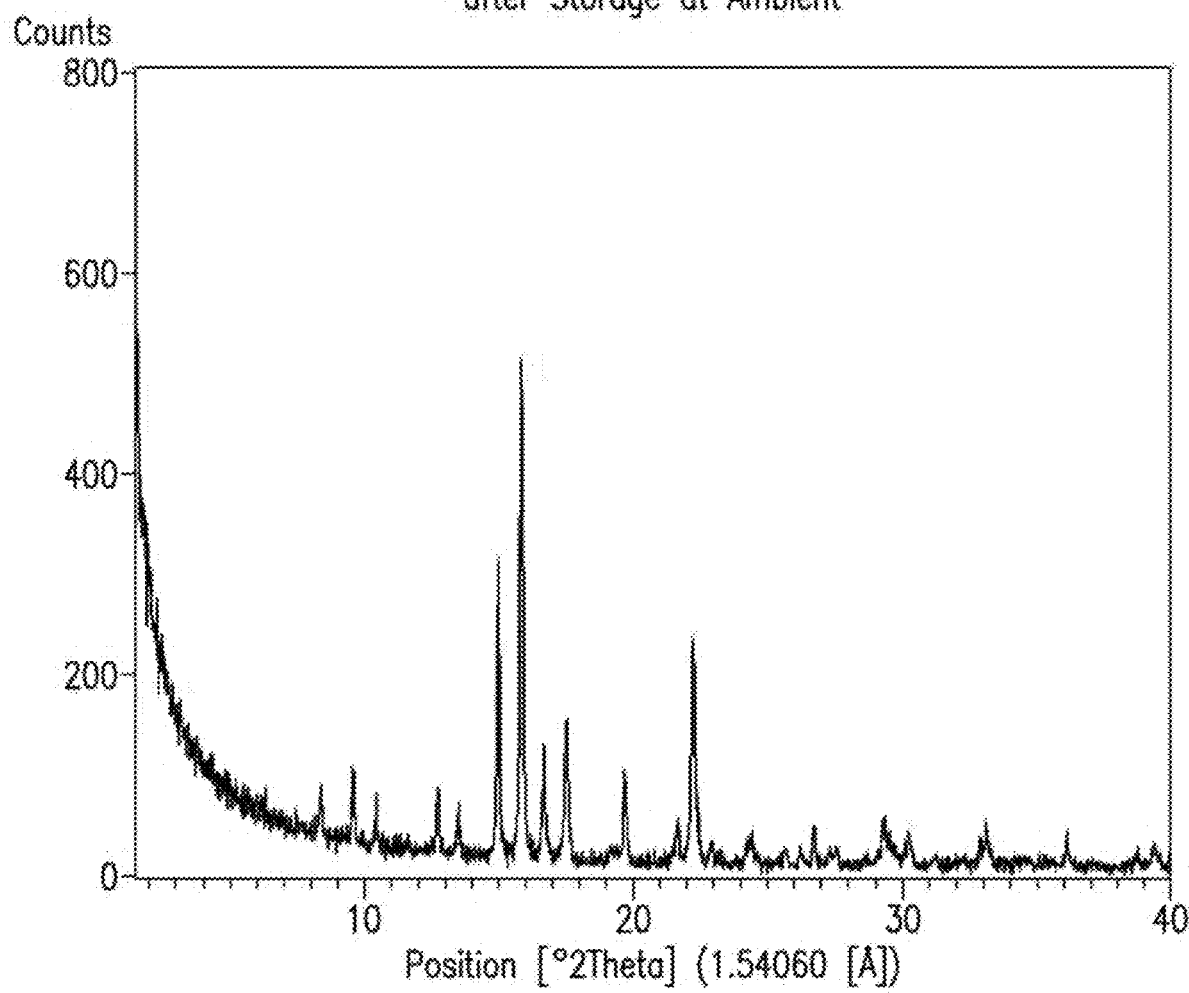

FIG. 49 provides a representative XRPD pattern of Form B of HCl salt of Compound (I-S) after storage at ambient.

Figure 50:
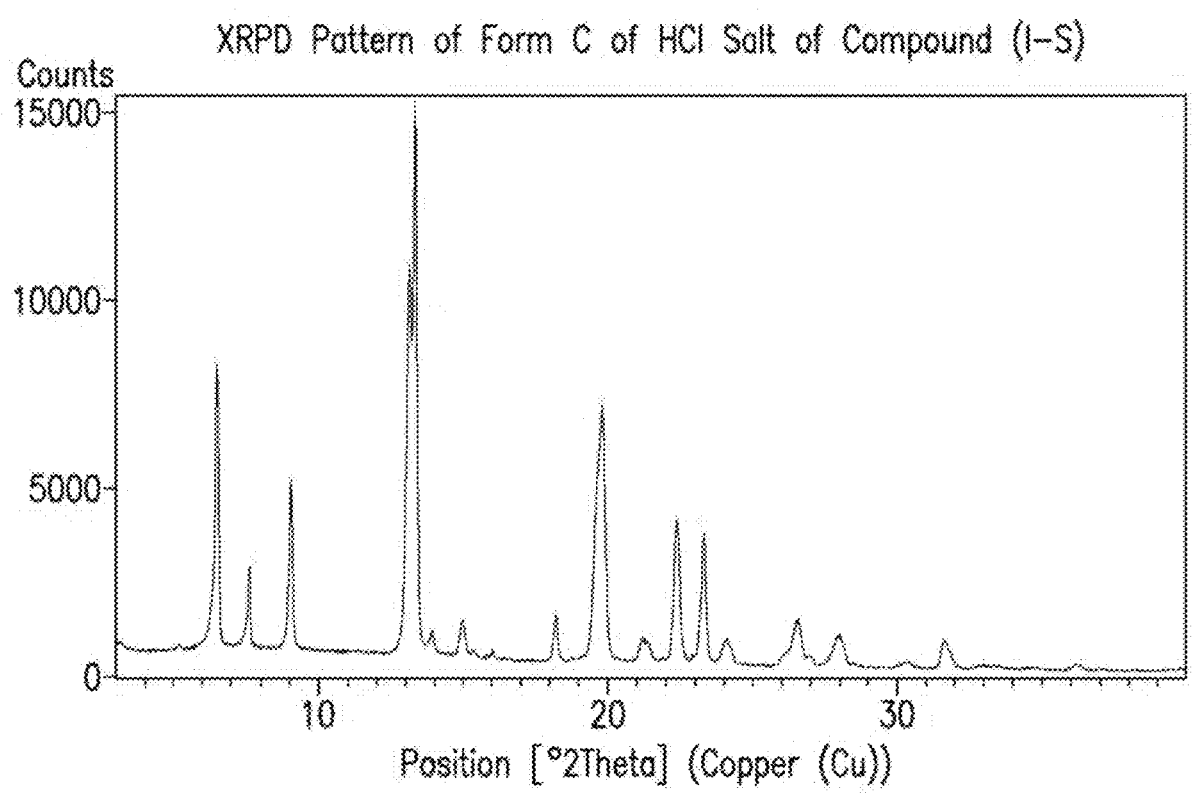

FIG. 50 provides a representative XRPD pattern of Form C of HCl salt of Compound (I-S).

Figure 51:
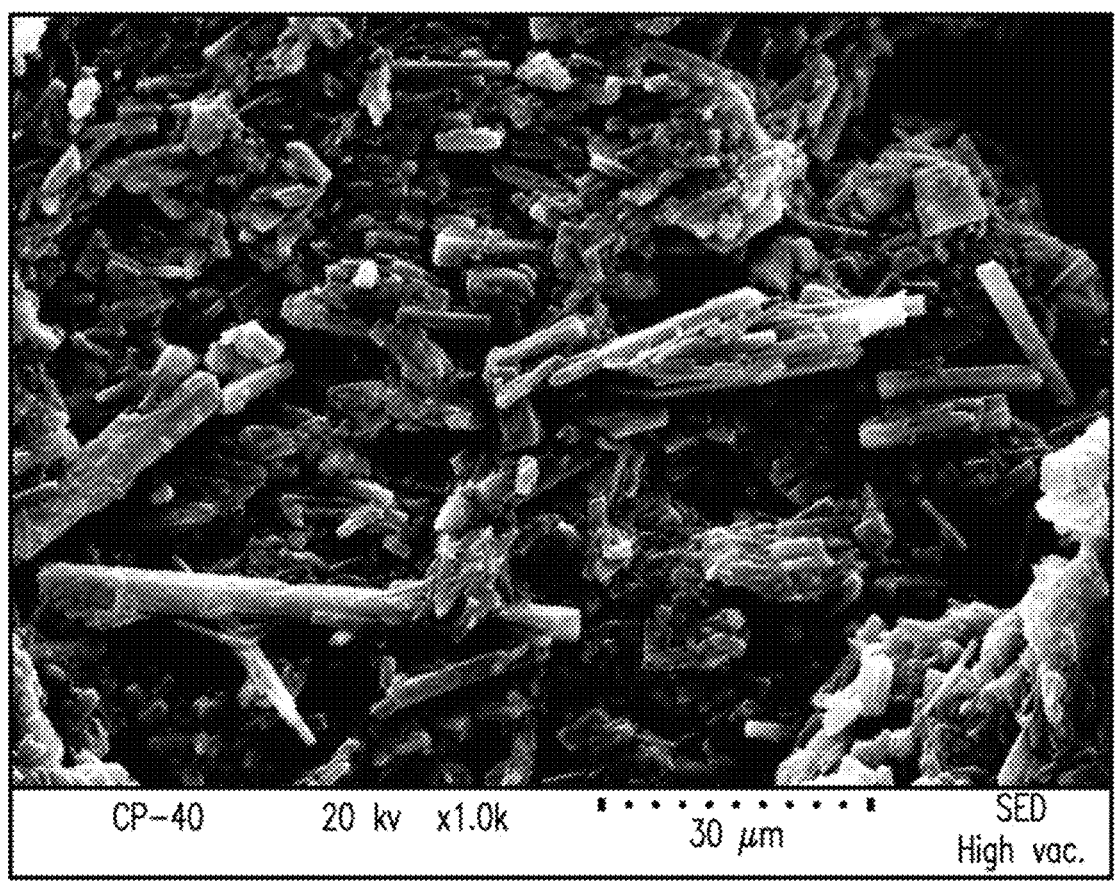

FIG. 51 provides a representative crystal habit of Form C of HCl salt of Compound (I-S).

Figure 52:
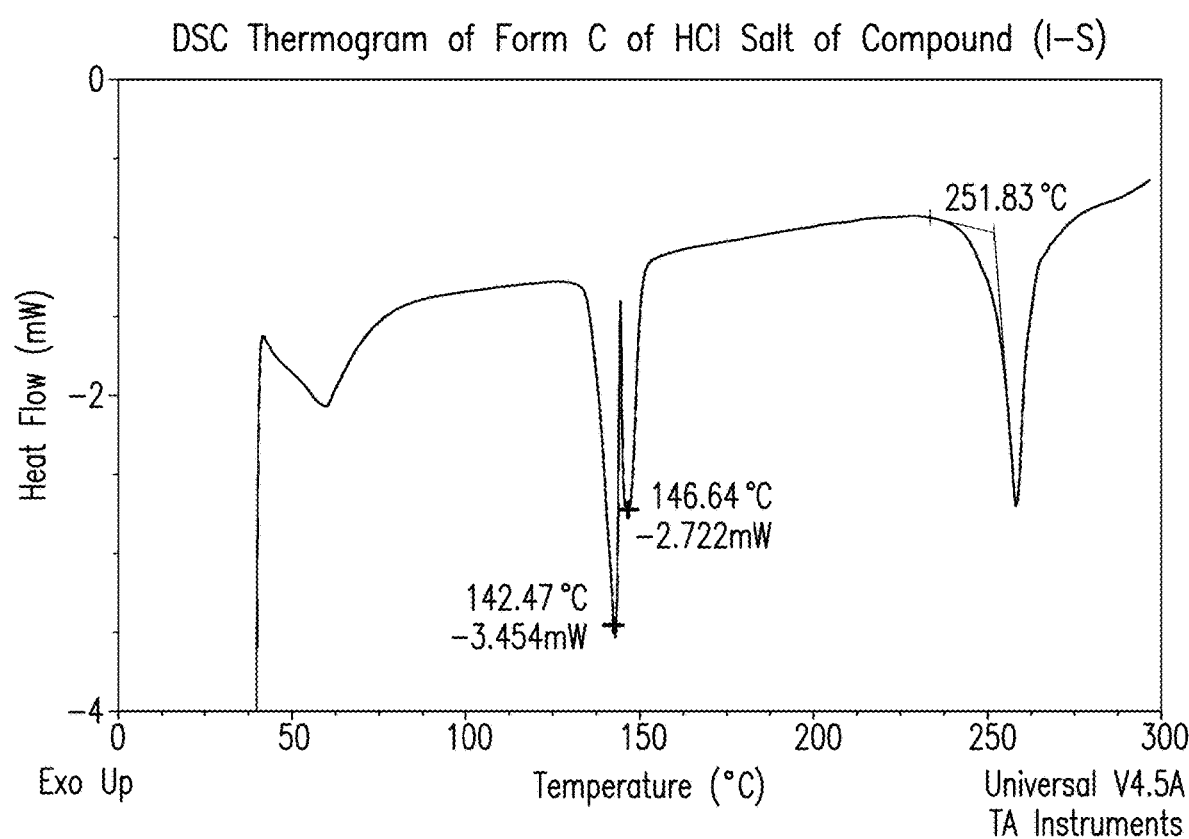

FIG. 52 provides a representative DSC thermogram of Form C of HCl salt of Compound (I-S).

Figure 53:
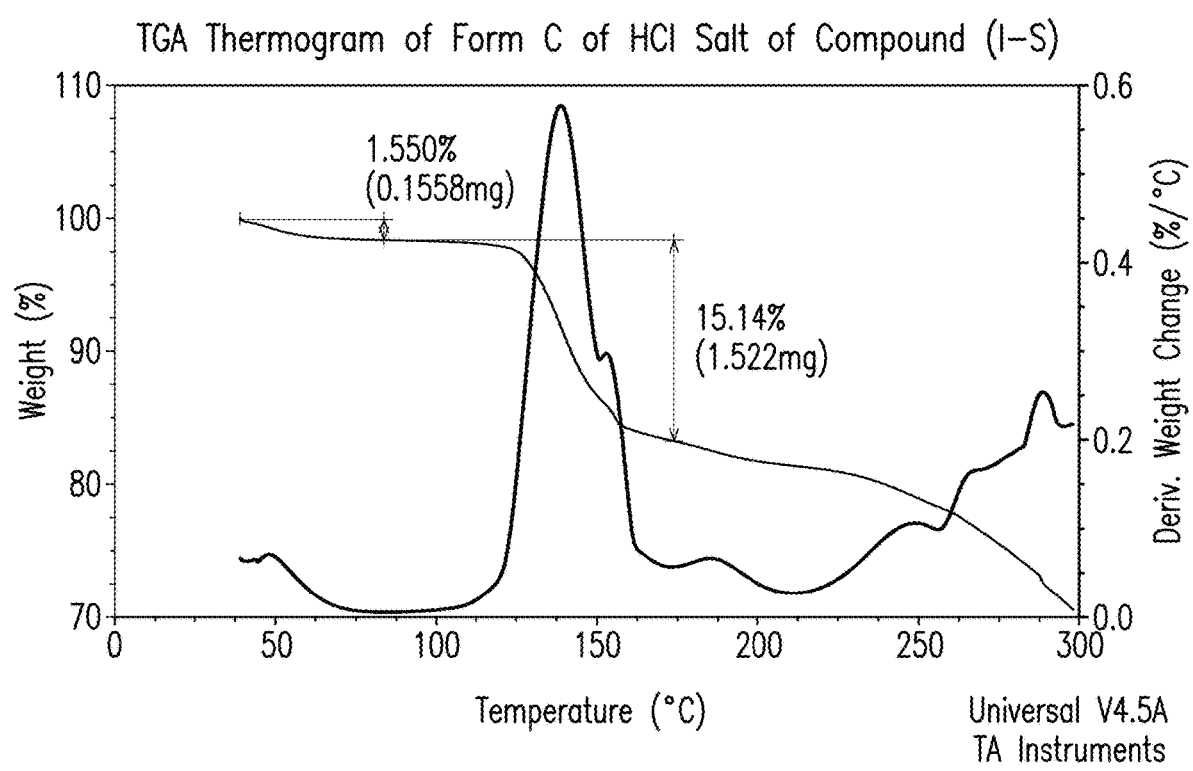

FIG. 53 provides a representative TGA thermogram of Form C of HCl salt of Compound (I-S).

Figure 54:
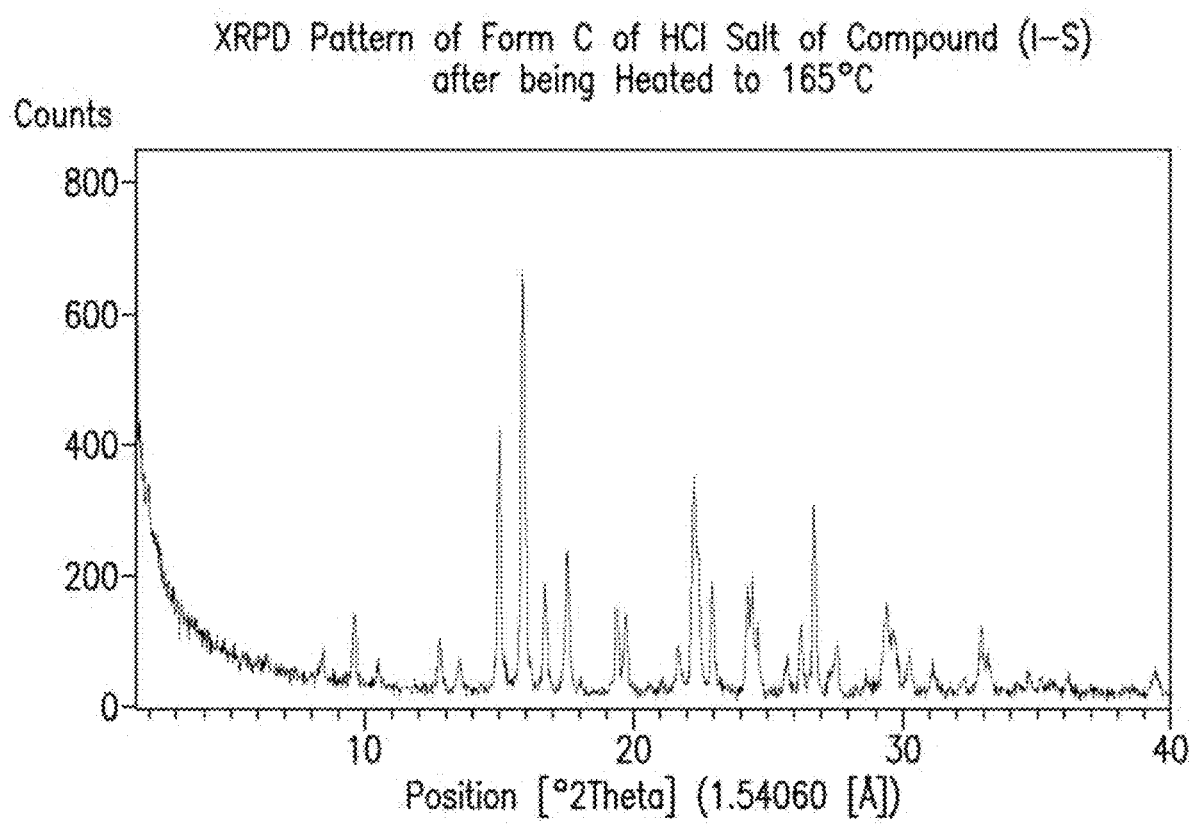

FIG. 54 provides a representative XRPD pattern of Form C of HCl salt of Compound (I-S) after being heated to 165° C.

Figure 55:
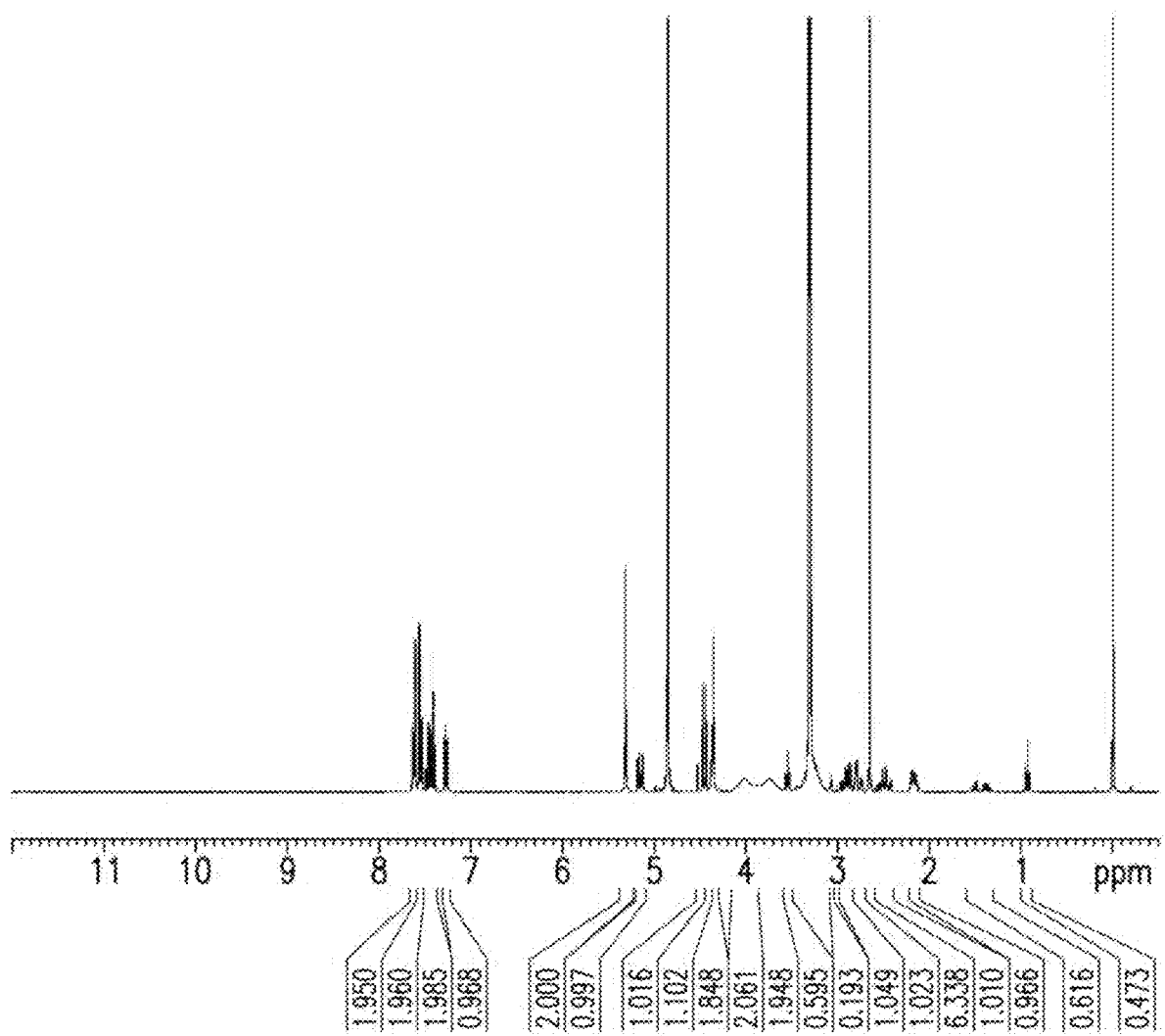

FIG. 55 provides a representative $^1$H-NMR spectrum of Form C of HCl salt of Compound (I-S).

Figure 56:
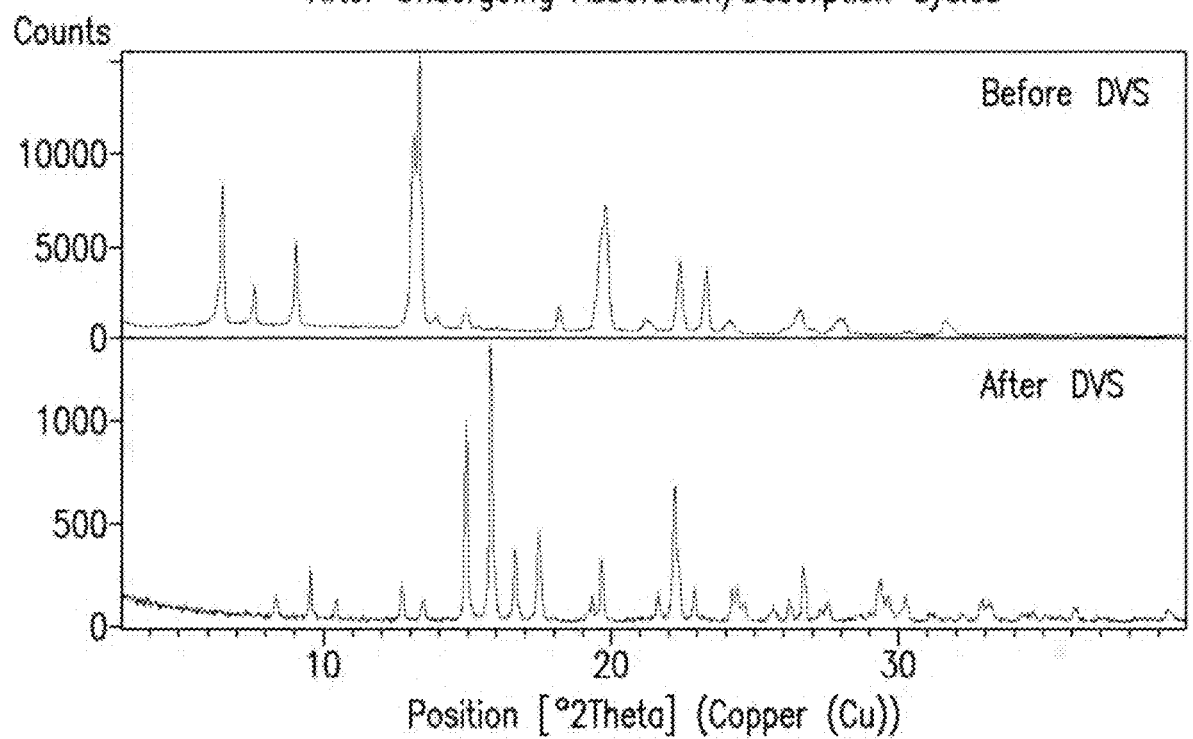

FIG. 56 provides representative XRPD patterns of Form C of HCl salt of Compound (I-S) before and after undergoing absorption/desorption cycles.

Figure 57:
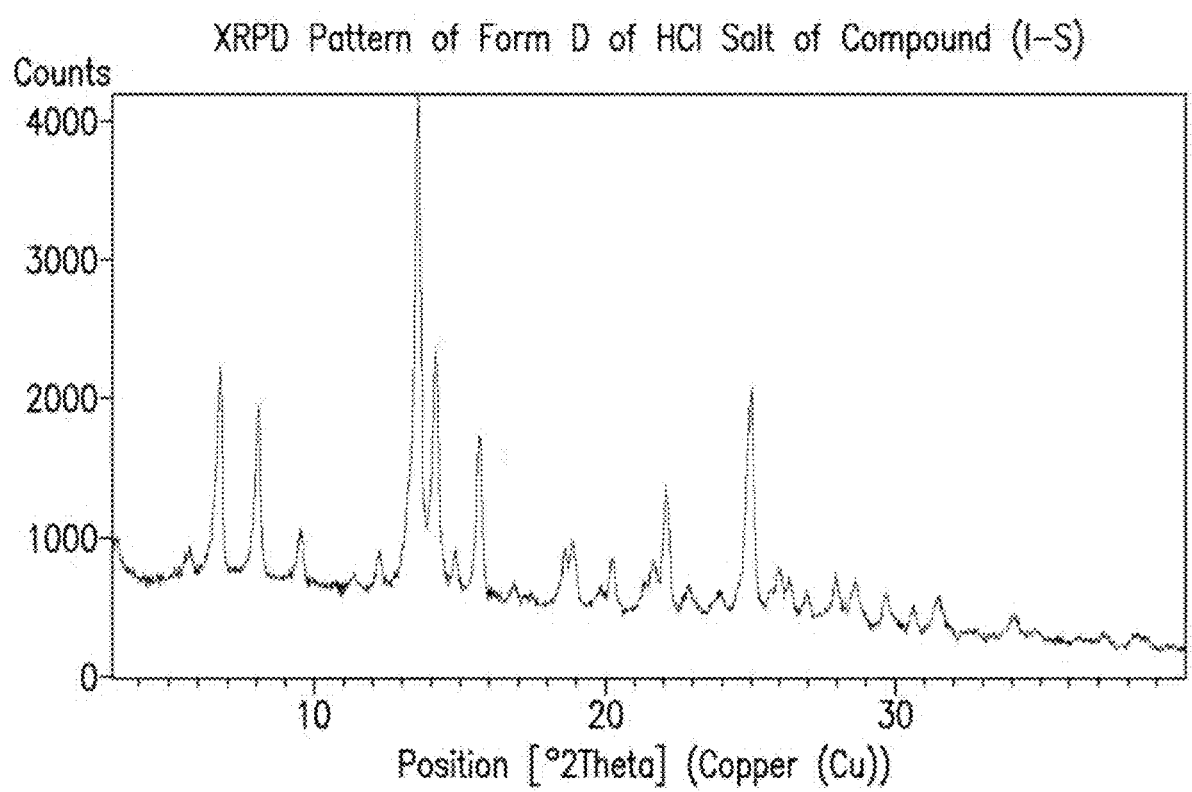

FIG. 57 provides a representative XRPD pattern of Form D of HCl salt of Compound (I-S).

Figure 58:
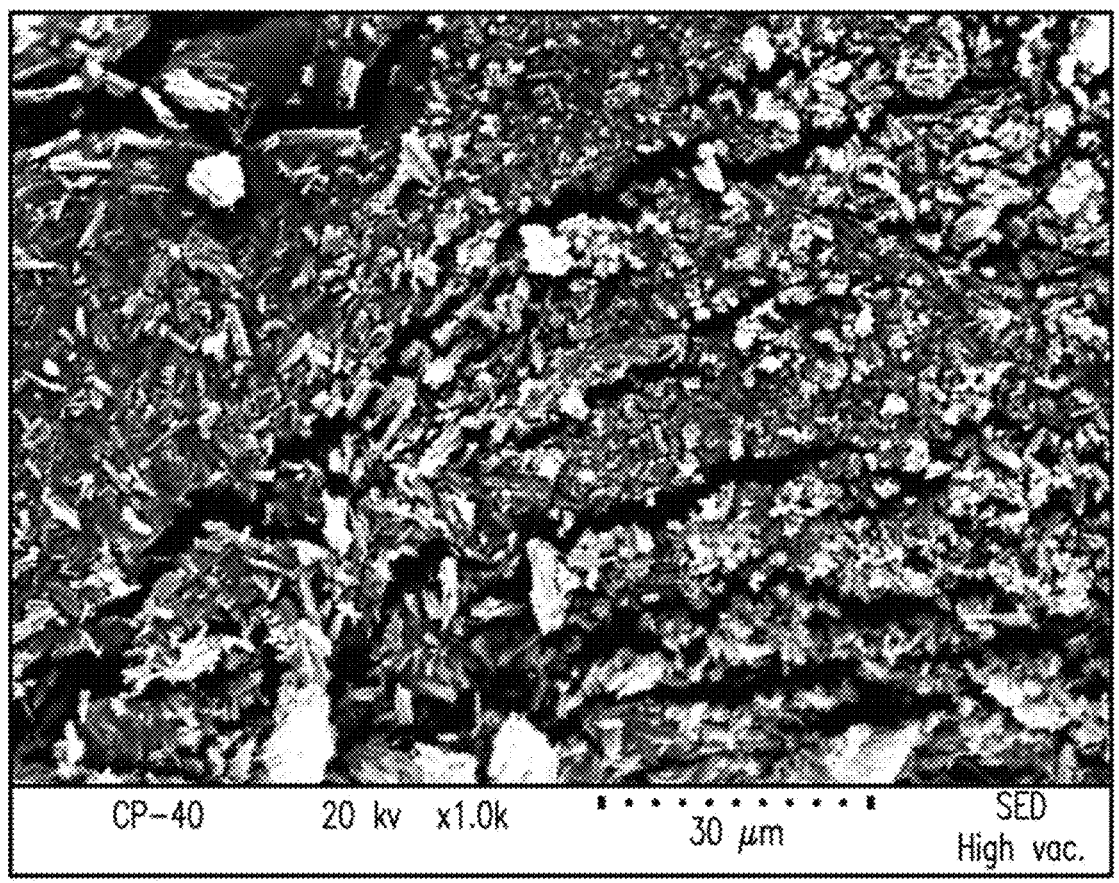

FIG. 58 provides a representative crystal habit of Form D of HCl salt of Compound (I-S).

Figure 59:
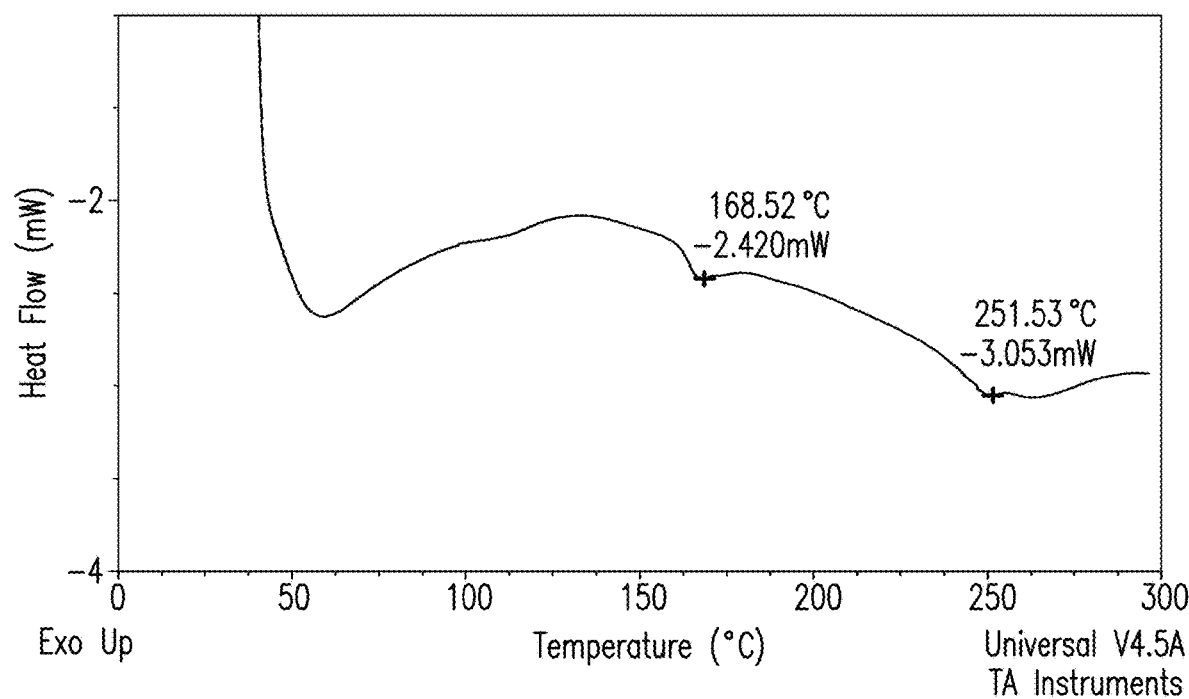

FIG. 59 provides a representative DSC thermogram of Form D of HCl salt of Compound (I-S).

Figure 60:
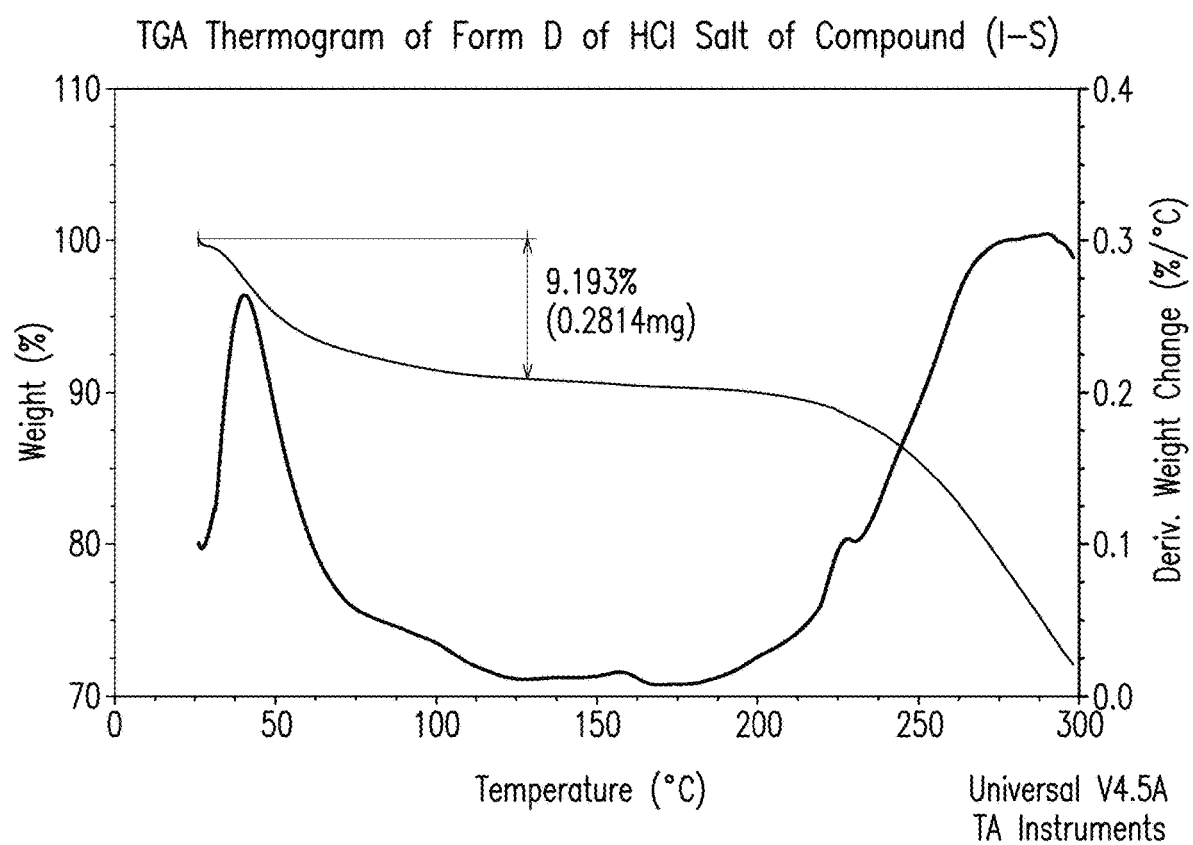

FIG. 60 provides a representative TGA thermogram of Form D of HCl salt of Compound (I-S).

Figure 61:
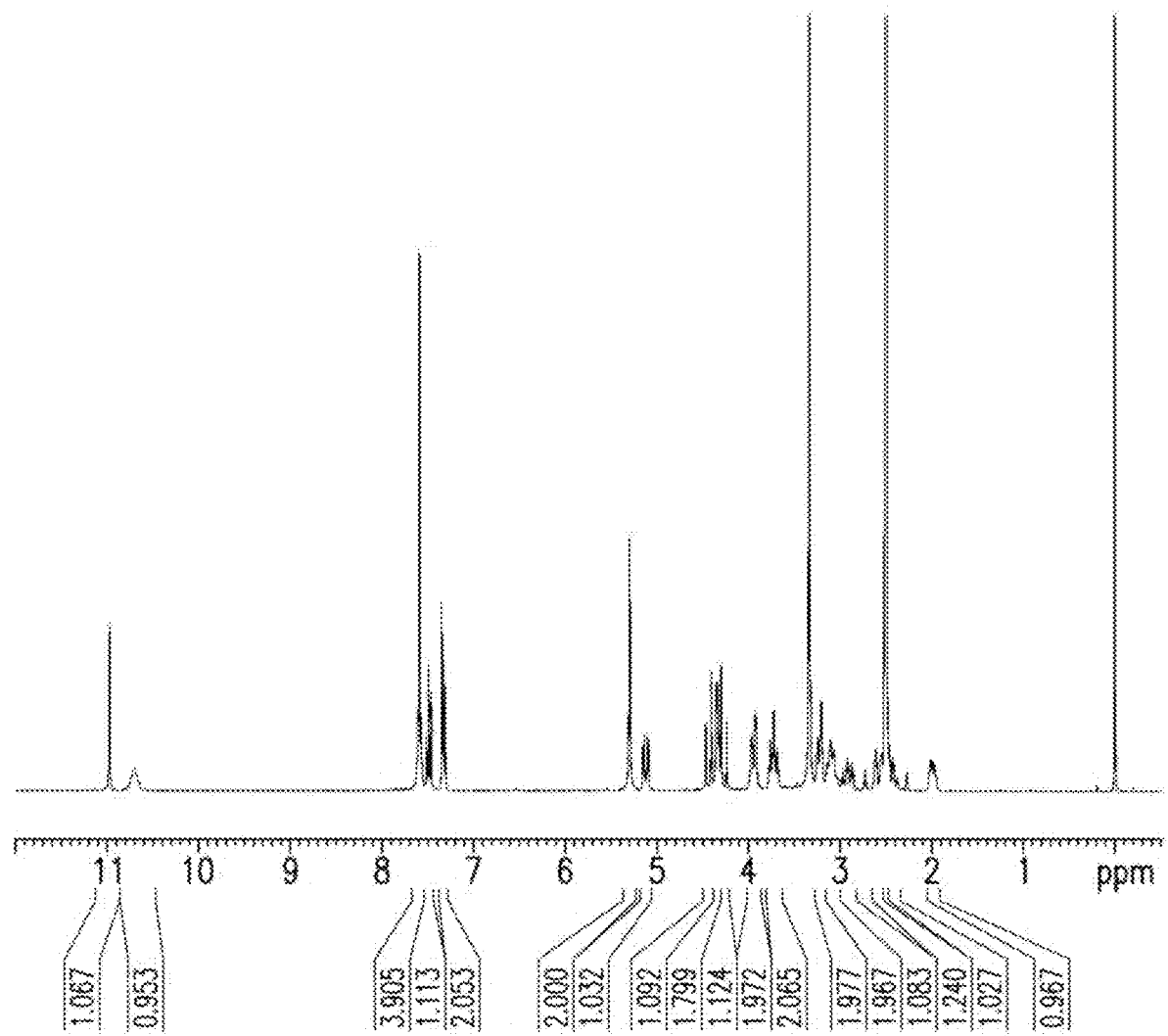

FIG. 61 provides a representative $^1$H-NMR spectrum of Form D of HCl salt of Compound (I-S).

Figure 62:
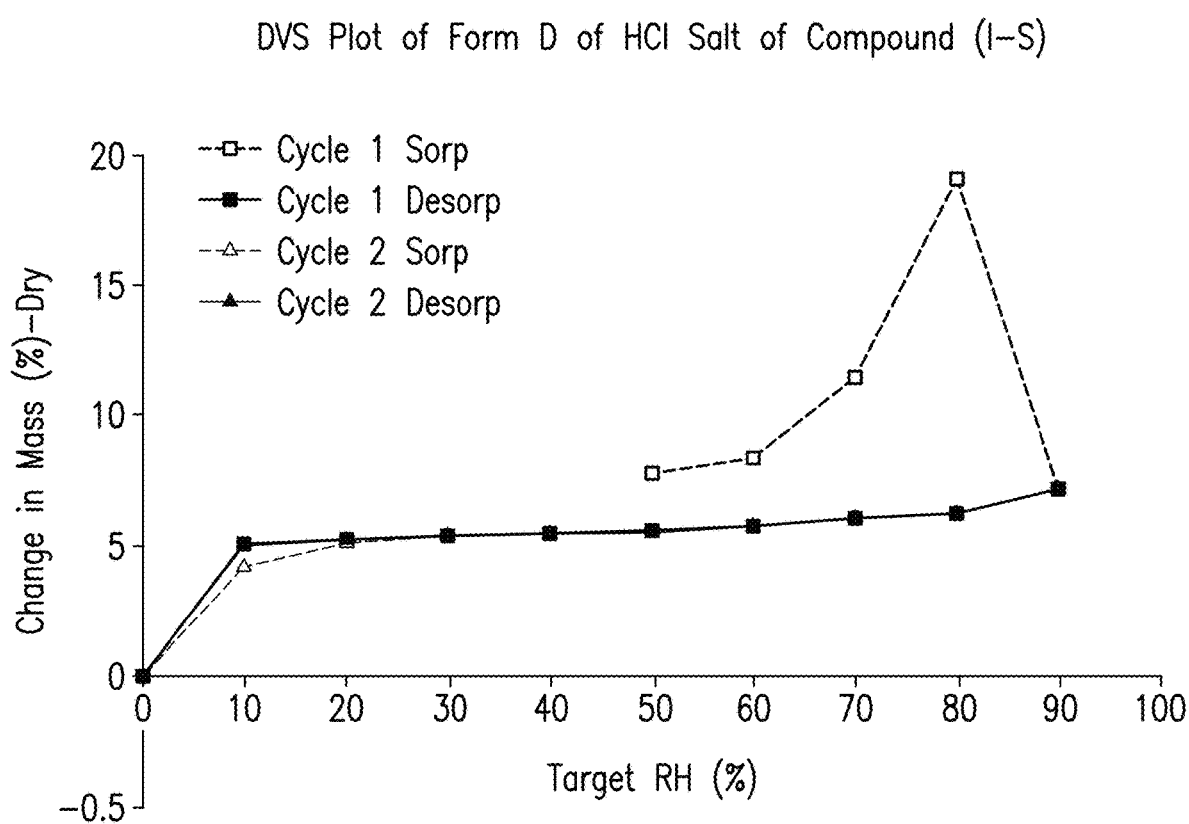

FIG. 62 provides a representative DVS plot of Form D of HCl salt of Compound (I-S).

Figure 63:
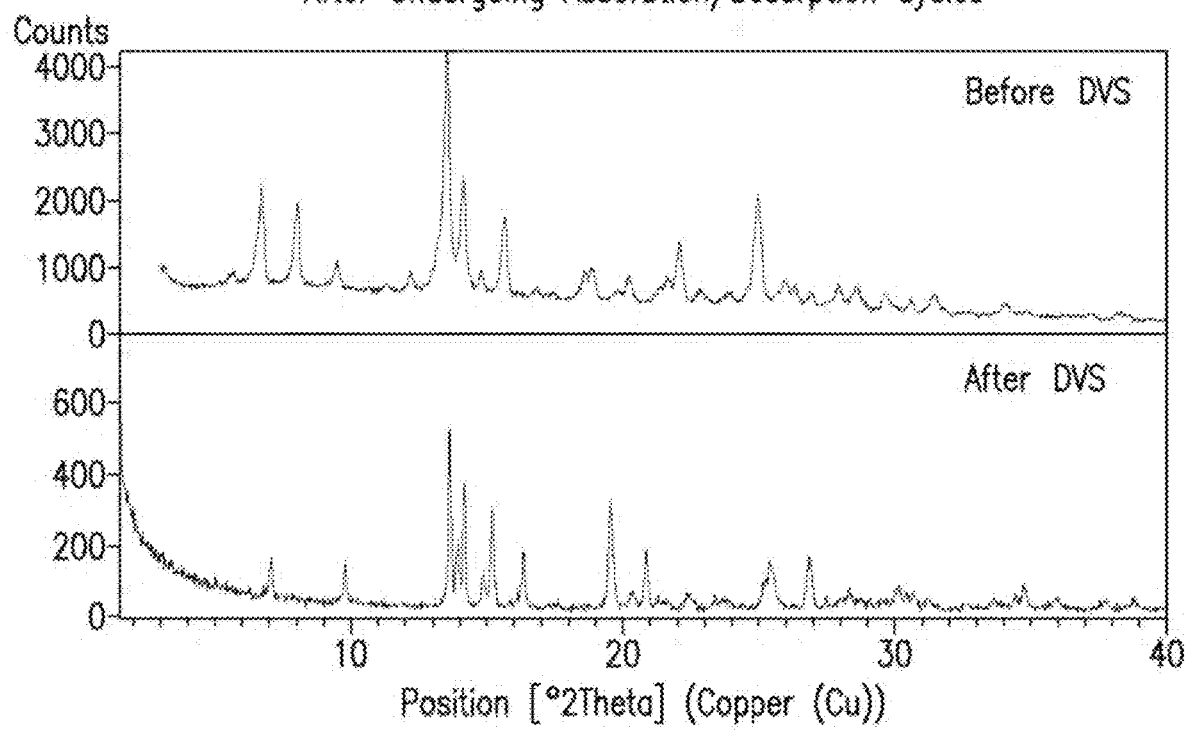

FIG. 63 provides representative XRPD patterns of Form D of HCl salt of Compound (I-S) before and after undergoing absorption/desorption cycles.

Figure 64:
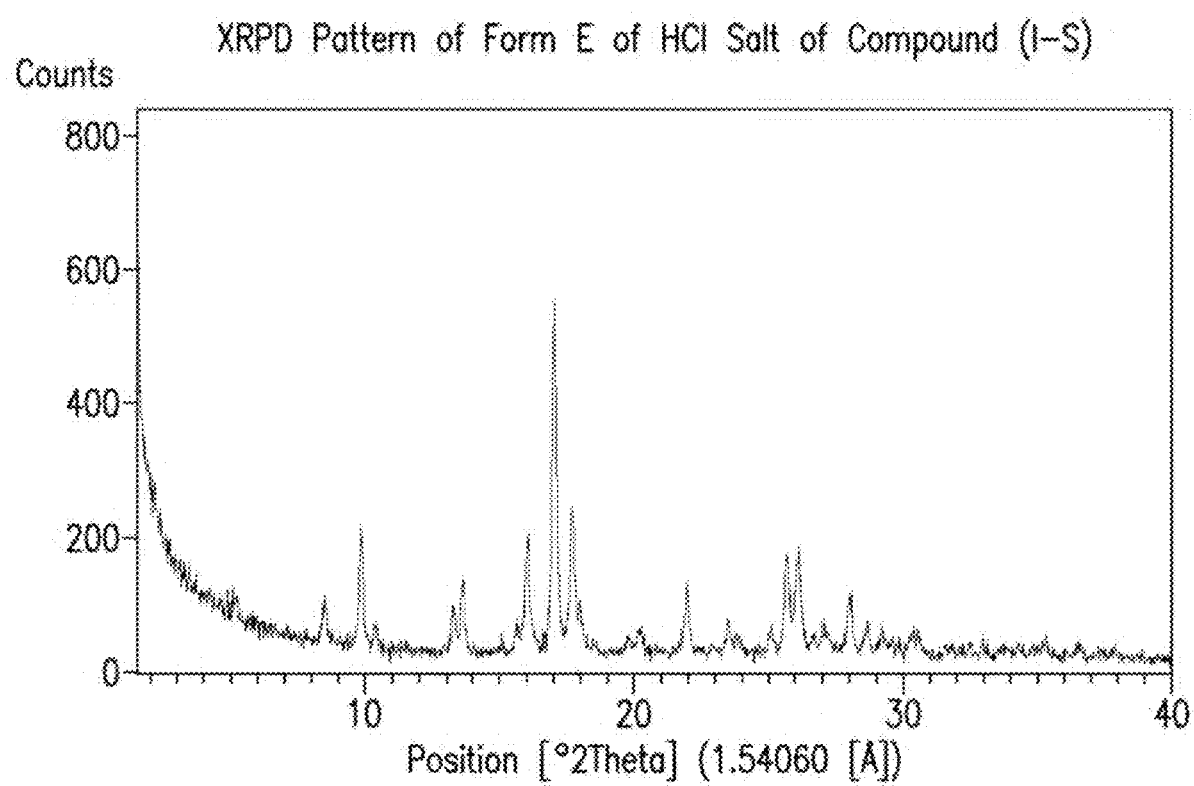

FIG. 64 provides a representative XRPD pattern of Form E of HCl salt of Compound (I-S).

Figure 65:
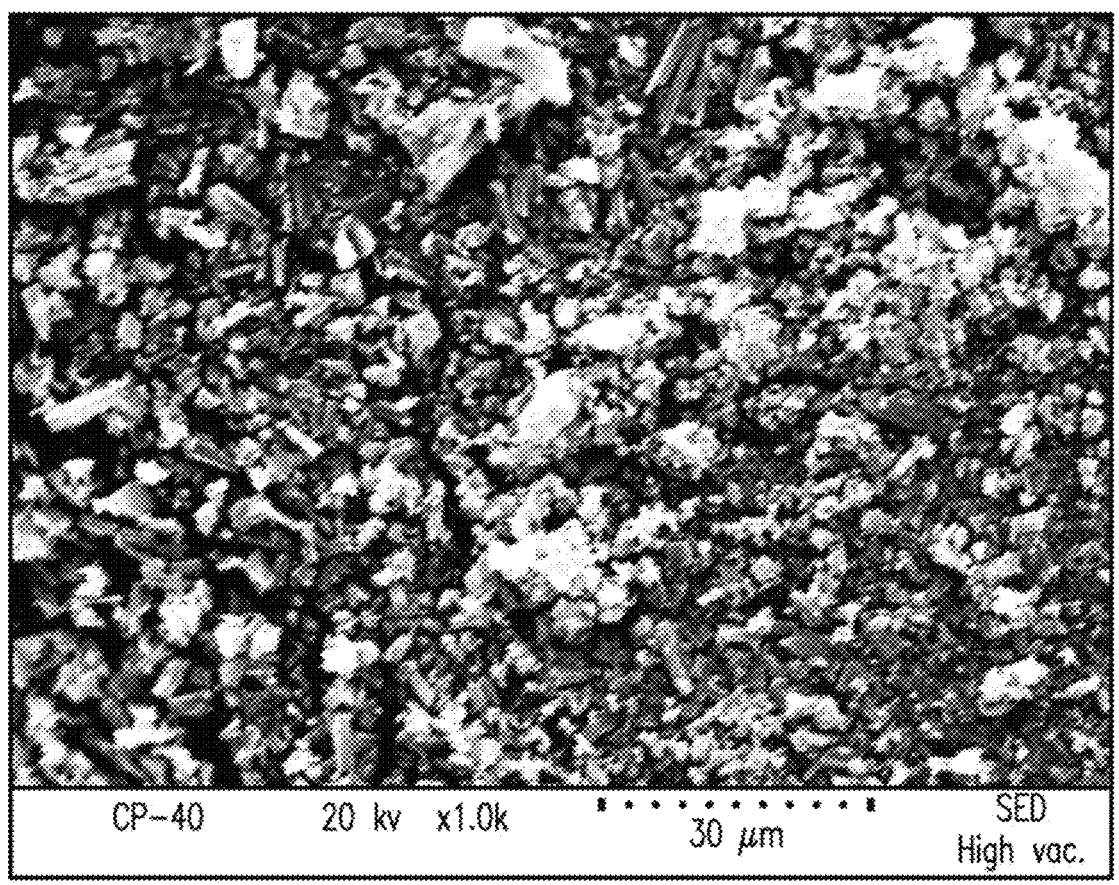

FIG. 65 provides a representative crystal habit of Form E of HCl salt of Compound (I-S).

Figure 66:
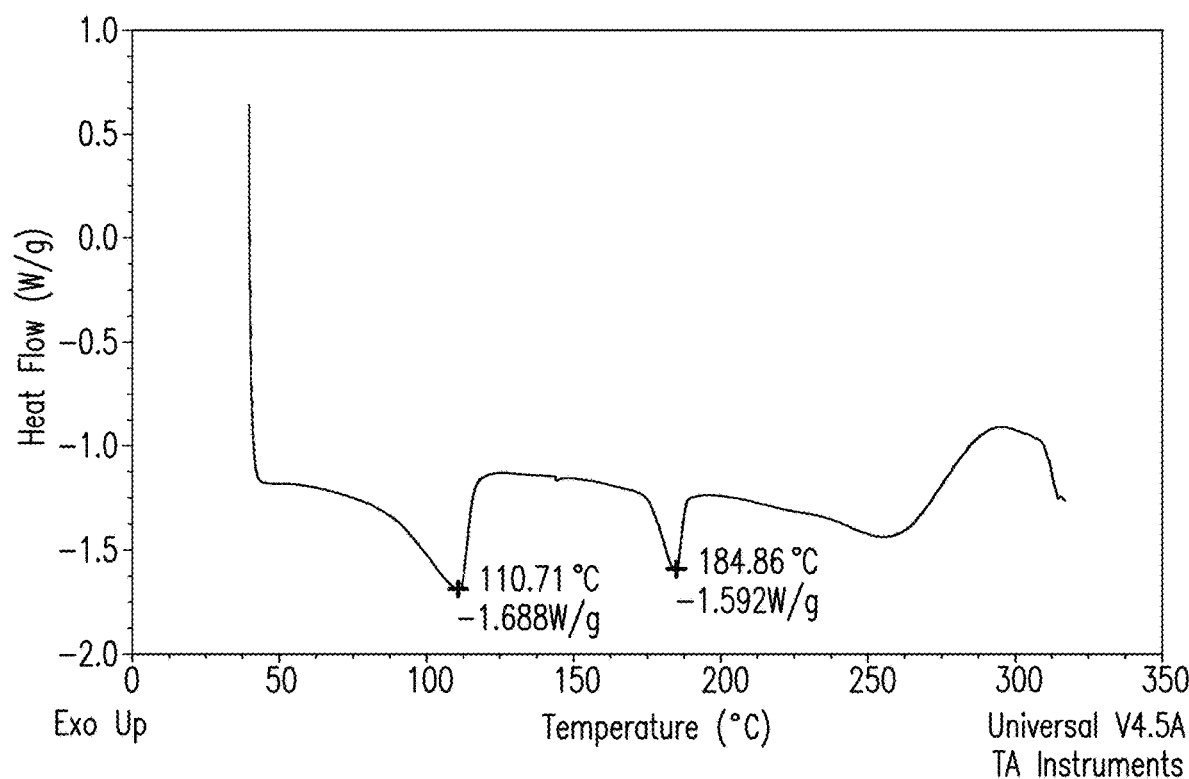

FIG. 66 provides a representative DSC thermogram of Form E of HCl salt of Compound (I-S).

Figure 67:
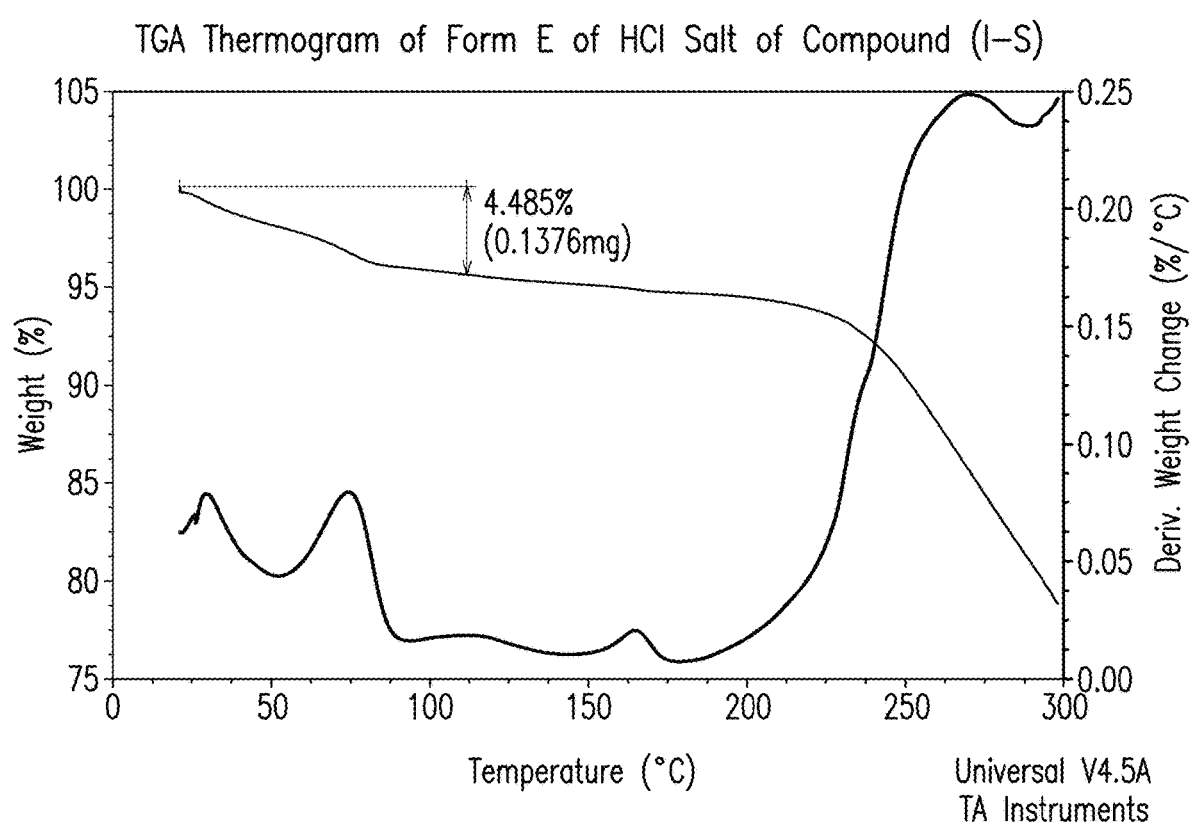

FIG. 67 provides a representative TGA thermogram of Form E of HCl salt of Compound (I-S).

Figure 68:
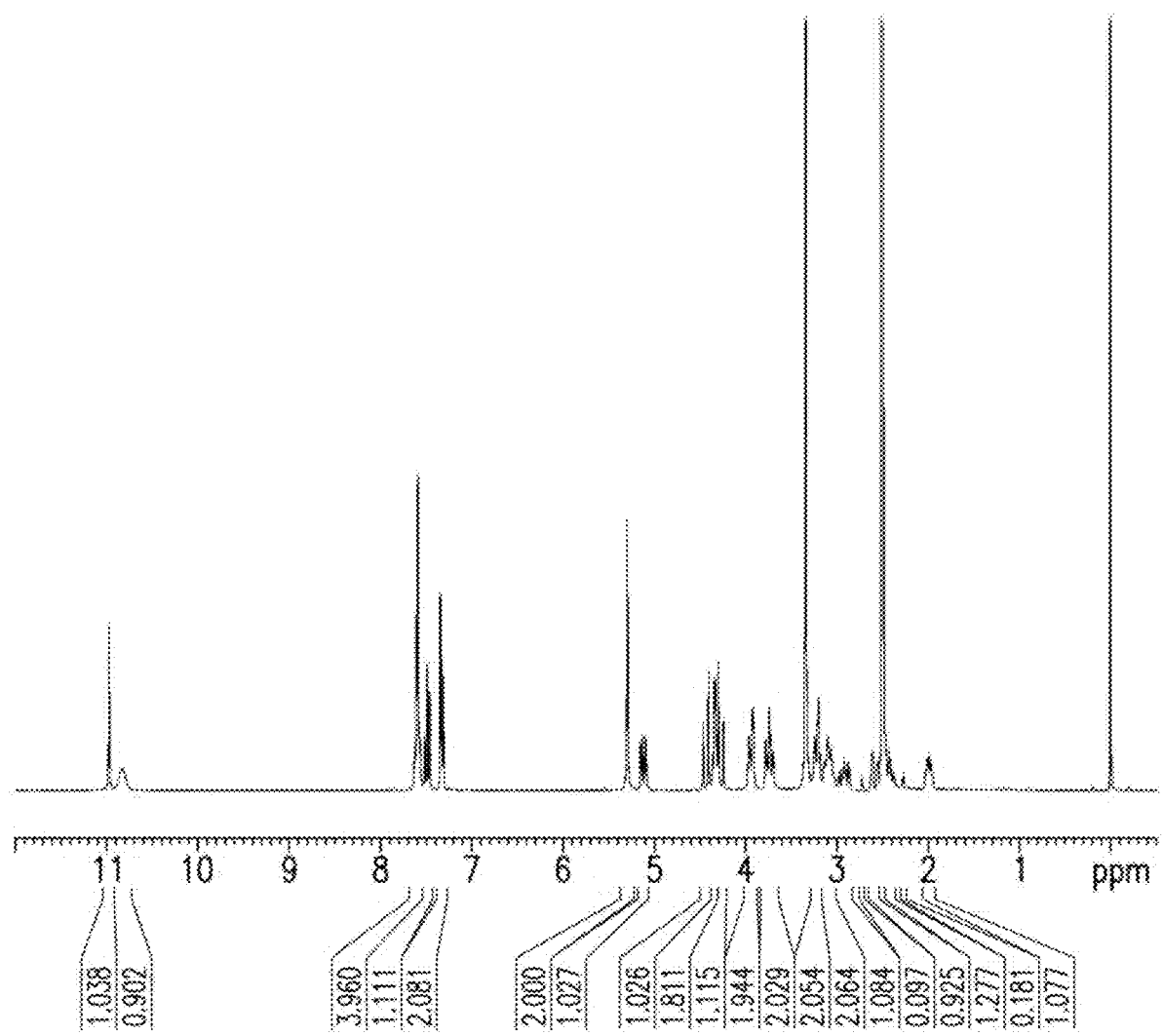

FIG. 68 provides a representative $^1$H-NMR spectrum of Form E of HCl salt of Compound (I-S).

Figure 69:
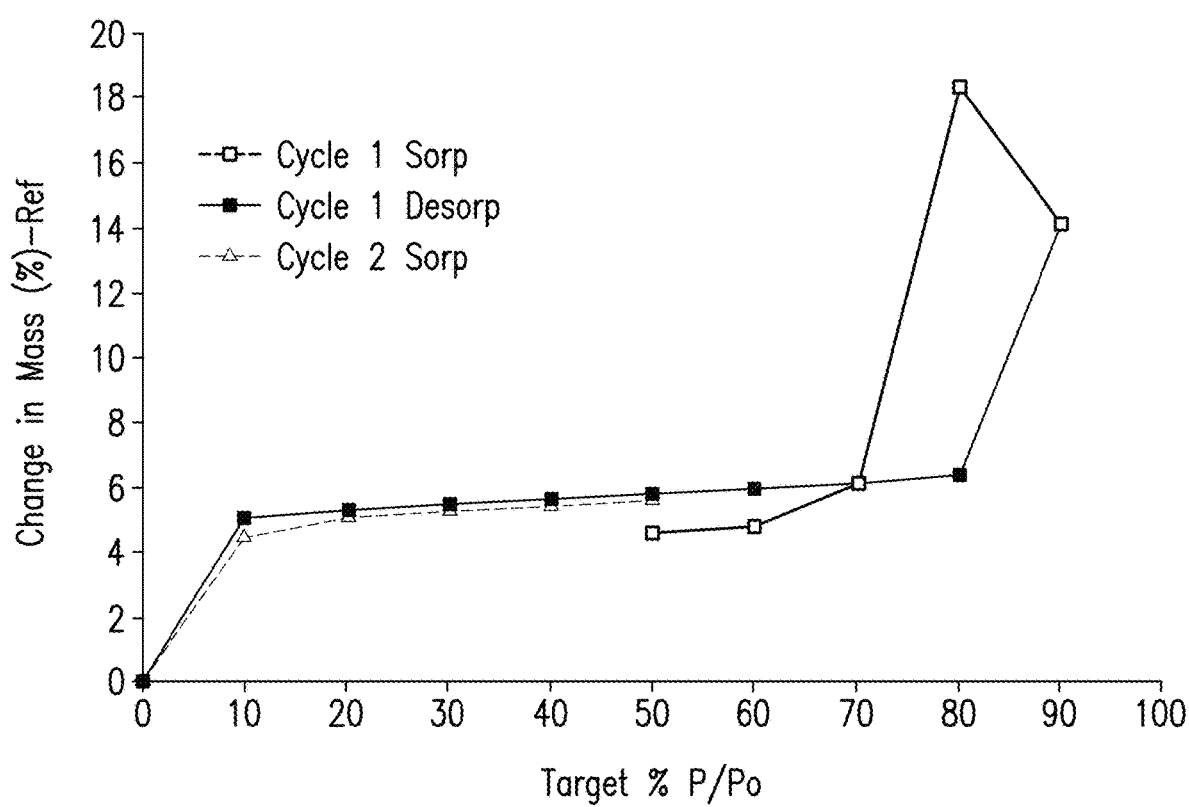

FIG. 69 provides a representative DVS plot of Form E of HCl salt of Compound (I-S).

Figure 70:
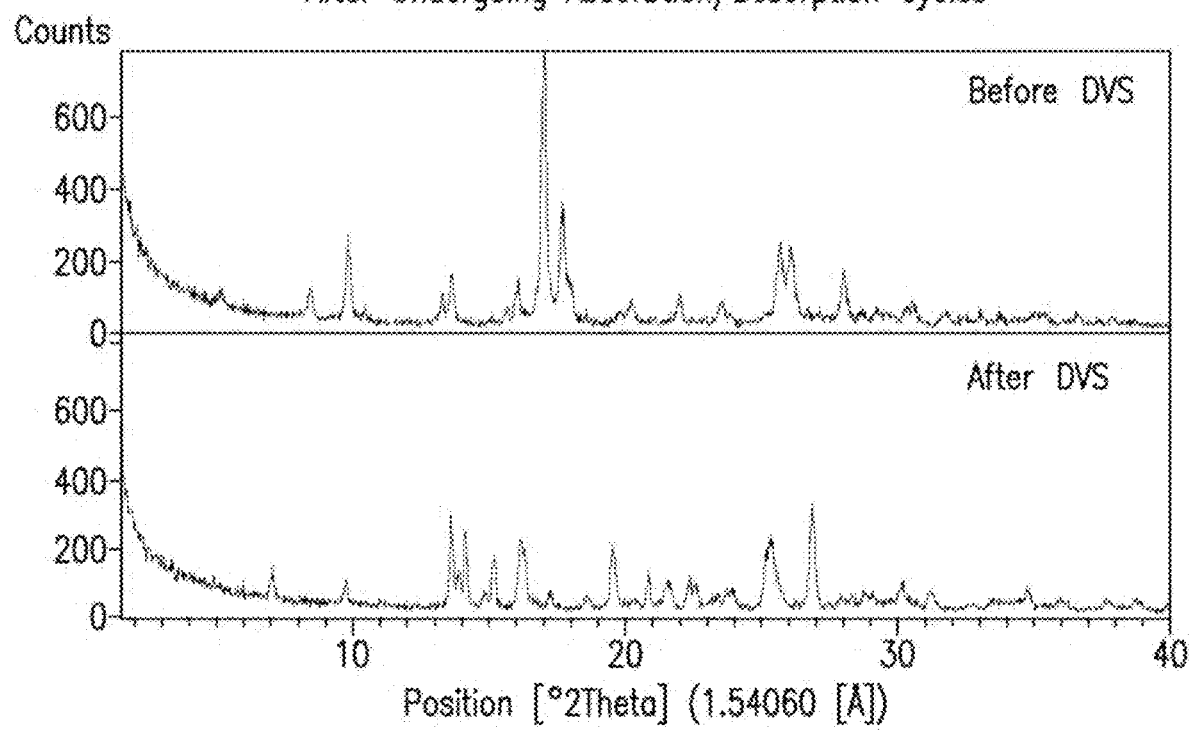

FIG. 70 provides representative XRPD patterns of Form E of HCl salt of Compound (I-S) before and after undergoing absorption/desorption cycles.

Figure 71:
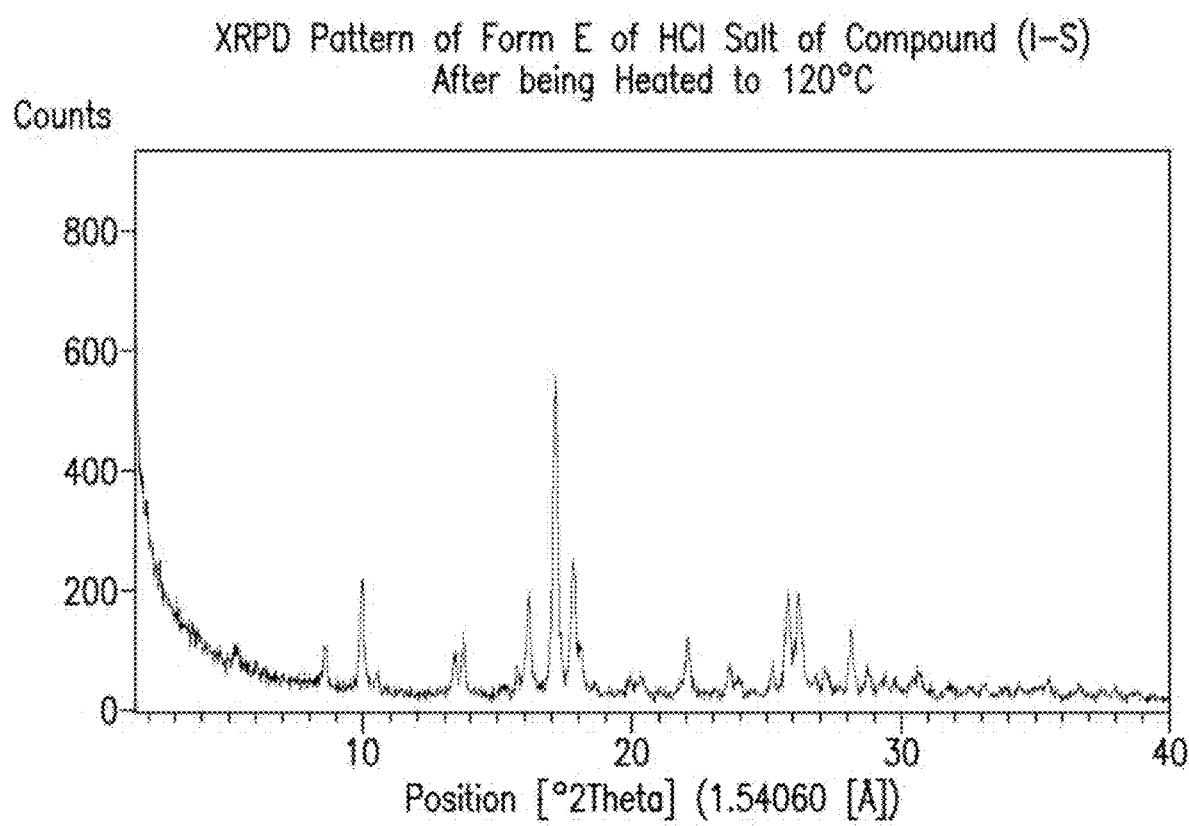

FIG. 71 provides a representative XRPD pattern of Form E of HCl salt of Compound (I-S) after being heated to 120° C.

Figure 72:
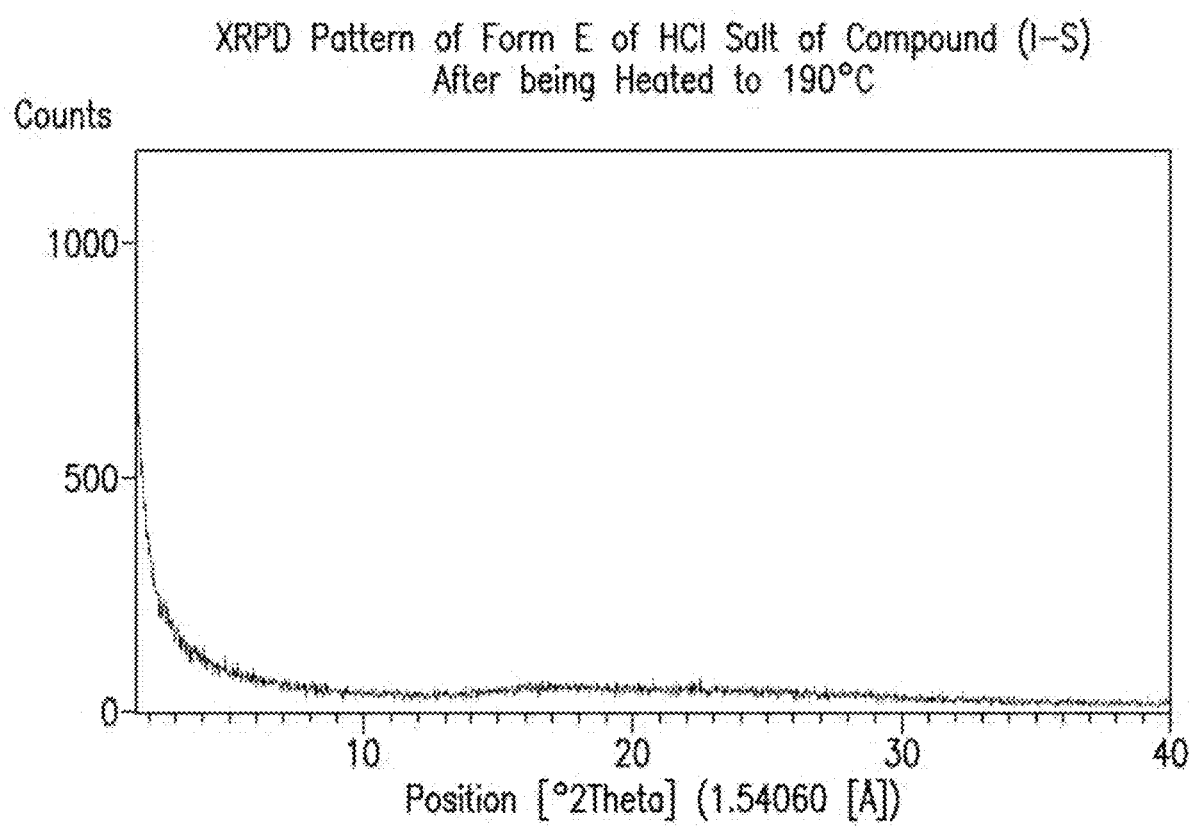

FIG. 72 provides a representative XRPD pattern of Form E of HCl salt of Compound (I-S) after being heated to 190° C.

Figure 73:
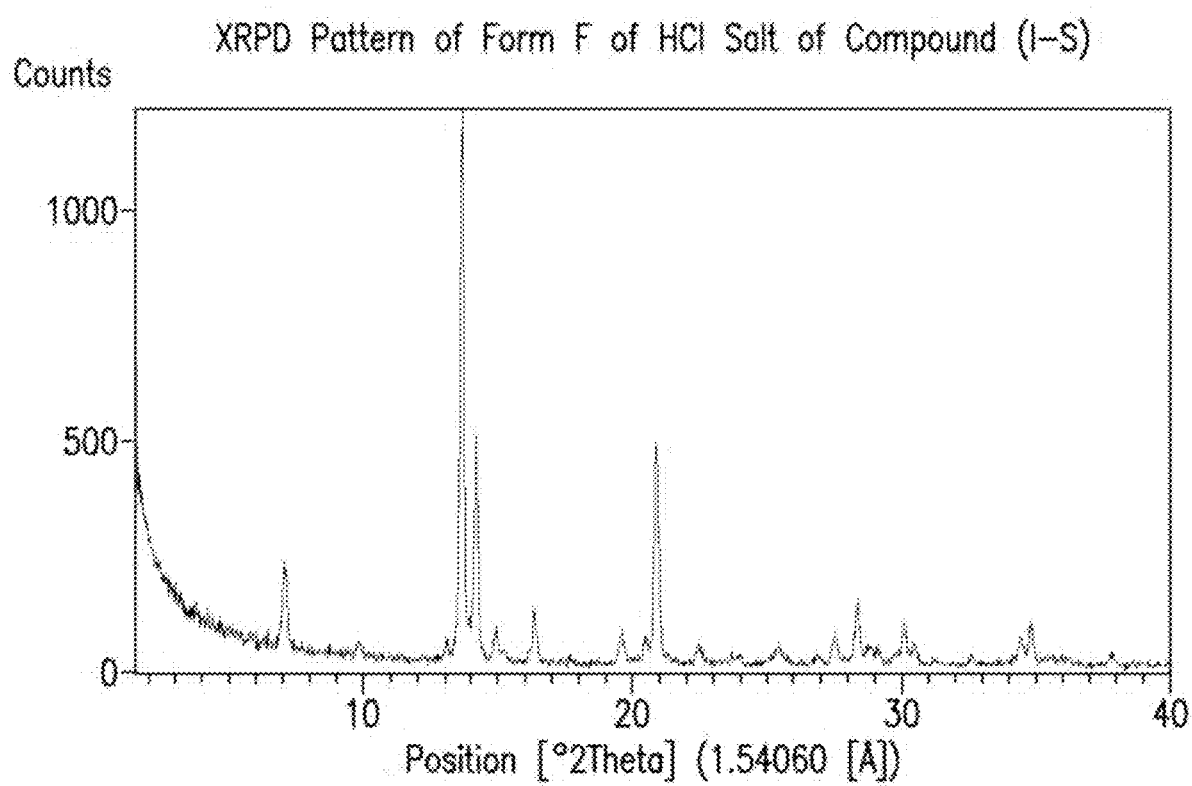

FIG. 73 provides a representative XRPD pattern of Form F of HCl salt of Compound (I-S).

Figure 74:
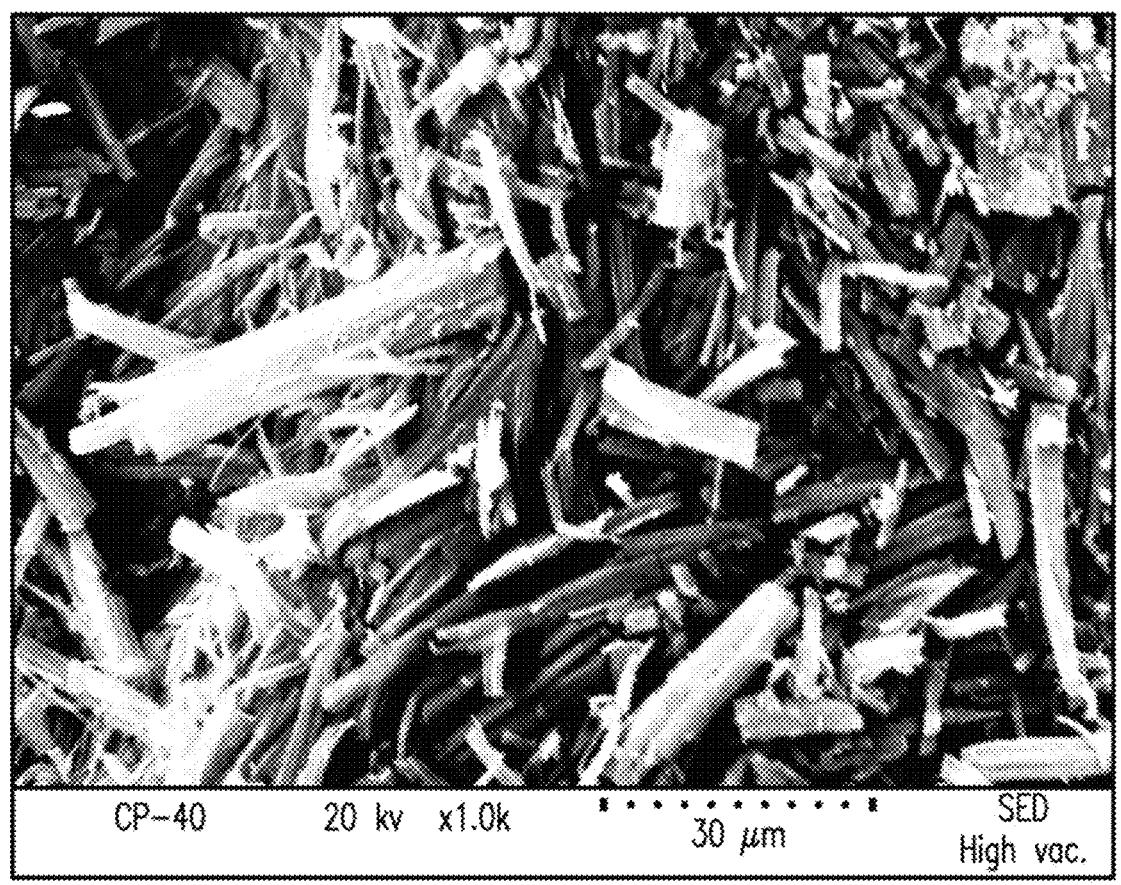

FIG. 74 provides a representative crystal habit of Form F of HCl salt of Compound (I-S).

Figure 75:
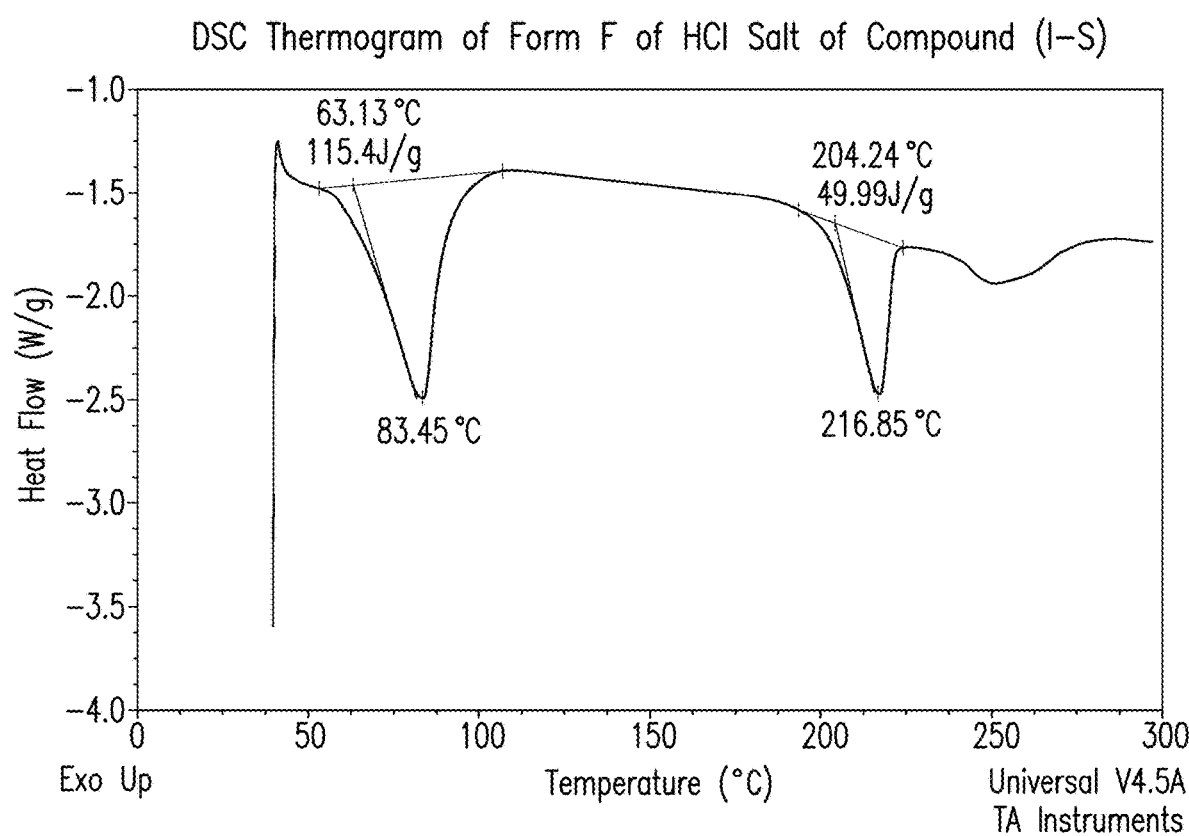

FIG. 75 provides a representative DSC thermogram of Form F of HCl salt of Compound (I-S).

Figure 76:
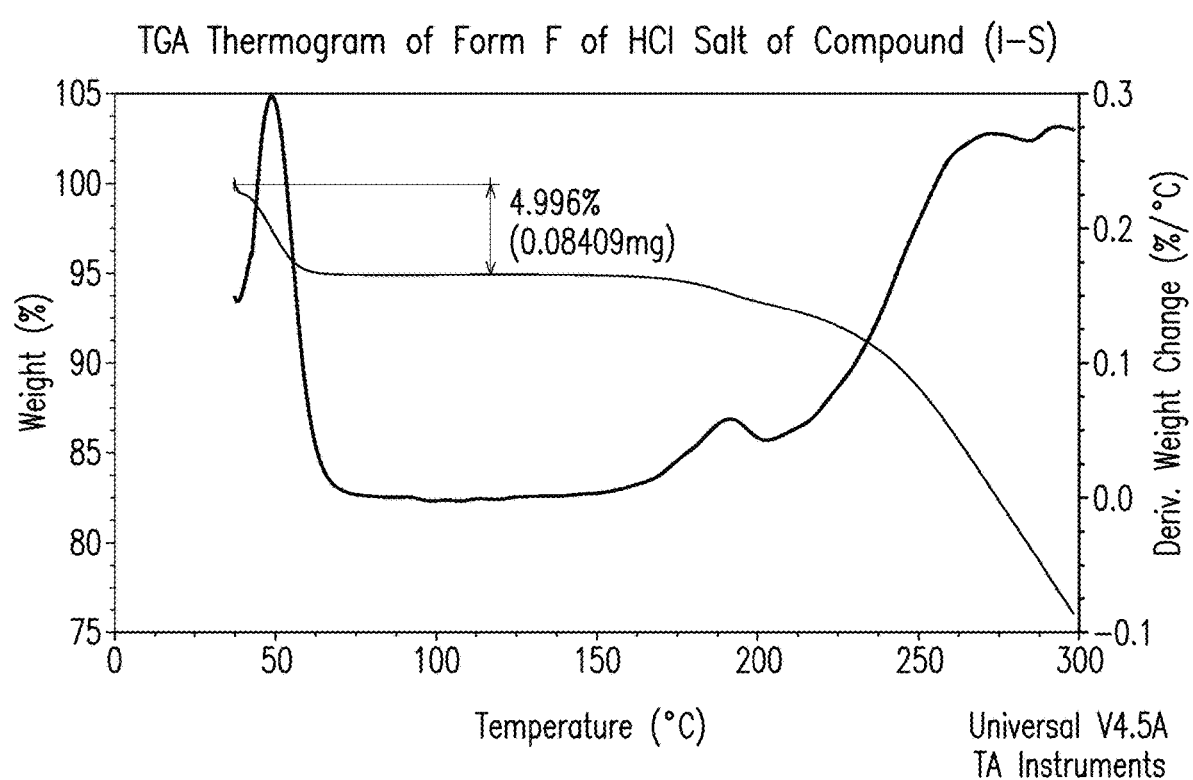

FIG. 76 provides a representative TGA thermogram of Form F of HCl salt of Compound (I-S).

Figure 77:
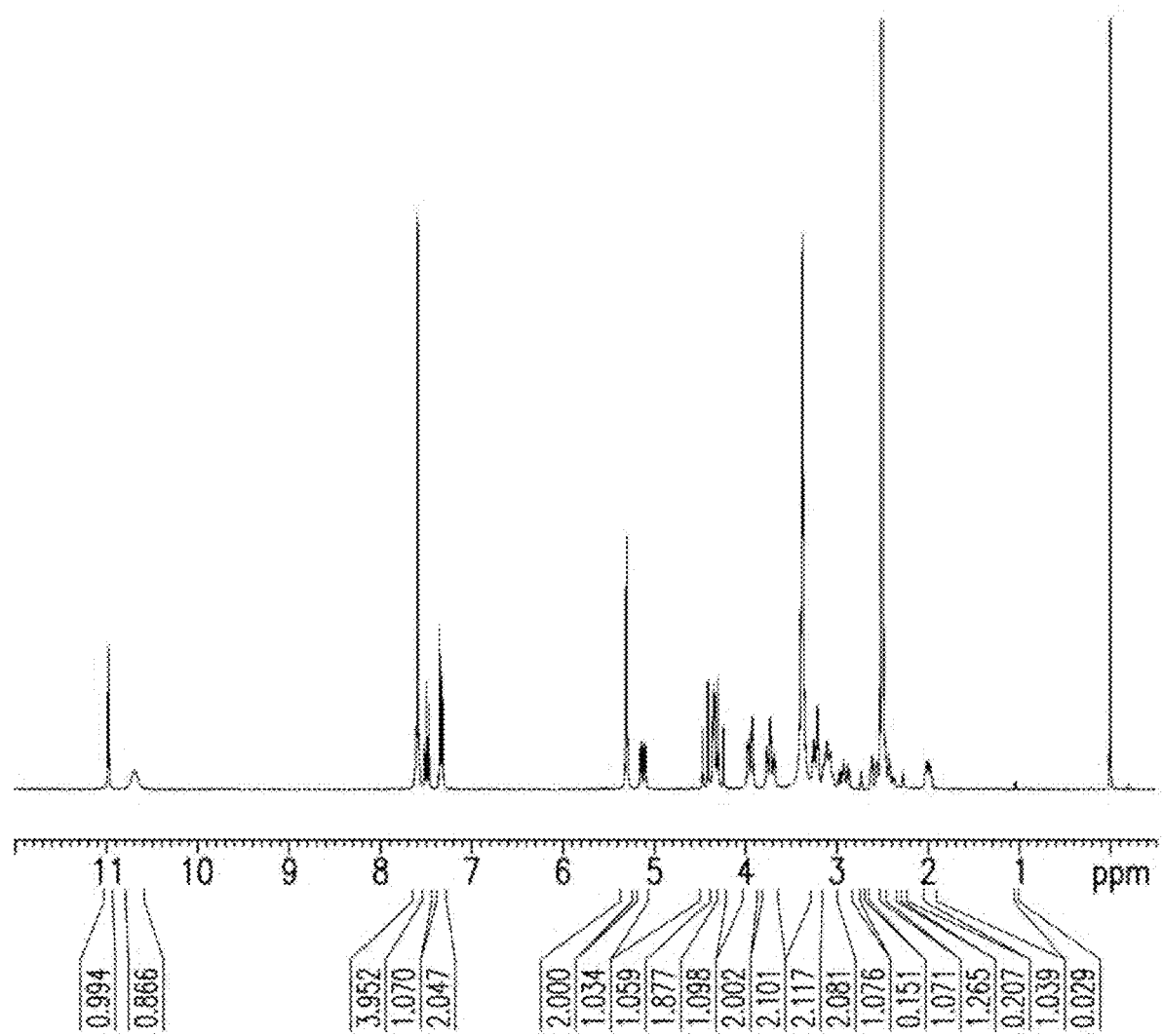

FIG. 77 provides a representative $^1$H-NMR spectrum of Form F of HCl salt of Compound (I-S).

Figure 78:
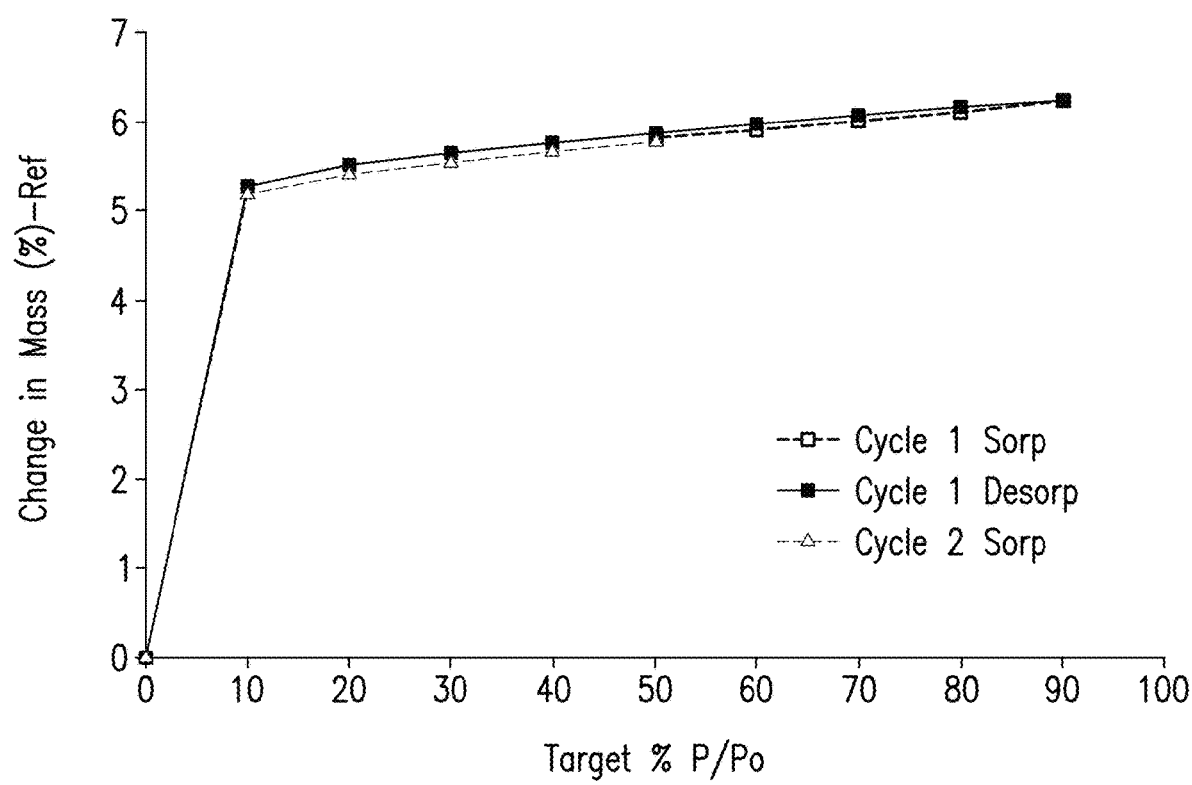

FIG. 78 provides a representative DVS plot of Form F of HCl salt of Compound (I-S).

Figure 79:
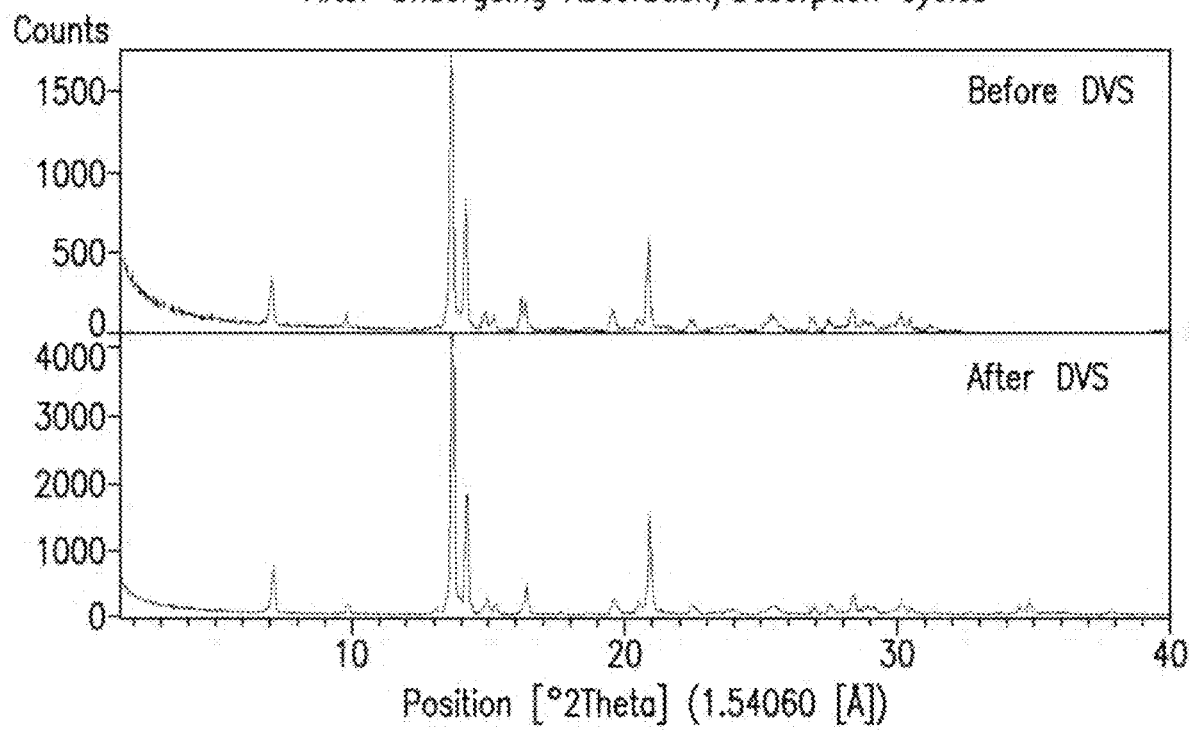

FIG. 79 provides representative XRPD patterns of Form F of HCl salt of Compound (I-S) before and after undergoing absorption/desorption cycles.

Figure 80:
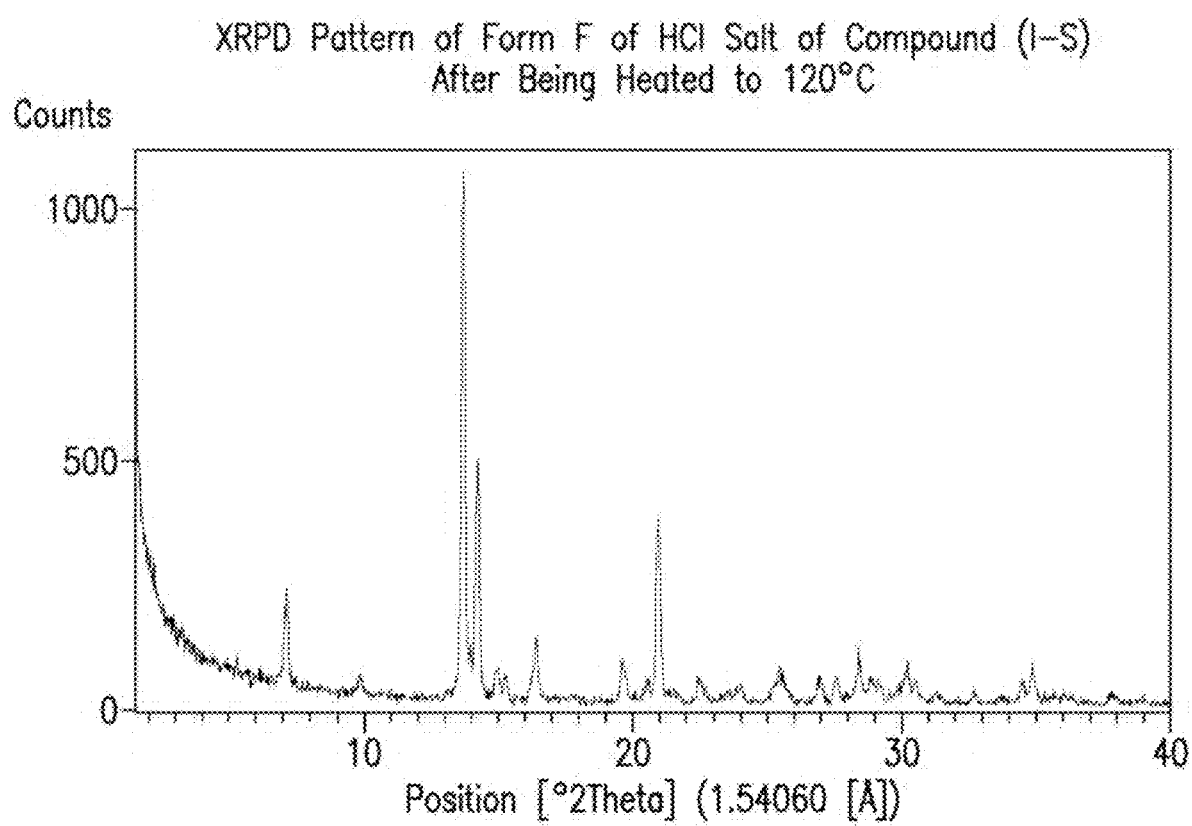

FIG. 80 provides a representative XRPD pattern of Form F of HCl salt of Compound (I-S) after being heated to 120° C.

Figure 81:
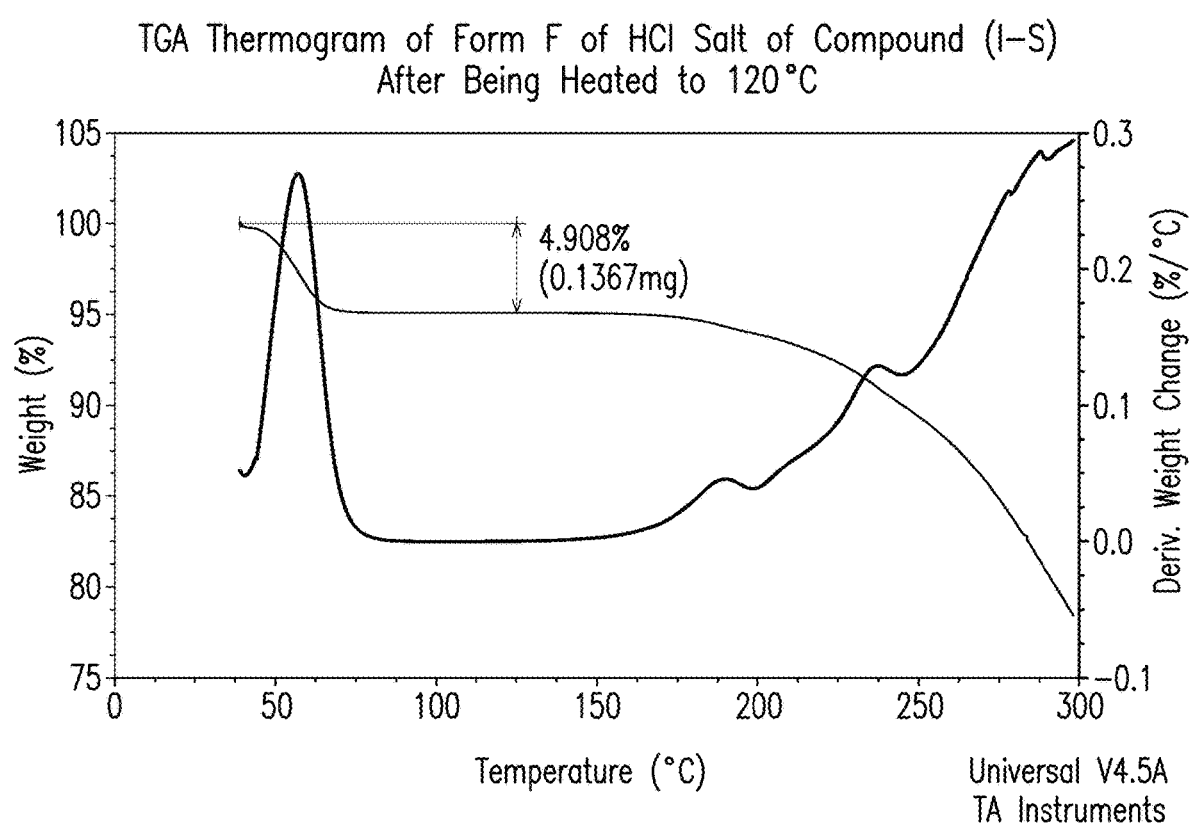

FIG. 81 provides a representative TGA thermogram of Form F of HCl salt of Compound (I-S) after being heated to 120° C.

Figure 82:
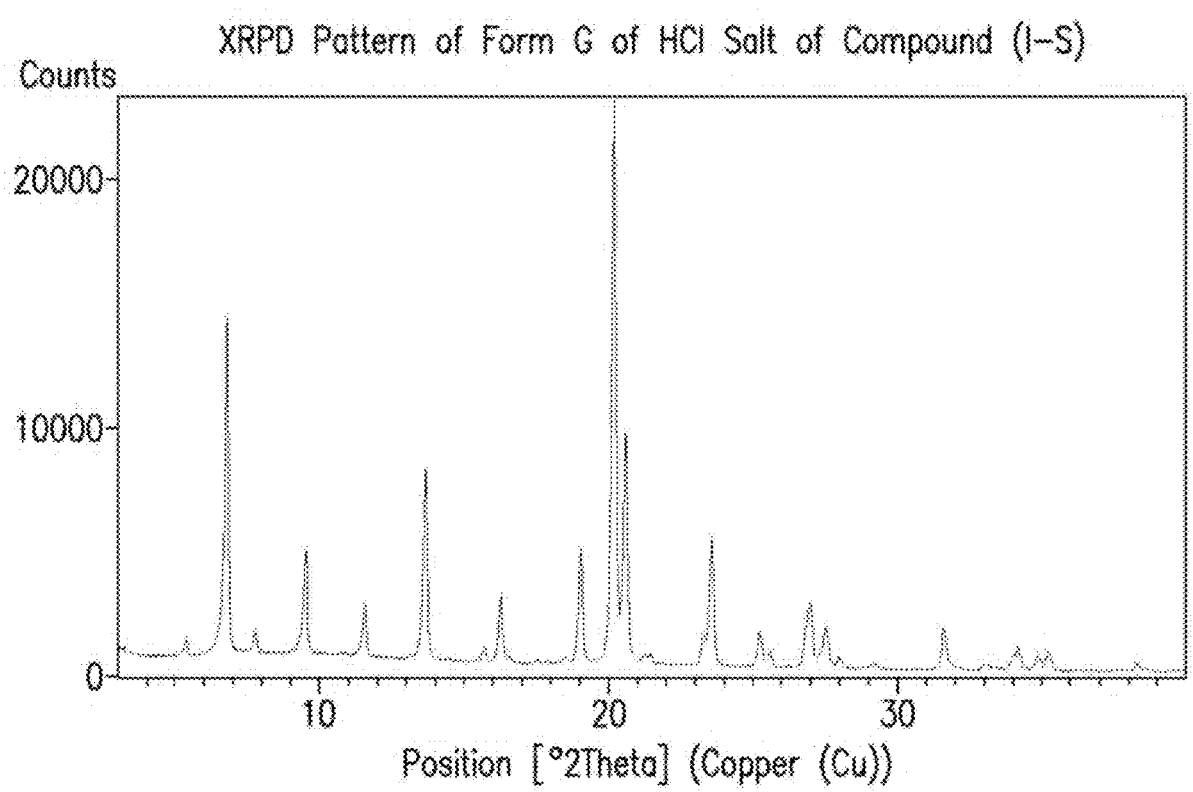

FIG. 82 provides a representative XRPD pattern of Form G of HCl salt of Compound (I-S).

Figure 83:
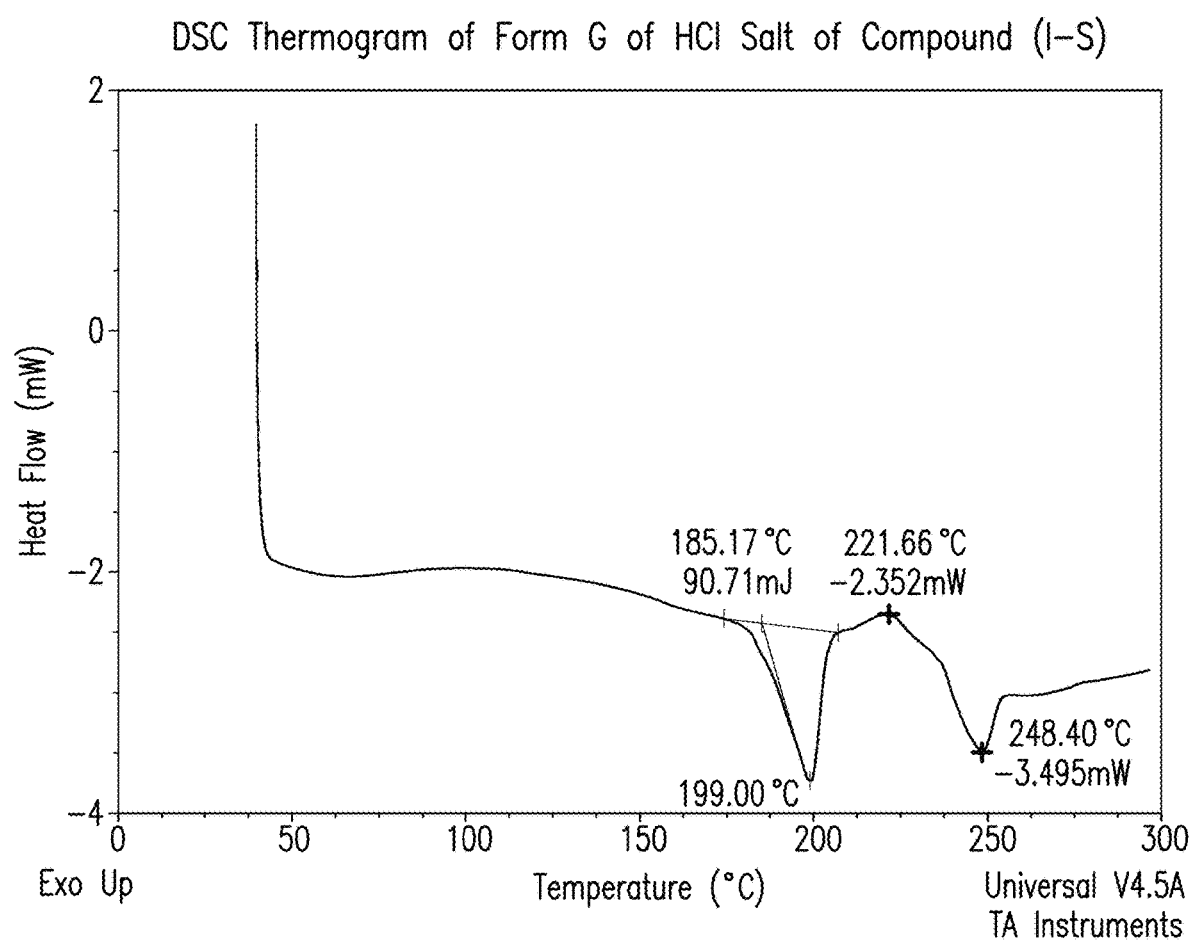

FIG. 83 provides a representative DSC thermogram of Form G of HCl salt of Compound (I-S).

Figure 84:
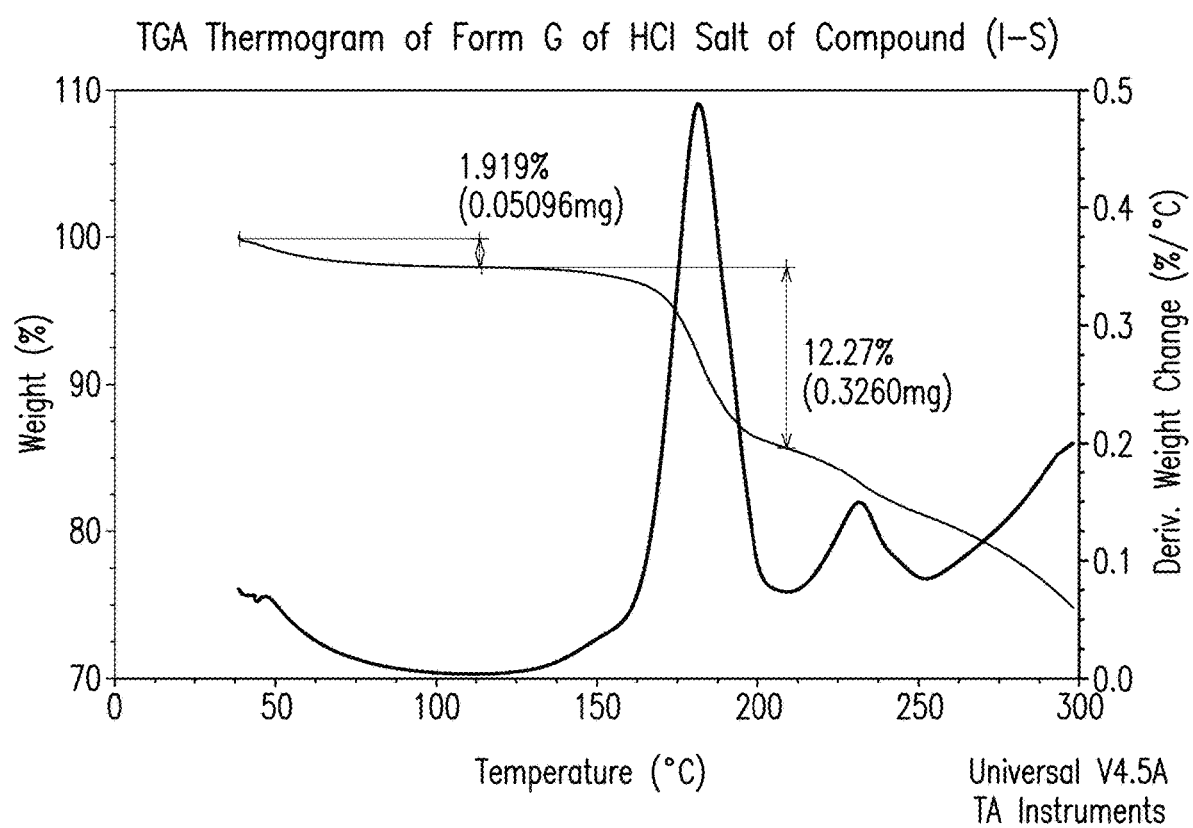

FIG. 84 provides a representative TGA thermogram of Form G of HCl salt of Compound (I-S).

Figure 85:
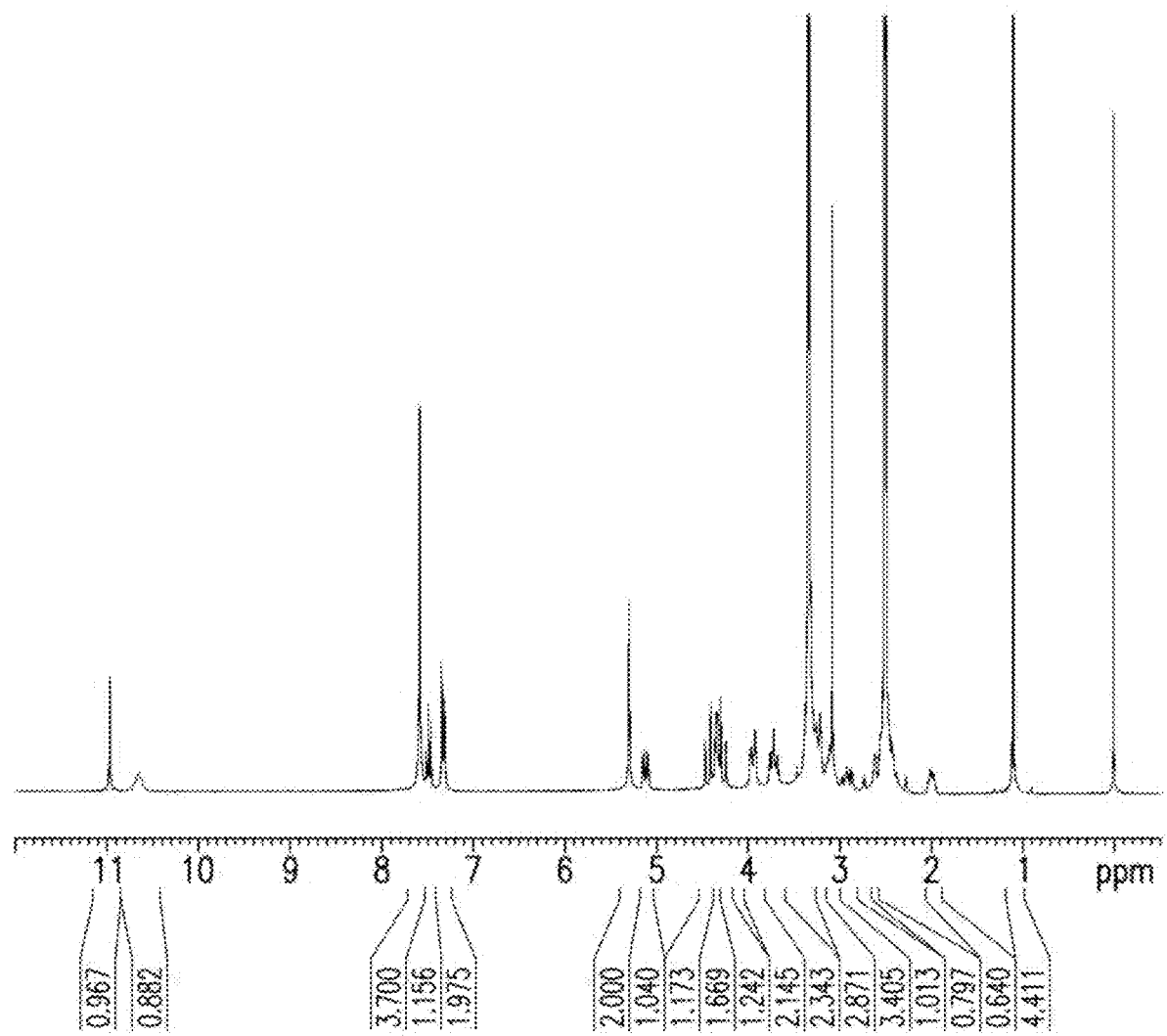

FIG. 85 provides a representative $^1$H-NMR spectrum of Form G of HCl salt of Compound (I-S).

Figure 86:
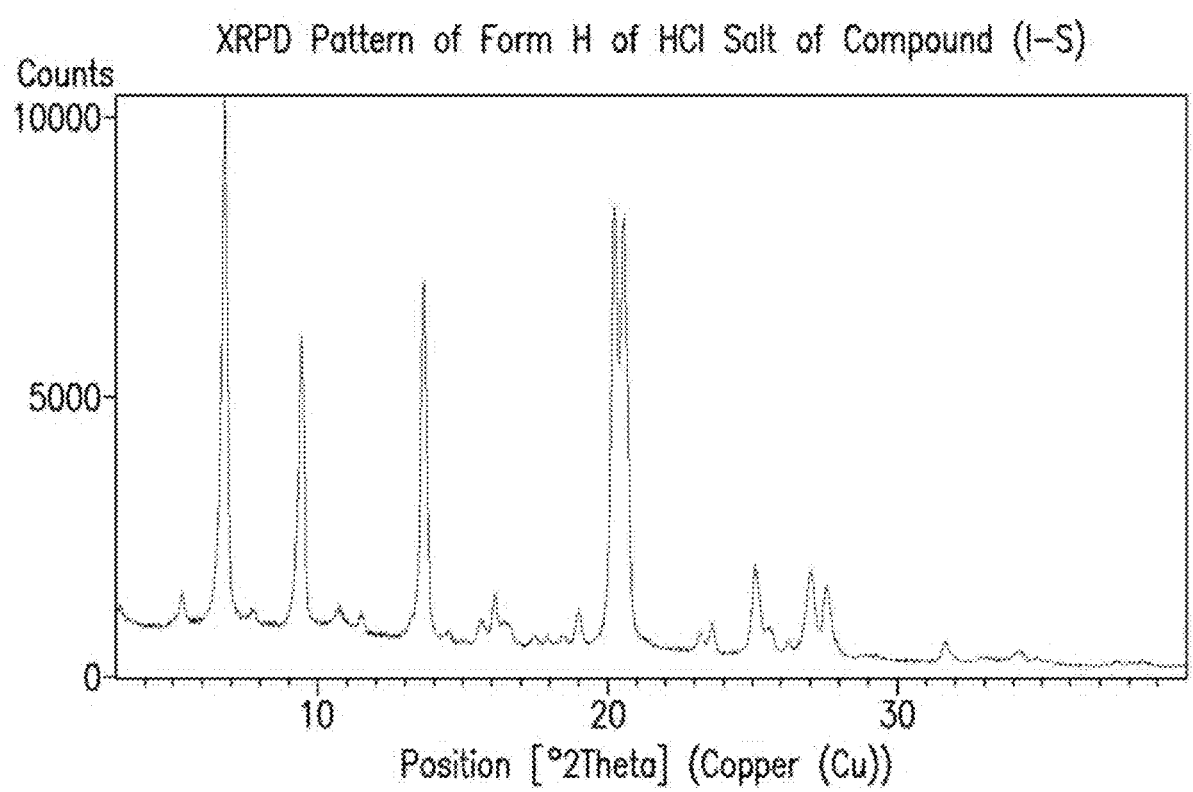

FIG. 86 provides a representative XRPD pattern of Form H of HCl salt of Compound (I-S).

Figure 87:
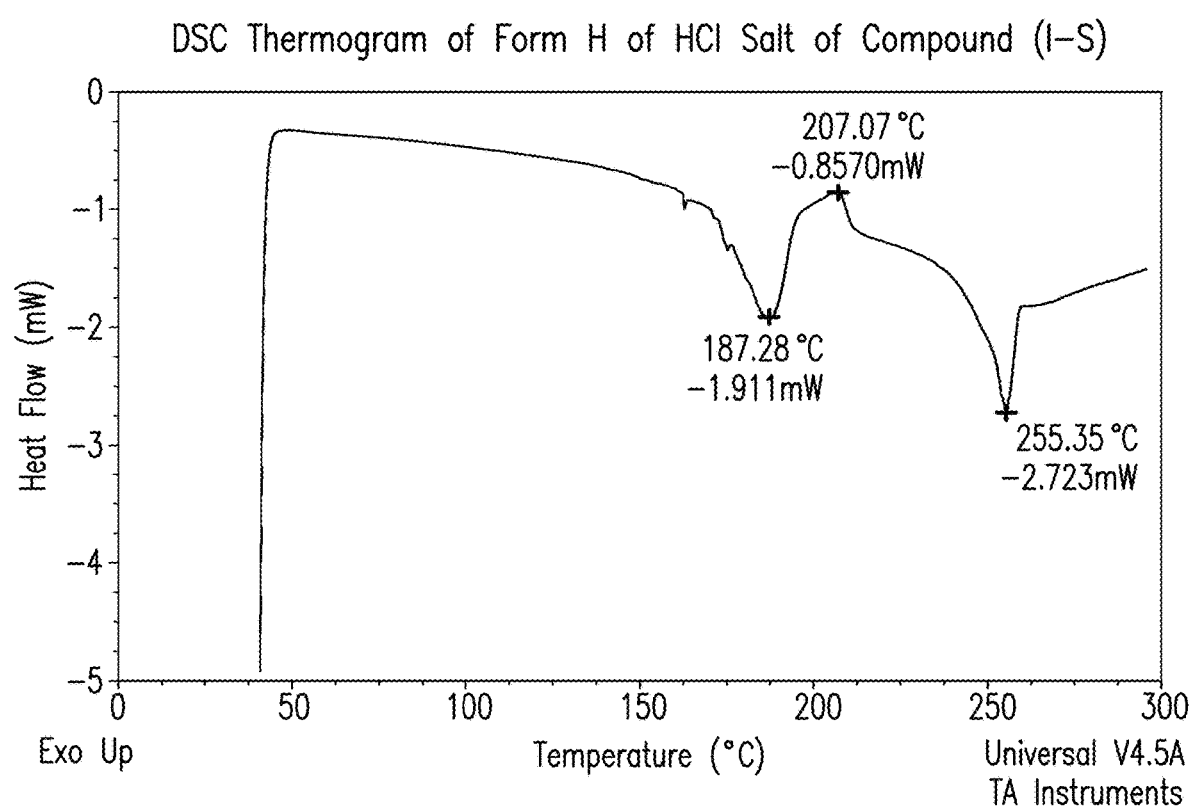

FIG. 87 provides a representative DSC thermogram of Form H of HCl salt of Compound (I-S).

Figure 88:
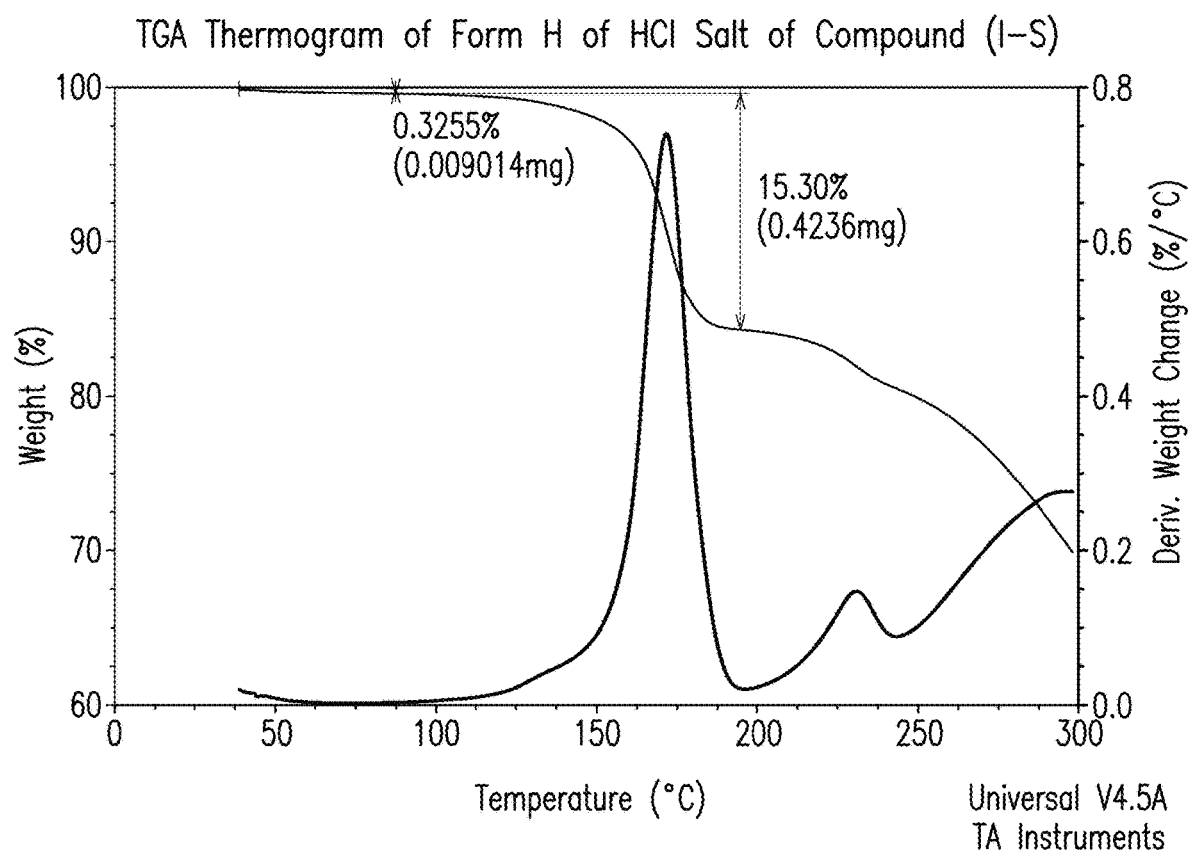

FIG. 88 provides a representative TGA thermogram of Form H of HCl salt of Compound (I-S).

Figure 89:
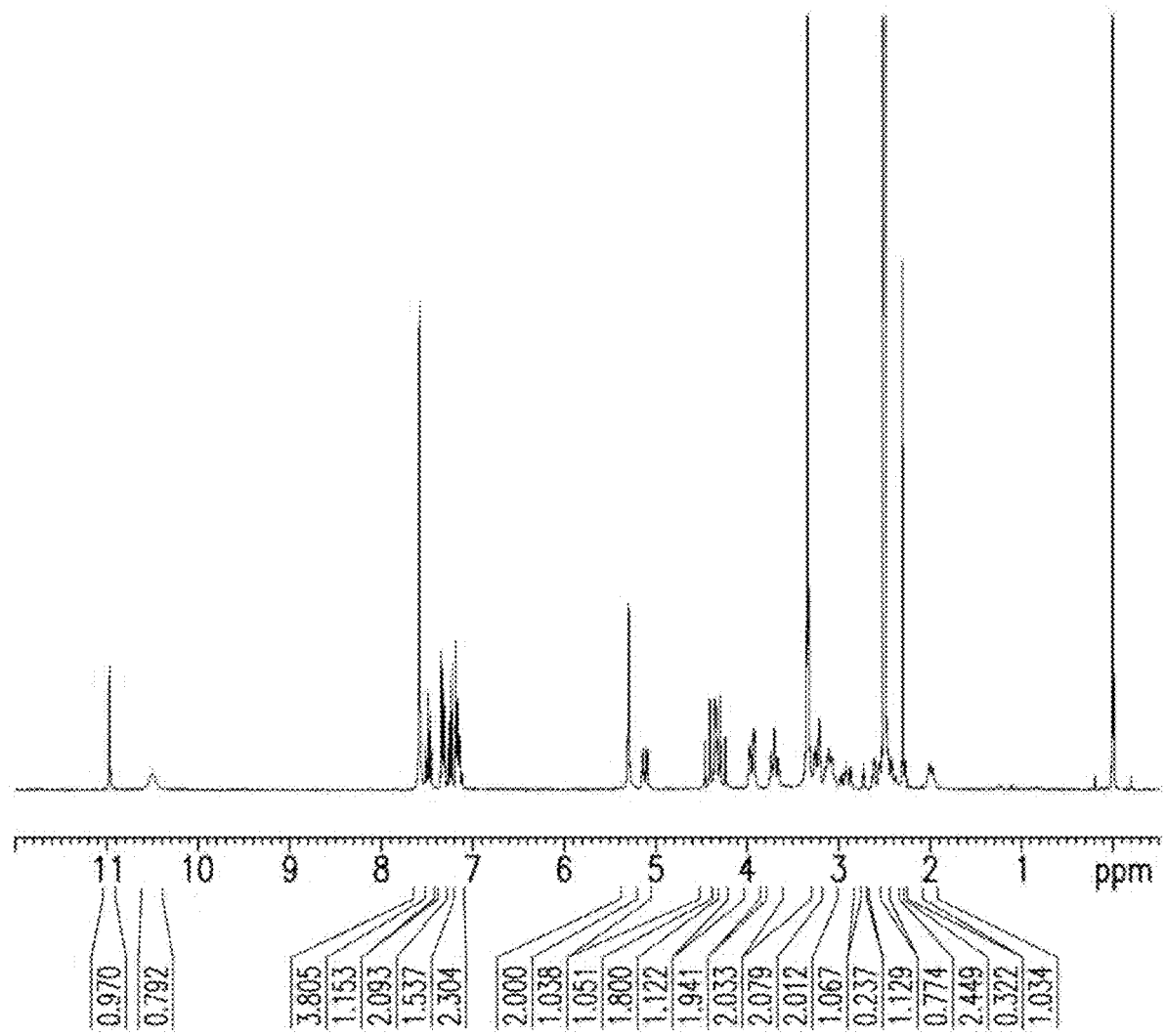

FIG. 89 provides a representative $^1$H-NMR spectrum of Form H of HCl salt of Compound (I-S).

Figure 90:
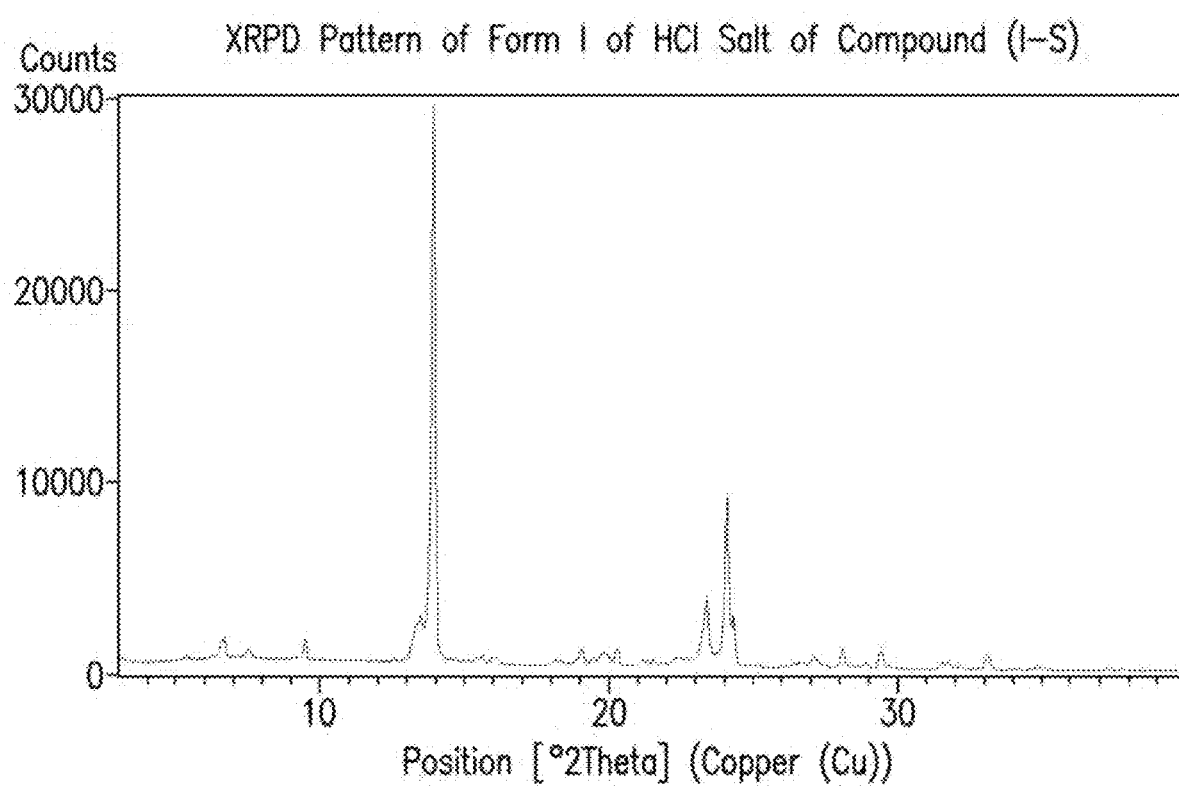

FIG. 90 provides a representative XRPD pattern of Form I of HCl salt of Compound (I-S).

Figure 91:
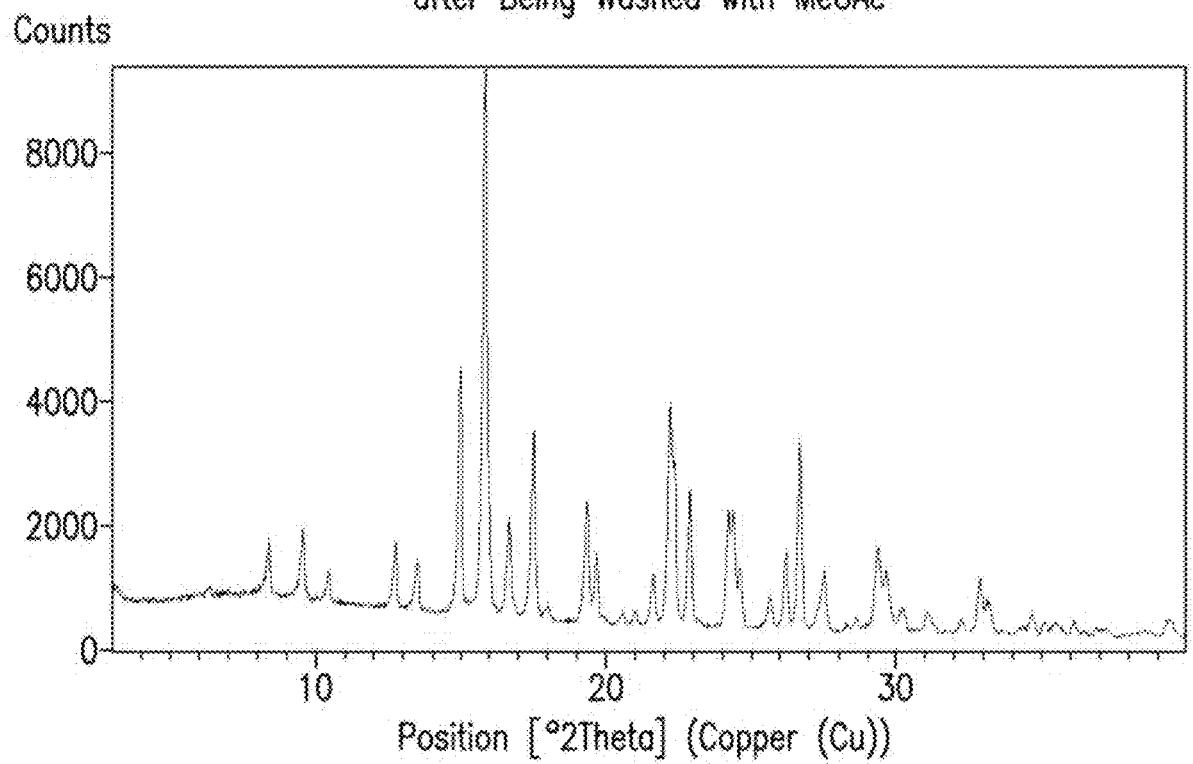

FIG. 91 provides a representative XRPD pattern of Form I of HCl salt of Compound (I-S) after being washed with MeOAc.

Figure 92:
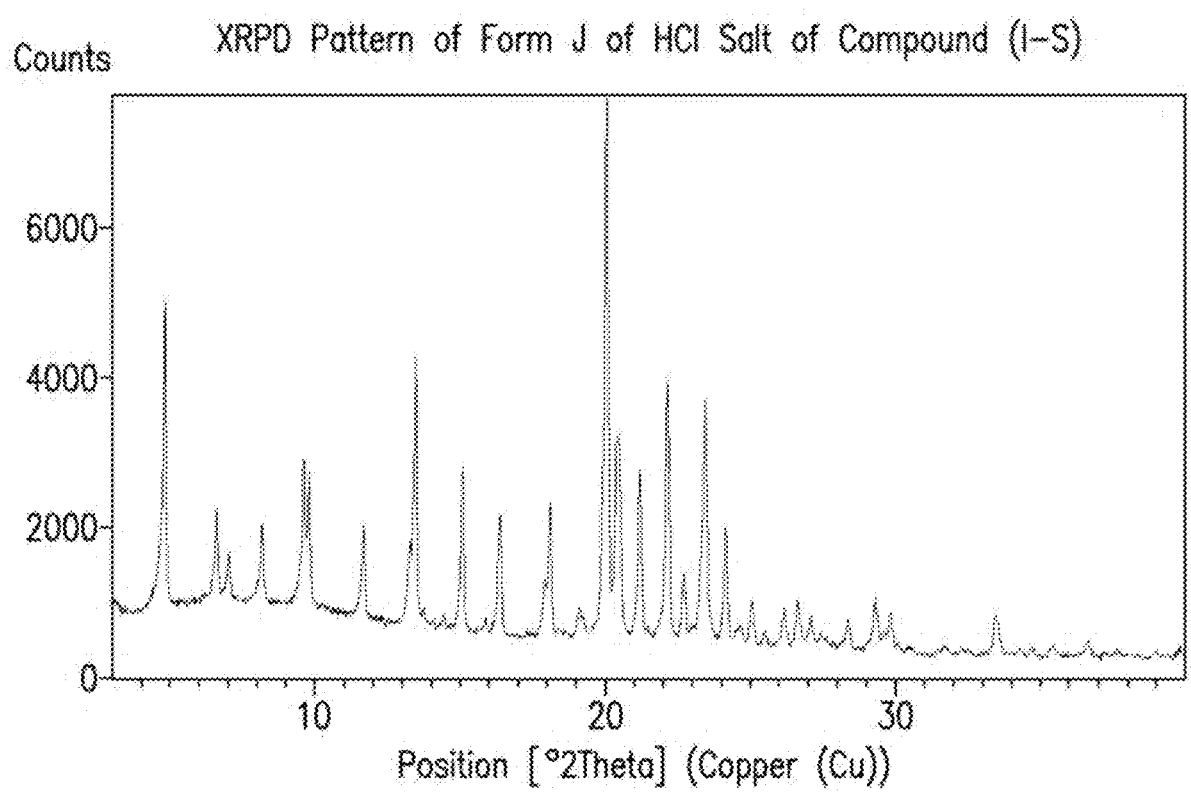

FIG. 92 provides a representative XRPD pattern of Form J of HCl salt of Compound (I-S).

Figure 93:
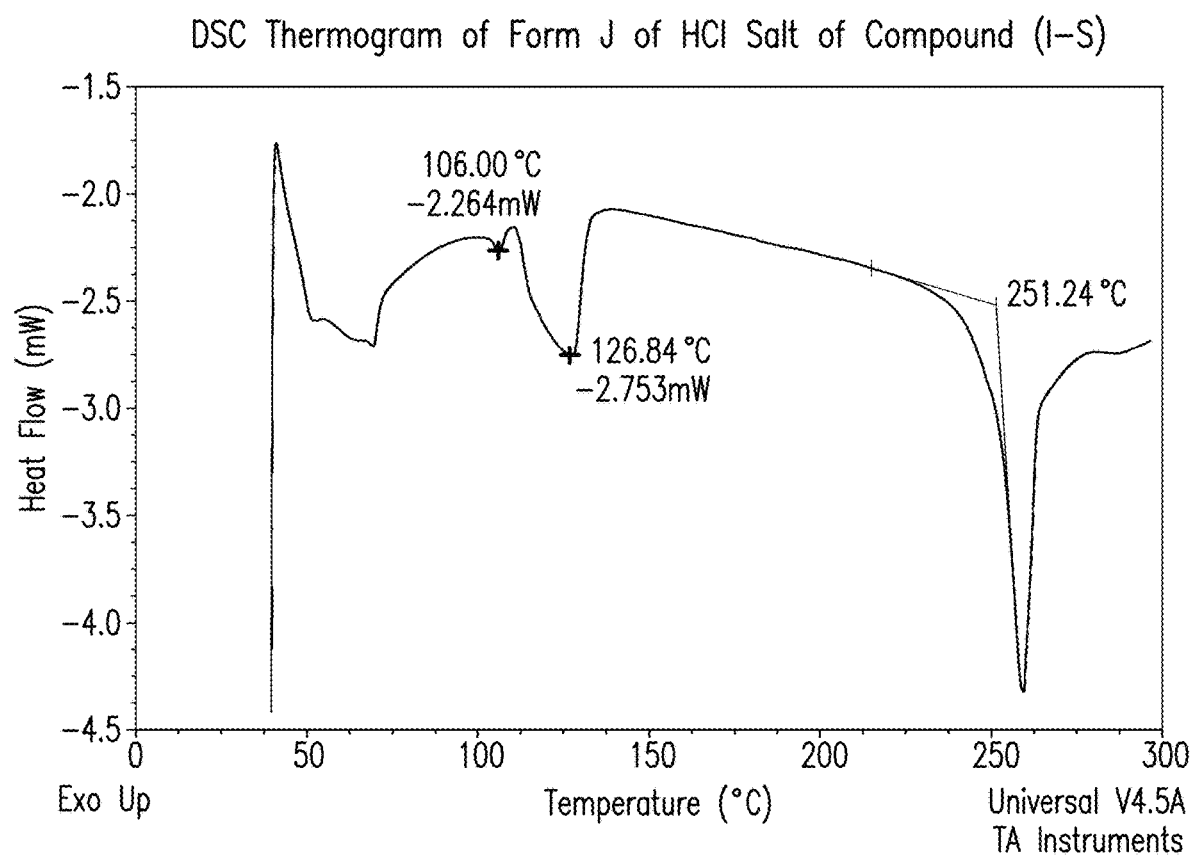

FIG. 93 provides a representative DSC thermogram of Form J of HCl salt of Compound (I-S).

Figure 94:
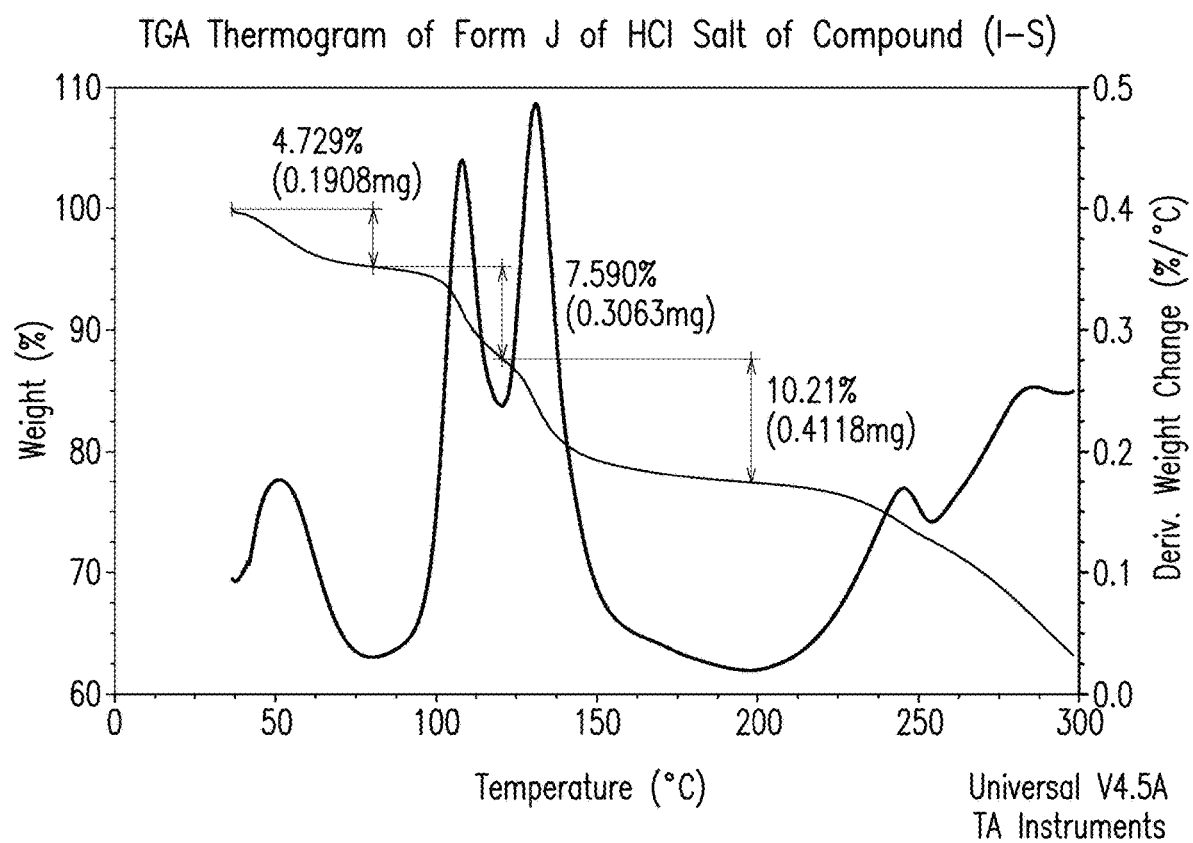

FIG. 94 provides a representative TGA thermogram of Form J of HCl salt of Compound (I-S).

Figure 95:
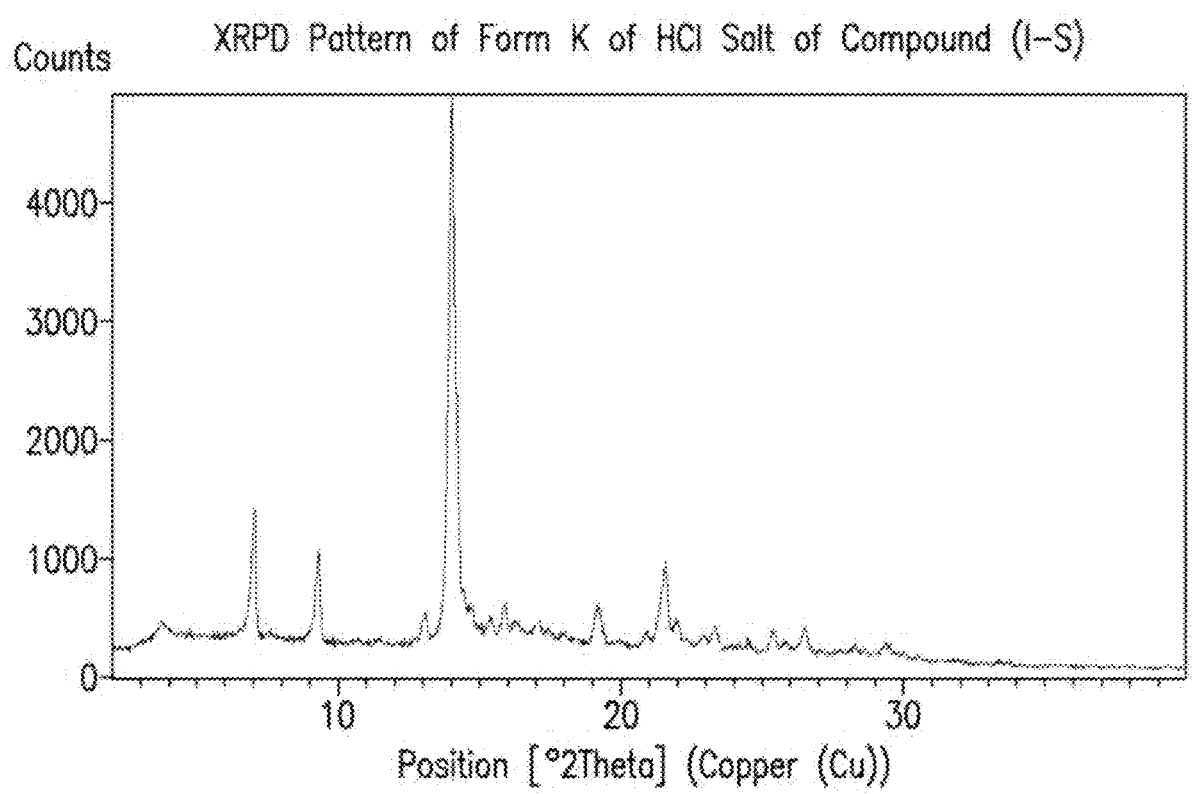

FIG. 95 provides a representative XRPD pattern of Form K of HCl salt of Compound (I-S).

Figure 96:
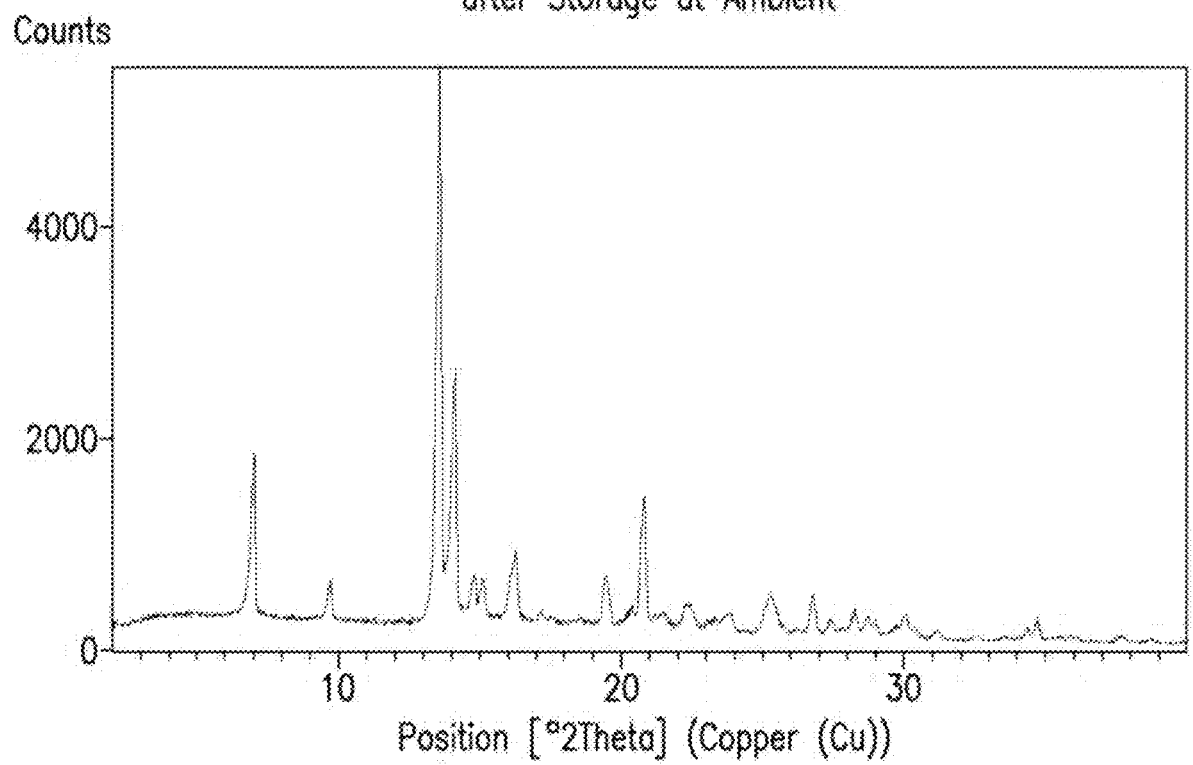

FIG. 96 provides a representative XRPD pattern of Form K of HCl salt of Compound (I-S) after storage at ambient.

Figure 97:
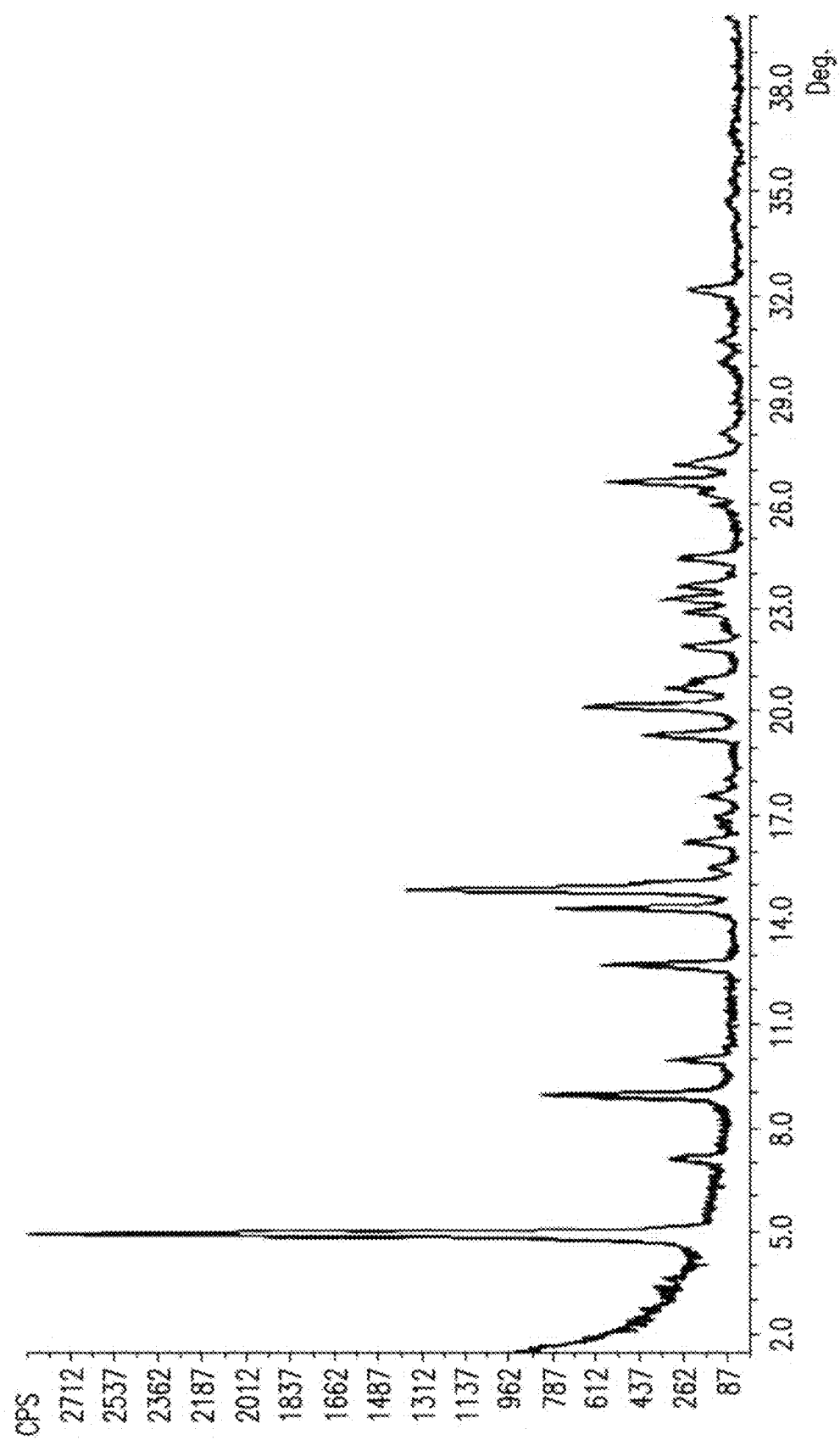

FIG. 97 provides a representative XRPD pattern of an anhydrate of racemic Compound (I).

Figure 98A:
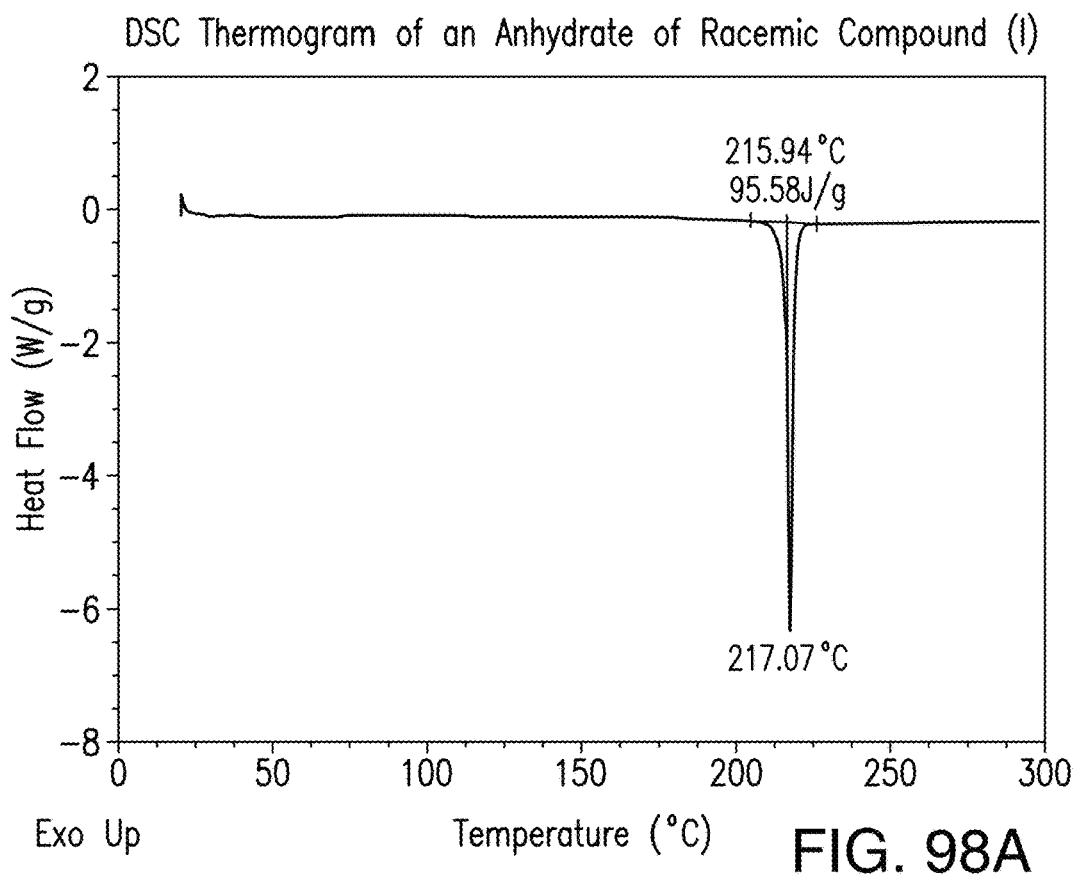

FIG. 98A provides a representative DSC thermogram of an anhydrate of racemic Compound (I).

Figure 98B:
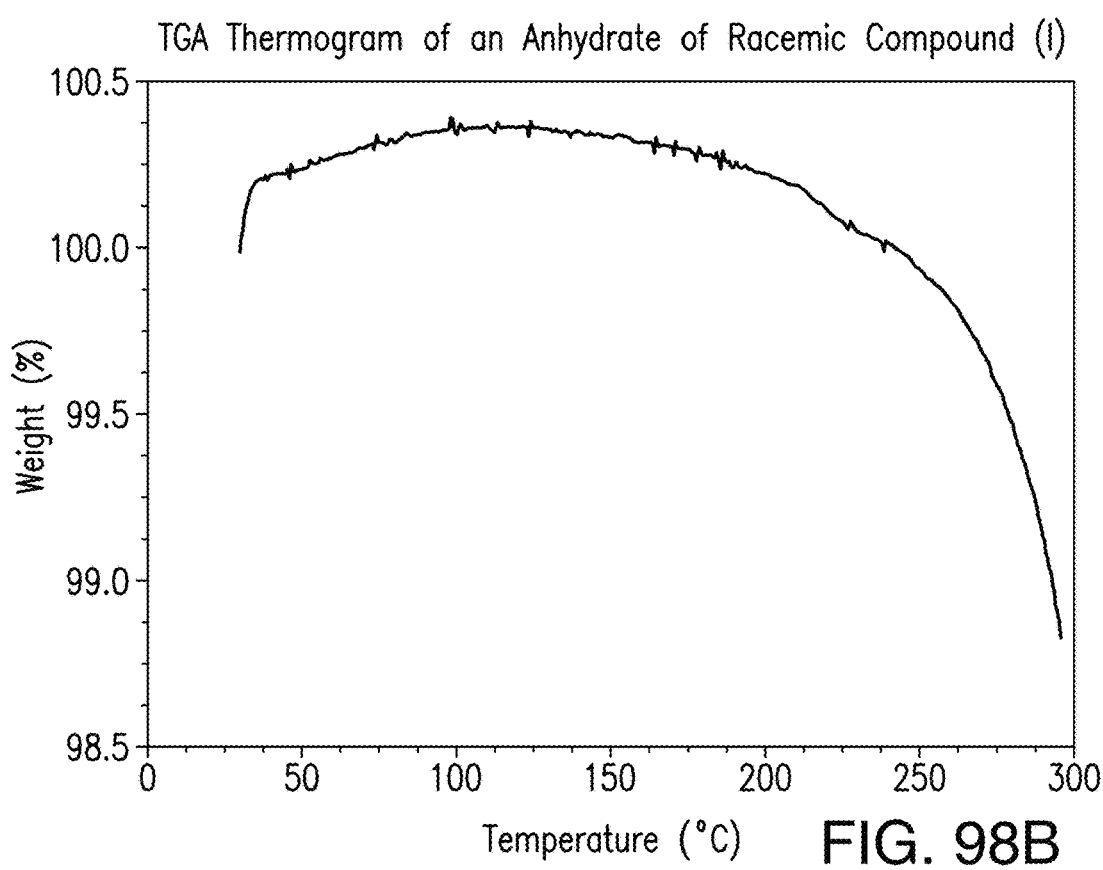

FIG. 98B provides a representative TGA thermogram of an anhydrate of racemic Compound (I).

Figure 99:
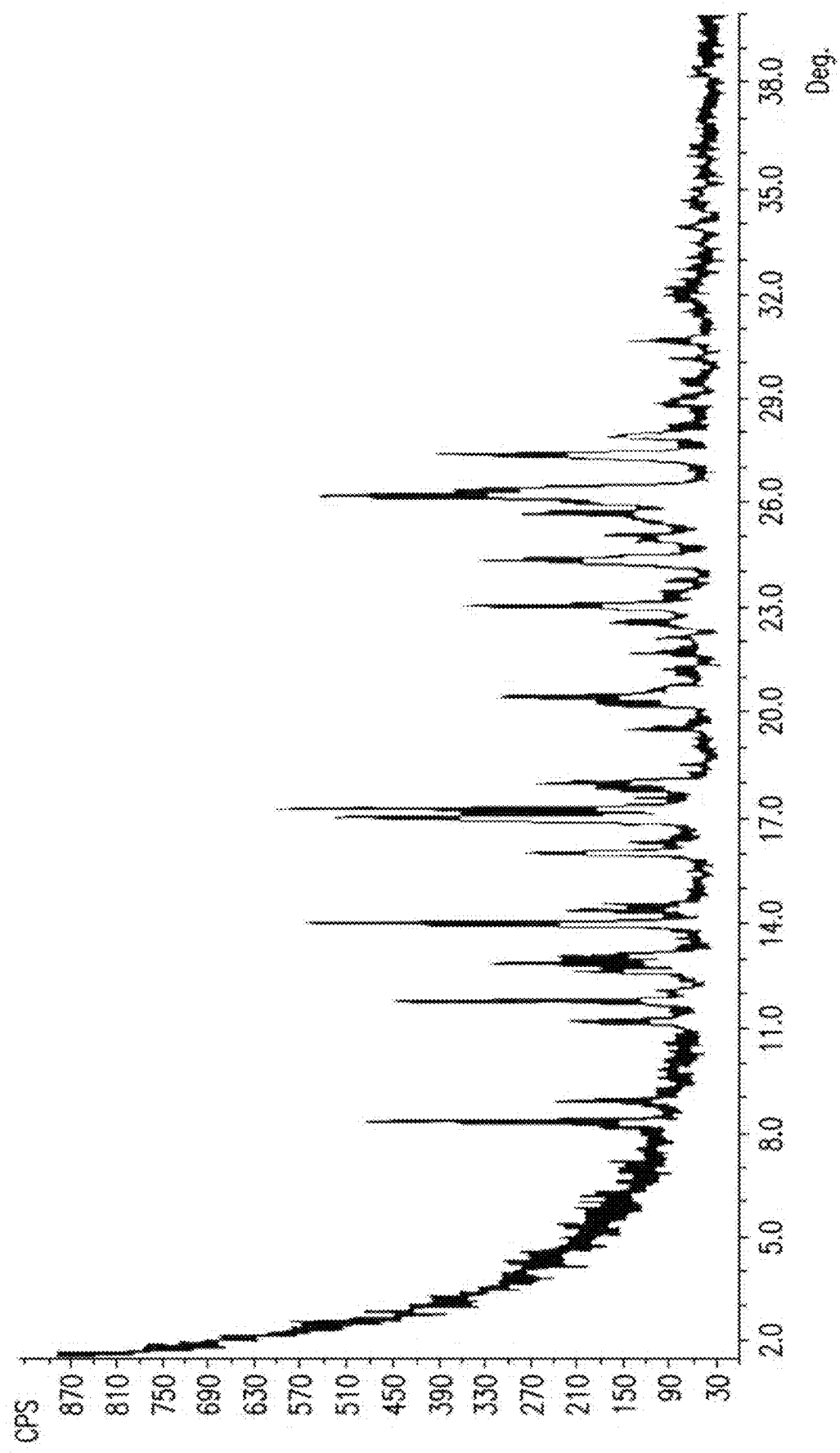

FIG. 99 provides a representative XRPD pattern of a hydrate of racemic Compound (I).

Figure 100A:
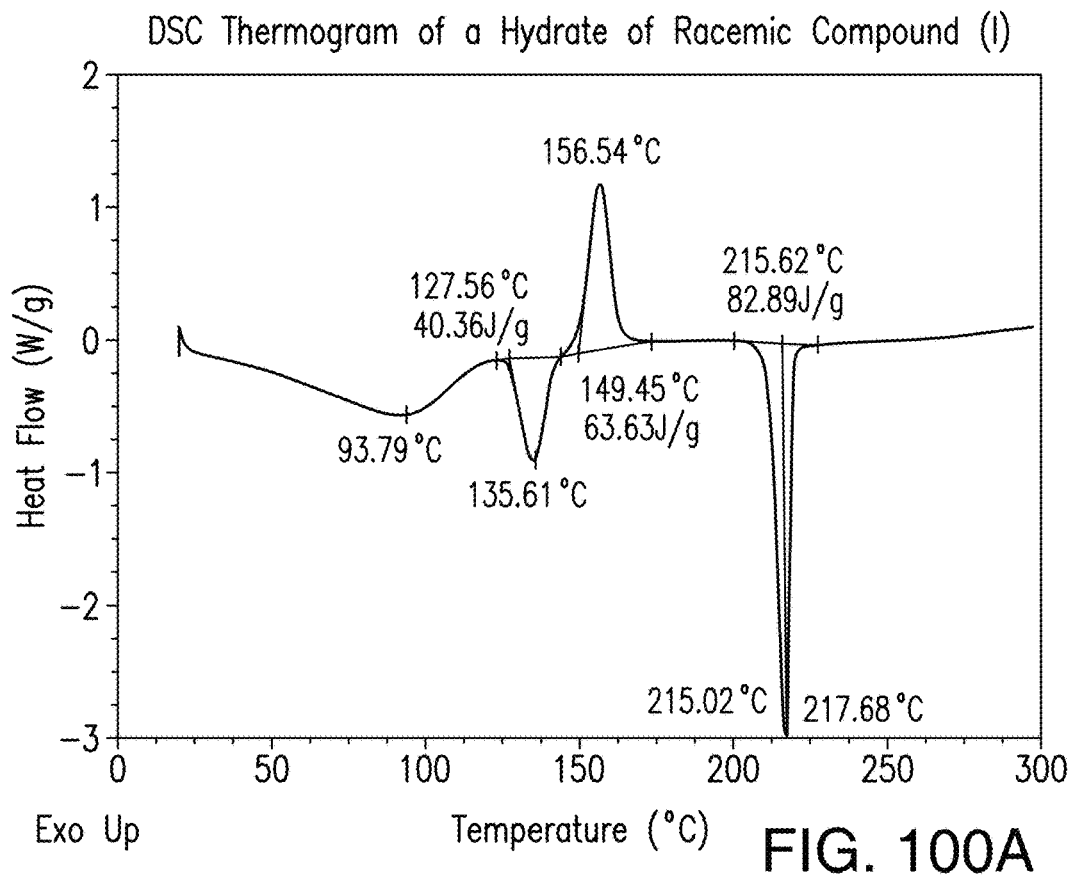

FIG. 100A provides a representative DSC thermogram of a hydrate of racemic Compound (I).

Figure 100B:
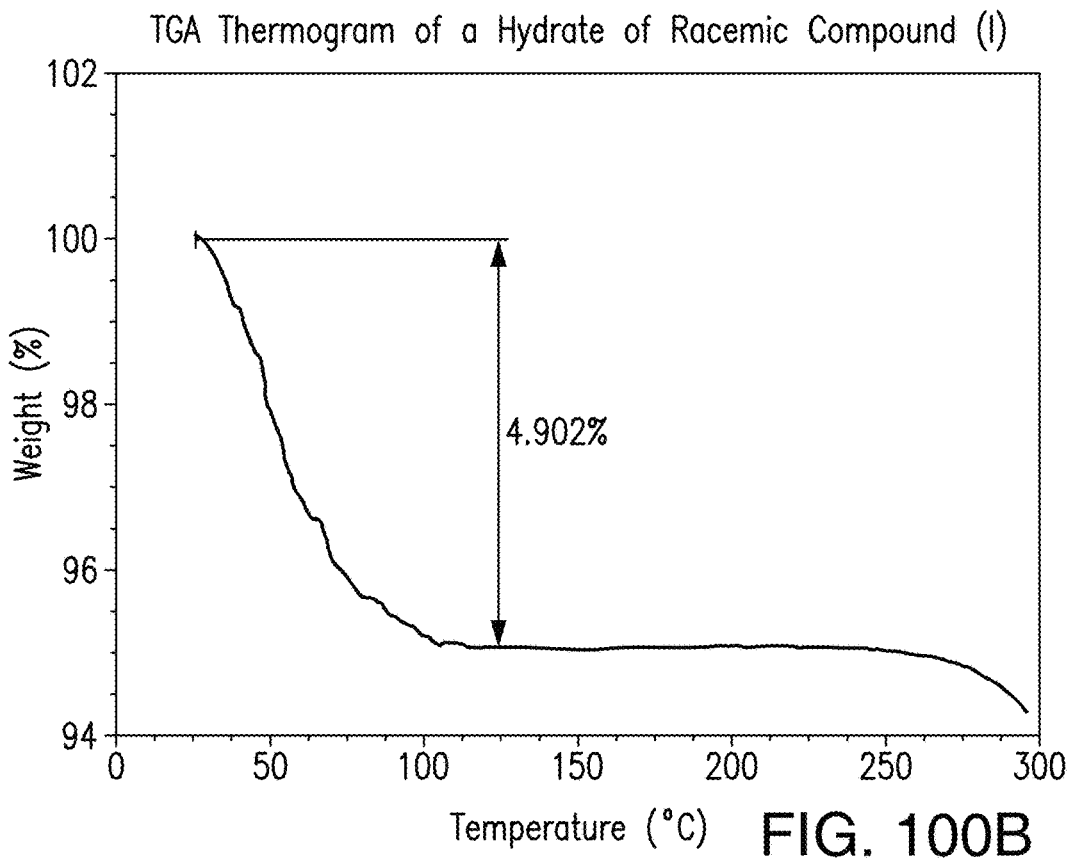

FIG. 100B provides a representative TGA thermogram of a hydrate of racemic Compound (I).

Figure 101:
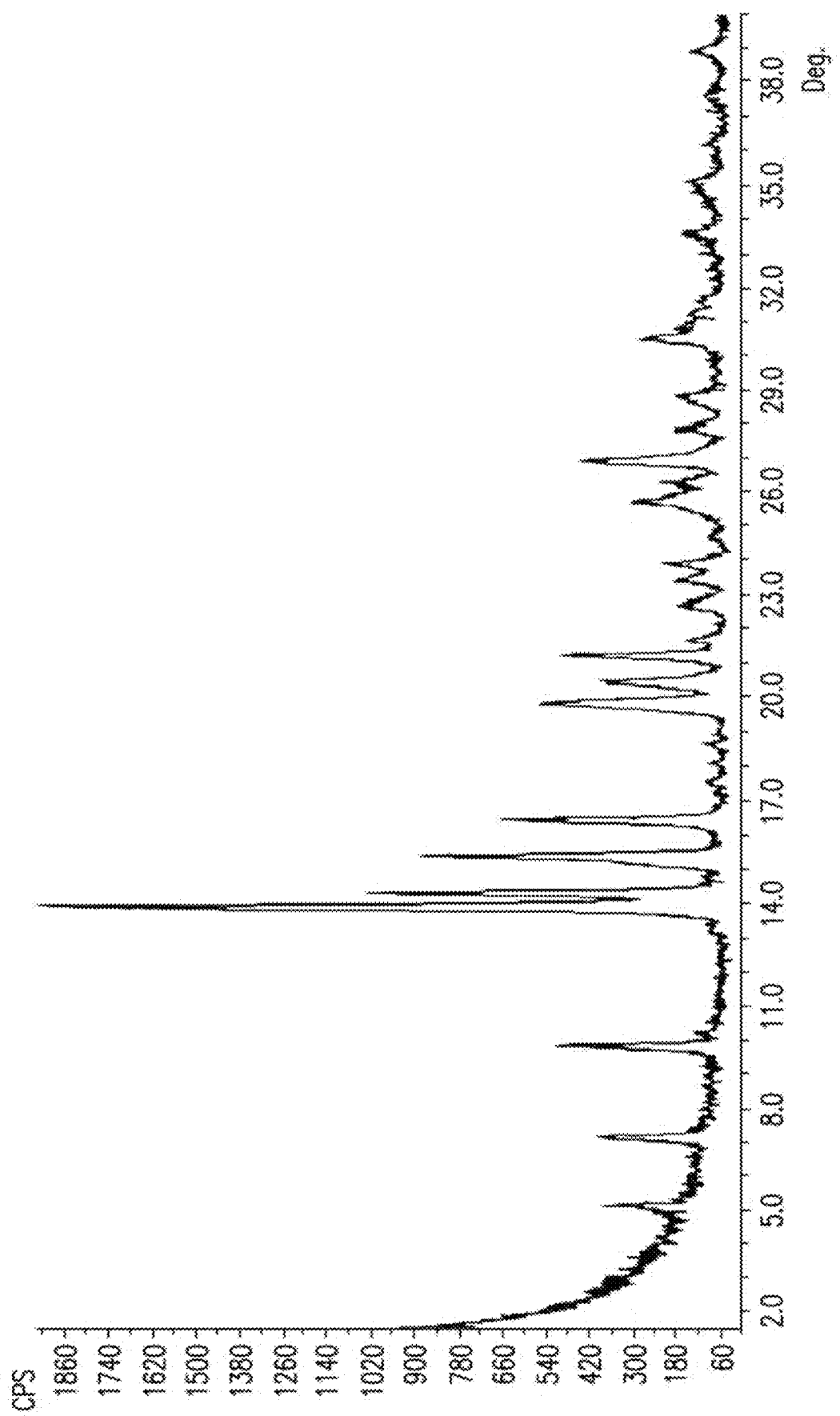

FIG. 101 provides a representative XRPD pattern of a hydrate of HCl salt of racemic Compound (I).

Figure 102A:
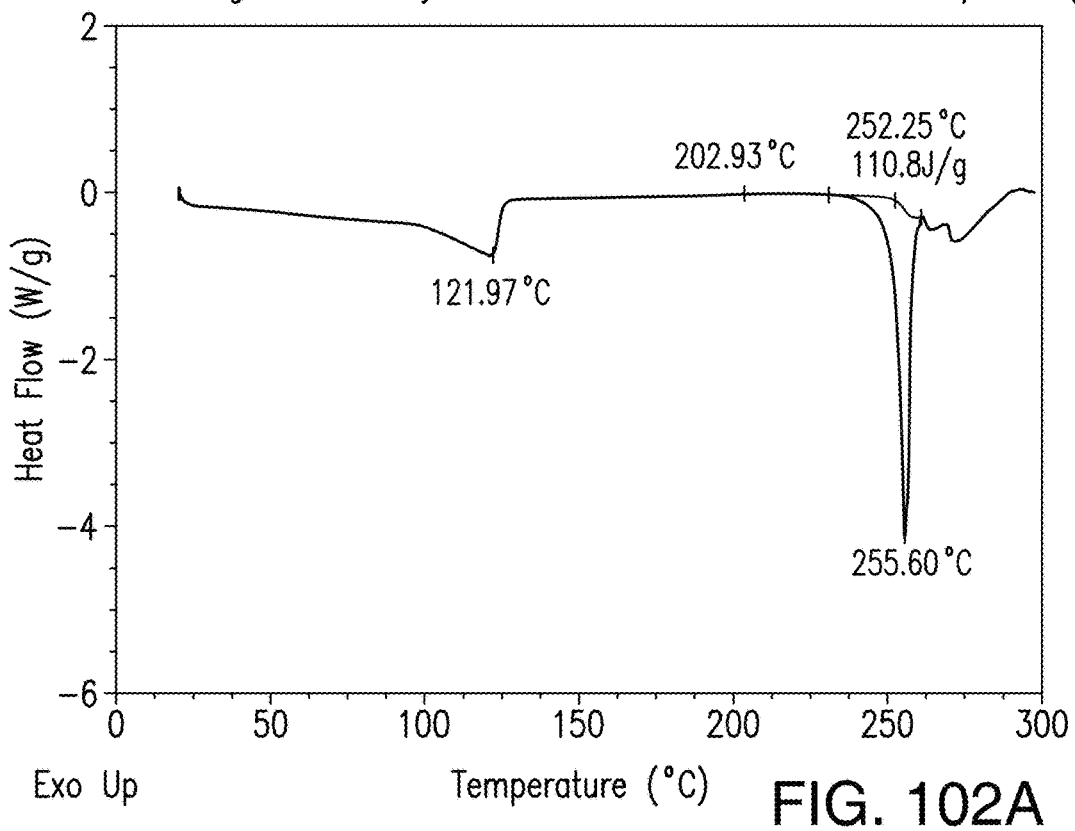

FIG. 102A provides a representative DSC thermogram of a hydrate of HCl salt of racemic Compound (I).

Figure 102B:
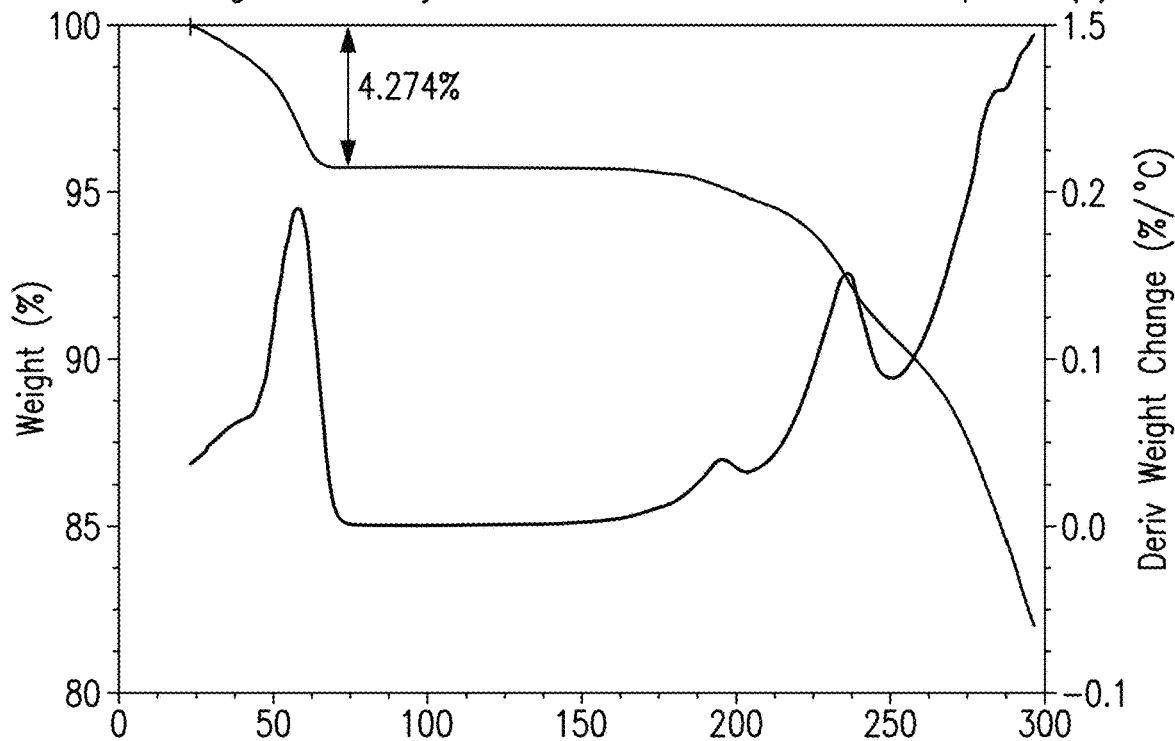

FIG. 102B provides a representative TGA thermogram of a hydrate of HCl salt of racemic Compound (I).

Figure 103:
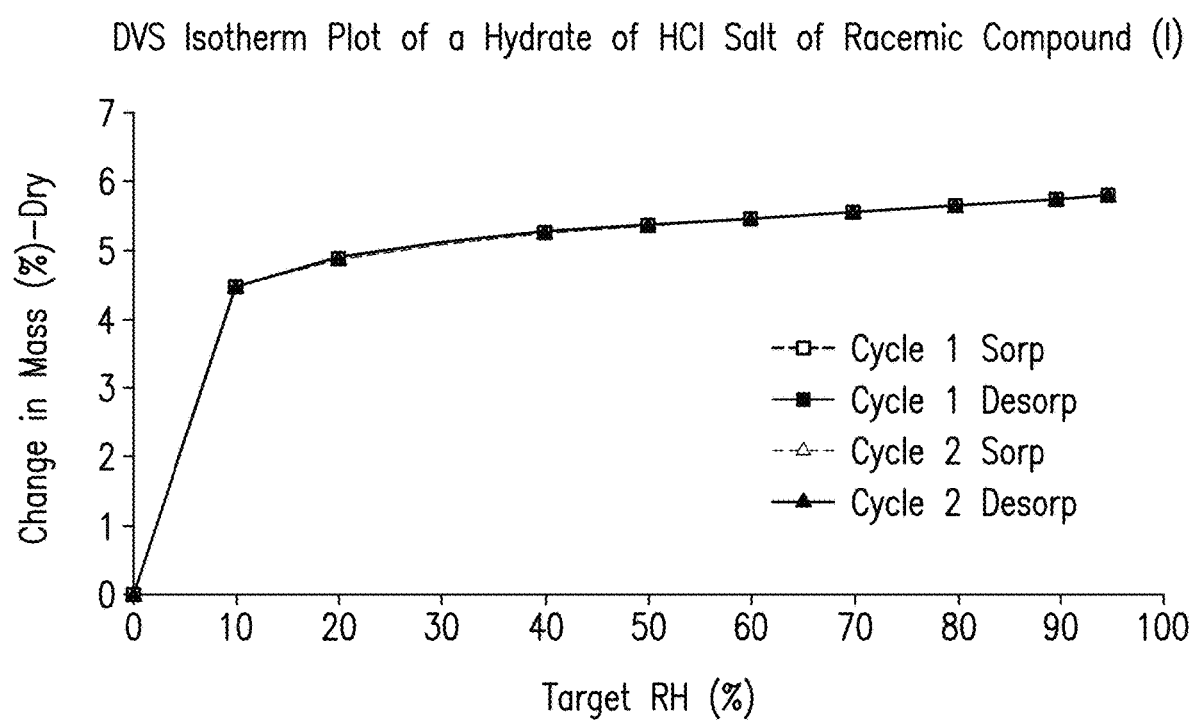

FIG. 103 provides a representative DVS plot of a hydrate of HCl salt of racemic Compound (I).

Figure 104:
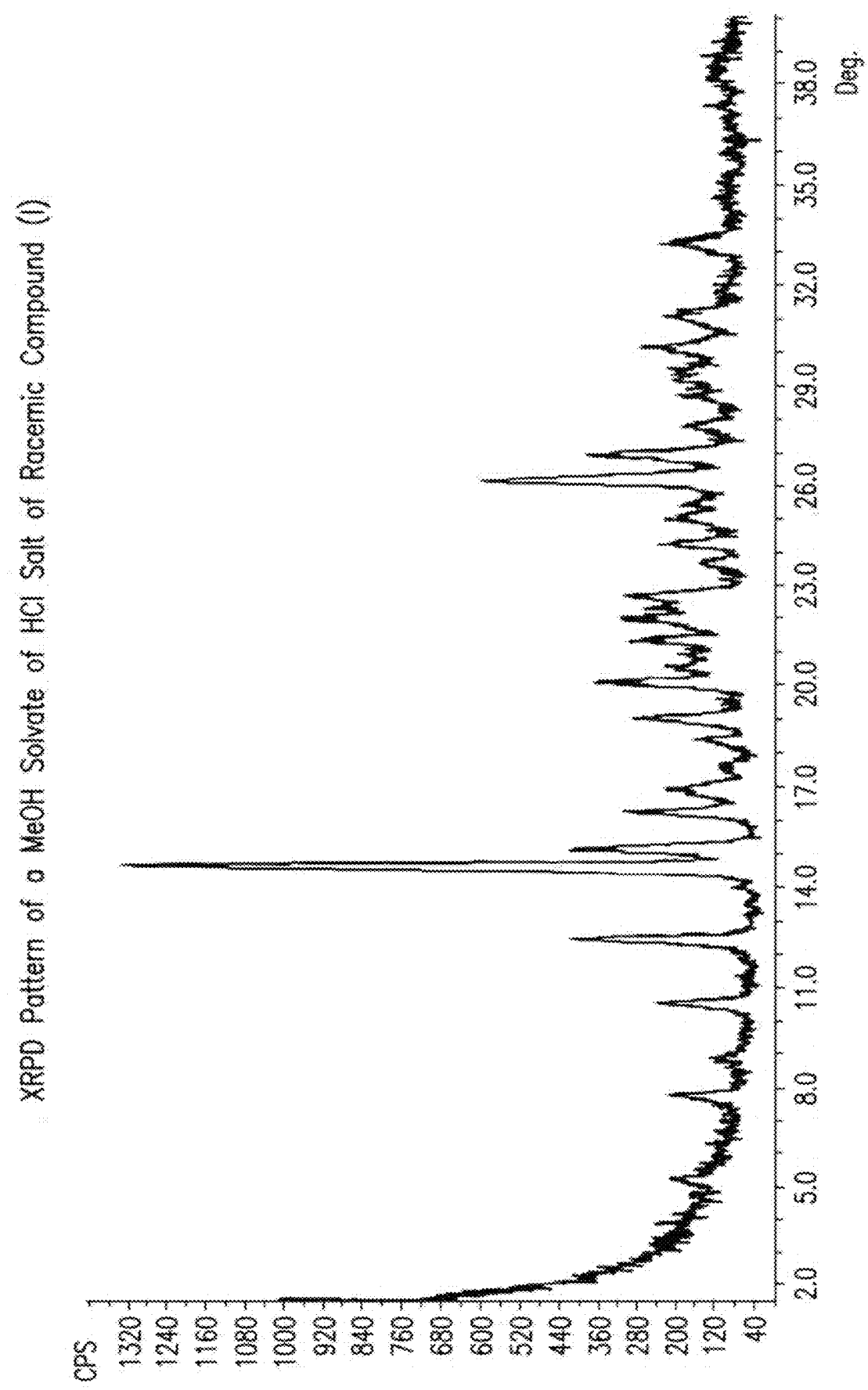

FIG. 104 provides a representative XRPD pattern of a MeOH solvate of HCl salt of racemic Compound (I).

Figure 105:
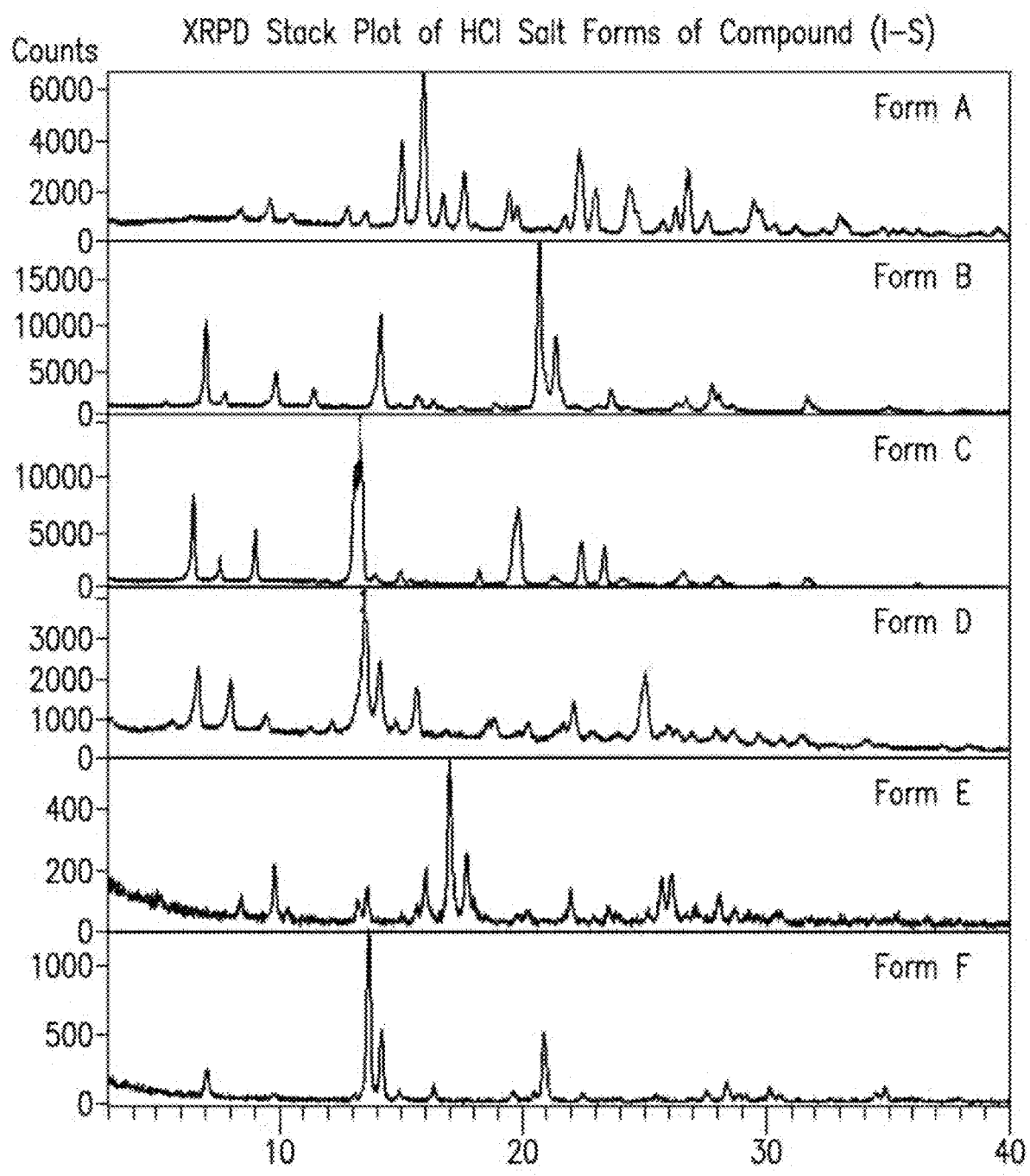
Figure 105:
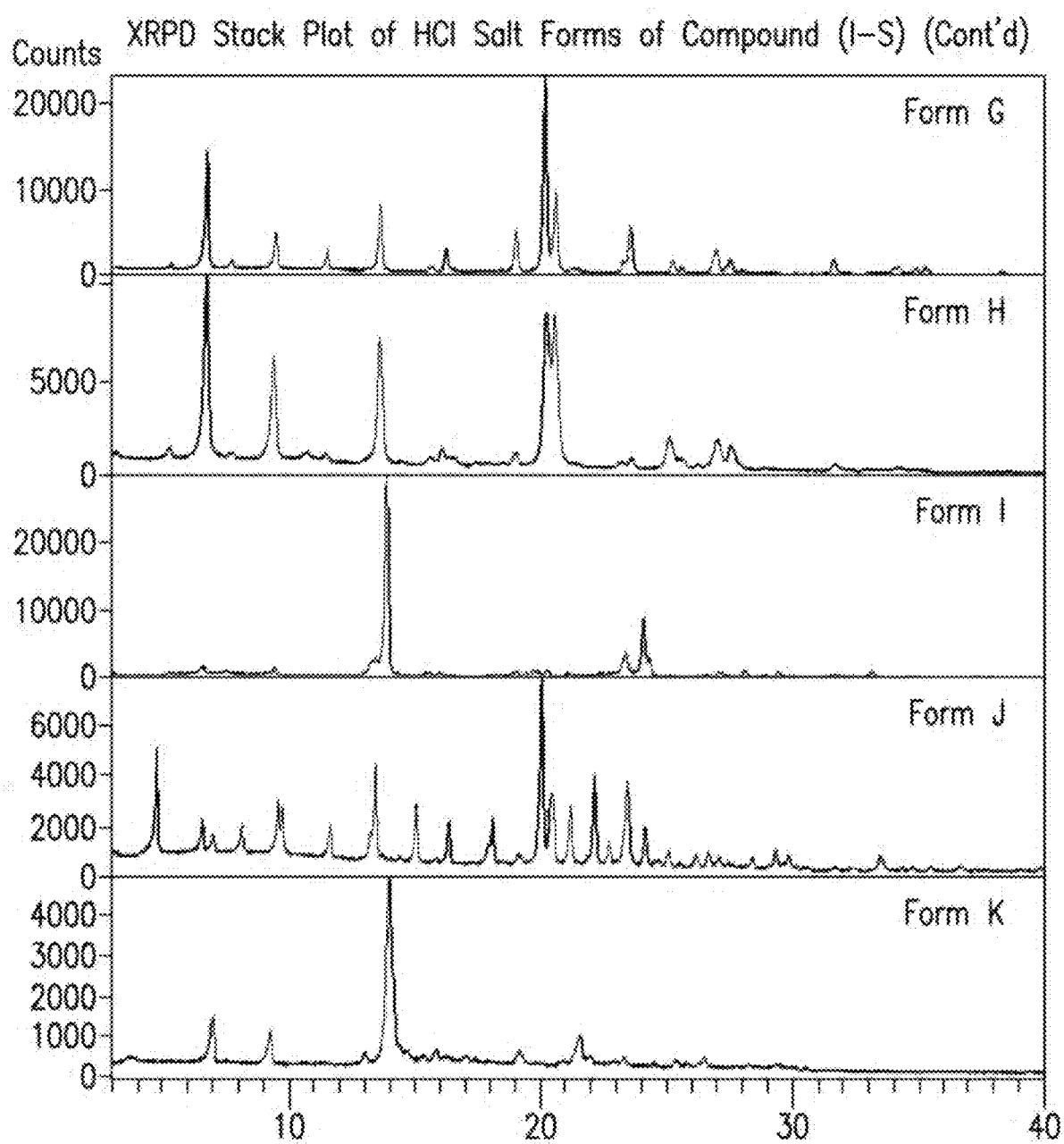

FIG. 105 provides a representative XRPD stack plot of HCl salt forms of Compound (I-S).

Figure 106:
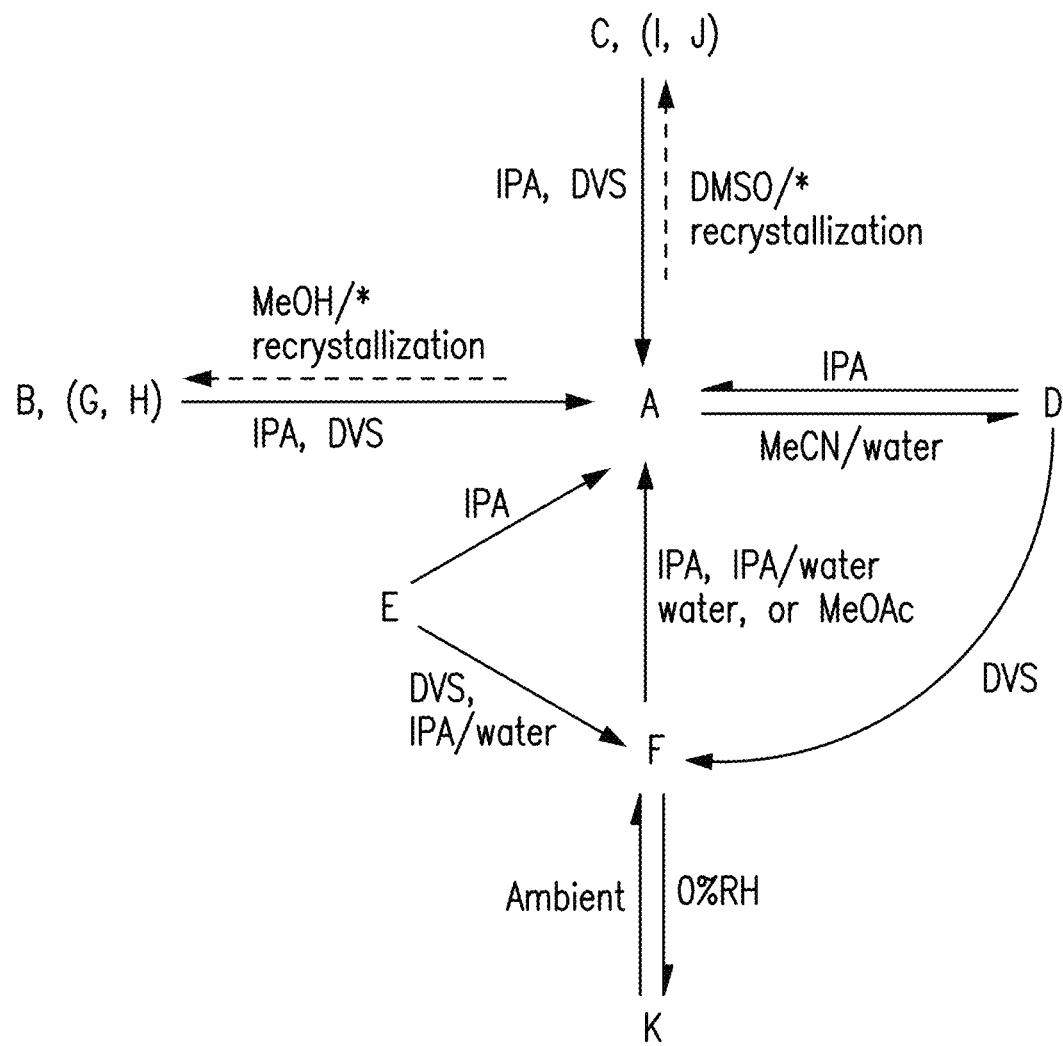

FIG. 106 provides an interconversion diagram of Form A-K of HCl salt of Compound (I-S).

5. DETAILED DESCRIPTION

5.1 Salts and Solid Forms of Compound (I-S) and Syntheses Thereof

Compound (I-S) is the (S) stereoisomer of 3-(4-((4-(morpholinomethyl)benzyl)oxy)-1-oxoisoindolin-2-yl)piperidine-2,6-dione. Methods of preparing racemic 3-(4-((4-(morpholinomethyl)benzyl)oxy)-1-oxoisoindolin-2-yl) piperidine-2,6-dione have been reported in U.S. Patent Publication No. 2011/0196150, which is incorporated herein by reference in its entirety. Compound (I-S) has the following structure:

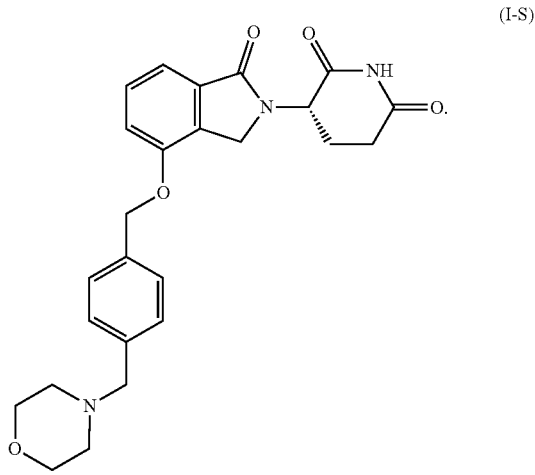 [SMILES: O=C1CC[C@H](N2Cc3c(OCc4ccc(CN5CCOCC5)cc4)cccc3C2=O)C(=O)N1]

(I-S)

Provided herein are salts of Compound (I-S). In some embodiments, Compound (I-S) is a salt of H-X, wherein X is F, Cl, Br, I, $RSO_3$, or $RCO_2$, wherein R is alkyl, aryl, substituted alkyl, substituted aryl, or hydroxy. In some embodiments, Compound (I-S) is a tartrate salt, e.g., D or L, or hemi-tartrate salt. In some embodiments, the salt is a hydrochloric acid, benzenesulfonic acid, p-toluenesulfonic acid, (+) camphorsulfonic acid salt, D-tartaric acid, or L-tartaric acid salt. In some embodiments, the salt is a carbonate salt or a sulfate salt. Without being limited by any particular theory, the acids are associated with the basic nitrogen of the nitrogen on the morpholine ring of Compound (I-S).

Also provided herein are solid forms of Compound (I-S) and of salts of Compound (I-S). In some embodiments, the solid form is an anhydrate, hydrate, or solvate. In some embodiments, the solvate is a tetrahydrofuran or dimethyl sulfoxide solvate.

As used herein and unless otherwise specified, the terms "solid form" and related terms refer to a physical form which is not predominantly in a liquid or a gaseous state. Solid forms may be crystalline, amorphous or mixtures thereof. In particular embodiments, solid forms may be liquid crystals.

In some embodiments, Compound (I-S) is a single component or multiple component solid form. A "single-component" solid form comprising Compound (I-S) consists essentially of Compound (I-S). A "multiple-component" solid form comprising Compound (I-S) comprises a significant quantity of one or more additional species, such as ions and/or molecules, within the solid form. For example, in particular embodiments, a crystalline multiple-component solid form comprising Compound (I-S) further comprises one or more species non-covalently bonded at regular positions in the crystal lattice. In one embodiment, a multiple component solid form provided herein is a co-crystal.

As used herein and unless otherwise specified, the term "crystalline" and related terms used herein, when used to describe a substance, modification, material, component or product, unless otherwise specified, mean that the substance, modification, material, component or product is substantially crystalline as determined by X-ray diffraction. See, e.g., *Remington: The Science and Practice of Pharmacy*, $21^{st}$ edition, Lippincott, Williams and Wilkins, Baltimore, Md. (2005); *The United States Pharmacopeia*, $23^{rd}$ edition, 1843-1844 (1995).

As used herein and unless otherwise specified, the term "crystal forms" and related terms herein refer to solid forms that are crystalline. Crystal forms include single-component crystal forms and multiple-component crystal forms, and include, but are not limited to, polymorphs, solvates, hydrates, and other molecular complexes, as well as salts, solvates of salts, hydrates of salts, other molecular complexes of salts, and polymorphs thereof. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

Also provided herein are polymorphs of various salts of Compound (I-S). As used herein and unless otherwise specified, the terms "polymorphs," "polymorphic forms" and related terms herein, refer to two or more crystal forms that consist essentially of the same molecule, molecules or ions. Like different crystal forms, different polymorphs may have different physical properties such as, for example, melting temperatures, heats of fusion, solubilities, dissolution rates and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to a thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (for example, one polymorph might be more likely to form solvates or might be difficult to filter and wash free of impurities, and particle shape and size distribution might be different between polymorphs).

As used herein and unless otherwise specified, the term "solvate" and "solvated," refer to a crystal form of a substance which contains solvent. The term "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. As used herein, a tilde (i.e., "~") preceding a numerical value or range of values indicates "about" or "approximately."

In some embodiments, the solid forms, e.g., crystal or amorphous forms, described herein are substantially pure, i.e., substantially free of other solid forms and/or of other chemical compounds, containing less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

Solid forms may exhibit distinct physical characterization data that are unique to a particular solid form, such as the crystal forms described herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms described herein by performing one of these characterization techniques and determining whether the resulting data "matches" the reference data provided herein, which is identified as being characteristic of a particular solid form. Characterization data that "matches" those of a reference solid form is understood by those skilled in the art to correspond to the same solid form as the reference solid form. In analyzing whether data "match," a person of ordinary skill in the art understands that particular characterization data points may vary to a reasonable extent while still describing a given solid form, due to, for example, experimental error and routine sample-to-sample analysis.

The solid forms provided herein may be crystalline, amorphous, or an intermediate form. The crystal forms described herein, therefore, may have varying degrees of crystallinity or lattice order. The solid forms described herein are not limited by any particular degree of crystallinity or lattice order, and may be 0-100% crystalline. Methods of determining the degree of crystallinity are known to those of ordinary skill in the, such as those described in Suryanarayanan, R., *X-Ray Power Diffractometry*, Physical Characterization of Pharmaceutical Salts, H. G. Brittain, Editor, Mercel Dekkter, Murray Hill, N.J., 1995, pp. 187-199, which is incorporated herein by reference in its entirety. In some embodiments, the solid forms described herein are about 0, 5, 10, 15, 20, 25, 30, 35, 40, 45, 50, 55, 60, 65, 70, 75, 80, 85, 90, 95 or 100% crystalline.

(1) Freebase Anhydrate

Provided herein is an anhydrate of Compound (I-S). In some embodiments, the anhydrate is obtained by heating a mixture of Compound (I-S) and acetonitrile. In some embodiments, the anhydrate is obtained by heating a mixture of Compound (I-S) and acetonitrile to about 40° C. and subsequently cooling the mixture to about room temperature. In some embodiments, the anhydrate is obtained by heating a mixture of Compound (I-S) and acetonitrile to about 40° C., subsequently cooling the mixture to about room temperature, and isolating the anhydrate by filtration.

Without being limited by any particular theory, in some embodiments, the anhydrate has the following formula:

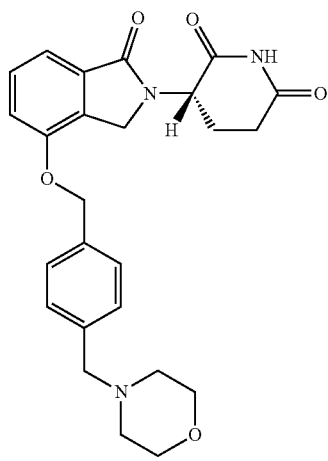 [SMILES: O=C1CC[C@H](N2Cc3c(OCc4ccc(CN5CCOCC5)cc4)cccc3C2=O)C(=O)N1]

A representative XRPD pattern of the anhydrate of Compound (I-S) is provided in FIG. 1.

In some embodiments, provided herein is a solid form comprising Compound (I-S) characterized by XRPD peaks located at 1, 2, 3, 4, 5, 6, 7, or all of the following or approximately the following positions: 4.76, 7.15, 8.72, 12.10, 14.31, 14,96, 19.06, and 26.11 degrees 2θ. In one embodiment, the solid form is characterized by 3 of the peaks. In another embodiment, the solid form is characterized by 5 of the peaks. In another embodiment, the solid form is characterized by all of the peaks.

In some embodiments, provided herein is a solid form comprising Compound (I-S) having an XRPD pattern comprising peaks at approximately 4.76, 8.72, 14.31, and 14.96 degrees 2θ. In certain embodiments, the solid form further comprises peaks at approximately 7.15, 12.10, 19.06, and 26.11 degrees 2θ. In some embodiments, the solid form comprises peaks at 4.76, 7.15, 8.72, 12.10, 14.31, 14.96, 19.06, and 26.11 degrees 2θ.

In some embodiments, provided herein is a solid form comprising Compound (I-S), wherein the solid form is characterized by an XRPD diffraction pattern which matches the XRPD pattern presented in FIG. 1.

Representative thermal characteristics of the anhydrate are provided in FIG. 2 and FIG. 3. A representative differential scanning calorimetry (DSC) thermogram is presented in FIG. 2. In some embodiments, provided herein is a solid form comprising Compound (I-S) that exhibits a thermal event, as characterized by DSC, with a peak temperature of about 133° C. and an onset temperature of about 127° C., with a peak temperature of about 155° C., or with a peak temperature of about 215° C. In some embodiments, provided herein is a solid form comprising Compound (I-S) that exhibits thermal events, as characterized by DSC, with a peak temperature of about 133° C. and an onset temperature of about 127° C., with a peak temperature of about 155° C., and with a peak temperature of about 215° C. In certain embodiments, the event with a peak temperature of about 133° C. corresponds to melting. In certain embodiments, the event with a peak temperature of about 155° C. corresponds to epimerization and crystallization. In certain embodiments, the event with a peak temperature of about 215° C. corresponds to melting. In some embodiments, provided herein is a solid form comprising Compound (I-S), wherein the solid form is characterized by a DSC thermogram which matches the DSC thermogram presented in FIG. 2.

A representative thermal gravimetric analysis curve of the anhydrate is provided in FIG. 3, which exhibits no substantial change of the total sample weight upon heating from about 25 to about 150° C. In some embodiments, provided herein is a solid form comprising Compound (I-S), wherein the solid form is characterized by a TGA thermogram which matches the TGA thermogram presented in FIG. 3.

A representative DVS isotherm plot of the anhydrate is provided in FIG. 4. In some embodiments, provided herein is a solid form comprising Compound (I-S), wherein the solid form is characterized by a DVS isotherm plot which matches the DVS isotherm plot presented in FIG. 4.

(ii) Freebase Hydrate

Provided herein is a hydrate of Compound (I-S). Furthermore, provided herein is a solid form comprising Compound (I-S) and water. In some embodiments, the solid form is obtained by heating a mixture of Compound (I-S) and water. In some embodiments, the solid form is obtained by heating a mixture of Compound (I-S) and water to about 50° C. and subsequently cooling the mixture to about room temperature. In some embodiments, the solid form is obtained by heating a mixture of Compound (I-S) and water to about 50° C., subsequently cooling the mixture to about room temperature, and isolating the solid form by filtration. In some embodiments, the molar ratio of Compound (I-S) to water is approximately 2:1 to 1:2. In some embodiments, the molar ratio of Compound (I-S) to water is approximately 1:1.

Without being limited by any particular theory, in some embodiments the hydrate has the following formula:

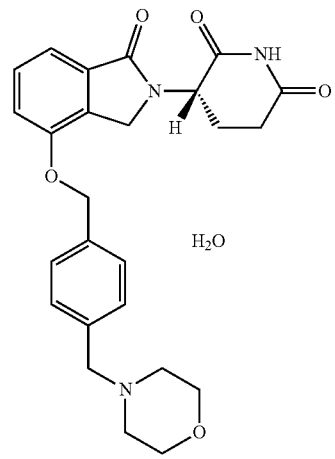 [SMILES: O=C1CC[C@H](N2Cc3c(OCc4ccc(CN5CCOCC5)cc4)cccc3C2=O)C(=O)N1 ; O]

A representative XRPD pattern of a hydrate of Compound (I-S) is provided in FIG. 5.

In some embodiments, provided herein is a solid form comprising Compound (I-S) and water characterized by XRPD peaks located at 1, 2, 3, 4, 5, 6, 7, 8, 9, 10, 11, 12, or all of the following or approximately the following positions: 8.31, 11.80, 13.42, 13.79, 15.92, 17.15, 17.37, 18.31, 20.41, 22.07, 25.58, 26.00, and 27.14 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by all of the peaks.

In some embodiments, provided herein is a solid form comprising Compound (I-S) and water having an XRPD pattern comprising peaks at approximately 8.31, 11.80, and 17.37 degrees 2θ. In certain embodiments, the solid form further comprises peaks at approximately 13.79, 17.15, 26.00 degrees 2θ. In one embodiment, the solid form comprises peaks at approximately 8.31, 11.80, 13.42, 13.79, 15.92, 17.15, 17.37, 18.31, 20.41, 22.07, 25.58, 26.00, and 27.14 degrees 2θ.

In some embodiments, provided herein is a solid form comprising Compound (I-S) and water, wherein the solid form is characterized by an XRPD diffraction pattern which matches the XRPD pattern presented in FIG. 5.

Representative thermal characteristics of the hydrate are provided in FIG. 6 and FIG. 7. A representative differential scanning calorimetry (DSC) thermogram is presented in FIG. 6 ° C. In some embodiments, provided herein is a solid form comprising Compound (I-S) and water that exhibits a thermal event, as characterized by DSC, with a peak temperature of about 110° C., with a peak temperature of about 188° C. and an onset temperature of about 180° C., or with a peak temperature of about 220° C. and an onset temperature of about 217° C. In some embodiments, provided herein is a solid form comprising Compound (I-S) and water that exhibits thermal events, as characterized by DSC, with a peak temperature of about 110° C., with a peak temperature of about 188° C. and an onset temperature of about 180° C., and with a peak temperature of about 220° C. and an onset temperature of about 217° C. In some embodiments, provided herein is a solid form comprising Compound (I-S) and water, wherein the solid form is characterized by a DSC thermogram which matches the DSC thermogram presented in FIG. 6.

A representative thermal gravimetric analysis curve of the hydrate is provided in FIG. 7, which exhibits a weight loss of about 5.43% of the total sample weight upon heating from about 30 to about 150° C. In some embodiments, provided herein is a solid form comprising Compound (I-S) and water, wherein the solid form is characterized by a TGA thermogram which matches the TGA thermogram presented in FIG. 7.

(iii) Freebase THF Solvate

Provided herein is a tetrahydrofuran (THF) solvate of Compound (I-S). Furthermore, provided herein is a solid form comprising Compound (I-S) and THF. In some embodiments, the solid form is obtained by heating a mixture of Compound (I-S) and THF. In some embodiments, the solid form is obtained by heating a mixture of Compound (I-S) and THF to about 40° C. and subsequently cooling the mixture to about room temperature. In some embodiments, the solid form is obtained by heating a mixture of Compound (I-S) and THF to about 40° C., subsequently cooling the mixture to about room temperature, and isolating the solid form by filtration. In some embodiments, the molar ratio of Compound (I-S) to THF is approximately 2:1 to 1:2. In some embodiments, the molar ratio of Compound (I-S) to THF is approximately 1:1.

Without being limited by any particular theory, in some embodiments, the solvate has the following formula:

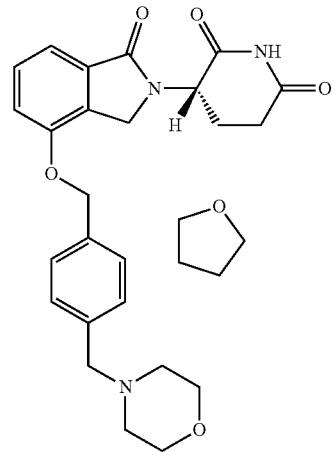

A representative XRPD pattern of a THF solvate of Compound (I-S) is provided in FIG. 8.

In some embodiments, provided herein is a solid form comprising Compound (I-S) and THF characterized by XRPD peaks located at 1, 2, 3, 4, 5, 6, 7, 8, 9, 10, 11, 12, 13, 14 or all of the following or approximately the following positions: 6.03, 8.65, 10.40, 11.80, 15.12, 17.71, 17.90, 18.23, 18.59, 20.49, 20.89, 22.16, 23.24, 26.47, and 29.14 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising Compound (I-S) and THF having an XRPD pattern comprising peaks at approximately 11.80, 20.89, and 22.16 degrees 2θ. In certain embodiments, the solid form further comprises peaks at approximately 6.03 and 18.59 degrees 2θ. In one embodiment, the solid form comprises peaks at approximately 6.03, 8.65, 10.40, 11.80, 15.12, 17.71, 17.90, 18.23, 18.59, 20.49, 20.89, 22.16, 23.24, 26.47, and 29.14 degrees 2θ.

In some embodiments, provided herein is a solid form comprising Compound (I-S) and THF, wherein the solid form is characterized by an XRPD diffraction pattern which matches the XRPD pattern presented in FIG. 8.

Representative thermal characteristics of the solvate are provided in FIG. 9 and FIG. 10. A representative differential scanning calorimetry (DSC) thermogram is presented in FIG. 9. In some embodiments, provided herein is a solid form comprising Compound (I-S) and THF that exhibits a thermal event, as characterized by DSC, with a peak temperature of about 114° C. and an onset temperature of about 105° C., with a peak temperature of about 177° C. and an onset temperature of about 171° C., or with a peak temperature of about 219° C. and an onset temperature of about 219° C. In some embodiments, provided herein is a solid form comprising Compound (I-S) and THF that exhibits thermal events, as characterized by DSC, with a peak temperature of about 114° C. and an onset temperature of about 105° C., with a peak temperature of about 177° C. and an onset temperature of about 171° C., and with a peak temperature of about 219° C. and an onset temperature of about 219° C. In some embodiments, provided herein is a solid form comprising Compound (I-S) and THF, wherein the solid form is characterized by a DSC thermogram which matches the DSC thermogram presented in FIG. 9.

A representative thermal gravimetric analysis curve of the solvate is provided in FIG. 10, which exhibits a weight loss of about 11.51% of the total sample weight upon heating from about 50 to about 175° C. In some embodiments, provided herein is a solid form comprising Compound (I-S) and THF, wherein the solid form is characterized by a TGA thermogram which matches the TGA thermogram presented in FIG. 10.

(iv) Besylate

Provided herein is a solid form comprising a besylate salt of Compound (I-S). In some embodiments, the solid form is obtained by heating a mixture of Compound (II), solvent, and benzenesulfonic acid, followed by crystallization.

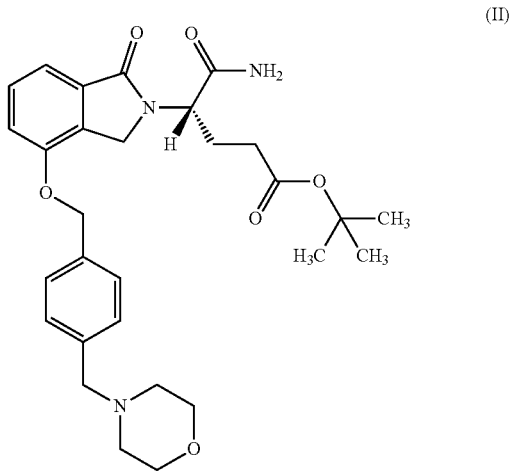 [SMILES: CC(C)(C)OC(=O)CC[C@@H](C(N)=O)N1Cc2c(OCc3ccc(CN4CCOCC4)cc3)cccc2C1=O]

(II)

In some embodiments, the solvent is acetonitrile. In some embodiments, the solid form is obtained by the steps of (1) heating a mixture of Compound (II), benzenesulfonic acid, and acetonitrile to about 82° C. and (2) crystallization. In some embodiments, the solid form is isolated by filtration.

In some embodiments, the molar ratio of Compound (I-S) to benzenesulfonic acid in the solid form is approximately 2:1 to 1:2. In some embodiments, the molar ratio is approximately 1:1.

Without being limited by any particular theory, in some embodiments, the besylate has the following formula:

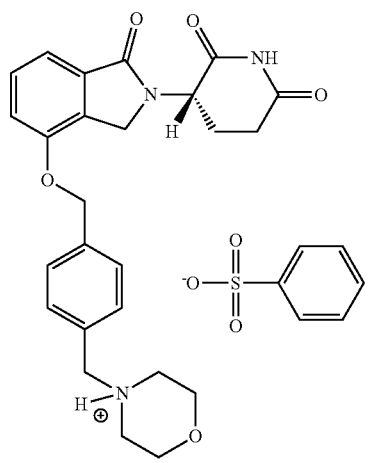

A representative XRPD pattern of the besylate Compound (I-S) is provided in FIG. 11.

In some embodiments, provided herein is a solid form comprising a besylate salt of Compound (I-S) characterized by XRPD peaks located at 1, 2, 3, 4, 5, 6, 7, 8, 9, 10, 11, 12, 13, 14, 15, 16, 17, 18, 19, 20, 21, 22, 23, 24, 25 or all of the following or approximately the following positions 7.06, 7.69, 9.51, 9.99, 15.48, 15.92, 16.42, 18.28, 19.07, 20.36, 20.71, 21.34, 21.66, 22.33, 22.52, 23.60, 23.96, 24.31, 24.44, 25.14, 25.32, 26.02, 27.58, 27.99, 28.36, and 29.82 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by 15 of the peaks. In some embodiments, the solid form is characterized by 17 of the peaks. In some embodiments, the solid form is characterized by all of the peaks.

In some embodiments, provided herein is a solid form comprising besylate of Compound (I-S) having an XRPD pattern comprising peaks at approximately 19.07, 20.71, and 23.96 degrees 2θ. In certain embodiments, the solid form further comprises peaks at approximately 15.48 and 15.92 degrees 2θ. In one embodiment, the solid form comprises peaks at approximately 7.06, 7.69, 9.51, 9.99, 15.48, 15.92, 16.42, 18.28, 19.07, 20.36, 20.71, 21.34, 21.66, 22.33, 22.52, 23.60, 23.96, 24.31, 24.44, 25.14, 25.32, 26.02, 27.58, 27.99, 28.36, and 29.82 degrees 2θ.

In some embodiments, provided herein is a solid form comprising a besylate salt of Compound (I-S), wherein the solid form is characterized by an XRPD diffraction pattern which matches the XRPD pattern presented in FIG. 11.

Representative thermal characteristics of the besylate are provided in FIG. 12 and FIG. 13. A representative differential scanning calorimetry (DSC) thermogram is presented in FIG. 12. In some embodiments, provided herein is a solid form comprising a besylate salt of Compound (I-S) that exhibits a thermal event, as characterized by DSC, with a peak temperature of about 220° C. and an onset temperature of about 211° C. In some embodiments, provided herein is a solid form comprising a besylate salt of Compound (I-S), wherein the solid form is characterized by a DSC thermogram which matches the DSC thermogram presented in FIG. 12.

A representative thermal gravimetric analysis curve of the besylate salt of Compound (I-S) is provided in FIG. 13, which exhibits no substantial change of the total sample weight upon heating from about 30 to about 125° C. In some embodiments, provided herein is a solid form comprising a besylate salt of Compound (I-S), wherein the solid form is characterized by a TGA thermogram which matches the TGA thermogram presented in FIG. 13.

A representative DVS isotherm plot of the besylate salt of Compound (I-S) is provided in FIG. 14. In some embodiments, provided herein is a solid form comprising a besylate salt of Compound (I-S), wherein the solid form is characterized by a DVS isotherm plot which matches the DVS isotherm plot presented in FIG. 14.

A representative $^1$H-NMR spectrum of the besylate salt of Compound (I-S) is provided in FIG. 15. In some embodiments, provided herein is a solid form comprising a besylate salt of Compound (I-S), wherein the solid form is characterized by a $^1$H-NMR spectrum which matches the $^1$H-NMR spectrum presented in FIG. 15.

(v) Besylate DMSO Solvate

Provided herein is a solid form comprising a DMSO solvate of the besylate salt of Compound (I-S).

In some embodiments, the solid form is obtained by contacting a besylate salt of Compound (I-S) with in DMSO and solvent. In some embodiments, the solvent in ethyl acetate.

In some embodiments, the molar ratio of Compound (I-S) to benzenesulfonic acid in the solid form is approximately 2:1 to 1:2. In some embodiments, the molar ratio is approximately 1:1.

In some embodiments, the molar ratio of Compound (I-S) to DMSO in the solid form is approximately 2:1 to 1:2. In some embodiments, the molar ratio is approximately 1:1.

Without being limited by any particular theory, in some embodiments, the solvate has the following formula:

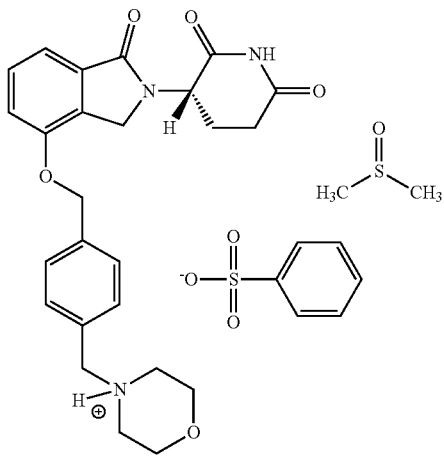

A representative XRPD pattern of the solvate is provided in FIG. 16.

In some embodiments, provided herein is a solid form comprising a DMSO solvate of a besylate salt of Compound (I-S) characterized by XRPD peaks located at 1, 2, 3, 4, 5, 6, 7, 8, 9, 10, 11, 12, 13, 14, 15 or all of the following or approximately the following positions 7.31, 12.17, 14.94, 16.02, 16.58, 16.88, 18.14, 20.02, 21.10, 22.68, 23.04, 24.22, 24.49, 24.99, 26.70, and 28.52 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising a DMSO solvate of a besylate of Compound (I-S) having an XRPD pattern comprising peaks at approximately 16.88, 18.14, and 20.02 degrees 2θ. In certain embodiments, the solid form further comprises peaks at approximately 7.31 and 24.49 degrees 2θ. In one embodiment, the solid form comprises peaks at approximately 7.31, 12.17, 14.94, 16.02, 16.58, 16.88, 18.14, 20.02, 21.10, 22.68, 23.04, 24.22, 24.49, 24.99, 26.70, and 28.52 degrees 2θ.

In some embodiments, provided herein is a solid form comprising a DMSO solvate of a besylate salt of Compound (I-S), wherein the solid form is characterized by an XRPD diffraction pattern which matches the XRPD pattern presented in FIG. 26.

Representative thermal characteristics of the DMSO solvate are provided in FIG. 17 and FIG. 18. A representative differential scanning calorimetry (DSC) thermogram is presented in FIG. 17. In some embodiments, provided herein is a solid form comprising a DMSO solvate of a besylate salt of Compound (I-S) that exhibits a thermal event, as characterized by DSC, with a peak temperature of about 146° C. and an onset temperature of about 143° C. In some embodiments, provided herein is a solid form comprising a DMSO solvate of a besylate salt of Compound (I-S), wherein the solid form is characterized by a DSC thermogram which matches the DSC thermogram presented in FIG. 17.

A representative thermal gravimetric analysis curve of the DMSO solvate of the besylate salt of Compound (I-S) is provided in FIG. 18, which exhibits no substantial change of the total sample weight upon heating from about 15 to about 110° C. In some embodiments, provided herein is a solid form comprising a DMSO solvate of a besylate salt of Compound (I-S), wherein the solid form is characterized by a TGA thermogram which matches the TGA thermogram presented in FIG. 18.

A representative spectrum of the DMSO solvate of the besylate salt of Compound (I-S) is provided in FIG. 19. In some embodiments, provided herein is a solid form comprising a DMSO solvate of a besylate salt of Compound (I-S), wherein the solid form is characterized by a $^1$H-NMR spectrum which matches the $^1$H-NMR spectrum presented in FIG. 19.

(vi) D-Tartrate

Provided herein is a solid form comprising a D-tartrate salt of Compound (I-S).

In some embodiments, the solid form is obtained by heating a mixture of Compound (I-S) with D-tartaric acid and solvent. In some embodiments, the solvent in acetonitrile. In some embodiments, the mixture is heated to about 70° C. In some embodiments, solvent is acetonitrile and the mixture is heated to about 70° C. for about 5 hours, then maintained at about 50° C. for about 14 hours, and subsequently cooled. In some embodiments, the solid form is isolated by filtration.

In some embodiments, the molar ratio is approximately 1:1.

Without being limited by any particular theory, in some embodiments, the tartrate has the following formula:

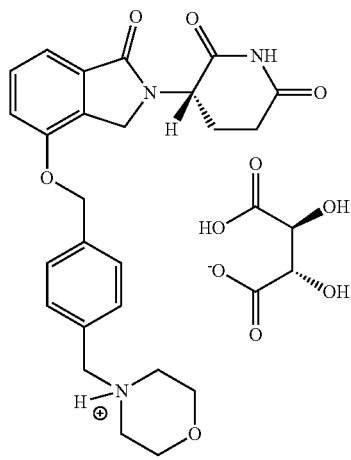

A representative XRPD pattern of the tartrate salt is provided in FIG. 20.

In some embodiments, provided herein is a solid form comprising a D-tartrate salt of Compound (I-S) characterized by XRPD peaks located at 1, 2, 3, 4, 5, 6, 7, 8, or all of the following or approximately the following positions 6.84, 17.00, 18.01, 19.25, 19.73, 20.51, 21.25, 21.67, and 25.86 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by all of the peaks.

In some embodiments, provided herein is a solid form comprising a D-tartrate salt of Compound (I-S) having an XRPD pattern comprising peaks at approximately 17.00, 19.73, and 25.86 degrees 2θ. In certain embodiments, the solid form further comprises peaks at approximately 19.25 and 21.25 degrees 2θ. In one embodiment, the solid form comprises peaks at approximately positions 6.84, 17.00, 18.01, 19.25, 19.73, 20.51, 21.25, 21.67, and 25.86 degrees 2θ.

In some embodiments, provided herein is a solid form comprising a D-tartrate salt of Compound (I-S), wherein the solid form is characterized by an XRPD diffraction pattern which matches the XRPD pattern presented in FIG. 20.

Representative thermal characteristics of the D-tartrate salt are provided in FIG. 21A and FIG. 21B. A representative differential scanning calorimetry (DSC) thermogram is presented in FIG. 21A. In some embodiments, provided herein is a solid form comprising a D-tartrate salt of Compound (I-S) that exhibits a thermal event, as characterized by DSC, with a peak temperature of about 181° C. In some embodiments, provided herein is a solid form comprising a D-tartrate salt of Compound (I-S), wherein the solid form is characterized by a DSC thermogram which matches the DSC thermogram presented in FIG. 21A.

A representative thermal gravimetric analysis curve of the D-tartrate salt is provided in FIG. 21B, which exhibits a weight loss of about 28.91% of the total sample weight upon heating from about 140 to about 250° C. In some embodiments, provided herein is a solid form comprising a D-tartrate salt of Compound (I-S), wherein the solid form is characterized by a TGA thermogram which matches the TGA thermogram presented in FIG. 21B.

A representative spectrum of the D-tartrate salt of Compound (I-S) is provided in FIG. 22. In some embodiments, provided herein is a solid form comprising a D-tartrate salt of Compound (I-S), wherein the solid form is characterized by a $^1$H-NMR spectrum which matches the $^1$H-NMR spectrum presented in FIG. 22.

(vii) Hemi D-Tartrate

Provided herein is a solid form comprising a hemi D-tartrate salt of Compound (I-S).

In some embodiments, the solid form is obtained by heating a mixture of Compound (I-S) with D-tartaric acid and solvent. In some embodiments, the solvent in acetonitrile. In some embodiments, the mixture is heated to about 60° C. In some embodiments, solvent is acetonitrile and the mixture is heated to about 60° C. for about 1 hour, then maintained at about 75° C. for about 1 hour, and subsequently cooled. In some embodiments, the solid form is isolated by filtration.

In some embodiments, the molar ratio of Compound (I-S) to tartaric acid in the solid form is approximately 2:1.

Without being limited by any particular theory, in some embodiments, the hemi tartrate has the following formula:

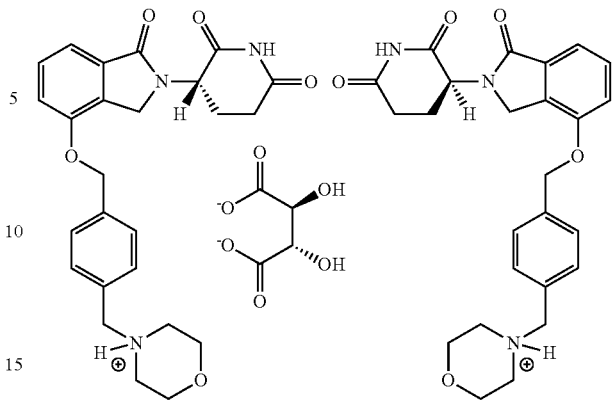

A representative XRPD pattern of the hemi tartrate salt is provided in FIG. 23.

In some embodiments, provided herein is a solid form comprising a hemi D-tartrate salt of Compound (I-S) characterized by XRPD peaks located at 1, 2, 3, 4, 5, 6, 7, 8, 9, 10, 11, 12, 13, 14, 15 or all of the following or approximately the following positions 6.21, 6.47, 9.94, 12.32, 12.91, 16.32, 16.64, 17.73, 19.09, 19.78, 19.88, 21.32, 24.60, 25.89, 26.00, and 27.54 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising a hemi D-tartrate salt of Compound (I-S) having an XRPD pattern comprising peaks at approximately 6.21, 12.91, and 16.32 degrees 2θ. In certain embodiments, the solid form further comprises peaks at approximately 12.32 and 19.09 degrees 2θ. In one embodiment, the solid form comprises peaks at approximately positions 66.21, 6.47, 9.94, 12.32, 12.91, 16.32, 16.64, 17.73, 19.09, 19.78, 19.88, 21.32, 24.60, 25.89, 26.00, and 27.54 degrees 2θ.

In some embodiments, provided herein is a solid form comprising a hemi D-tartrate salt of Compound (I-S), wherein the solid form is characterized by an XRPD diffraction pattern which matches the XRPD pattern presented in FIG. 23.

Representative thermal characteristics of the hemi D-tartrate salt are provided in FIG. 24A and FIG. 24B. A representative differential scanning calorimetry (DSC) thermogram is presented in FIG. 24A. In some embodiments, provided herein is a solid form comprising a hemi D-tartrate salt of Compound (I-S) that exhibits a thermal event, as characterized by DSC, with a peak temperature of about 111° C., or with a peak temperature of about 169° C. In some embodiments, provided herein is a solid form comprising a hemi D-tartrate salt of Compound (I-S) that exhibits thermal events, as characterized by DSC, with a peak temperature of about 111° C., and with a peak temperature of about 169° C. In some embodiments, provided herein is a solid form comprising a hemi D-tartrate salt of Compound (I-S), wherein the solid form is characterized by a DSC thermogram which matches the DSC thermogram presented in FIG. 24A.

A representative thermal gravimetric analysis curve of the hemi D-tartrate salt is provided in FIG. 24B, which exhibits a weight loss of about 4.60% of the total sample weight upon heating from about 20 to about 150° C. In some embodiments, provided herein is a solid form comprising a hemi D-tartrate salt of Compound (I-S), wherein the solid form is characterized by a TGA thermogram which matches the TGA thermogram presented in FIG. 24B.

A representative $^1$H-NMR spectrum of the hemi D-tartrate salt is provided in FIG. 25. In some embodiments, provided herein is a solid form comprising a hemi-D-tartrate salt of Compound (I-S), wherein the solid form is characterized by a $^1$H-NMR spectrum which matches the $^1$H-NMR spectrum presented in FIG. 25.

(viii) L-Tartrate

Provided herein is a solid form comprising a L-tartrate salt of Compound (I-S).

In some embodiments, the solid form is obtained by heating a mixture of Compound (I-S) with L-tartaric acid and solvent. In some embodiments, the solvent in 2-propanol. In some embodiments, the mixture is heated to about 50° C. In some embodiments, the solid form is isolated by filtration.

In some embodiments, the molar ratio of Compound (I-S) to L-tartaric acid is approximately 1:1.

Without being limited by any particular theory, in some embodiments, the tartrate has the following formula:

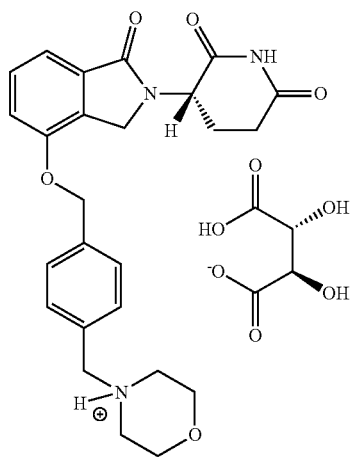

A representative XRPD pattern of the tartrate is provided in FIG. 26.

In some embodiments, provided herein is a solid form comprising a L-tartrate salt of Compound (I-S) characterized by XRPD peaks located at 1, 2, 3, 4, 5, 6, 7, 8, 9, 10, 11, or all of the following or approximately the following positions 6.27, 7.21, 10.90, 11.97, 14.41, 15.32, 17.08, 17.75, 18.79, 20.82, 23.40, and 25.28 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by all of the peaks.

In some embodiments, provided herein is a solid form comprising a L-tartrate salt of Compound (I-S) having an XRPD pattern comprising peaks at approximately 6.27, 10.90, and 15.32 degrees 2θ. In certain embodiments, the solid form further comprises peaks at approximately 11.97, 14.41, and 17.08 degrees 2θ. In one embodiment, the solid form comprises peaks at approximately positions 6.27, 7.21, 10.90, 11.97, 14.41, 15.32, 17.08, 17.75, 18.79, 20.82, 23.40, and 25.28 degrees 2θ.

In some embodiments, provided herein is a solid form comprising a L-tartrate salt of Compound (I-S), wherein the solid form is characterized by an XRPD diffraction pattern which matches the XRPD pattern presented in FIG. 26.

Representative thermal characteristics of the L-tartrate salt are provided in FIG. 27A and FIG. 27B. A representative differential scanning calorimetry (DSC) thermogram is presented in FIG. 27A. In some embodiments, provided herein is a solid form comprising a L-tartrate salt of Compound (I-S) that exhibits a thermal event, as characterized by DSC, with a peak temperature of about 114° C., or with a peak temperature of about 123° C. In some embodiments, provided herein is a solid form comprising a L-tartrate salt of Compound (I-S) that exhibits thermal events, as characterized by DSC, with a peak temperature of about 114° C., and with a peak temperature of about 123° C. In some embodiments, provided herein is a solid form comprising a L-tartrate salt of Compound (I-S), wherein the solid form is characterized by a DSC thermogram which matches the DSC thermogram presented in FIG. 27A.

A representative thermal gravimetric analysis curve of the L-tartrate salt is provided in FIG. 27B, which exhibits a weight loss of about 3.76% of the total sample weight upon heating from about 25 to about 125° C. In some embodiments, provided herein is a solid form comprising a L-tartrate salt of Compound (I-S), wherein the solid form is characterized by a TGA thermogram which matches the TGA thermogram presented in FIG. 27B.

A representative $^1$H-NMR spectrum of the L-tartrate salt is provided in FIG. 28. In some embodiments, provided herein is a solid form comprising a L-tartrate salt of Compound (I-S), wherein the solid form is characterized by a $^1$H-NMR spectrum which matches the $^1$H-NMR spectrum presented in FIG. 28.

(ix) Tosylate

Provided herein is a solid form comprising a tosylate salt of Compound (I-S).

In some embodiments, the solid form is obtained by heating a mixture of Compound (I-S), solvent, and p-toluenesulfonic acid hydrate. In some embodiments, the solvent is acetonitrile. In some embodiments, the solid form is obtained by the steps of (1) heating a mixture of acetonitrile, Compound (I-S), and p-toluenesulfonic acid hydrate to 70° C. for about 1.5 hr; (2) subsequently maintaining a temperature of about 50° C. for about 5 hr; and (3) finally maintaining a temperature of about 20° C. for about 15 hr. In some embodiments, the solid form is isolated by filtration.

In some embodiments, the molar ratio of Compound (I-S) to p-toluenesulfonic acid in the solid form is approximately 2:1 to 1:2. In some embodiments, the molar ratio is approximately 1:1.

Without being limited by any particular theory, in some embodiments, the besylate has the following formula:

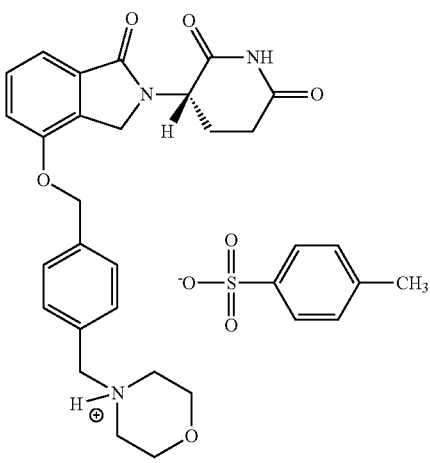

A representative XRPD pattern of the tosylate of Compound (I-S) is provided in FIG. 29.

In some embodiments, provided herein is a solid form comprising a tosylate salt of Compound (I-S) characterized by XRPD peaks located at 1, 2, 3, 4, 5, 6, 7, 8, 9, 10, 11, 12, 13, 14, 15, 16, 17, 18, or all of the following or approximately the following positions 7.41, 9.22, 9.77, 15.41, 18.70, 18.84, 19.25, 20.66, 20.89, 21.98, 22.37, 22.97, 23.83, 24.36, 24.89, 25.29, 25.55, 27.69, and 28.08 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by 15 of the peaks. In some embodiments, the solid form is characterized by 17 of the peaks. In some embodiments, the solid form is characterized by all of the peaks.

In some embodiments, provided herein is a solid form comprising tosylate of Compound (I-S) having an XRPD pattern comprising peaks at approximately 9.77, 15.41, and 19.25 degrees 2θ. In certain embodiments, the solid form further comprises peaks at approximately 7.41 and 22.97 degrees 2θ. In one embodiment, the solid form comprises peaks at approximately 77.41, 9.22, 9.77, 15.41, 18.70, 18.84, 19.25, 20.66, 20.89, 21.98, 22.37, 22.97, 23.83, 24.36, 24.89, 25.29, 25.55, 27.69, and 28.08 degrees 2θ.

In some embodiments, provided herein is a solid form comprising a tosylate salt of Compound (I-S), wherein the solid form is characterized by an XRPD diffraction pattern which matches the XRPD pattern presented in FIG. 29.

Representative thermal characteristics of the tosylate salt are provided in FIG. 30A and FIG. 30B. A representative differential scanning calorimetry (DSC) thermogram is presented in FIG. 30A. In some embodiments, provided herein is a solid form comprising a tosylate salt of Compound (I-S) that exhibits a thermal event, as characterized by DSC, with a peak temperature of about 242° C. and an onset temperature of about 237° C. In some embodiments, provided herein is a solid form comprising a tosylate salt of Compound (I-S), wherein the solid form is characterized by a DSC thermogram which matches the DSC thermogram presented in FIG. 30A.

A representative thermal gravimetric analysis curve of the tosylate salt is provided in FIG. 30B, which exhibits no substantial change of the total sample weight upon heating from about 25 to about 150° C. In some embodiments, provided herein is a solid form comprising a tosylate salt of Compound (I-S), wherein the solid form is characterized by a TGA thermogram which matches the TGA thermogram presented in FIG. 30B.

A representative $^1$H-NMR spectrum of the tosylate salt is provided in FIG. 31. In some embodiments, provided herein is a solid form comprising a tosylate salt of Compound (I-S), wherein the solid form is characterized by a $^1$H-NMR spectrum which matches the $^1$H-NMR spectrum presented in FIG. 31.

(x) (+) Camphorsulfonic Acid

Provided herein is a solid form comprising a (+) camphorsulfonic acid salt of Compound (I-S).

In some embodiments, the solid form is obtained by heating a mixture of Compound (I-S), solvent, and (+) camphorsulfonate.

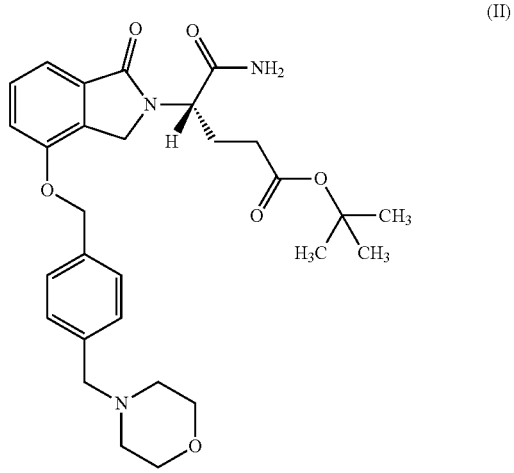 [SMILES: CC(C)(C)OC(=O)CC[C@@H](C(N)=O)N1Cc2c(OCc3ccc(CN4CCOCC4)cc3)cccc2C1=O]

(II)

In some embodiments, the solvent is ethyl acetate. In some embodiments, the solid form is obtained by the steps of (1) heating a mixture of Compound (II), (+) camphorsulfonate, and ethyl acetate to reflux for about 28 hours and removing water. In some embodiments, water is removed via Dean stark apparatus.

In some embodiments, the molar ratio of Compound (I-S) to (+) camphorsulfonic acid in the solid form is approximately 2:1 to 1:2. In some embodiments, the molar ratio is approximately 1:1.

Without being limited by any particular theory, in some embodiments, the (+) camphorsulfonic acid salt has the following formula:

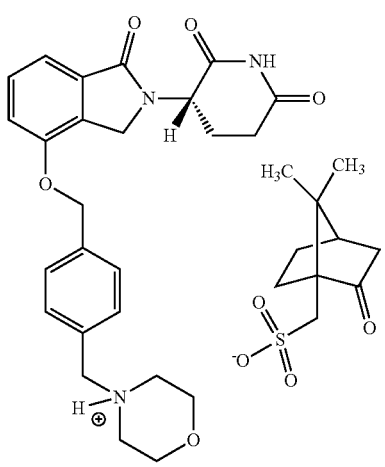

A representative XRPD pattern of the (+) camphorsulfonic acid salt of Compound (I-S) is provided in FIG. 32.

In some embodiments, provided herein is a solid form comprising a (+) camphorsulfonic acid salt of Compound (I-S) characterized by XRPD peaks located at 1, 2, 3, 4, 5, 6, 7, 8, 9, 10, 11, 12, 13, 14, 15, or all of the following or approximately the following positions 5.61, 9.05, 11.12, 13.97, 14.61, 15.34, 16.12, 16.35, 16.82, 17.20, 17.52, 18.67, 20.92, 21.53, 26.40, and 27.34 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by 11 of the peaks. In some embodiments, the solid form is characterized by 13 of the peaks. In some embodiments, the solid form is characterized by all of the peaks.

In some embodiments, provided herein is a solid form comprising (+) camphorsulfonic acid salt of Compound (I-S) having an XRPD pattern comprising peaks at approximately 9.05, 14.61, and 16.82 degrees 2θ. In certain embodiments, the solid form further comprises peaks at approximately 13.97, 15.34, and 16.35 degrees 2θ. In one embodiment, the solid form comprises peaks at approximately 5.61, 9.05, 11.12, 13.97, 14.61, 15.34, 16.12, 16.35, 16.82, 17.20, 17.52, 18.67, 20.92, 21.53, 26.40, and 27.34 degrees 2θ.

In some embodiments, provided herein is a solid form comprising a (+) camphorsulfonic acid salt of Compound (I-S), wherein the solid form is characterized by an XRPD diffraction pattern which matches the XRPD pattern presented in FIG. 32.

Representative thermal characteristics of the (+) camphorsulfonic acid salt are provided in FIG. 33 and FIG. 34. A representative differential scanning calorimetry (DSC) thermogram is presented in FIG. 33. In some embodiments, provided herein is a solid form of a (+) camphorsulfonic acid salt of Compound (I-S) that exhibits a thermal event, as characterized by DSC, with a peak temperature of about 195° C. and an onset temperature of about 181° C., or with a peak temperature of about 251° C. In some embodiments, provided herein is a solid form of a (+) camphorsulfonic acid salt of Compound (I-S) that exhibits thermal events, as characterized by DSC, with a peak temperature of about 195° C. and an onset temperature of about 181° C., and with a peak temperature of about 251° C. In some embodiments, provided herein is a solid form comprising a (+) camphorsulfonic acid salt of Compound (I-S), wherein the solid form is characterized by a DSC thermogram which matches the DSC thermogram presented in FIG. 33.

A representative thermal gravimetric analysis curve of the (+) camphorsulfonic acid salt of Compound (I-S) is provided in FIG. 34, which exhibits a weight loss of about 1.79% of the total sample weight upon heating from about 25 to about 150° C. In some embodiments, provided herein is a solid form comprising a (+) camphorsulfonic acid salt of Compound (I-S), wherein the solid form is characterized by a TGA thermogram which matches the TGA thermogram presented in FIG. 34.

A representative $^1$H-NMR spectrum of the (+) camphorsulfonic acid salt of Compound (I-S) is provided in FIG. 35. In some embodiments, provided herein is a solid form comprising a (+) camphorsulfonic acid salt of Compound (I-S), wherein the solid form is characterized by a $^1$H-NMR spectrum which matches the $^1$H-NMR spectrum presented in FIG. 35.

5.2 Various Solid Forms of Compound (I-S) HCl Salt and Syntheses Thereof

Provided herein are solid forms of the HCl salt of Compound (I-S). In some embodiments, the solid forms are crystalline. In some embodiments, the solid form is a hydrate, anhydrate, or solvate. Certain solid form of the HCl salt of Compound (I-S) have been described above.

Provided herein are various polymorphic forms of the HCl salt of Compound (I-S).

(i) Form A

Provided herein is the Form A crystal form of the HCl salt of Compound (I-S).

A representative XRPD pattern of Form A is provided in FIG. 36. In some embodiments, provided herein is a solid form comprising a HCl salt of Compound (I-S) characterized by XRPD peaks located at 1, 2, 3, 4, 5, 6, 7, 8, 9, 10, 11, 12, 13, 14, 15, 16, 17, 18, 19, 20 or all of the following or approximately the following positions: 9.69, 12.82, 15.09, 15.94, 16.76, 17.65, 19.44, 19.80, 22.30, 22.47, 22.95, 23.02, 24.29, 24.48, 24.70, 26.27, 26.77, 27.60, 29.43, 29.72, and 32.91 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by 15 of the peaks. In some embodiments, the solid form is characterized by all of the peaks.

In some embodiments, provided herein is a solid form comprising a HCl salt of Compound (I-S) having an XRPD pattern comprising peaks at approximately 15.09, 15.94, and 22.30 degrees 2θ. In certain embodiments, the solid form further comprises peaks at approximately 17.65, 22.47, and 26.77 degrees 2θ. In one embodiment, the solid form comprises peaks at approximately 9.69, 12.82, 15.09, 15.94, 16.76, 17.65, 19.44, 19.80, 22.30, 22.47, 22.95, 23.02, 24.29, 24.48, 24.70, 26.27, 26.77, 27.60, 29.43, 29.72, and 32.91 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 36.

In some embodiments, the Form A crystal form has an irregular rod crystal habit. A representative crystal habit is presented in FIG. 37.

Representative thermal characteristics of the Form A crystal form of the HCl salt of Compound (I-S) are shown in FIG. 38 and FIG. 39. A representative differential scanning calorimetry (DSC) thermogram is presented in FIG. 38. In some embodiments, provided herein is a solid form comprising a HCl salt of Compound (I-S) that exhibits a thermal event, as characterized by DSC, with a peak temperature of about 261° C. and an onset temperature of about 256° C. Without being limited by any particular theory, the event corresponds to melting and/or decomposition. In some embodiments, provided herein is a solid form comprising a HCl salt of Compound (I-S), wherein the solid form is characterized by a DSC thermogram which matches the DSC thermogram presented in FIG. 38.

A representative thermal gravimetric analysis curve of Form A is provided in FIG. 39, which exhibits a weight loss of about 0.16% of the total sample weight upon heating from about 25 to about 120° C. In certain embodiments, provided herein is a solid form comprising a HCl salt of Compound (I-S), wherein the solid form is characterized by a TGA thermogram which matches the TGA thermogram presented in FIG. 39.

A representative $^1$H-NMR spectrum of the Form A crystal form is presented in FIG. 40. In certain embodiments, provided herein is a solid form comprising a HCl salt of Compound (I-S), wherein the solid form is characterized by a $^1$H-NMR spectrum which matches the $^1$H-NMR spectrum presented in FIG. 40.

A representative DVS isotherm plot is provided in FIG. 41. In certain embodiments, provided herein is a solid form comprising a HCl salt of Compound (I-S), wherein the solid form is characterized by a DVS isotherm plot which matches the DVS isotherm plot presented in FIG. 41. In some embodiments, a mass change of about 1.8% occurs between a relative humidity (RH) between 0% and 95%. Representative XRPD patterns of the Form A crystal form before and after it undergoes adsorption/desorption cycles are presented in FIG. 42. In one embodiment, the Form A crystal remains as the Form A crystal after it undergoes adsorption/desorption cycles.

In some embodiments, the Form A crystal form remains as the Form A crystal form after application of 2000-psi for about 1 minute. A representative XRPD pattern of Form A after application of 2000-psi for about 1 minute is presented in FIG. 43. In one embodiment, the Form A crystal form remains as the Form A crystal form after application of 2000-psi for about 1 minute.

In some embodiments, the Form A crystal form is an anhydrate.

Further properties of the Form A crystal form are provided in the Examples section.

(ii) Form B

Provided herein is the Form B crystal form of the HCl salt of Compound (I-S).

In some embodiments, the Form B crystal form is obtained by recrystallization of a Form A crystal form in MeOH.

A representative XRPD pattern of Form B is provided in FIG. 44. In some embodiments, provided herein is a solid form comprising a HCl salt of Compound (I-S) characterized by XRPD peaks located at 1, 2, 3, 4, 5, 6, 7, 8, 9, 10, 11, 12, 13, 14, 15 or all of the following or approximately the following positions: 7.11, 7.87, 9.93, 11.48, 13.90, 14.20, 15.71, 20.71, 20.96, 21.36, 23.61, 26.68, 27.69, 27.76, 28.05, and 31.63 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising a HCl salt of Compound (I-S) having an XRPD pattern comprising peaks at approximately 7.11, 14.20, and 20.71 degrees 2θ. In certain embodiments, the solid form further comprises peaks at approximately 9.93 and 21.36 degrees 2θ. In one embodiment, the solid form comprises peaks at approximately 7.11, 7.87, 9.93, 11.48, 13.90, 14.20, 15.71, 20.71, 20.96, 21.36, 23.61, 26.68, 27.69, 27.76, 28.05, and 31.63 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 44.

In some embodiments, the Form B crystal form has an irregular rod crystal habit. A representative crystal habit is presented in FIG. 45.

Representative thermal characteristics of the Form B crystal form of the HCl salt of Compound (I-S) are shown in FIG. 46 and FIG. 47. A representative differential scanning calorimetry (DSC) thermogram is presented in FIG. 46. In some embodiments, provided herein is a solid form comprising a HCl salt of Compound (I-S) that exhibits a thermal event, as characterized by DSC, with a peak temperature of about 174° C. and an onset temperature of about 170° C., or with a peak temperature of about 250° C. In some embodiments, provided herein is a solid form comprising a HCl salt of Compound (I-S) that exhibits thermal events, as characterized by DSC, with a peak temperature of about 174° C. and an onset temperature of about 170° C., and with a peak temperature of about 250° C. Without being limited by any particular theory, the event with a peak temperature of about 174° C. corresponds to melting, and the event with a peak temperature of about 250° C. corresponds to decomposition. In certain embodiments, provided herein is a solid form comprising a HCl salt of Compound (I-S), wherein the solid form is characterized by a DSC thermogram which matches the DSC thermogram presented in FIG. 46.

A representative thermal gravimetric analysis curve of Form B is provided in FIG. 47, which exhibits a weight loss of about 7.60% of the total sample weight upon heating from about 25 to about 125° C. In certain embodiments, provided herein is a solid form comprising a HCl salt of Compound (I-S), wherein the solid form is characterized by a TGA thermogram which matches the TGA thermogram presented in FIG. 47. Without being limited by any particular theory, the weight loss corresponds to a loss of water and/or solvent.

A representative $^1$H-NMR spectrum of the Form B crystal form is presented in FIG. 48. In certain embodiments, provided herein is a solid form comprising a HCl salt of Compound (I-S), wherein the solid form is characterized by a $^1$H-NMR spectrum which matches the $^1$H-NMR spectrum presented in FIG. 48.

In some embodiments, the Form B crystal form is a hydrate of the HCl salt of Compound (I-S).

In some embodiments, the Form B crystal form exhibits the XRPD diffraction pattern presented in FIG. 49 after being subjected to ambient storage. In one embodiment, the Form B crystal form converts to the Form A crystal form after being subjected to ambient storage.

Further properties of the Form B crystal form are provided in the Examples section.

(iii) Form C

Provided herein is the Form C crystal form of the HCl salt of Compound (I-S).

In some embodiments, the Form C crystal form is obtained by recrystallization of a HCl salt of Compound (I-S) in DMSO/n-BuOH, DMSO/MTBE, or DMSO BuOAC.

A representative XRPD pattern of Form C is provided in FIG. 50. In some embodiments, provided herein is a solid form comprising a HCl salt of Compound (I-S) characterized by XRPD peaks located at 1, 2, 3, 4, 5, 6, 7, 8, or all of the following or approximately the following positions: 6.55, 7.65, 9.09, 13.14, 13.37, 19.62, 19.80, 22.40, and 23.32 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by all of the peaks.

In some embodiments, provided herein is a solid form comprising a HCl salt of Compound (I-S) having an XRPD pattern comprising peaks at approximately 6.55, 13.14, and 13.37 degrees 2θ. In certain embodiments, the solid form further comprises peaks at approximately 9.09, 19.62, and 19.80 degrees 2θ. In one embodiment, the solid form comprises peaks at approximately 6.55, 7.65, 9.09, 13.14, 13.37, 19.62, 19.80, 22.40, and 23.32 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 50.

In some embodiments, the Form C crystal form has an irregular crystal habit. A representative crystal habit is presented in FIG. 51.

Representative thermal characteristics of the Form C crystal form of the HCl salt of Compound (I-S) are shown in FIG. 52 and FIG. 53. A representative differential scanning calorimetry (DSC) thermogram is presented in FIG. 52. In some embodiments, provided herein is a solid form comprising a HCl salt of Compound (I-S) that exhibits a thermal event, as characterized by DSC, with a peak temperature of about 142° C., with a peak temperature of about 147° C., or with an onset temperature of about 252° C. In some embodiments, provided herein is a solid form comprising a HCl salt of Compound (I-S) that exhibits thermal events, as characterized by DSC, with a peak temperature of about 142° C., with a peak temperature of about 147° C., and with an onset temperature of about 252° C. Without being limited by any particular theory, the event with an onset temperature of about 252° C. corresponds to melting and/or decomposition. In certain embodiments, provided herein is a solid form comprising a HCl salt of Compound (I-S), wherein the solid form is characterized by a DSC thermogram which matches the DSC thermogram presented in FIG. 52.

A representative thermal gravimetric analysis curve of Form C is provided in FIG. 53, which exhibits a weight loss of 1.55% of the total sample weight upon heating from about 30 to about 80° C., and a weight loss of 15.14% of the total sample weight upon heating from about 80 to about 175° C. In certain embodiments, provided herein is a solid form comprising a HCl salt of Compound (I-S), wherein the solid form is characterized by a TGA thermogram which matches the TGA thermogram presented in FIG. 53. Without being limited by any particular theory, the weight loss corresponds to a loss of water and/or solvent.

In some embodiments, the Form C crystal form exhibits the XRPD diffraction pattern presented in FIG. 54 after being subjected to heating to 165° C. In one embodiment, the Form C crystal form converts to the Form A crystal form after being subjected to heating at 165° C.

A representative $^1$H-NMR spectrum of the Form C crystal form is presented in FIG. 55. In certain embodiments, provided herein is a solid form comprising a HCl salt of Compound (I-S), wherein the solid form is characterized by a $^1$H-NMR spectrum which matches the $^1$H-NMR spectrum presented in FIG. 55.

In some embodiments, the Form C crystal form is a DMSO solvate of the HCl salt of Compound (I-S).

In some embodiments, the Form C crystal form converts to the Form A crystal form upon exposure to high humidity, e.g., higher than 70% RH, e.g., in a DVS instrument. Representative XRPD diffraction patterns of the Form C crystal form before and after exposure to high humidity in a DVS instrument are presented in FIG. 56.

Further properties of the Form C crystal form are provided in the Examples section.

(iv) Form D

Provided herein is the Form D crystal form of the HCl salt of Compound (I-S).

In some embodiments, the Form D crystal form is obtained by equilibration of Form A in MeCN/water (95:5).

A representative XRPD pattern of Form D is provided in FIG. 57. In some embodiments, provided herein is a solid form comprising a HCl salt of Compound (I-S) characterized by XRPD peaks located at 1, 2, 3, 4, 5, 6, 7, 8, 9, 10, 11, 12, 13, 14, 15, 16 or all of the following or approximately the following positions: 6.82, 8.07, 9.56, 12.23, 13.52, 14.16, 14.82, 15.71, 18.61, 18.85, 20.27, 21.65, 22.06, 25.00, 25.99, 27.93, and 28.62 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by 15 of the peaks. In some embodiments, the solid form is characterized by all of the peaks.

In some embodiments, provided herein is a solid form comprising a HCl salt of Compound (I-S) having an XRPD pattern comprising peaks at approximately 13.52, 14.16, and 25.00 degrees 2θ. In certain embodiments, the solid form further comprises peaks at approximately 6.82, 8.07, and 15.71 degrees 2θ. In one embodiment, the solid form comprises peaks at approximately 6.82, 8.07, 9.56, 12.23, 13.52, 14.16, 14.82, 15.71, 18.61, 18.85, 20.27, 21.65, 22.06, 25.00, 25.99, 27.93, and 28.62 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 57.

In some embodiments, the Form D crystal form has an irregular crystal habit. A representative crystal habit is presented in FIG. 58.

Representative thermal characteristics of the Form D crystal form of the HCl salt of Compound (I-S) are shown in FIG. 59 and FIG. 60. A representative differential scanning calorimetry (DSC) thermogram is presented in FIG. 59. In some embodiments, provided herein is a solid form comprising a HCl salt of Compound (I-S) that exhibits a thermal event, as characterized by DSC, with a peak temperature of about 60° C., with a peak temperature of about 169° C., or with a peak temperature of about 252° C. In some embodiments, provided herein is a solid form comprising a HCl salt of Compound (I-S) that exhibits thermal events, as characterized by DSC, with a peak temperature of about 60° C., with a peak temperature of about 169° C., and with a peak temperature of about 252° C. Without being limited by any particular theory, the thermal event with a peak temperature of about 60° C. corresponds to water and/or solvent loss, the thermal event with a peak temperature of about 169° C. corresponds to melting, and the thermal event with a peak temperature of about 252° C. corresponds to decomposition. In certain embodiments, provided herein is a solid form comprising a HCl salt of Compound (I-S), wherein the solid form is characterized by a DSC thermogram which matches the DSC thermogram presented in FIG. 59.

A representative thermal gravimetric analysis curve of Form D is provided in FIG. 60, which exhibits a weight loss of about 9.19% of the total sample weight upon heating from about 25 to about 125° C. In certain embodiments, provided herein is a solid form comprising a HCl salt of Compound (I-S), wherein the solid form is characterized by a TGA thermogram which matches the TGA thermogram presented in FIG. 60. Without being limited by any particular theory, the weight loss corresponds to a loss of water and/or solvent.

A representative $^1$H-NMR spectrum of the Form D crystal form is presented in FIG. 61. In certain embodiments, provided herein is a solid form comprising a HCl salt of Compound (I-S), wherein the solid form is characterized by a $^1$H-NMR spectrum which matches the $^1$H-NMR spectrum presented in FIG. 61.

A representative DVS isotherm plot is provided in FIG. 62. In certain embodiments, provided herein is a solid form comprising a HCl salt of Compound (I-S), wherein the solid form is characterized by a DVS isotherm plot which matches the DVS isotherm plot presented in FIG. 62. In some embodiments, a mass change of about 11% relative to dry mass occurs between a relative humidity (RH) between 50% and 80%, and a mass change of about 12% between 80-90% relative humidity during absorption. Without being limited by any particular theory, the mass change between 80-90% RH corresponds to transformation of the solid form.

Representative XRPD patterns of the Form D crystal form before and after it undergoes adsorption/desorption cycles are presented in FIG. 63. In one embodiment, the Form D crystal form converts to the Form F crystal form after it undergoes adsorption/desorption cycles.

In some embodiments, the Form D crystal form is a hydrate of the HCl salt of Compound (I-S).

Further properties of the Form D crystal form are provided in the Examples section.

(v) Form E

Provided herein is the Form E crystal form of the HCl salt of Compound (I-S).

In some embodiments, the Form E crystal form is obtained by heating a mixture of Compound (I-S), HCl, water, and acetonitrile at about 45° C., followed by cooling. In some embodiments, the Form E crystal form is obtained by a method comprising the steps of: (1) heating a mixture of Compound (I-S), acetonitrile, and water at about 45° C.; (2) adding HCl to the mixture; (3) cooling the mixture to about room temperature to induce precipitation; (4) reheating the mixture to about 45° C.; and (4) cooling the mixture to about room temperature. In certain embodiments, the Form E crystal form is isolated by filtration.

A representative XRPD pattern of Form E is provided in FIG. 64. In some embodiments, provided herein is a solid form comprising a HCl salt of Compound (I-S) characterized by XRPD peaks located at 1, 2, 3, 4, 5, 6, 7, 8, 9, 10 or all of the following or approximately the following positions: 8.48, 9.82, 13.27, 13.64, 16.05, 17.06, 17.73, 21.96, 25.71, 26.15, and 28.03 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by all of the peaks.

In some embodiments, provided herein is a solid form comprising a HCl salt of Compound (I-S) having an XRPD pattern comprising peaks at approximately 9.82, 17.06, and 17.73 degrees 2θ. In certain embodiments, the solid form further comprises peaks at approximately 16.05, 25.71, and 26.15 degrees 2θ. In one embodiment, the solid form comprises peaks at approximately 8.48, 9.82, 13.27, 13.64, 16.05, 17.06, 17.73, 21.96, 25.71, 26.15, and 28.03 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 64.

In some embodiments, the Form E crystal form has an irregular crystal habit. A representative crystal habit is presented in FIG. 65.

Representative thermal characteristics of the Form E crystal form of the HCl salt of Compound (I-S) are shown in FIG. 66 and FIG. 67. A representative differential scanning calorimetry (DSC) thermogram is presented in FIG. 66. In some embodiments, provided herein is a solid form comprising a HCl salt of Compound (I-S) that exhibits a thermal event, as characterized by DSC, with a peak temperature of about 111° C., with a peak temperature of about 185° C., or with a peak temperature of about 250° C. In some embodiments, provided herein is a solid form comprising a HCl salt of Compound (I-S) that exhibits thermal events, as characterized by DSC, with a peak temperature of about 111° C., with a peak temperature of about 185° C., and with a peak temperature of about 250° C. Without being limited by any particular theory, the event with a peak temperature of about 250° C. corresponds to melting and/or decomposition. In certain embodiments, provided herein is a solid form comprising a HCl salt of Compound (I-S), wherein the solid form is characterized by a DSC thermogram which matches the DSC thermogram presented in FIG. 66.

A representative thermal gravimetric analysis curve of Form E is provided in FIG. 67, which exhibits a weight loss of about 4.49% upon heating from about 25 to about 120° C. Without being limited by any particular theory, in some embodiments, the weight loss corresponds to a Karl Fischer result showing a 4.2 wt % of water. In certain embodiments, provided herein is a solid form comprising a HCl salt of Compound (I-S), wherein the solid form is characterized by a TGA thermogram which matches the TGA thermogram presented in FIG. 67.

A representative $^1$H-NMR spectrum of the Form E crystal form is presented in FIG. 68. In certain embodiments, provided herein is a solid form comprising a HCl salt of Compound (I-S), wherein the solid form is characterized by a $^1$H-NMR spectrum which matches the $^1$H-NMR spectrum presented in FIG. 68.

A representative DVS isotherm plot is provided in FIG. 69. In certain embodiments, provided herein is a solid form comprising a HCl salt of Compound (I-S), wherein the solid form is characterized by a DVS isotherm plot which matches the DVS isotherm plot presented in FIG. 69. In some embodiments, a mass change of about 14% relative to dry mass occurs between a relative humidity (RH) between 50% and 80%. In some embodiments, a mass change is observed between 80-90% relative humidity during absorption. Without being limited by any particular theory, the mass change between 80-90% RH corresponds to transformation of the solid form.

Representative XRPD patterns of the Form E crystal form before and after it undergoes adsorption/desorption cycles are presented in FIG. 70. In one embodiment, the Form E crystal form converts to the Form F crystal form after it undergoes adsorption/desorption cycles.

In some embodiments, the Form E crystal form converts to Form A in an IPA slurry. In some embodiments, the Form E crystal form converts to Form F in IPA/water mixtures.

A representative XRPD pattern of the Form E crystal form taken after it is heated to 120° C. is presented in FIG. 71. In one embodiment, the Form E crystal form remains as the Form E crystal form after it is heated to 120° C. A representative XRPD pattern of Form E after it is heated to 190° C. is presented in FIG. 72. In one embodiment, the Form E crystal form converts to an amorphous form after it is heated to 190° C.

In some embodiments, the Form E crystal form is a hydrate.

Further properties of the Form E crystal form are provided in the Examples section.

(vi) Form F

Provided herein is the Form F crystal form of the HCl salt of Compound (I-S).

In some embodiments, the Form F crystal form is obtained by heating a mixture of Compound (I-S), HCl, water, and 2-propanol at about 40° C., followed by cooling and crystallization. In some embodiments, crystallization is induced by addition of 2-propanol. In certain embodiments, the Form F crystal form is isolated by filtration. In some embodiments, the Form F crystal form is obtained by slurrying Form E in an IPA/water mixture.

A representative XRPD pattern of Form F is provided in FIG. 73. In some embodiments, provided herein is a solid form comprising a HCl salt of Compound (I-S) characterized by XRPD peaks located at 1, 2, 3, 4, 5, 6, 7, 8, 9, 10 or all of the following or approximately the following positions: 7.10, 13.71, 14.22, 14.94, 16.35, 19.56, 20.87, 27.55, 28.36, 30.10, and 34.81 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 9 of the peaks. In some embodiments, the solid form is characterized by all of the peaks.

In some embodiments, provided herein is a solid form comprising a HCl salt of Compound (I-S) having an XRPD pattern comprising peaks at approximately 13.71, 14.22, and 20.87 degrees 2θ. In certain embodiments, the solid form further comprises peaks at approximately 7.10, 16.35, and 28.36 degrees 2θ. In one embodiment, the solid form comprises peaks at approximately 7.10, 13.71, 14.22, 14.94, 16.35, 19.56, 20.87, 27.55, 28.36, 30.10, and 34.81 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 73.

In some embodiments, the Form F crystal form has an irregular rod crystal habit. A representative crystal habit is presented in FIG. 74.

Representative thermal characteristics of the Form F crystal form of the HCl salt of Compound (I-S) are shown in FIG. 75 and FIG. 76. A representative differential scanning calorimetry (DSC) thermogram is presented in FIG. 75. In some embodiments, provided herein is a solid form comprising a HCl salt of Compound (I-S) that exhibits a thermal event, as characterized by DSC, with a peak temperature of about 83° C. and an onset temperature of about 63° C., with a peak temperature of about 217° C. and an onset temperature of about 204° C., or with a peak temperature of about 250° C. In some embodiments, provided herein is a solid form comprising a HCl salt of Compound (I-S) that exhibits thermal events, as characterized by DSC, with a peak temperature of about 83° C. and an onset temperature of about 63° C., with a peak temperature of about 217° C. and an onset temperature of about 204° C., and with a peak temperature of about 250° C. In certain embodiments, provided herein is a solid form comprising a HCl salt of Compound (I-S), wherein the solid form is characterized by a DSC thermogram which matches the DSC thermogram presented in FIG. 75.

A representative thermal gravimetric analysis curve of Form F is provided in FIG. 76, which exhibits a weight loss of 5.00% of the total sample weight upon heating from about 30 to about 110° C. Without being limited by any particular theory, in some embodiments, the weight loss corresponds to a Karl Fischer result showing a 5.3 wt % of water. In certain embodiments, provided herein is a solid form comprising a HCl salt of Compound (I-S), wherein the solid form is characterized by a TGA thermogram which matches the TGA thermogram presented in FIG. 76.

A representative $^1$H-NMR spectrum of the Form F crystal form is presented in FIG. 77. In certain embodiments, provided herein is a solid form comprising a HCl salt of Compound (I-S), wherein the solid form is characterized by a $^1$H-NMR spectrum which matches the $^1$H-NMR spectrum presented in FIG. 77.

A representative DVS isotherm plot is provided in FIG. 78. In certain embodiments, provided herein is a solid form comprising a HCl salt of Compound (I-S), wherein the solid form is characterized by a DVS isotherm plot which matches the DVS isotherm plot presented in FIG. 78. In some embodiments, a mass change of about 6.3% relative to dry mass occurs between a relative humidity (RH) between 0% and 90%. In some embodiments, water content is stabilized between 5.2 and 6.3 wt % from 10 to 90% was determined by DVS, which, in certain embodiments, corresponds to approximately 1.5-1.9 molar equivalents of water.

Representative XRPD patterns of the Form F crystal form before and after it undergoes adsorption/desorption cycles are presented in FIG. 79. In one embodiment, the Form F crystal form remains as the Form F crystal form after it undergoes adsorption/desorption cycles.

In some embodiments, the Form F crystal form converts to Form A when in IPA slurry.

A representative XRPD pattern of the Form F crystal form taken after it is heated to 120° C. is presented in FIG. 80. A representative TGA pattern of the Form F crystal form taken after it is heated to 120° C. is presented in FIG. 81. In one embodiment, the Form F crystal form remains as the Form F crystal form after it is heated to 120° C.

In some embodiments, the Form F crystal form is a hydrate. In some embodiments, the Form F crystal form is a sesqui hydrate.

Further properties of the Form F crystal form are provided in the Examples section.

(vii) Form G

Provided herein is the Form G crystal form of the HCl salt of Compound (I-S).

In some embodiments, the Form G crystal form is obtained by recrystallization of Form A in MeOH/MTBE.

A representative XRPD pattern of Form G is provided in FIG. 82. In some embodiments, provided herein is a solid form comprising a HCl salt of Compound (I-S) characterized by XRPD peaks located at 1, 2, 3, 4, 5, 6, 7, 8, 9, 10, 11, 12, 13, 14, 15 or all of the following or approximately the following positions: 6.85, 7.81, 9.56, 11.59, 13.69, 16.30, 19.05, 20.20, 20.60, 23.25, 23.57, 25.26, 26.81, 26.99, 27.51, and 31.57 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising a HCl salt of Compound (I-S) having an XRPD pattern comprising peaks at approximately 6.85, 20.20, and 20.60 degrees 2θ. In certain embodiments, the solid form further comprises peaks at approximately 9.56, 13.69, 19.05, and 23.57 degrees 2θ. In one embodiment, the solid form comprises peaks at approximately 6.85, 7.81, 9.56, 11.59, 13.69, 16.30, 19.05, 20.20, 20.60, 23.25, 23.57, 25.26, 26.81, 26.99, 27.51, and 31.57 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 82.

Representative thermal characteristics of the Form G crystal form of the HCl salt of Compound (I-S) are shown in FIG. 83 and FIG. 84. A representative differential scanning calorimetry (DSC) thermogram is presented in FIG. 83. In some embodiments, provided herein is a solid form comprising a HCl salt of Compound (I-S) that exhibits a thermal event, as characterized by DSC, with a peak temperature of about 199° C. and an onset temperature of about 185° C., or with a peak temperature of about 248° C. and an onset temperature of about 222° C. In some embodiments, provided herein is a solid form comprising a HCl salt of Compound (I-S) that exhibits thermal events, as characterized by DSC, with a peak temperature of about 199° C. and an onset temperature of about 185° C., and with a peak temperature of about 248° C. and an onset temperature of about 222° C. In certain embodiments, provided herein is a solid form comprising a HCl salt of Compound (I-S), wherein the solid form is characterized by a DSC thermogram which matches the DSC thermogram presented in FIG. 83.

A representative thermal gravimetric analysis curve of Form G is provided in FIG. 84, which exhibits a weight loss of about 1.92% of the total sample weight upon heating from about 30 to about 110° C., and a weight loss of about 12.27% of the total sample weight upon heating from about 110 to about 210° C. Without being limited by any particular theory, in some embodiments, the weight loss of about 1.92% corresponds to a loss of water and or solvent, and the weight loss of 12.27% corresponds to desolvation. In certain embodiments, provided herein is a solid form comprising a HCl salt of Compound (I-S), wherein the solid form is characterized by a TGA thermogram which matches the TGA thermogram presented in FIG. 84.

A representative $^1$H-NMR spectrum of the Form G crystal form is presented in FIG. 85. In certain embodiments, provided herein is a solid form comprising a HCl salt of Compound (I-S), wherein the solid form is characterized by a $^1$H-NMR spectrum which matches the $^1$H-NMR spectrum presented in FIG. 85.

In some embodiments, the Form G crystal form is a solvate. In some embodiments, the Form G crystal form is a MTBE solvate. In certain embodiments, the solvate contains about 0.5 molar equivalents of MTBE relative to Compound (I-S).

Further properties of the Form G crystal form are provided in the Examples section.

(viii) Form H

Provided herein is the Form H crystal form of the HCl salt of Compound (I-S).

In some embodiments, the Form H crystal form is obtained by recrystallization of Form A in MeOH/toluene.

A representative XRPD pattern of Form H is provided in FIG. 86. In some embodiments, provided herein is a solid form comprising a HCl salt of Compound (I-S) characterized by XRPD peaks located at 1, 2, 3, 4, 5, 6, 7, 8 or all of the following or approximately the following positions: 6.83, 9.47, 13.63, 16.13, 20.19, 20.58, 25.08, 26.99, and 27.55 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by all of the peaks.

In some embodiments, provided herein is a solid form comprising a HCl salt of Compound (I-S) having an XRPD pattern comprising peaks at approximately 6.83, 20.19, and 20.58 degrees 2θ. In certain embodiments, the solid form further comprises peaks at approximately 9.47 and 13.63 degrees 2θ. In one embodiment, the solid form comprises peaks at approximately 6.83, 9.47, 13.63, 16.13, 20.19, 20.58, 25.08, 26.99, and 27.55 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 86.

Representative thermal characteristics of the Form H crystal form of the HCl salt of Compound (I-S) are shown in FIG. 87 and FIG. 88. A representative differential scanning calorimetry (DSC) thermogram is presented in FIG. 87. In some embodiments, provided herein is a solid form comprising a HCl salt of Compound (I-S) that exhibits a thermal event, as characterized by DSC, with a peak temperature of about 187° C., or with a peak temperature of about 255° C. In some embodiments, provided herein is a solid form comprising a HCl salt of Compound (I-S) that exhibits thermal events, as characterized by DSC, with a peak temperature of about 187° C., and with a peak temperature of about 255° C. In certain embodiments, provided herein is a solid form comprising a HCl salt of Compound (I-S), wherein the solid form is characterized by a DSC thermogram which matches the DSC thermogram presented in FIG. 87.

A representative thermal gravimetric analysis curve of Form H is provided in FIG. 88, which exhibits a weight loss of about 0.33% of the total sample weight upon heating from about 25 to about 80° C., and a weight loss of about 15.30% of the total sample weight upon heating from about 80 to about 200° C. Without being limited by any particular theory, the weight loss of 15.30% corresponds to desolvation. In certain embodiments, provided herein is a solid form comprising a HCl salt of Compound (I-S), wherein the solid form is characterized by a TGA thermogram which matches the TGA thermogram presented in FIG. 88.

A representative $^1$H-NMR spectrum of the Form H crystal form is presented in FIG. 89. In certain embodiments, provided herein is a solid form comprising a HCl salt of Compound (I-S), wherein the solid form is characterized by a $^1$H-NMR spectrum which matches the 41-NMR spectrum presented in FIG. 89.

In some embodiments, the Form H crystal form is a solvate. In some embodiments, the Form G crystal form is a toluene solvate.

Further properties of the Form H crystal form are provided in the Examples section.

(ix) Form I

Provided herein is the Form I crystal form of the HCl salt of Compound (I-S).

In some embodiments, the Form I crystal form is obtained by recrystallization of Form A in DMSO/MeCN or DMSO/acetone.

A representative XRPD pattern of Form I is provided in FIG. 90. In some embodiments, provided herein is a solid form comprising a HCl salt of Compound (I-S) characterized by XRPD peaks located at 1, 2, 3, 4, 5 or all of the following or approximately the following positions: 13.29, 13.51, 13.95, 23.39, 24.10, and 24.30 degrees 2θ. In some embodiments, the solid form is characterized by 3 of the peaks. In some embodiments, the solid form is characterized by 5 of the peaks. In some embodiments, the solid form is characterized by all of the peaks.

In some embodiments, provided herein is a solid form comprising a HCl salt of Compound (I-S) having an XRPD pattern comprising peaks at approximately 13.95, 23.39, and 24.10 degrees 2θ. In certain embodiments, the solid form further comprises peaks at approximately 13.51 and 24.30 degrees 2θ. In one embodiment, the solid form comprises peaks at approximately 13.29, 13.51, 13.95, 23.39, 24.10, and 24.30 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 90.

In some embodiments, the Form I crystal form exhibits the XRPD pattern presented in FIG. 91 after being washed with MeOAc. In one embodiment, the Form I crystal converts to the Form A crystal after being washed with MeOAc.

In some embodiments, the Form I crystal form is a solvate.

Further properties of the Form I crystal form are provided in the Examples section.

(x) Form J

Provided herein is the Form J crystal form of the HCl salt of Compound (I-S).

In some embodiments, the Form J crystal form is obtained by recrystallization of Form A in DMSO/THF.

A representative XRPD pattern of Form J is provided in FIG. 92. In some embodiments, provided herein is a solid form comprising a HCl salt of Compound (I-S) characterized by XRPD peaks located at 1, 2, 3, 4, 5, 6, 7, 8, 9, 10, 11, 12, 13, 14, 15, 16, 17, 18, 19 or all of the following or approximately the following positions: 4.86, 6.66, 7.08, 8.22, 9.65, 9.82, 11.70, 13.26, 13.48, 15.11, 16.39, 18.12, 20.06, 20.39, 20.51, 21.20, 22.15, 22.72, 23.45, and 24.15 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by 15 of the peaks. In some embodiments, the solid form is characterized by all of the peaks.

In some embodiments, provided herein is a solid form comprising a HCl salt of Compound (I-S) having an XRPD pattern comprising peaks at approximately 4.86, 13.48, and 20.06 degrees 2θ. In certain embodiments, the solid form further comprises peaks at approximately 20.39, 22.15, and 23.45 degrees 2θ. In one embodiment, the solid form comprises peaks at approximately 4.86, 6.66, 7.08, 8.22, 9.65, 9.82, 11.70, 13.26, 13.48, 15.11, 16.39, 18.12, 20.06, 20.39, 20.51, 21.20, 22.15, 22.72, 23.45, and 24.15 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 92.

Representative thermal characteristics of the Form J crystal form of the HCl salt of Compound (I-S) are shown in FIG. 93 and FIG. 94. A representative differential scanning calorimetry (DSC) thermogram is presented in FIG. 93. In some embodiments, provided herein is a solid form comprising a HCl salt of Compound (I-S) that exhibits a thermal event, as characterized by DSC, with a peak temperature of about 70° C., with a peak temperature of about 106° C., with a peak temperature of about 127° C., or with an onset temperature of about 251° C. In some embodiments, provided herein is a solid form comprising a HCl salt of Compound (I-S) that exhibits thermal events, as characterized by DSC, with a peak temperature of about 70° C., with a peak temperature of about 106° C., with a peak temperature of about 127° C., and with an onset temperature of about 251° C. In certain embodiments, provided herein is a solid form comprising a HCl salt of Compound (I-S), wherein the solid form is characterized by a DSC thermogram which matches the DSC thermogram presented in FIG. 93.

A representative thermal gravimetric analysis curve of Form J is provided in FIG. 94, which exhibits a weight loss of about 4.73% of the total sample weight upon heating from about 25 to about 80° C., a weight loss of about 7.59% of the total sample weight upon heating from about 80 to about 120° C., and a weight loss of about 10.21% of the total sample weight upon heating from about 120 to about 200° C. Without being limited by any particular theory, the weight loss of about 4.73% corresponds to loss of water and/or solvent, the weight loss of about 7.59% and the weight loss of about 10.21% correspond to desolvation. In certain embodiments, provided herein is a solid form comprising a HCl salt of Compound (I-S), wherein the solid form is characterized by a TGA thermogram which matches the TGA thermogram presented in FIG. 94

In some embodiments, the Form J crystal form is a solvate.

Further properties of the Form J crystal form are provided in the Examples section.

(xi) Form K

Provided herein is the Form K crystal form of the HCl salt of Compound (I-S).

In some embodiments, the Form K crystal form is obtained by drying Form F at about 0% relative humidity. In one embodiment, the drying is performed by placing Form F in a chamber containing drierite for about 16 hours.

A representative XRPD pattern of Form K is provided in FIG. 95. In some embodiments, provided herein is a solid form comprising a HCl salt of Compound (I-S) characterized by XRPD peaks located at 1, 2, 3, 4, 5, 6, 7 or all of the following or approximately the following positions: 7.09, 9.35, 14.03, 14.22, 14.76, 15.91, 19.17, and 21.60 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by all of the peaks.

In some embodiments, provided herein is a solid form comprising a HCl salt of Compound (I-S) having an XRPD pattern comprising peaks at approximately 7.09, 14.03, and 14.22 degrees 2θ. In certain embodiments, the solid form further comprises peaks at approximately 9.35 and 21.60 degrees 2θ. In one embodiment, the solid form comprises peaks at approximately 7.09, 9.35, 14.03, 14.22, 14.76, 15.91, 19.17, and 21.60 degrees 2θ.

In certain embodiments, provided herein is a solid form comprising a HCl salt of Compound (I-S), wherein the solid form is characterized by an XRPD diffraction pattern which matches the XRPD diffraction pattern presented in FIG. 95.

A representative XRPD pattern of Form K after it is exposed to ambient conditions is provided in FIG. 96. In one embodiment, the Form K crystal converts to the Form F crystal after it is exposed to ambient condition.

Further properties of the Form K crystal form are provided in the Examples section.

(xii) Interconversion of HCl Forms

The interconversion of Form A-K is depicted in FIG. 106.

5.3 Salts and Solid Forms of Racemic Compound (I) and Syntheses Thereof

Provided herein are salts of racemic Compound (I). In some embodiments, racemic Compound (I) is a salt of H-X, wherein X is F, Cl, Br, I, RSO$_3$, or RCO$_2$, wherein R is alkyl, aryl, substituted alkyl, or substituted aryl. In some embodiments, the salt is a hydrochloric acid salt. Without being limited by any particular theory, the acids are associated with the basic nitrogen of the nitrogen on the morpholine ring of racemic Compound (I).

Also provided herein are solid forms of racemic Compound (I) and of salts of racemic Compound (I). In some embodiments, the solid form is an anhydrate, hydrate, or solvate. In some embodiments, the solvate is a methanol solvate.

(i) Freebase Anhydrate

Provided herein is an anhydrate of racemic Compound (I). In some embodiments, the anhydrate is obtained by heating a mixture of racemic Compound (I) and acetonitrile. In some embodiments, the anhydrate is obtained by heating a mixture of racemic Compound (I) and acetonitrile to about 40° C. and subsequently cooling the mixture to about room temperature. In some embodiments, the anhydrate is obtained by heating a mixture of racemic Compound (I) and acetonitrile to about 40° C., subsequently cooling the mixture to about room temperature, and isolating the anhydrate by filtration.

Without being limited by any particular theory, in some embodiments, the anhydrate has the following formula:

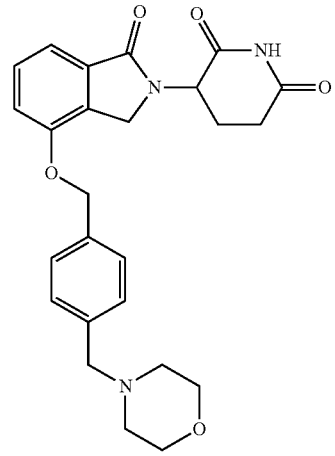 [SMILES: O=C1CCC(N2Cc3c(OCc4ccc(CN5CCOCC5)cc4)cccc3C2=O)C(=O)N1]

A representative XRPD pattern of the anhydrate of racemic Compound (I) is provided in FIG. 97.

In some embodiments, provided herein is a solid form comprising racemic Compound (I) characterized by XRPD peaks located at 1, 2, 3, 4, 5, 6, 7, 8, 9, 10, 11, 12, 13, 14, 15, 16, 17, 18 or all of the following or approximately the following positions: 4.95, 7.11, 8.96, 9.97, 12.67, 14.30, 14.83, 16.20, 19.26, 20.09, 20.61, 21.81, 22.82, 23.21, 23.58, 24.37, 26.57, 27.09, and 32.16 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by 15 of the peaks. In some embodiments, the solid form is characterized by all of the peaks.

In some embodiments, provided herein is a solid form comprising racemic Compound (I) having an XRPD pattern comprising peaks at approximately 4.95, 8.96, and 14.83 degrees 2θ. In certain embodiments, the solid form further comprises peaks at approximately 12.67, 14.30, 20.09, and 26.57 degrees 2θ. In some embodiments, the solid form comprises peaks at 4.95, 7.11, 8.96, 9.97, 12.67, 14.30, 14.83, 16.20, 19.26, 20.09, 20.61, 21.81, 22.82, 23.21, 23.58, 24.37, 26.57, 27.09, and 32.16 degrees 2θ.

In some embodiments, provided herein is a solid form comprising racemic Compound (I), wherein the solid form is characterized by an XRPD diffraction pattern which matches the XRPD pattern presented in FIG. 97.

Representative thermal characteristics of the anhydrate are provided in FIG. 98A and FIG. 98B. A representative differential scanning calorimetry (DSC) thermogram is presented in FIG. 98A. In some embodiments, provided herein is a solid form comprising racemic Compound (I) that exhibits a thermal event, as characterized by DSC, with a peak temperature of about 217° C. and an onset temperature of about 216° C. In certain embodiments, the event corresponds to melting. In some embodiments, provided herein is a solid form comprising racemic Compound (I), wherein the solid form is characterized by a DSC thermogram which matches the DSC thermogram presented in FIG. 98A.

A representative thermal gravimetric analysis curve of the anhydrate is provided in FIG. 98B, which exhibits no substantial change of the total sample weight upon heating from about 25 to about 200° C. In some embodiments, provided herein is a solid form comprising racemic Compound (I), wherein the solid form is characterized by a TGA thermogram which matches the TGA thermogram presented in FIG. 98B.

(ii) Freebase Hydrate

Provided herein is a hydrate of racemic Compound (I). In some embodiments, the hydrate is obtained by heating a mixture of racemic Compound (I), acetonitrile, and water. In some embodiments, the hydrate is obtained by heating a mixture of racemic Compound (I), acetonitrile, and water to about 40° C. and subsequently cooling the mixture to about room temperature. In some embodiments, the hydrate is obtained by heating a mixture of racemic Compound (I), acetonitrile, and water to about 40° C., subsequently cooling the mixture to about room temperature, and isolating the hydrate by filtration. In some embodiments, the volume ratio of acetonitrile to water used in the preparation of the hydrate is about 1:1. In some embodiments, the hydrate has a molar ratio of racemic Compound (I) to water of approximately 2:1 to 1:2. In some embodiments, the hydrate has a molar ratio of racemic Compound (I) to water of approximately 1:1.

Without being limited by any particular theory, in some embodiments, the hydrate has the following formula:

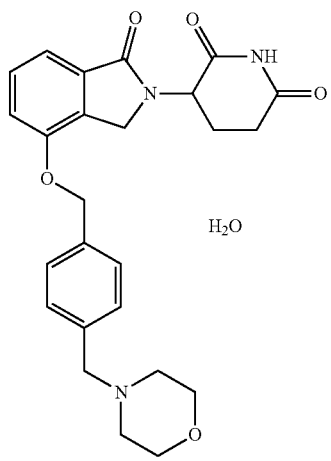 [SMILES: O=C1CCC(N2Cc3c(OCc4ccc(CN5CCOCC5)cc4)cccc3C2=O)C(=O)N1 ; O]

A representative XRPD pattern of the hydrate of racemic Compound (I) is provided in FIG. 99.

In some embodiments, provided herein is a solid form comprising racemic Compound (I) and water characterized by XRPD peaks located at 1, 2, 3, 4, 5, 6, 7, 8, 9, 10, 11, 12, 13, 14, 15 or all of the following or approximately the following positions: 8.34, 8.95, 11.79, 12.88, 14.01, 16.02, 17.01, 17.28, 18.00, 20.46, 23.05, 24.37, 25.71, 26.21, 26.38, and 27.37 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising racemic Compound (I) and water having an XRPD pattern comprising peaks at approximately 14.01, 17.28, and 26.21 degrees 2θ. In certain embodiments, the solid form further comprises peaks at approximately 8.34, 11.79, and 17.01 degrees 2θ. In some embodiments, the solid form comprises peaks at 8.34, 8.95, 11.79, 12.88, 14.01, 16.02, 17.01, 17.28, 18.00, 20.46, 23.05, 24.37, 25.71, 26.21, 26.38, and 27.37 degrees 2θ.

In some embodiments, provided herein is a solid form comprising racemic Compound (I) and water, wherein the solid form is characterized by an XRPD diffraction pattern which matches the XRPD pattern presented in FIG. 99.

Representative thermal characteristics of the hydrate are provided in FIG. 100A and FIG. 100B. A representative differential scanning calorimetry (DSC) thermogram is presented in FIG. 100A. In some embodiments, provided herein is a solid form comprising racemic Compound (I) and water that exhibits a thermal event, as characterized by DSC, with a peak temperature of about 94° C., with a peak temperature of about 137° C. and an onset temperature of about 128° C., with a peak temperature of about 157° C. and an onset temperature of about 149° C., or with a peak temperature of about 218° C. and an onset temperature of about 215° C. In some embodiments, provided herein is a solid form comprising racemic Compound (I) and water that exhibits thermal events, as characterized by DSC, with a peak temperature of about 94° C., with a peak temperature of about 137° C. and an onset temperature of about 128° C., with a peak temperature of about 157° C. and an onset temperature of about 149° C., and with a peak temperature of about 218° C. and an onset temperature of about 215° C. Without being limited by any particular theory, the event with a peak temperature of about 94° C. corresponds to melting, the event with an onset temperature of about 149° C. corresponds to recrystallization, and the event with an onset temperature of about 215° C. corresponds to melting. In some embodiments, provided herein is a solid form comprising racemic Compound (I) and water, wherein the solid form is characterized by a DSC thermogram which matches the DSC thermogram presented in FIG. 100A.

A representative thermal gravimetric analysis curve of the hydrate is provided in FIG. 100B, which exhibits a weight loss of about 4.90% of the total sample weight upon heating from about 25 to about 125° C. In some embodiments, provided herein is a solid form comprising racemic Compound (I) and water, wherein the solid form is characterized by a TGA thermogram which matches the TGA thermogram presented in FIG. 100B.

(iii) Hydrochloride Hydrates

Provided herein is a hydrate of the hydrochloride salt of racemic Compound (I). Provided herein is a solid form comprising a hydrochloride salt of racemic Compound (I) and water. In some embodiments, the solid form is obtained by heating a mixture of a hydrochloride salt of racemic Compound (I), isopropanol, and water. In some embodiments, the solid form is obtained by heating a mixture of a hydrochloride salt of racemic Compound (I), isopropanol, and water to about 50° C., and subsequently cooling the mixture to about room temperature. In some embodiments, the solid form is obtained by heating a mixture of a hydrochloride salt of racemic Compound (I), isopropanol, and water to about 50° C., subsequently cooling the mixture to about room temperature, and isolating the solid form by filtration. In some embodiments, the volume ratio of isopropanol to water used in the preparation of the solid form is about 4:1. In some embodiments, the solid form has a molar ratio of racemic Compound (I) to HCl of approximately 2:1 to 1:2. In some embodiments, the solid form has a molar ratio of racemic Compound (I) to HCl of approximately 1:1. In some embodiments, the solid form has a molar ratio of racemic Compound (I) to water of approximately 2:1 to 1:2. In some embodiments, the solid form has a molar ratio of racemic Compound (I) to water of approximately 1:1.

Without being limited by any particular theory, in some embodiments, the hydrochloride salt hydrate has the following formula:

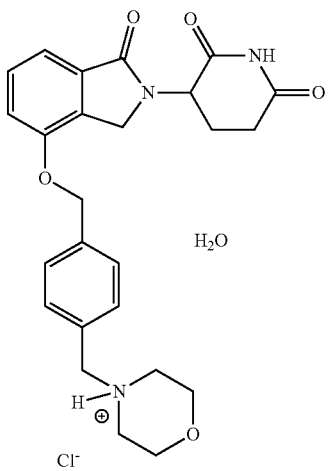

A representative XRPD pattern of a hydrate HCl salt of racemic Compound (I) is provided in FIG. 101.

In some embodiments, provided herein is a solid form comprising a HCl salt of racemic Compound (I) and water characterized by XRPD peaks located at 1, 2, 3, 4, 5, 6, 7, 8, 9, 10, 11 or all of the following or approximately the following positions: 5.17, 7.17, 9.84, 13.88, 14.30, 15.36, 16.42, 19.82, 20.48, 21.22, 25.74, and 26.95 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by all of the peaks.

In some embodiments, provided herein is a solid form comprising a HCl salt of racemic Compound (I) and water having an XRPD pattern comprising peaks at approximately 13.88, 14.30, and 15.36 degrees 2θ. In certain embodiments, the solid form further comprises peaks at approximately 9.84, 16.42, and 19.82 degrees 2θ. In one embodiment, the solid form comprises peaks at approximately 5.17, 7.17, 9.84, 13.88, 14.30, 15.36, 16.42, 19.82, 20.48, 21.22, 25.74, and 26.95 degrees 2θ.

In some embodiments, provided herein is a solid form comprising a HCl salt of racemic Compound (I) and water, wherein the solid form is characterized by an XRPD diffraction pattern which matches the XRPD pattern presented in FIG. 101.

Representative thermal characteristics of the hydrate are provided in FIG. 102A and FIG. 102B. A representative differential scanning calorimetry (DSC) thermogram is presented in FIG. 102A. In some embodiments, provided herein is a solid form comprising a HCl salt of racemic Compound (I) and water that exhibits a thermal event, as characterized by DSC, with a peak temperature of about 122° C., or with a peak temperature of about 255° C. and an onset temperature of about 252° C. In some embodiments, provided herein is a solid form comprising a HCl salt of racemic Compound (I) and water that exhibits thermal events, as characterized by DSC, with a peak temperature of about 122° C., and with a peak temperature of about 255° C. and an onset temperature of about 252° C. Without being limited by any particular theory, the event with an onset temperature of about 252° C. corresponds to melting/decomposition. In some embodiments, provided herein is a solid form comprising a HCl salt of racemic Compound (I) and water, wherein the solid form is characterized by a DSC thermogram which matches the DSC thermogram presented in FIG. 102A.

A representative thermal gravimetric analysis curve of the hydrate of the HCl salt of racemic Compound (I) is provided in FIG. 102B, which exhibits a weight loss of about 4.27% of the total sample weight upon heating from about 25 to about 100° C. In some embodiments, provided herein is a solid form comprising a HCl salt of racemic Compound (I) and water, wherein the solid form is characterized by a TGA thermogram which matches the TGA thermogram presented in FIG. 102B.

A representative DVS isotherm plot of the hydrate of the HCl salt of racemic Compound (I) is provided in FIG. 103. In some embodiments, provided herein is a solid form comprising a HCl salt of racemic Compound (I) and water, wherein the solid form is characterized by a DVS isotherm plot which matches the DVS isotherm plot presented in FIG. 103.

(iv) Hydrochloride MeOH Solvate

Provided herein is a MeOH solvate of the hydrochloride salt of racemic Compound (I). Provided herein is a solid form comprising a hydrochloride salt of racemic Compound (I) and MeOH. In some embodiments, the solid form is obtained by heating a mixture of a hydrochloride salt of racemic Compound (I) and methanol. In some embodiments, the solid form is obtained by heating a mixture of a hydrochloride salt of racemic Compound (I) and methanol to about 50° C., and subsequently cooling the mixture to about room temperature. In some embodiments, the solid form is obtained by heating a mixture of a hydrochloride salt of racemic Compound (I) and methanol to about 50° C., subsequently cooling the mixture to about room temperature, and isolating the solid form by filtration. In some embodiments, the methanol used in the preparation of the solid form is pre-dried on 3-A molecular sieves. In some embodiments, the solid form has a molar ratio of racemic Compound (I) to HCl of approximately 2:1 to 1:2. In some embodiments, the solid form has a molar ratio of racemic Compound (I) to HCl of approximately 1:1. In some embodiments, the solid form has a molar ratio of racemic Compound (I) to methanol of approximately 2:1 to 1:2. In some embodiments, the solid form has a molar ratio of racemic Compound (I) to methanol of approximately 1:1.

Without being limited by any particular theory, in some embodiments, the hydrochloride salt hydrate has the following formula:

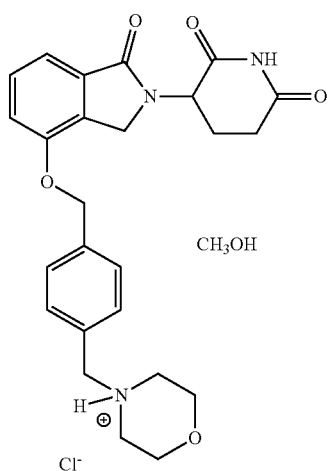

A representative XRPD pattern of a MeOH solvate of HCl salt of racemic Compound (I) is provided in FIG. 104.

In some embodiments, provided herein is a solid form comprising a HCl salt of racemic Compound (I) and methanol characterized by XRPD peaks located at 1, 2, 3, 4, 5, 6, 7, 8, 9, 10, 11, 12, 13, 14, 15, 16 or all of the following or approximately the following positions: 7.73, 10.45, 12.38, 14.54, 15.06, 16.18, 18.95, 20.00, 21.26, 21.97, 22.24, 22.30, 22.61, 24.17, 26.10, 26.86, and 30.13 degrees 2θ. In some embodiments, the solid form is characterized by 3 of the peaks. In some embodiments, the solid form is characterized by 5 of the peaks. In some embodiments, the solid form is characterized by 7 of the peaks. In some embodiments, the solid form is characterized by 10 of the peaks. In some embodiments, the solid form is characterized by 13 of the peaks. In some embodiments, the solid form is characterized by all of the peaks.

In some embodiments, provided herein is a solid form comprising a HCl salt of racemic Compound (I) and methanol having an XRPD pattern comprising peaks at approximately 12.38, 14.54, and 26.10 degrees 2θ. In certain embodiments, the solid form further comprises peaks at approximately 15.06, 20.00, and 26.86 degrees 2θ. In one embodiment, the solid form comprises peaks at approximately 7.73, 10.45, 12.38, 14.54, 15.06, 16.18, 18.95, 20.00, 21.26, 21.97, 22.24, 22.30, 22.61, 24.17, 26.10, 26.86, and 30.13 degrees 2θ.

In some embodiments, provided herein is a solid form comprising a HCl salt of racemic Compound (I) and methanol, wherein the solid form is characterized by an XRPD diffraction pattern which matches the XRPD pattern presented in FIG. 104.

In one embodiment, a MeOH solvate of HCl salt of racemic Compound (I) converts to a hydrate of HCl salt of racemic Compound (I) upon exposure to ambient moisture.

5.4 Methods of Treatment, Prevention, and Management

Provided herein are methods of treating, preventing, and/or managing various diseases or disorders using a solid form of Compound (I), a salt of Compound (I), a solid form of a salt of Compound (I), or a stereoisomer thereof.

Examples of diseases or disorders include, but are not limited to, cancer, disorders associated with angiogenesis, pain including, but not limited to, Complex Regional Pain Syndrome ("CRPS"), Macular Degeneration ("MD") and related syndromes, skin diseases, immunodeficiency disorders, dysfunctional sleep and related disorders, hemoglobinopathy and related disorders (e.g., anemia), TNFα related disorders, and other various diseases and disorders.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder.

As used herein, unless otherwise specified, the term "preventing" refers to the treatment with or administration of a compound provided herein, with or without other additional active compound, prior to the onset of symptoms, particularly to patients at risk of cancer and/or other disorders described herein. The term "prevention" includes the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. In certain cases, the beneficial effects that a subject derives from a prophylactic or therapeutic agent do not result in a cure of the disease or disorder.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to inhibit or reduce a symptom of a disease or to prevent recurrence of a disease. A prophylactically effective amount of a compound means an amount of therapeutic agent, alone or in combination with other agents, which provides a prophylactic benefit in the inhibition or reduction of a symptom of a disease or recurrence of a disease. The term "prophylactically effective amount" can encompass an amount that improves overall prophylaxis or enhances the prophylactic efficacy of another prophylactic agent.

In one embodiment, provided herein is a method of treating and preventing cancer, which comprises administering to a patient a solid form of Compound (I), a salt of Compound (I), a solid form of a salt of Compound (I), or a stereoisomer thereof.

In another embodiment, provided herein is method of managing cancer, which comprises administering to a patient a solid form of Compound (I), a salt of Compound (I), a solid form of a salt of Compound (I), or a stereoisomer thereof.

Also provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

As used herein, the term "cancer" includes, but is not limited to, solid tumors and blood born tumors. Specific examples of cancer include, but are not limited to, cancers of skin (e.g., melanoma); lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing or managing either primary or metastatic tumors.

Other specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistant to chemotherapy or radiation.

In certain embodiments, the cancer is a blood borne tumor. In certain embodiments, the blood borne tumor is metastatic. In certain embodiments, the blood borne tumor is drug resistant. In certain embodiments, the cancer is myeloma, leukemia or lymphoma.

In one embodiment, provided herein are methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. publication no. 2006/0030594, published Feb. 9, 2006, which is incorporated in its entirety by reference. In one embodiment, the cancer is acute myelogenous leukemia or acute myeloid leukemia. In another embodiment, provided herein are methods of treating, preventing, and/or managing myeloid proliferative diseases or myeloid dysplastic syndrome using a solid form of Compound (I), a salt of Compound (I), a solid form of a salt of Compound (I), or a stereoisomer thereof.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another embodiment, provided herein are methods of treating, preventing or managing various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), follicular lymphoma, and any type of the mantle cell lymphomas that can be seen under the microscope (nodular, diffuse, blastic and mantle zone lymphoma). In one embodiment, the cancer is diffuse large B-Cell lymphoma, follicular lymphoma, or mantle cell lymphoma. In one embodiment, provided herein are methods for the treatment or management of non-Hodgkin's lymphoma (NHL), including but not limited to, diffuse large B-cell lymphoma (DLBCL), using prognostic factors.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Examples of MD and related syndromes include, but are not limited to, those described in U.S. patent publication no. 2004/0091455, published May 13, 2004, which is incorporated herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

Examples of skin diseases include, but are not limited to, keratoses and related symptoms, skin diseases or disorders characterized with overgrowths of the epidermis, scleroderma, cutaneous vasculitis, acne, and wrinkles.

Examples of immunodeficiency disorders include, but are not limited to, those described in U.S. application Ser. No. 11/289,723, filed Nov. 30, 2005. Specific examples include, but not limited to, adenosine deaminase deficiency, antibody deficiency with normal or elevated Igs, ataxia-telangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of dysfunctional sleep and related syndromes include, but are not limited to, those disclosed in U.S. publication no. 2005/0222209A1, published Oct. 6, 2005, which is incorporated herein by reference. Specific examples include, but are not limited to, snoring, sleep apnea, insomnia, narcolepsy, restless leg syndrome, sleep terrors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral sclerosis, multiple sclerosis, Huntington's Disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; Amyotrophic Lateral Sclerosis (ALS); CNS trauma and myoclonus.

Examples of hemoglobinopathy and related disorders include, but are not limited to, those described in U.S. publication no. 2005/0143420A1, published Jun. 30, 2005, which is incorporated herein by reference. Specific examples include, but are not limited to, hemoglobinopathy, sickle cell anemia, and any other disorders related to the differentiation of CD34+ cells.

Examples of TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, rheumatoid spondylitis, osteoarthritis, psoriatic arthritis and other arthritic conditions, septic shock, sepsis, endotoxic shock, graft versus host disease, wasting, Crohn's disease, ulcerative colitis, multiple sclerosis, systemic lupus erythromatosis, ENL in leprosy, HIV, AIDS, and opportunistic infections in AIDS; disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

Also provided herein are methods of treating, preventing, and/or managing diseases, disorders and/or conditions associated with immune-related and inflammatory diseases comprising administering a therapeutically effective amount of a solid form of Compound (I), a salt of Compound (I), a solid form of a salt of Compound (I), or a stereoisomer thereof. In certain embodiments, the disease is selected from lupus, scleroderma, Sjögren syndrome, ANCA-induced vasculitis, anti-phospholipid syndrome and myasthenia gravis. In certain embodiments, the disease is scleroderma or lupus.

In certain embodiments, provided herein are methods of treating, preventing, and/or managing scleroderma or a symptom thereof, comprising administering a therapeutically effective amount of a solid form of Compound (I), a salt of Compound (I), a solid form of a salt of Compound (I), or a stereoisomer thereof, to a patient having scleroderma.

In certain embodiments, provided herein are methods of preventing scleroderma or a symptom thereof, comprising administering an effective amount of a solid form of Compound (I), a salt of Compound (I), a solid form of a salt of Compound (I), or a stereoisomer thereof, to a patient at risk of having scleroderma.

In certain embodiments, the scleroderma is localized, systemic, limited or diffuse scleroderma.

In certain embodiments, the systemic scleroderma comprises CREST syndrome (Calcinosis, Raynaud's syndrome, esophagaeal dysfunction or dysmotility, sclerodactyly, telangiectasia). Scleroderma is also known as systemic sclerosis or progressive systemic sclerosis. In certain embodiments, provided herein are methods of treating or preventing Raynaud's disease or syndrome. In certain embodiments, systemic sclerosis comprises scleroderma lung disease, scleroderma renal crisis, cardiac manifestations, muscular weakness (including fatigue or limited CREST), gastrointestinal dysmotility and spasm, and abnormalities in the central, peripheral and autonomic nervous system (including carpal tunnel syndrome followed by trigeminal neuralgia). It also includes general disability, including depression, and impact on quality of life.

In certain embodiments, limited scleroderma is limited to the hands, the face, neck, or combinations thereof.

In certain embodiments, diffuse scleroderma comprises skin tightening and also occurs above the wrists (or elbows). In certain embodiments, the diffuse systemic sclerosis is sine scleroderma, comprising internal organ fibrosis, but no skin tightening; or familial progressive systemic sclerosis.

In one embodiment, scleroderma is not associated with wasting, such as disease-related wasting.

In one embodiment, provided herein are methods for the reduction, inhibition, or prevention of one or more of the following symptoms of scleroderma: (i) gradual hardening, thickening, and tightening of the skin (e.g., in extremities, such as hands, face, and feet); (ii) skin discoloration; (iii) numbness of extremities; (iv) shiny skin; (v) small white lumps under the surface of the skin that erupt into a chalky white fluid; (vi) Raynaud's esophagaeal dysfunction (pain, numbness, and/or color changes in the hands caused by spasm of the blood vessels upon exposure to cold or emotional stress); (vii) telangiectasia (red spots on, e.g., the hands, palms, forearms, face, and lips); (viii) pain and/or stiffness of the joints; (ix) swelling of the hands and feet; (x) itching of the skin; (xi) stiffening and curling of the fingers; (xii) ulcers (sores) on the outside of certain joints, such as knuckles and elbows; (xiii) digestive problems, such as heartburn, difficulty in swallowing, diarrhea, irritable bowel, and constipation; (xiv) fatigue and weakness; (xv) shortness of breath; (xvi) arthritis; (xvii) hair loss; (xviii) internal organ problems; (xix) digital ulcers; or (xx) digital autoamputation, comprising administering an effective amount of a solid form of Compound (I), a salt of Compound (I), a solid form of a salt of Compound (I), or a stereoisomer thereof, to a patient in need thereof.

Without being limited by any particular theory, it is believed that a solid form of Compound (I), a salt of Compound (I), a solid form of a salt of Compound (I), or a stereoisomer thereof, enhances Th1 immune response, and suppresses Th2 immune response, which may result in anti-fibrotic effects in the skin.

Further provided herein are methods for improving or reducing the skin thickness of a patient having scleroderma comprising administering an effective amount of a solid form of Compound (I), a salt of Compound (I), a solid form of a salt of Compound (I), or a stereoisomer thereof, to the patient. In one embodiment, the skin thickness is reduced by about 20%, about 25%, about 30%, about 40%, about 50%, about 60%, about 70% about 80%, about 90% or more.

Further provided herein are methods for achieving one or more clinical endpoints associated with scleroderma comprising administering an effective amount of a solid form of Compound (I), a salt of Compound (I), a solid form of a salt of Compound (I), or a stereoisomer thereof, to a patient in need thereof.

Further provided herein are methods for increasing the overall survival, objective response rate, time to progression, progression-free survival and/or time-to-treatment failure of a patient having scleroderma comprising administering an effective amount of a solid form of Compound (I), a salt of Compound (I), a solid form of a salt of Compound (I), or a stereoisomer thereof, to the patient.

Further provided herein are methods for decreasing mortality, respiratory mortality and/or respiratory hospitalization of a patient having scleroderma comprising administering an effective amount of a solid form of Compound (I), a salt of Compound (I), a solid form of a salt of Compound (I), or a stereoisomer thereof, to the patient.

Further provided herein are methods for improving the modified Rodnan skin score of a patient having scleroderma comprising administering an effective amount of a solid form of Compound (I), a salt of Compound (I), a solid form of a salt of Compound (I), or a stereoisomer thereof, to the patient. In one embodiment, the improvement in modified Rodnan skin score is 5, 10, 15 or 20 points or more.

Further provided herein are methods for improving or reducing the skin thickness of a patient having scleroderma comprising administering an effective amount of a solid form of Compound (I), a salt of Compound (I), a solid form of a salt of Compound (I), or a stereoisomer thereof, to the patient. In one embodiment, the skin thickness is reduced by about 20%, about 25%, about 30%, about 40%, about 50%, about 60%, about 70% about 80%, about 90% or more.

Further provided herein are methods for improving or reducing skin induration of a patient having scleroderma comprising administering an effective amount of a solid form of Compound (I), a salt of Compound (I), a solid form of a salt of Compound (I), or a stereoisomer thereof, to the patient.

Further provided herein are methods for improving the dermatology quality of life index of a patient having scleroderma comprising administering an effective amount of a solid form of Compound (I), a salt of Compound (I), a solid form of a salt of Compound (I), or a stereoisomer thereof, to the patient.

Further provided herein are methods for improving the pulmonary function of a patient having scleroderma comprising administering an effective amount of a solid form of Compound (I), a salt of Compound (I), a solid form of a salt of Compound (I), or a stereoisomer thereof, to the patient.

Further provided herein are methods for improving the carbon monoxide diffusing capacity of a patient having scleroderma comprising administering an effective amount of a solid form of Compound (I), a salt of Compound (I), a solid form of a salt of Compound (I), or a stereoisomer thereof, to the patient. In one embodiment, the carbon monoxide diffusing capacity of a patient is improved by an improvement in the diffusing capacity of the lung for carbon monoxide (DLco) of about 10%, about 20%, about 25%, about 30%, about 40%, about 50%, about 60%, about 70% about 80%, about 90% or more.

Further provided herein are methods for improving the Mahler Dyspnea index of a patient having scleroderma comprising administering an effective amount of a solid form of Compound (I), a salt of Compound (I), a solid form of a salt of Compound (I), or a stereoisomer thereof, to the patient. In one embodiment, the improvement in Mahler Dyspnea index is 4, 5, 6, 7, 8, 9 or 10 points or more.

Further provided herein are methods for improving the Saint George's Respiratory Questionnaire score of a patient having scleroderma comprising administering an effective amount of a solid form of Compound (I), a salt of Compound (I), a solid form of a salt of Compound (I), or a stereoisomer thereof, to the patient. In one embodiment, the improvement in Saint George's Respiratory Questionnaire score is 4, 8, 12, 16, 20, 24, 28, 32, 36, 40, 44, 48, 52 points or more.

Further provided herein are methods for improving the UCLA scleroderma clinical trial consortium gastrointestinal tract score of a patient having scleroderma comprising administering an effective amount of a solid form of Compound (I), a salt of Compound (I), a solid form of a salt of Compound (I), or a stereoisomer thereof, to the patient.

Further provided herein are methods for treating or preventing digital ulcer of a patient or patient population having scleroderma comprising administering an effective amount of a solid form of Compound (I), a salt of Compound (I), a solid form of a salt of Compound (I), or a stereoisomer thereof, to the patient.

Further provided herein are methods improving flow-mediated dilatation of a patient having scleroderma comprising administering an effective amount of a solid form of Compound (I), a salt of Compound (I), a solid form of a salt of Compound (I), or a stereoisomer thereof, to the patient.

Further provided herein are methods improving or increasing the six minute walk distance of a patient having scleroderma comprising administering an effective amount of a solid form of Compound (I), a salt of Compound (I), a solid form of a salt of Compound (I), or a stereoisomer thereof, to the patient. In one embodiment, the improvement in the six minute walk distance is about 200 meters, about 250 meters, about 300 meters, about 350 meters, about 400 meters or more.

In certain embodiments, provided herein are methods of treating, preventing, and/or managing lupus erythematosus or a symptom thereof, comprising administering a therapeutically effective amount of a solid form of Compound (I), a salt of Compound (I), a solid form of a salt of Compound (I), or a stereoisomer thereof, to a patient having lupus erythematosus.

In one embodiment, provided herein are methods of preventing lupus erythematosus or a symptom thereof, comprising administering an effective amount of a solid form of Compound (I), a salt of Compound (I), a solid form of a salt of Compound (I), or a stereoisomer thereof, to a patient at risk of having lupus erythematosus.

In certain embodiments, provided herein are methods for treating, preventing, and/or managing systemic lupus erythematosus (SLE), cutaneous lupus erythematosus (CLE), discoid lupus erythematosus (DLE), or drug-induced lupus.

The phrase "Systemic lupus erythematosus" is interchangeably used herein with SLE and lupus and refers to all manifestations of the disease as known in the art (including remissions and flares). In SLE, abnormal hyperactivity of B lymphocytes and massive abnormal production of immunoglobulin gamma (IgG) auto-antibodies play a key role. This pathological process results in sequestration and destruction of Ig-coated cells, fixation and cleaving of complement proteins, and release of chemotaxins, vasoactive peptides and destructive enzymes into tissues (Hahn B H. Systemic Lupus Erythematosus. In: Kasper D L, Braunwald E, Fauci A S, Hauser S L, Longo D L, Jameson, J L, editors. In: *Harrison's Principles of Internal Medicine* (16th edition). New York (US): McGraw-Hill; 2005. pp. 1960-196'7).

Symptoms of SLE vary from person to person, and may come and go. In most patients, the symptoms include joint pain and swelling. Frequently affected joints are the fingers, hands, wrists, and knees. Some patients develop arthritis. Other common symptoms include: chest pain when taking a deep breath, fatigue, fever with no other cause, general discomfort, uneasiness, or ill feeling (malaise), hair loss, mouth sores, swollen lymph nodes, sensitivity to sunlight, skin rash—a "butterfly" rash over the cheeks and bridge of the nose affects about half of people with SLE, in some patients, the rash gets worse in sunlight, and the rash may also be widespread.

Other symptoms depend on what part of the body is affected, and may include the following:

Brain and nervous system: headaches, numbness, tingling, seizures, vision problems, personality changes, Digestive tract: abdominal pain, nausea, and vomiting, Heart: abnormal heart rhythms (arrhythmias), Lung: coughing up blood and difficulty breathing, and Skin: patchy skin color, fingers that change color when cold (Raynaud's phenomenon).

Some patients only have skin symptoms. This is called discoid lupus.

In one embodiment, provided herein are methods of treating moderate, severe, or very severe SLE. The term "severe SLE" as used herein refers to an SLE condition where the patient has one or more severe or life-threatening symptoms (such as hemolytic anemia, extensive heart or lung involvement, kidney disease, or central nervous system involvement).

Further provided herein are methods for achieving one or more clinical endpoints associated with SLE comprising administering an effective amount of a solid form of Compound (I), a salt of Compound (I), a solid form of a salt of Compound (I), or a stereoisomer thereof, to a patient in need thereof.

Further provided herein are methods for increasing the overall survival, objective response rate, time to progression, progression-free survival and/or time-to-treatment failure of a patient having SLE comprising administering an effective amount of a solid form of Compound (I), a salt of Compound (I), a solid form of a salt of Compound (I), or a stereoisomer thereof, to the patient.

In certain embodiment, a solid form of Compound (I), a salt of Compound (I), a solid form of a salt of Compound (I), or a stereoisomer thereof, acts as an inhibitor of primary human memory CD19+ B-cell differentiation to the plasmablast stage. Without being limited by any particular theory, it is believed that a solid form of Compound (I), a salt of Compound (I), a solid form of a salt of Compound (I), or a stereoisomer thereof, blocks cells at a premature stage thereby decreasing the numbers of plasmablasts that are capable of producing high levels of immunoglobulin. A functional consequence of this effect is reduced immunoglobulin G (IgG) and immunoglobulin M (IgM) production in these differentiation cultures.

In certain embodiments, a solid form of Compound (I), a salt of Compound (I), a solid form of a salt of Compound (I), or a stereoisomer thereof, inhibits of the ability of primary human memory CD19+ B-cells to differentiate to the plasmablast stage. In certain embodiments, a solid form of Compound (I), a salt of Compound (I), a solid form of a salt of Compound (I), or a stereoisomer thereof, has no significant effect on mature CD138+ plasma cells in short term cultures. In certain embodiments, a solid form of Compound (I), a salt of Compound (I), a solid form of a salt of Compound (I), or a stereoisomer thereof, inhibits B cell differentiation factors including interferon regulatory factor 4 (IRF4), lymphocyte-induced maturation protein (BLIMP), X-box-protein-1 (XBP-1) and B cell lymphoma 6 (Bcl6).

Further provided herein are methods of treating, managing, or preventing other immune-related diseases or conditions using a solid form of Compound (I), a salt of Compound (I), a solid form of a salt of Compound (I), or a stereoisomer thereof. In certain embodiments, for example, provided herein is a method of treating an individual having a disease or disorder, wherein the disease or disorder is caused by, or is associated with, an inappropriate or undesirable immune response, e.g., a disease, disorder or condition that can be treated beneficially by immunosuppression, comprising administering to the individual a solid form of Compound (I), a salt of Compound (I), a solid form of a salt of Compound (I), or a stereoisomer thereof.

In various specific embodiments, said immune-related disease is one or more of selected from Sjögren syndrome, ANCA-induced vasculitis, anti-phospholipid syndrome, myasthenia gravis, Addison's disease, alopecia areata, ankylosing spondylitis, antiphospholipid antibody syndrome, antiphospholipid syndrome (primary or secondary), asthma, autoimmune gastritis, autoimmune hemolytic anemia, autoimmune hepatitis, autoimmune inner ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatrical pemphigoid (e.g., mucous membrane pemphigoid), cold agglutinin disease, degos disease, dermatitis hepatiformis, essential mixed cryoglobulinemia, Goodpasture's syndrome, Graves' disease, Guillain-Barre syndrome, Hashimoto's thyroiditis (Hashimoto's disease; autoimmune thyroditis), idiopathic pulmonary fibrosis, idiopathic thrombocytopenia purpura, IgA nephropathy, juvenile arthritis, lichen planus, Ménière disease, mixed connective tissue disease, morephea, narcolepsy, neuromyotonia, pediatric autoimmune neuropsychiatric disorders (PANDAs), pemphigus vulgaris, pernicious anemia, polyarteritis nodosa, polychondritis, polymyalgia rheumatica, primary agammaglobulinemia, primary biliary cirrhosis, Raynaud disease (Raynaud phenomenon), Reiter's syndrome, relapsing polychondritis, rheumatic fever, Sjogren's syndrome, stiff-person syndrome (Moersch-Woltmann syndrome), Takayasu's arteritis, temporal arteritis (giant cell arteritis), uveitis, vasculitis (e.g., vasculitis not associated with lupus erythematosus), vitiligo, and/or Wegener's granulomatosis.

In other embodiments, provided herein is the use of the salts or solid forms in various immunological applications in combination with a vaccination, for example, as vaccine adjuvant. Although any methods and manners of use of the salts or solid forms provided herein in combination with a vaccine are contemplated herein, a non-limiting example of such uses is the use of the salts or solid forms provided herein as vaccine adjuvants, according to the administration regimens disclosed in U.S. Provisional Application No. 60/712,823, filed Sep. 1, 2005, which is incorporated herein in its entirety by reference. These embodiments also relate to the uses of salts and solid forms provided herein in combination with vaccines to treat or prevent cancer or infectious diseases, and other various uses of compounds provided herein, such as, but not limited to, reduction or desensitization of allergic reactions.

Doses the salts or solid forms provided herein vary depending on factors such as: specific indication to be treated, prevented, or managed; age and condition of a patient; and amount of second active agent used, if any. In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiment, a therapeutically or prophylactically effective amount is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg every other day.

In certain embodiments, the therapeutically or prophylactically effective amount is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of a solid form of Compound (I), a salt of Compound (I), a solid form of a salt of Compound (I), or a stereoisomer thereof, for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day to patients with NHL (e.g., DLBCL). In a particular embodiment, the compound can be administered in an amount of about 10 mg/day to patients with NHL (e.g., DLBCL).

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/ cder/cancer/animalframe.htm). For example, a dose of 1 mg/kg/day for a 65 kg human is approximately equal to 38 mg/m$^2$/day.

In certain embodiments, the amount of the compound administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a solid form of Compound (I), a salt of Compound (I), a solid form of a salt of Compound (I), or a stereoisomer thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the compound administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of a solid form of Compound (I), a salt of Compound (I), a solid form of a salt of Compound (I), or a stereoisomer thereof. In certain embodiments, the patient to be treated with one of the methods provided herein has been treated with anticancer therapy prior to the administration of a solid form of Compound (I), a salt of Compound (I), a solid form of a salt of Compound (I), or a stereoisomer thereof. In certain embodiments, the patient to be treated with one of the methods provided herein has developed drug resistance to the anticancer therapy.

The methods provided herein encompass treating a patient regardless of patient's age, although some diseases or disorders are more common in certain age groups. Further provided herein is a method for treating a patient who has undergone surgery in an attempt to treat the disease or condition at issue, as well in one who has not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

Depending on the disease to be treated and the subject's condition, a solid form of Compound (I), a salt of Compound (I), a solid form of a salt of Compound (I), or a stereoisomer thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A solid form of Compound (I), a salt of Compound (I), a solid form of a salt of Compound (I), or a stereoisomer thereof, may be formulated, alone or together, in suitable dosage unit with pharmaceutically acceptable excipients, carriers, adjuvants and vehicles, appropriate for each route of administration.

In one embodiment, a solid form of Compound (I), a salt of Compound (I), a solid form of a salt of Compound (I), or a stereoisomer thereof, is administered orally. In another embodiment, a solid form of Compound (I), a salt of Compound (I), a solid form of a salt of Compound (I), or a stereoisomer thereof, is administered parenterally. In yet another embodiment, a solid form of Compound (I), a salt of Compound (I), a solid form of a salt of Compound (I), or a stereoisomer thereof, is administered intravenously.

a solid form of Compound (I), a salt of Compound (I), a solid form of a salt of Compound (I), or a stereoisomer thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MM scan and other commonly accepted evaluation modalities.

a solid form of Compound (I), a salt of Compound (I), a solid form of a salt of Compound (I), or a stereoisomer thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound is administered once or more than once each day, for example, for a period of time. The term "continuous" is intended to mean that a therapeutic compound, is administered daily for an uninterrupted period of at least 10 days to 52 weeks. The term "intermittent" or "intermittently" as used herein is intended to mean stopping and starting at either regular or irregular intervals. For example, intermittent administration of a solid form of Compound (I), a salt of Compound (I), a solid form of a salt of Compound (I), or a stereoisomer thereof, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a solid form of Compound (I), a salt of Compound (I), a solid form of a salt of Compound (I), or a stereoisomer thereof, is administered once a day. In another embodiment, a solid form of Compound (I), a salt of Compound (I), a solid form of a salt of Compound (I), or a stereoisomer thereof, is administered twice a day. In yet another embodiment, a solid form of Compound (I), a salt of Compound (I), a solid form of a salt of Compound (I), or a stereoisomer thereof, is administered three times a day. In still another embodiment, a solid form of Compound (I), a salt of Compound (I), a solid form of a salt of Compound (I), or a stereoisomer thereof, is administered four times a day.

In certain embodiments, a solid form of Compound (I), a salt of Compound (I), a solid form of a salt of Compound (I), or a stereoisomer thereof, is administered once per day from one day to six months, from one week to three months, from one week to four weeks, from one week to three weeks, or from one week to two weeks. In certain embodiments, a solid form of Compound (I), a salt of Compound (I), a solid form of a salt of Compound (I), or a stereoisomer thereof, is administered once per day for one week, two weeks, three weeks, or four weeks. In one embodiment, a solid form of Compound (I), a salt of Compound (I), a solid form of a salt of Compound (I), or a stereoisomer thereof, is administered once per day for one week. In another embodiment, a solid form of Compound (I), a salt of Compound (I), a solid form of a salt of Compound (I), or a stereoisomer thereof, is administered once per day for two weeks. In yet another embodiment, a solid form of Compound (I), a salt of Compound (I), a solid form of a salt of Compound (I), or a stereoisomer thereof, is administered once per day for three weeks. In still another embodiment, a solid form of Compound (I), a salt of Compound (I), a solid form of a salt of Compound (I), or a stereoisomer thereof, is administered once per day for four weeks.

5.5 Clinical Trials Endpoints for Cancer Approval

"Overall survival" is defined as the time from randomization until death from any cause, and is measured in the intent-to-treat population. Overall survival should be evaluated in randomized controlled studies. Demonstration of a statistically significant improvement in overall survival can be considered to be clinically significant if the toxicity profile is acceptable, and has often supported new drug approval.

Several endpoints are based on tumor assessments. These endpoints include disease free survival (DFS), objective response rate (ORR), time to progression (TTP), progression-free survival (PFS), and time-to-treatment failure (TTF). The collection and analysis of data on these time-dependent endpoints are based on indirect assessments, calculations, and estimates (e.g., tumor measurements).

Generally, "disease free survival" (DFS) is defined as the time from randomization until recurrence of tumor or death from any cause. Although overall survival is a conventional endpoint for most adjuvant settings, DFS can be an important endpoint in situations where survival may be prolonged, making a survival endpoint impractical. DFS can be a surrogate for clinical benefit or it can provide direct evidence of clinical benefit. This determination is based on the magnitude of the effect, its risk-benefit relationship, and the disease setting. The definition of DFS can be complicated, particularly when deaths are noted without prior tumor progression documentation. These events can be scored either as disease recurrences or as censored events. Although all methods for statistical analysis of deaths have some limitations, considering all deaths (deaths from all causes) as recurrences can minimize bias. DFS can be overestimated using this definition, especially in patients who die after a long period without observation. Bias can be introduced if the frequency of long-term follow-up visits is dissimilar between the study arms or if dropouts are not random because of toxicity.

"Objective response rate" (ORR) is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study. If available, standardized criteria should be used to ascertain response. A variety of response criteria have been considered appropriate (e.g., RECIST criteria) (Therasse et al., (2000) *J. Natl. Cancer Inst*, 92: 205-16). The significance of ORR is assessed by its magnitude and duration, and the percentage of complete responses (no detectable evidence of tumor).

"Time to progression" (TTP) and "progression-free survival" (PFS) have served as primary endpoints for drug approval. TTP is defined as the time from randomization until objective tumor progression; TTP does not include deaths. PFS is defined as the time from randomization until objective tumor progression or death. Compared with TTP, PFS is the preferred regulatory endpoint. PFS includes deaths and thus can be a better correlate to overall survival. PFS assumes patient deaths are randomly related to tumor progression. However, in situations where the majority of deaths are unrelated to cancer, TTP can be an acceptable endpoint.

As an endpoint to support drug approval, PFS can reflect tumor growth and be assessed before the determination of a survival benefit. Its determination is not confounded by subsequent therapy. For a given sample size, the magnitude of effect on PFS can be larger than the effect on overall survival. However, the formal validation of PFS as a surrogate for survival for the many different malignancies that exist can be difficult. Data are sometimes insufficient to allow a robust evaluation of the correlation between effects on survival and PFS. Cancer trials are often small, and proven survival benefits of existing drugs are generally modest. The role of PFS as an endpoint to support licensing approval varies in different cancer settings. Whether an improvement in PFS represents a direct clinical benefit or a surrogate for clinical benefit depends on the magnitude of the effect and the risk-benefit of the new treatment compared to available therapies.

"Time-to-treatment failure" (TTF) is defined as a composite endpoint measuring time from randomization to discontinuation of treatment for any reason, including disease progression, treatment toxicity, and death. TTF is not recommended as a regulatory endpoint for drug approval. TTF does not adequately distinguish efficacy from these additional variables. A regulatory endpoint should clearly distinguish the efficacy of the drug from toxicity, patient or physician withdrawal, or patient intolerance.

5.6 Second Active Agents

A salt or solid form provided herein can be combined with other pharmacologically active compounds ("second active agents") in methods and compositions provided herein. Certain combinations may work synergistically in the treatment of particular types diseases or disorders, and conditions and symptoms associated with such diseases or disorders. Salt or solid form can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetlyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); PI3K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, anticancer agents and antibiotics (e.g., clarithromycin).

In certain embodiments, large molecule active agents are biological molecules, such as naturally occurring or artificially made proteins. Proteins that are particularly useful in this disclosure include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; GC-CSF, BCG, cancer antibodies, and EPO.

Particular proteins that can be used in the methods and compositions of the disclosure include, but are not limited to: filgrastim, which is sold in the United States under the trade name NEUPOGEN® (Amgen, Thousand Oaks, Calif.); sargramostim, which is sold in the United States under the trade name LEUKINE® (Immunex, Seattle, Wash.); and recombinant EPO, which is sold in the United States under the trade name EPGEN® (Amgen, Thousand Oaks, Calif.).

Inhibitors of ActRII receptors or activin-ActRII inhibitors may be used in the methods and compositions provided herein. Inhibitors of ActRII receptors include ActRIIA inhibitors and ActRIIB inhibitors. Inhibitors of ActRII receptors can be polypeptides comprising activin-binding domains of ActRII. In certain embodiments, the activin-binding domain comprising polypeptides are linked to an Fc portion of an antibody (i.e., a conjugate comprising an activin-binding domain comprising polypeptide of an ActRII receptor and an Fc portion of an antibody is generated). In certain embodiments, the activin-binding domain is linked to an Fc portion of an antibody via a linker, e.g., a peptide linker. Examples of such non-antibody proteins selected for activin or ActRIIA binding and methods for design and selection of the same are found in WO/2002/088171, WO/2006/055689, WO/2002/032925, WO/2005/037989, US 2003/0133939, and US 2005/0238646, each of which is incorporated herein by reference in its entirety. In one embodiment, the inhibitor of ActRII receptors is ACE-11. In another embodiment, the inhibitor of ActRII receptors is ACE-536.

Recombinant and mutated forms of GM-CSF can be prepared as described in U.S. Pat. Nos. 5,391,485; 5,393,870; and 5,229,496; the disclosure of each of which is incorporated herein by reference in its entirety. Recombinant and mutated forms of G-CSF can be prepared as described in U.S. Pat. Nos. 4,810,643; 4,999,291; 5,528,823; and 5,580,755; the disclosure of each of which is incorporated herein by reference in its entirety.

This disclosure encompasses the use of native, naturally occurring, and recombinant proteins. The disclosure further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with the compounds provided herein include monoclonal and polyclonal antibodies. Examples of antibodies include, but are not limited to, trastuzumab (HERCEPTIN®), rituximab (RITUXAN®), bevacizumab (AVASTIN™), pertuzumab (OMNITARG™), tositumomab (BEXXAR®), edrecolomab (PANOREX®), panitumumab and G250. The compounds provided herein can also be combined with or used in combination with anti-TNF-α antibodies.

Large molecule active agents may be administered in the form of anti-cancer vaccines. For example, vaccines that secrete, or cause the secretion of, cytokines such as IL-2, SCF, CXC14 (platelet factor 4), G-CSF, and GM-CSF can be used in the methods, pharmaceutical compositions, and kits of the disclosure. See, e.g., Emens, L. A., et al., *Curr. Opinion Mol. Ther.* 3(1):77-84 (2001).

Second active agents that are small molecules can also be used to alleviate adverse effects associated with the administration of the compounds provided herein. However, like some large molecules, many are believed to be capable of providing a synergistic effect when administered with (e.g., before, after or simultaneously) the compounds provided herein. Examples of small molecule second active agents include, but are not limited to, anti-cancer agents, antibiotics, immunosuppressive agents, and steroids.

Specific second active compounds that can be combined with compounds provided herein vary depending on the specific indication to be treated, prevented or managed.

For instance, for the treatment, prevention or management of cancer, second active agents include, but are not limited to: semaxanib; cyclosporin; etanercept; doxycycline; bortezomib; lapatinib (Tykerb®); abraxane; ace-11; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; stem cell treatments such as PDA-001; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevee), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In one embodiment, the second active agent is proteasome inhibitor. In one embodiment, the proteasome inhibitor is bortezomib, disulfiram, epigallocatechin-3-gallate, salinosporamide A, carfilzomib, ONX 0912, CEP-18770, or MLN9708.

In one embodiment, the second active agent is HDAC inhibitor. In one embodiment, the HDAC inhibitor is vorinostat, romidepsin, panobinostat, valproic acid, belinostat, mocetinostat, abexinostat, entinostat, SB939, resminostat, givinostat, CUDC-101, AR-42, CHR-2845, CHR-3996, 4SC-202, CG200745, ACY-1215, sulforaphane, kevetrin, or trichostatin A.

In one embodiment, the second active agent is mitotic inhibitor. In one embodiment, the mitotic inhibitor is taxanes, vinca alkaloids, or colchicines. In one embodiment, the taxane is paclitaxel (Abraxane) or docetaxel. In one embodiment, the vinca alkaloid is vinblastine, vincristine, vindesine, or vinorelbine.

Specific second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In another embodiment, examples of specific second agents according to the indications to be treated, prevented, or managed can be found in the following references, all of which are incorporated herein in their entireties: U.S. Pat. Nos. 6,281,230 and 5,635,517; U.S. publication nos. 2004/0220144, 2004/0190609, 2004/0087546, 2005/0203142, 2004/0091455, 2005/0100529, 2005/0214328, 2005/0239842, 2006/0154880, 2006/0122228, and 2005/0143344; and U.S. provisional application No. 60/631,870.

Examples of second active agents that may be used for the treatment, prevention and/or management of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the Physician's Desk Reference 2003. Specific examples include, but are not limited to, salicylic acid acetate (Aspirin®), celecoxib (Celebrex®), Enbrel®, ketamine, gabapentin (Neurontin®), phenytoin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavir), imipramine (Tofranil®), doxepin (Sinequan®), clomipramine (Anafranil®), fluoxetine (Prozac®), sertraline (Zoloft®), naproxen, nefazodone (Serzone®), venlafaxine (Effexor®), trazodone (Desyrer), bupropion (Wellbutrin®), mexiletine, nifedipine, propranolol, tramadol, lamotrigine, vioxx, ziconotide, ketamine, dextromethorphan, benzodiazepines, baclofen, tizanidine and phenoxybenzamine.

Examples of second active agents that may be used for the treatment, prevention and/or management of macular degeneration and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2a, pentoxifylline, tin etiopurpurin, motexafin, lucentis, lutetium, 9-fluoro-11,21-dihydroxy-16, 17-1-methylethylidinebis (oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632, 984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited herein are incorporated in their entireties by reference.

Examples of second active agents that may be used for the treatment, prevention and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment, prevention and/or management of immunodeficiency disorders include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-a), antibodies (e.g., anti-CD40 and IgM), oligonucleotides containing unmethylated CpG motifs, and vaccines (e.g., viral and tumor peptide vaccines).

Examples of second active agent that may be used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, a-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of hemoglobinopathy and related disorders include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; hydroxy urea; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Administration of a salt or solid form provided herein and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One of administration for compounds provided herein is oral. Routes of administration for the second active agents or ingredients are known to those of ordinary skill in the art. See, e.g., *Physicians' Desk Reference* ($60^{th}$ ed., 2006).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. Salts and solid forms provided herein and other active ingredients can be administered to a patient prior to, during, or after the occurrence of the adverse effect associated with conventional therapy.

5.7 Cycling Therapy

In certain embodiments, the prophylactic or therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, a salt or solid form provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a salt or solid form provided herein is administered for a greater number of cycles than would typically cause dose-limiting toxicity in a patient to whom a second active ingredient is not also being administered.

In one embodiment, a salt or solid form provided herein is administered daily and continuously for three or four weeks at a dose of from about 0.1 mg to about 500 mg per day, followed by a rest of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In one embodiment, a salt or solid form provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

5.8 Pharmaceutical Compositions and Dosage Forms

Pharmaceutical compositions can be used in the preparation of individual, single unit dosage forms. Pharmaceutical compositions and dosage forms provided herein comprise a salt or solid form provided herein. Pharmaceutical compositions and dosage forms can further comprise one or more excipients.

Pharmaceutical compositions and dosage forms provided herein can also comprise one or more additional active ingredients. Examples of optional second, or additional, active ingredients are disclosed above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences*, $20^{th}$ ed., Mack Publishing, Easton Pa. (2000).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

5.8.1 Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 20th ed., Mack Publishing, Easton Pa. (2000).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a salt or solid form provided herein, anhydrous lactose, microcrystalline cellulose, polyvinylpyrrolidone, stearic acid, colloidal anhydrous silica, and gelatin.

5.8.2 Controlled Release Dosage Forms

Active ingredients such as the compounds, salts and solid forms provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus, the compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In one embodiment, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, Medical Applications of Controlled Release, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

5.8.3 Parenteral Dosage Forms

Parenteral dosage forms can be administered to patients by various routes including, but not limited to, subcutaneous, intravenous (including bolus injection), intramuscular, and intraarterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Salts and solid forms that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

5.8.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16$^{th}$, 18$^{th}$ and 20$^{th}$ eds., Mack Publishing, Easton Pa. (1980, 1990 and 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., Remington's Pharmaceutical Sciences, 16$^{th}$, 18$^{th}$ and 20$^{th}$ eds., Mack Publishing, Easton Pa. (1980, 1990 and 2000).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition

5.9 Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise additional active ingredients such as oblimersen (Genasense), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6. EXAMPLES

6.1 Salts and Solvates of Compound (I-S)

6.1.1 Synthesis of Compound (I-S)

Besylate of Compound (I-S) (75 g, 1×) and sodium bicarbonate (11.4 g, 0.15×) were added to methyl acetate (1350 mL, 18×) and water (300 mL, 4×) in a 3 liter jacketed bottom drop vessel with overhead agitation and nitrogen blanket. The mixture was agitated at 15 to 25° C. until the solid dissolved. The mixture was settled and split. Water (75 mL, 1×) was added to the organic phase, agitated for 5 minutes at 15 to 25° C., settled, and split. The organic layer was dried to provide Compound (I-S).

6.1.2 Freebase Anhydrate

In a vial, ~50 mg of Compound (I-S) and ~250 μL of acetonitrile were heated to ~40° C., then cooled to room temperature. The resulting slurry was filtered, affording Compound (I-S) freebase anhydtrate solids.

6.1.3 Freebase Hydrate

In a vial, ~150 mg of Compound (I-S) and ~1.5 mL water were heated to 50° C., and then cooled to room temperature. The resulting slurry was filtered, affording Compound (I-S) freebase hydrate solids.

6.1.4 Freebase THF Solvate

In a vial, ~50 mg of Compound (I-S) and ~250 μL THF were heated to 40° C., then cooled to room temperature. The resulting slurry was filtered, affording a THF solvate of Compound (I-S).

6.1.5 Besylate

Compound (II) (175 g, 1×) and benzenesulfonic acid (68.7 g 0.39×) were charged to acetonitrile (1400 mL, 8×)

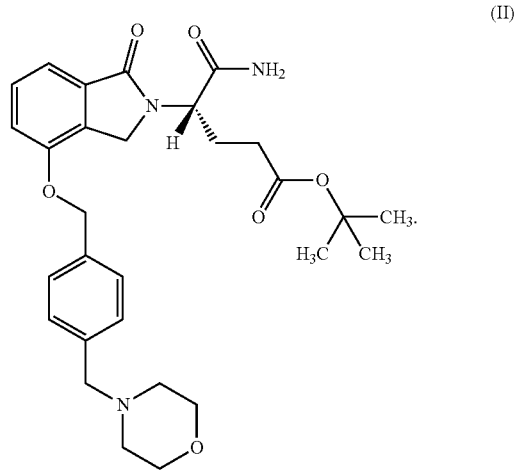 [SMILES: CC(C)(C)OC(=O)CC[C@@H](C(N)=O)N1Cc2c(OCc3ccc(CN4CCOCC4)cc3)cccc2C1=O]

(II)

The mixture was distilled at 90° C. at a rate of 1 to 3× volume of acetonitrile per hour for 4 hours. Seeds (1.75 g, 0.01×, as a slurry in 17.5 mL of acetonitrile) were added. The mixture was continuously distilled at a rate of 1 to 3× volume of acetonitrile per hour for 4 to 5 additional hours (8 to 9 hours total). The mixture was cooled to 15 to 25° C. over about 1 to 4 hours, and agitated at 15 to 25° C. for at least 1 hour. The solid was filtered, washed with acetonitrile (350 mL, 2×), and dried under reduced pressure at 35 to 50° C. with nitrogen bleed, to afford the besylate salt of Compound (I-S).

6.1.6 Besylate DMSO Solvate 5 g of the besylate salt of Compound (I-S) is dissolved in 10 mL dimethylsulfoxide and 10 mL ethyl acetate. 50 mL of ethyl acetate was added over about 5 hours at room temperature, and the mixture was agitated for 15 hours at room temperature. The reaction mixture is filtered to obtain the solvate, which is washed with 10 mL of ethyl acetate.

6.1.7 D-Tartrate 250 mg of Compound (I-S) was charged to 5 mL of acetonitrile. 83 mg (1 molar equivalent) of D-tartaric acid is charged. The reaction mixture was heated to 70° C., maintained at that temperature for 2 hours, then 50° C. for 14 hours, then cooled to 20° C. The D-tartrate was filtered and dried under vacuum.

6.1.8 Hemi D-Tartrate 2 g of Compound (I-S) and 0.71 g of D-tartaric acid was added to 30 mL of acetonitrile. The mixture was heated for 60° C. for 1 hour and then 75° C. for 1 hour. The mixture was then cooled to 20° C., and the hemi D-tartrate was collected.

6.1.9 L Tartrate

To a vial, 100 mg of Compound (I-S), 120 mg L-(+) tartaric acid solution (25% w/w in water), and 2 mL 2-propanol were added. The slurry was then heated to 50° C., then cooled to room temperature. The slurry was then filtered and dried, affording the tartrate.

6.1.10 Tosylate 250 mg of Compound (I-S) was charged to acetonitrile. 106 mg (1 equivalent) of p-toluenesulfonic acid hydrate was charged to the mixture. The mixture was agitated for 1.5 hour at 70° C., 5 hr at 50° C., and 15 hr at 20° C. The solids were then filtered to obtain the tosylate.

6.1.11 (+) Camphorsulfonic Acid Salt 2 g of Compound (II) (3.82 mmol), 1.15 g (4.97 mmol) of (+) camphorsulfonate was charged to 20 mL ethyl acetate.

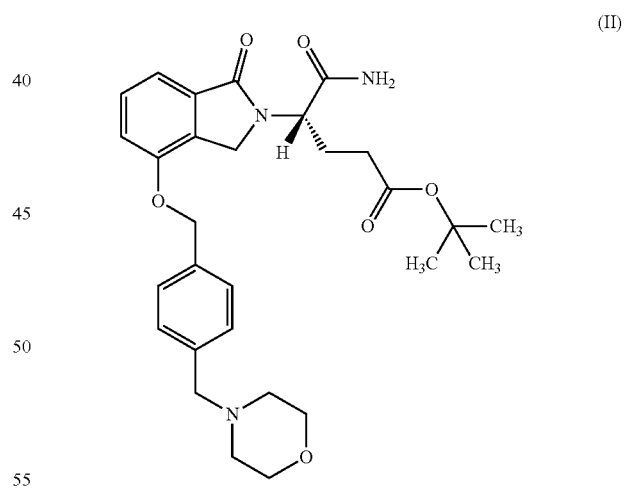

(II)

The mixture was heated to reflux for 28 hours, and the water was removed via Dean Stark apparatus. The mixture was then cooled and filtered to afford the (+) camphorsulfonic acid salt.

6.2 Polymorph Screen of HCL Salt of Compound (I-S)

A polymorph screen of the Compound (I-S) HCl (hydrochloride) salt was performed to investigate whether different solid forms of the Compound (I-S) HCl salt could be generated under various conditions, such as different solvents, temperature and humidity changes.

A total of eleven unique crystalline forms were found for the HCl salt in this polymorphism study. Form A was only anhydrate form found in this study. All other forms were found to be either hydrate or solvate.

A polymorph screen was initiated in an attempt to generate as many solid forms as possible. Characterization of the crystal forms produced during the screen was performed by X-ray powder diffraction (XRPD), differential scanning calorimetry (DSC), thermogravimetric analysis (TGA), Miniature Scanning Electron Microscope (Mini SEM) and dynamic vapor sorption (DVS). Information on solubility in aqueous and various common organic solvents was also obtained. A description of the experimental procedures employed in the screen are described below.

6.2.1 Approximate Solubility

The solvents used in the polymorph screen were either HPLC or reagent grade, including acetone, acetonitrile (MeCN), MeCN/water (1:1), n-butanol (n-BuOH), absolute ethanol (EtOH), ethanol/water (1:1), methanol (MeOH), 2-propanol (IPA), ethyl acetate (EtOAc), dichloromethane (DCM), methyl ethyl ketone (MEK), methyl t-butyl ether (MTBE), heptane, toluene, methyl acetate (MeOAc), tetrahydrofuran (THF), THF/water (1:1) and water. A weighed sample of the Compound (I-S) HCl salt (about 100 mg) was treated with a known volume of a test solvent. The resulting mixture was agitated for at least 24 hours at room temperature. If all of the solids appeared to be dissolved by visual inspection, the estimated solubility was calculated based on the total volume of solvent used to give a complete solution. If solids were present, a known volume of filtrate was evaporated to dryness and the weight of the residue was measured to estimate the solubility.

6.2.2 Equilibrium/Slurry and Evaporation

Equilibration and evaporation experiments were carried out by adding an excess of the HCl salt to up to 2 mL of a test solvent. The resulting mixture was agitated for at least 24 hours at room temperature and 50° C. separately. Upon reaching equilibrium, the saturated supernatant solution was removed, filtered using 0.45 μm PTFE filters and allowed to evaporate in an open vial under nitrogen at room temperature and 50° C., respectively. The solid resulting from the equilibration was isolated and air-dried before analysis.

6.2.3 Recrystallization

For cooling recrystallization, the selected solvent (MeOH) was saturated with the HCl salt at 60° C. The solution was stirred at 60° C. for 10 minutes, filtered using a 0.45 μm PTFE syringe filter, and then cooled to room temperature at 20° C./min stay overnight. The solution was placed into a refrigerator for 5 days. The solid resulting from the recrystallization was isolated and air-dried before analysis.

For anti-solvent recrystallization, the selected solvents (DMSO and MeOH) were saturated with the HCl salt at 60° C. Once the solid was completely dissolved, a portion of the solution was filtered into an anti-solvent (Acetone, MeCN, BuOAc, n-BuOH, MTBE, toluene or THF). The mixture of DMSO/MTBE and DMSO/THF were stirred at room temperature overnight. The rest of solutions was placed into a refrigerator for 5 days. The solid resulting from the recrystallization was isolated and air-dried before analysis.

6.2.4 Characterization

(A) X-Ray Powder Diffraction (XRPD)

All of the solid samples generated in the polymorph screen were analyzed by XRPD. XRPD analysis was conducted on a PANalytical Empyrean or a Thermo ARL X'TRA X-ray powder diffractometer using Cu Kα radiation at 1.54 Å.

The PANalytical Empyrean instrument was equipped with a fine focus X-ray tube. The voltage and amperage of the X-ray generator were set at 45 kV and 40 mA, respectively. The divergence slits were set at $\frac{1}{16}°$ and $\frac{1}{8}°$, and the receiving slits was set at $\frac{1}{16}°$. Diffracted radiation was measured using a Pixel 2D detector. A theta-two theta continuous scan was set at step size 0.013 or 0.026 from 3° to 40° 2θ with sample spinning rate at 4. A sintered alumina standard was used to check the peak positions.

The Thermo ARL X'TRA instrument was equipped with a fine focus X-ray tube. The voltage and amperage of the X-ray generator were set at 45 kV and 40 mA, respectively. The divergence slits were set at 4 mm and 2 mm and the measuring slits were set at 0.5 mm and 0.2 mm. Diffracted radiation was measured using a Peltier-cooled Si (Li) solid-state detector. A theta-two theta continuous scan at 2.40°/min (0.5 sec/0.02° step) from 1.5° to 40° 2θ was used. A sintered alumina standard was used to check the peak positions.

(B) Differential Scanning Calorimetry (DSC)

DSC analyses were performed on a TA instrument Q2000 Differential Scanning calorimeter. Indium was used as the calibration standard. Approximately 2-5 mg of sample was placed into a DSC pan. The sample was heated under nitrogen at a rate of 10° C./min, up to a final temperature of 300° C. Melting points were reported as the extrapolated onset temperatures.

(C) Thermogravimetric Analysis (TGA)

TGA analyses were performed on a TA instrument Q5000 Thermogravimetric Analyzer. Calcium oxalate was used for a performance check. Approximately 2-10 mg of accurately weighed sample was placed on a pan and loaded into the TGA furnace. The sample was heated under nitrogen at a rate of 10 degrees C./min, up to a final temperature of 300 degrees C.

(D) Miniature Scanning Electron Microscope (Mini SEM)

Morphology analysis of the samples was carried out on an Even Mini SEM. Small amounts of samples were dispersed on a sample holder, and then coating with gold viewed with 200× and 1000× magnification.

(E) Dynamic Vapor Sorption (DVS)

Hygroscopicity was determined on a Surface Measurement Systems DVS. Typically a sample size of 5-30 mg was loaded into the DVS instrument sample pan and the sample was analyzed on a DVS automated sorption analyzer at room temperature. The relative humidity was increased from 0% to 90% RH at 10% RH step, then at 95% RH. The relative humidity was then decreased in a similar manner to accomplish a full adsorption/desorption cycle. For hydrated forms, the analysis started at 50% RH and increased to 90% RH at 10% RH step. The relative humidity was then decreased in a similar manner to 0% RH followed by increasing to 50% RH.

(F) Nuclear Magnetic Resonance (NMR)

$^1$H NMR spectra were obtained on a Bruker 300 MHz NMR spectrometer. Samples were dissolved in DMSO-d6 and analyzed with 64 to 128 scans. The Form C sample was dissolved in MeOD.

6.2.5 Results

Approximate solubility of the HCl salt Form A, in various solvents at ambient temperature was estimated as described. The results are summarized in Table 1.

TABLE 1

Approximate Solubility of HCl Salt Form A in Selected Solvents at Room Temperature.

| Solvent | Approximate Solubility (mg/mL) |
|---|---|
| Acetone | <1 |
| CH$_3$CN | <1 |
| n-BuOH | <1 |
| EtOH | ~1 |
| MeOH | ~10 |
| IPA | ~1 |
| EtOAc | <1 |
| MEK | <1 |
| CH$_2$Cl$_2$ | <1 |
| MTBE | <1 |
| Heptane | <1 |
| Toluene | <1 |
| MeOAc | <1 |
| THF | <1 |
| H$_2$O | >50 |
| CH$_3$CN/H$_2$O (1:1) | >50 |
| EtOH/H$_2$O (1:1) | >50 |
| THF/H$_2$O (1:1) | >50 |
| DMSO | >50 |

The HCl salt was found to be most soluble (greater than 50 mg/mL) in MeCN/water (1:1), EtOH/water (1:1), THF/water (1:1), and water. The HCl salt showed moderate solubility in MeOH. The HCl salt showed low or very low solubility (around or less than 1 mg/mL) in acetone, MeCN, n-BuOH, EtOH, IPA, EtOAc, MEK, DCM, MTBE, heptane, MeOAc, toluene and THF.

The XRPD pattern of the HCl salt drug substance used to generate samples in the polymorph screen is shown in FIG. 94 and FIG. 35. The crystalline pattern was designated as Form A.

Equilibration experiments were performed at room temperature and 50° C. using the HCl salt Form A as starting material. The results are summarized in Table 2.

TABLE 2

Equilibration of Form A at Room Temperature and 50° C.

| Solvent | Form by XRPD | |
|---|---|---|
| | RT | 50° C. |
| Acetone | A | A |
| CH$_3$CN | A | A |
| n-BuOH | A | A |
| EtOH | A | A |
| MeOH | A | A |
| IPA | A | A |
| EtOAc | A | A |
| MEK | A | A |
| CH$_2$Cl$_2$ | A | n/a |
| MTBE | A | A |
| Heptane | A | A |

TABLE 2-continued

Equilibration of Form A at Room Temperature and 50° C.

| Solvent | Form by XRPD | |
|---|---|---|
| | RT | 50° C. |
| Toluene | A | A |
| MeOAc | A | A |
| THF | A | A |
| H$_2$O | n/a | n/a |
| CH$_3$CN/H$_2$O (1:1) | n/a | n/a |
| EtOH/H$_2$O (1:1) | n/a | n/a |
| THF/H$_2$O (1:1) | n/a | n/a |
| Acetone/H$_2$O (95:5) | A | n/a |
| MeCN/H$_2$O (95:5) | D | n/a |
| EtOH/H$_2$O (95:5) | A | n/a |
| IPA/H$_2$O (95:5) | A | n/a |
| MeOAc/H$_2$O (95:5) | A | n/a |
| THF/H$_2$O (95:5) | A | n/a | n/a: all solid went in solution or experiment not performed.

All of the solids isolated from non-aqueous solvents after 24 h of slurry were confirmed to be Form A by XRPD. Since all solid in aqueous or 50/50 mixtures of aqueous/organic solvent mixtures went in solution, additional equilibration experiments were performed in organic/water mixtures containing 5% of water at room temperature, including acetone/water, MeCN/water, EtOH/water, IPA/water, MeOAc/water and THF/water. All solids isolated were confirmed to be Form A by)(RFD, except for the solid from MeCN/water. The unique XRPD pattern obtained from this condition was designated as Form D Evaporation experiments were performed at room temperature and 50° C. The results are summarized in Table 3.

TABLE 3

Evaporation of Form A at Room Temperature and 50° C.

| Solvent | Form by XRPD | |
|---|---|---|
| | RT | 50° C. |
| Acetone | — | — |
| CH$_3$CN | — | — |
| n-BuOH | — | — |
| EtOH | — | — |
| MeOH | — | A |
| IPA | — | — |
| EtOAc | — | — |
| MEK | — | — |
| CH$_2$Cl$_2$ | — | — |
| MTBE | — | — |
| Heptane | — | — |
| Toluene | — | — |
| MeOAc | — | A |
| THF | — | — |
| H$_2$O | Amorphous | Amorphous |
| CH$_3$CN/H$_2$O | Amorphous | Amorphous |
| EtOH/H$_2$O | Amorphous | Amorphous |
| THF/H$_2$O | Amorphous | Amorphous |

—Not analyzable

Since the solubility of the HCl salt was low in most organic testing solvents, residual solids obtained from these solvents were not enough for any analysis. Evaporation from MeOH and MeOAc afforded solids that were confirmed to be Form A by XRPD. The solids isolated from water or water/organic mixtures evaporation at room temperature and 50° C. all showed amorphous XRPD pattern.

Cooling recrystallization and recrystallizations with anti-solvents were performed. MeOH was used as single solvent for cooling recrystallization. For anti-solvent recyclization, DMSO or MeOH was used as primary solvent, and acetone, MeCN, MTBE, BuOAc, n-BuOH, toluene or THF used as anti-solvent. The results are summarized in Table 4.

TABLE 4

Summary of Recrystallization Experiments.

| Primary solvent | Anti-Solvent | Solvent ratio | Form by XRPD |
|---|---|---|---|
| MeOH | n/a | n/a | B |
| MeOH | CH₃CN | 1:3 | n/a |
| MeOH | BuOAc | 1:3 | n/a |
| MeOH | MTBE | 1:3 | G |
| MeOH | Toluene | 1:3 | H |
| MeOH | THF | 1:3 | n/a |
| DMSO | CH₃CN | 1:10 | I |
| DMSO | BuOAc | 1:10 | C + peaks* |
| DMSO | n-BuOH | 1:10 | C |
| DMSO | MTBE | 1:10 | C + peaks* |
| DMSO | Acetone | 1:10 | I |
| DMSO | THF | 1:10 | J | n/a: not analyzable.
*additional diffraction peaks observed but not definitively identifiable.

Solid from MeOH showed unique XRPD pattern designated as Form B. The XRPD patterns for solids from MeOH//MTBE and MeOH/toluene showed similar diffraction peaks, but were later identified as different solid forms, designated as Form G and Form H, respectively. Solid from DMSO/n-BuOH, DMSO/MTBE and DMSO/BuOAc showed unique XRPD pattern designated as Form C. Solid from DMSO/Acetone or DMSO/MeCN showed unique XRPD pattern designated as Form I. And the pattern for solid from DMSO/THF was designated as Form J.

Further form conversion experiments were performed to determine interconversion among solid forms. Form conversion was also observed during further characterization of the solid forms. The results are summarized in Table 5.

TABLE 5

Stability and Form Transfer Experiments of HCl salt

| Starting Form | Solvent/Condition | Time at RT | XRPD Result |
|---|---|---|---|
| Form B | Exposed to ambient air | 1 week | Form A |
| Form C | MeOAc | 1 day | Form A |
| Form D | MeCN/water (95:5) | 10 day | Form D |
| Form B | After DVS | — | Form A |
| Form C | After DVS | — | Form A |
| Form D | After DVS | — | Form F |
| Form B | IPA | 24 h | Form A |
| Form C | IPA | 24 h | Form A |
| Form D | IPA | 24 h | Form A |
| Form E | IPA | 24 h | Form A |
| Form F | IPA | 10 days | Form A |
| Form I | MeoAc | 1 minute | Form A |

Competitive slurry experiments were carried out of Forms E and F. The results are summarized in Table 6.

TABLE 6

Summary of HCl Salt Form E and Form F Transformation.

| Starting Form | Solvent/Condition | Time at RT | XRPD Result |
|---|---|---|---|
| Form E | IPA/water (40/60) | Spontaneous | Form F |
| Form E | IPA/water (60/40) | Spontaneous | Form F |
| Form E | IPA/water (80/20) | Spontaneous | Form F |
| Form E | IPA/water (90/10) | Spontaneous | Form F |
| Form E | IPA/water (95/5) | Spontaneous | Form F |
| Form A + F | IPA/water (50/50) | 3 days | Form A |
| Form A + F | IPA/water (65/35) | 3 days | Form A |
| Form A + F | IPA/water (80/20) | 6 days | Form A |
| Form A + F | IPA/water (95/5) | 6 days | Form A |
| Form A + F | Water | 3 days | Form A |
| Form A + F | MeOAc saturated with water | 3 days | Form A |

6.2.6 Characterization of Polymorphic Forms

A total of eleven crystalline forms of the HCl salt were found during this polymorph screen study. The stack plot of XRPD patterns for these forms are shown in FIG. 105, and the physical characteristics are summarized in Table 7.

TABLE 7

Summary of Physical Characterization of HCl Salt Crystalline Forms.

| Form | Description | Representative conditions | DSC onset or peak (° C.) | TGA (wt %) | DVS or other comments |
|---|---|---|---|---|---|
| A | Anhydrate | salt formation in IPA/water/MeOAc | 256 (onset) | ~0.16 | 1.8 wt % water uptake from 0 to 90% RH |
| B | Hydrate/ solvate | MeOH recrystallization | ~80 (broad), 174 (endo), ~250 (peak) | 7.6 | Converts to Form A during exposure to ambient |
| C | Solvate/ hydrate | DMSO/(n-BuOH, MTBE or BuoAc) recrystallization | ~50 (broad), 142 (endo), 146 (endo), ~250 (onset) | 1.6, 15.1 | Converts to Form A at high humidity |
| D | Hydrate | MeCN/water slurry | ~60 (broad), 169 (endo), ~250 (onset) | 9.2 | Converts to Form F at high humidity during DVS experiment |
| E | Hydrate | salt formation in MeCN/water | 111 (broad), 185 (endo), ~250 (onset) | 4.5 | Converts to Form F during DVS experiment |
| F | Hydrate | salt formation in IPA/water | 83 (broad), 217 (endo), ~250 (onset) | 5.0 | 5.3~6.3 wt % water between 10 to 90% RH; 5.3 wt % mass change from 10 to 0% RH |
| G | Solvate/ hydrate | MeOH/MTBE recrystallization | 199 (endo), 248 (peak) | 1.9, 12.3 | Partially converted to Form A during DVS experiment |

TABLE 7-continued

Summary of Physical Characterization of HCl Salt Crystalline Forms.

| Form | Description | Representative conditions | DSC onset or peak (° C.) | TGA (wt %) | DVS or other comments |
|------|-------------|---------------------------|--------------------------|------------|------------------------|
| H | Solvate/hydrate | MeOH/Toluene recrystallization | 187 (endo), 255 (peak) | 0.3, 15.3 | n/a |
| I | Solvate/hydrate | DMSO/(MeCN, acetone) recrystallization | n/a | n/a | Converts to Form A upon exposure to ambient humidity |
| J | Solvate/hydrate | DMSO/THF recrystallization | ~70 (broad), 106 (endo), 127 (endo), 251 (onset) | 4.7, 7.6, 10.2 | n/a |
| K | Dehydrate | Dehydrated from Form F | n/a | n/a | Converts to Form F upon exposure to ambient humidity | n/a: not available.

(A) Form A

To a vial, 100 mg of a hydrate of the HCl salt of Compound (I-S) and 2 mL 2-propanol were added. The slurry was heated to 75° C. An additional 2 mL 2-propanol was added to thin out the resulting slurry. The batch was then cooled to room temperature and the slurry was filtered and dried, affording Form A, an anhydrate of a HCl salt of Compound (I-S). Form A was also found from most equilibration and evaporation experiments performed in this study. Form A had a crystalline XRPD pattern as shown in FIG. 36 and an irregular rod crystal habit as shown in FIG. 37. DSC and TGA thermograms of Form A are shown in FIG. 38 and FIG. 39, respectively. The DSC thermogram showed only one major event with an onset temperature of 256° C., corresponding to melt/decomposition. A TGA weight loss of 0.16% up to ~120° C. was observed. The $^1$H-NMR spectrum of Form A was consistent with Compound (I-S) structure with a small amount of residual solvent (FIG. 40). Without being limited by any particular theory, based on these data, Form A is an anhydrate.

The moisture sorption/desorption behavior of Form A was determined by DVS and the results are summarized in FIG. 41. A total mass change of 1.8% was observed between 0% RH and 95% RH, suggesting Form A is slightly hygroscopic. After undergoing the adsorption/desorption cycles, the XRPD diffractogram of the sample showed no change (FIG. 42).

The stability of Form A was further characterized by compression test and form transfer experiments. Upon application of 2000-psi pressure for about 1 minute, the material was still Form A (FIG. 43). Results from form transfer experiments (Tables 5 and 6) showed that all hydrate and solvate form will convert to Form A in IPA slurry. Furthermore Form A is also the more stable than hydrate forms in water and aqueous/organic mixtures studied. Without being limited by any particular theory, these results suggested that Form A is a stable anhydrate form of the HCl salt.

(B) Form B

Form B was obtained from recrystallization of Form A in MeOH. Form B had a crystalline XRPD pattern as shown in FIG. 44 and irregular rod crystal habit as shown in FIG. 45. DSC and TGA thermograms of Form B are shown in FIG. 46 and FIG. 47, respectively. The TGA weight loss of 7.6 wt % corresponded to broad DSC broad peak around 80° C. can be attributed to loss of water/solvent in Form B. The DSC thermogram also showed endothermic peaks at 174 and 250° C., respectively. The $^1$H-NMR spectrum was obtained for the Form B sample and did not show significant degradation or residual solvent (FIG. 48). Form B sample was found to have converted to Form A upon ambient storage (FIG. 49). Without being limited by any particular theory, based on available characterization data, Form B is a hydrate of the Compound (I-S) HCl salt.

(C) Form C

Form C was obtained from anti-solvent recrystallization in DMSO/n-BuOH, DMSO/MTBE or DMSO/BuOAc. Form C had a crystalline XRPD pattern as shown in FIG. 50 and irregular crystal habit as shown in FIG. 51. DSC and TGA thermograms of Form C are shown in FIG. 52 and FIG. 53, respectively. The TGA weight loss of 1.6 and 15.1 wt % corresponded to broad DSC endotherm around 50° C. and endotherms around 142-146° C., respectively, and can be attributed to loss of solvent/water in Form C. The DSC thermogram with an onset temperature of 251.8° C. was due to final melt/decomposition. To further confirm the desolvation event observed, a Form C sample was heated to 165° C. and tested for XRPD. The XRPD pattern of the heated sample was consistent with Form A (FIG. 54). The $^1$H-NMR spectrum of Form C was consistent with Compound I structure with approximately one molar equivalent (or ~13.9 wt %) of DMSO solvent (FIG. 55). Without being limited by any particular theory, Form C is a DMSO solvate.

The Form C sample was found to convert to Form A upon exposure to high humidity (higher than 70% RH) in the DVS instrument (FIG. 56). Form C was also found to convert to Form A in IPA slurry (Table 5).

(D) Form D

Form D was obtained from equilibration of Form A in MeCN/water (95:5). Form D had a crystalline XRPD pattern as shown in FIG. 57 and irregular crystal habit as shown in FIG. 58. DSC and TGA thermograms of Form D are shown in FIG. 59 and FIG. 60, respectively. The TGA weight loss of 9.2 wt % corresponded to the broad DSC endotherm around 60° C. The DSC thermogram also showed endothermic peaks at 169 and 250° C. The $^1$H-NMR spectrum of Form D was consistent with Compound (I-S) structure without significant degradation or residual solvent (FIG. 61). Without being limited by any particular theory, Form D is a hydrate.

The moisture sorption/desorption behavior of Form D was determined by DVS and the results are summarized in FIG. 62. Form D exhibited a mass change of ~11% relative to the dry mass when the relative humidity was increased from 50 to 80% RH, suggesting Form D is hygroscopic material. A steep mass change of ~12% was observed between 80-90% RH during adsorption, most likely due to transformation of solid form. After undergoing the adsorption/desorption cycles, the XRPD diffractogram of the sample showed that the material was changed from the initial Form D to Form F (FIG. 63). This result explained why the desorption curve and the second adsorption curve obtained for Form D were similar to those of Form F. These observations suggested that Form D was a less stable hydrate than Form F.

(E) Form E

To a flask, 1 g of Compound (I-S), 19 mL of acetonitrile, and 1 mL water were added and heated to 45° C. to dissolve the solid. Then approximately 0.4 mL of 6 M HCl was added and the batch was cooled to room temperature. The batch was held at room temperature until precipitation occurred, upon which the batch was reheated to 45° C. Then, the batch was cooled to room temperature, filtered, and dried, affording Form E, a hydrate of a HCl salt of Compound (I-S). Form E had a crystalline XRPD pattern as shown in FIG. 64 and irregular crystal habit as shown in FIG. 65. DSC and TGA thermograms of Form E are shown in FIG. 66 and FIG. 67, respectively. The TGA weight loss of 4.5 wt % corresponded to the broad DSC endotherm around 100° C. and also corresponded to the Karl Fischer result which showed 4.2 wt % of water. Without being limited by any particular theory, Form E is a hydrate. The DSC thermogram showed an endotherm around 185° C. and the final melt/decomposition around 250° C. The $^1$H-NMR spectrum of Form E was consistent with Compound (I-S) structure without significant degradation or residual solvent (FIG. 68).

The moisture sorption/desorption behavior of Form E was determined by DVS and the results are summarized in FIG. 69. Form E exhibited a mass change of ~14% relative to the dry mass when the relative humidity was increased from 50 to 80% RH, suggesting Form E is hygroscopic. A steep mass change was observed between 80-90% RH during adsorption, most likely due to transformation of solid form. After undergoing the adsorption/desorption cycles, the XRPD diffractogram of the sample showed that the material partially converted to Form F (FIG. 70).

Form E sample was heated to 120° C. and analyzed for XRPD. The resulted XRPD pattern was consistent with Form E, suggesting Form E lattice was stable upon moderate heating. Furthermore, a Form E sample was heated to 190° C. and resulted in an amorphous pattern, confirming that the endothermic event at 185° C. was corresponding to melting or collapsing of crystal lattices in Form E. Data are provided in FIGS. 71 and 82.

Form transfer experiments showed that Form E converted to Form A in IPA slurry (Table 5). Form E was also found to convert to Form F in various IPA/water mixtures (Table 6).

(F) Form F

To a flask, 2.5 g of Compound (I-S), 5 mL of 2-propanol and 7.5 mL water were added. Approximately 0.5 mL concentrated HCl was then added. The batch was heated to 40° C. and then cooled to 25° C. Approximately 50 mL 2-propanol was added dropwise, causing crystallization. The slurry was filtered and dried, affording a hydrate of a HCl salt of Compound (I-S). Form F was also spontaneously formed when Form E was slurried in IPA/water solvent mixtures. Form F had a crystalline XRPD pattern as shown in FIG. 73 and irregular rod crystal habit as shown in FIG. 74. DSC and TGA thermograms of Form F are shown in FIG. 75 and FIG. 76, respectively. The TGA weight loss of 5.0 wt % corresponded to the broad DSC endotherm around 83° C. and also corresponded to the Karl Fischer result which showed 5.3 wt % of water. Without being limited by any particular theory, Form F is a hydrate. The measured water content coincided with the theoretical water content of a sesqui-hydrate of the HCl Compound (I-S) salt. The DSC thermogram also showed an endotherm around 217° C. and the final decomposition around 250° C. The $^1$H-NMR spectrum of Form F was consistent with Compound (I-S) structure without significant degradation or residual solvent (FIG. 77).

The moisture sorption/desorption behavior of Form F was determined by DVS and the results are summarized in FIG. 78. Form F exhibited a total mass change of 6.3% relative to the dry mass when the relative humidity was increased from 0 to 90% RH. The water content was stabilized between 5.2 to 6.3 wt % from 10 to 90% RH, corresponding to approximately 1.5~1.8 molar equivalent of water. A steep mass change of 5.2 wt % was observed between 10-0% RH during desorption. After undergoing the adsorption/desorption cycles, the XRPD diffractogram of the sample showed that the material was unchanged from the initial Form F (FIG. 79).

The form transfer experiments showed that Form F convert to Form A when in IPA slurry (Table 5). Competitive slurry experiments listed in Table 6 also showed that Form F is less stable than Form A is various aqueous/IPA mixtures. To further probe the stability of Form F, a Form F sample was heated to 120° C. and analyzed for XRPD. The resulted XRPD pattern was consistent with Form F (FIG. 80). The TGA plot of the heated sample showed 4.9 wt % weight loss (FIG. 81), consistent with expected water content in Form F. Further, a Form F sample was placed in a chamber containing drierrite for 16 hours, the resulted solid provided a unique XRPD pattern designated as Form K.

(G) Form G

Form G was obtained from recrystallization of Form A in MeOH/MTBE. Form G had a crystalline XRPD pattern as shown in FIG. 82. The pattern showed some similarity to those of Form B and Form H, but was found to be a different solvate form. DSC and TGA thermograms of Form G are shown in FIG. 83 and FIG. 84, respectively. The initial TGA weight loss of 1.9 wt % corresponded to broad DSC broad peak around 60° C. and was likely attributed to loss of surface water/solvent in Form G. The major TGA weight loss of 12.3 wt % corresponded to the DSC endothermic peak at 199° C. The $^1$H-NMR spectrum was obtained for the Form G sample and showed approximately 0.5 molar equivalent (or ~8.3 wt %) of MTBE (FIG. 85). Without being limited by any particular theory, Form G is a MTBE solvate of the Compound (I-S) HCl salt.

(H) Form H

Form H was obtained from recrystallization of Form A in MeOH/toluene. Form H had a crystalline XRPD pattern as shown in FIG. 86. The pattern showed some similarity to Form B and was almost identical to Form G, but was found to be a different solvate form. DSC and TGA thermograms of Form H are shown in FIG. 87 and FIG. 88, respectively. The major TGA weight loss of 15.3 wt % corresponded to the DSC endothermic peak at 187° C. The $^1$H-NMR spectrum was obtained for the Form H sample and showed approximately 0.8 molar equivalent (or ~13.2 wt %) of toluene (FIG. 89). Without being limited by any particular theory, Form H is a toluene solvate of the Compound (I-S) HCl salt.

(I) Form I

Form I was obtained from recrystallization of Form A in DMSO/MeCN or DMSO/acetone. Form I had a crystalline XRPD pattern as shown in FIG. 90. The Form I was found to change to Form A. During crystallization experiments, some Form I solid was washed with MeOAc as an attempt to remove residual DMSO. The XRPD pattern of the resulted solid was consistent with Form A (FIG. 91). Without being limited by any particular theory, Form I is a solvate of the Compound (I-S) HCl salt.

(J) Form J

Form J was obtained from recrystallization of Form A in DMSO/THF. Form J had a crystalline XRPD pattern as shown in FIG. 92. DSC and TGA thermograms of Form J are shown in FIGS. 93 and 94, respectively. The initial TGA weight loss of 4.7 wt % corresponded to broad DSC broad peak around 70° C. and was likely attributed to loss of surface water/solvent in Form J. The TGA weight losses of 7.6 and 10.3 wt % corresponded to the DSC endothermic peaks at 106 and 127° C., respectively. Without being limited by any particular theory, Form J a solvate of the HCl salt.

(K) Form K

Form K was obtained from drying Form F at close to 0% RH condition. In detail, a Form F sample was placed in a chamber containing drierite for 16 hours. The resulted solid afforded a unique XRPD pattern, as shown in FIG. 95. Form K was not available as the Form was observed to convert to Form F after exposure to ambient condition (FIG. 96).

6.3 Salts and Solvates of Racemic Compound (I)

6.3.1 Freebase Anhydrate

In a vial, ~50 mg of racemic Compound (I) and ~250 uL acetonitrile were heated to 40° C., then cooled to room temperature. The resulting slurry was filtered, affording racemic Compound (I) freebase anhydrate solids.

6.3.2 Freebase Hydrate

In a vial, ~50 mg racemic Compound (I) and ~250 μL 1/1 acetonitrile/water were heated to 40° C., then cooled to room temperature. The resulting slurry was filtered, affording racemic Compound (I) freebase hydrate solids.

6.3.3 Hydrochloride Hydrate

In a vial, ~750 mg racemic Compound (I) hydrochloride and ~15 mL 80/20 isopropanol/water were heated to 50° C., then cooled to room temperature. The resulting slurry was filtered, affording racemic Compound (I) hydrochloride hydrate solids.

6.3.4 Hydrochloride Methanol Solvate

In a vial, ~70 mg racemic Compound (I) hydrochloride and 1 mL methanol dried on 3-A molecular sieves were added. The suspension was heated to 50° C., then cooled to room temperature. The resulting slurry was filtered, affording a wet solids of racemic Compound (I) hydrochloride methanol solvate. The product was converted to racemic Compound (I) hydrochloride hydrate upon exposure to ambient moisture.

6.4 Assays

6.4.1 TNFα Inhibition Assay in hPMBC

Human peripheral blood mononuclear cells (hPBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bio-products, Woodland, Calif., USA), 2 mM L-glutamine, 100 U/ml penicillin, and 100 μg/ml streptomycin (Life Technologies).

PBMC ($2 \times 10^5$ cells) are plated in 96-well flat-bottom Costar tissue culture plates (Corning, N.Y., USA) in triplicate. Cells are stimulated with LPS (from *Salmonella abortus equi*, Sigma cat. no. L-1887, St. Louis, Mo., USA) at 1 ng/ml final in the absence or presence of compounds. Compounds provided herein are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% $CO_2$, and supernatants are then collected, diluted with culture medium and assayed for TNFα levels by ELISA (Endogen, Boston, Mass., USA). $IC_{50}$s are calculated using non-linear regression, sigmoidal dose-response, constraining the top to 100% and bottom to 0%, allowing variable slope (GraphPad Prism v3.02).

6.4.2 IL-2 and MIP-3a Production by T Cells

PBMC are depleted of adherent monocytes by placing $1 \times 10^8$ PBMC in 10 ml complete medium (RPMI 1640 supplemented with 10% heat-inactivated fetal bovine serum, 2 mM L-glutamine, 100 U/ml penicillin, and 100 μg/ml streptomycin) per 10 cm tissue culture dish, in 37° C., 5% $CO_2$ incubator for 30-60 minutes. The dish is rinsed with medium to remove all non-adherent PBMC. T cells are purified by negative selection using the following antibody (Pharmingen) and Dynabead (Dynal) mixture for every $1 \times 10^8$ non-adherent PBMC: 0.3 ml Sheep anti-mouse IgG beads, 15 μl anti-CD16, 15 μl anti-CD33, 15 μl anti-CD56, 0.23 ml anti-CD19 beads, 0.23 ml anti-HLA class II beads, and 56 μl anti-CD14 beads. The cells and bead/antibody mixture is rotated end-over-end for 30-60 minutes at 4° C. Purified T cells are removed from beads using a Dynal magnet. Typical yield is about 50% T cells, 87-95% $CD3^+$ by flow cytometry.

Tissue culture 96-well flat-bottom plates are coated with anti-CD3 antibody OKT3 at 5 μg/ml in PBS, 100 μl per well, incubated at 37° C. for 3-6 hours, then washed four times with complete medium 100 μl/well just before T cells are added. Compounds are diluted to 20 times of final in a round bottom tissue culture 96-well plate. Final concentrations are about 10 μM to about 0.00064 μM. A 10 mM stock of compounds provided herein is diluted 1:50 in complete for the first 20x dilution of 200 μl in 2% DMSO and serially diluted 1:5 into 2% DMSO. Compound is added at 10 μl per 200 μl culture, to give a final DMSO concentration of 0.1%. Cultures are incubated at 37° C., 5% $CO_2$ for 2-3 days, and supernatants analyzed for IL-2 and MIP-3a by ELISA (R&D Systems). IL-2 and MIP-3a levels are normalized to the amount produced in the presence of an amount of a compound provided herein, and $EC_{50}$s calculated using non-linear regression, sigmoidal dose-response, constraining the top to 100% and bottom to 0%, allowing variable slope (GraphPad Prism v3.02).

6.4.3 Cell Proliferation Assay

Cell lines (e.g., Namalwa, MUTZ-5, UT-7, and various NHL cell lines) are obtained from the Deutsche Sammlung von Mikroorganismen und Zellkulturen GmbH (Braunschweig, Germany). The cell line KG-1 is obtained from the American Type Culture Collection (Manassas, Va., USA). Cell proliferation as indicated by $^3$H-thymidine incorporation is measured in all cell lines as follows.

Cells are plated in 96-well plates at 6000 cells per well in media. The cells are pre-treated with compounds at about 100, 10, 1, 0.1, 0.01, 0.001, 0.0001 and 0 μM in a final concentration of about 0.25% DMSO in triplicate at 37° C. in a humidified incubator at 5% $CO_2$ for 72 hours. One microcurie of $^3$H-thymidine (Amersham) is then added to each well, and cells are incubated again at 37° C. in a humidified incubator at 5% $CO_2$ for 6 hours. The cells are harvested onto UniFilter GF/C filter plates (Perkin Elmer) using a cell harvester (Tomtec), and the plates are allowed to dry overnight. Microscint 20 (Packard) (25 µl/well) is added, and plates are analyzed in TopCount NXT (Packard). Each well is counted for one minute. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope. (GraphPad Prism v3.02).

6.4.4 Immunoprecipitation and Immunoblot

Cells (e.g., various NHL cell lines) are treated with DMSO or an amount of a compound provided herein for 1 hour, then stimulated with 10 U/ml of Epo (R&D Systems) for 30 minutes. Cell lysates are prepared and either immunoprecipitated with Epo receptor Ab or separated immediately by SDS-PAGE. Immunoblots are probed with Akt, phospo-Akt (Ser473 or Thr308), phospho-Gabl (Y627), Gabl, IRS2, actin and IRF-1 Abs and analyzed on a Storm 860 Imager using ImageQuant software (Molecular Dynamics).

6.4.5 Cell Cycle Analysis

Cells are treated with DMSO or an amount of a compound provided herein overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

6.4.6 Apoptosis Analysis

Cells are treated with DMSO or an amount of a compound provided herein at various time points, then washed with annexin-V wash buffer (BD Biosciences). Cells are incubated with annexin-V binding protein and propidium iodide (BD Biosciences) for 10 minutes. Samples are analyzed using flow cytometry.

6.4.7 Luciferase Assay

Namalwa cells are transfected with 4 µg of AP1-luciferase (Stratagene) per $1\times10^6$ cells and 3 µl Lipofectamine 2000 (Invitrogen) reagent according to manufacturer's instructions. Six hours post-transfection, cells are treated with DMSO or an amount of a compound provided herein. Luciferase activity is assayed using luciferase lysis buffer and substrate (Promega) and measured using a luminometer (Turner Designs).

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

All of the patents, patent applications and publications referred to herein are incorporated herein in their entireties. Citation or identification of any reference in this application is not an admission that such reference is available as prior art to the claimed subject matter. The full scope of the invention is better understood with reference to the appended claims.

What is claimed:

1. A method of treating cancer, an immune-related disease or disorder, an inflammatory disease or disorder, or a symptom thereof in a subject, comprising administering to the subject a therapeutically effective amount of a solid form comprising a racemic Compound (I):

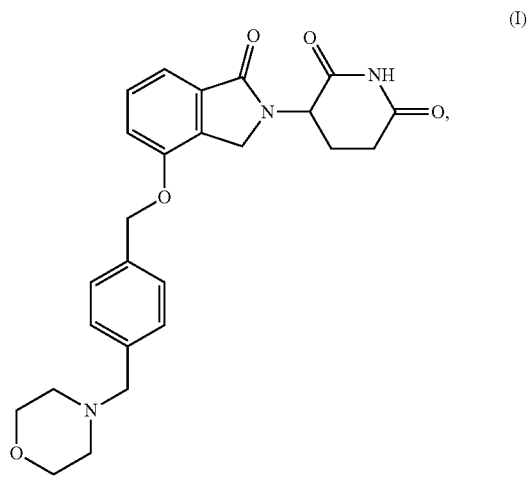 [SMILES: O=C1CCC(N2Cc3c(OCc4ccc(CN5CCOCC5)cc4)cccc3C2=O)C(=O)N1]

or a hydrate or anhydrate thereof, wherein the solid form is crystalline, wherein the solid form comprises a HCl salt of racemic Compound (I) and water, having an XRPD pattern comprising peaks at approximately 13.88, 14.30, and 15.36 degrees 2θ; or comprises a HCl salt of racemic Compound (I) and methanol, having an XRPD pattern comprising peaks at approximately 12.38, 14.54, and 26.10 degrees 2θ;

wherein the cancer, immune-related disease or disorder, or inflammatory disease or disorder is lupus, scleroderma, Sjögren syndrome, ANCA-induced vasculitis, anti-phospholipid syndrome, myasthenia gravis, or multiple myeloma.

2. The method of claim 1, wherein the solid form comprises a HCl salt of racemic Compound (I) and water, having an XRPD pattern comprising peaks at approximately 13.88, 14.30, and 15.36 degrees 2θ.

3. The method of claim 2, wherein the XRPD pattern further comprises peaks at approximately 9.84, 16.42, and 19.82 degrees 2θ.

4. The method of claim 2, wherein the XRPD pattern matches the XRPD pattern presented in FIG. 101.

5. The method of claim 1, wherein the solid form comprises a HCl salt of racemic Compound (I) and methanol, having an XRPD pattern comprising peaks at approximately 12.38, 14.54, and 26.10 degrees 2θ.

6. The method of claim 5, wherein the XRPD pattern further comprises peaks at approximately 15.06, 20.00, and 26.86 degrees 2θ.

7. The method of claim 5, wherein the XRPD pattern matches the XRPD pattern presented in FIG. 104.

8. The method of claim 1, wherein the immune-related or inflammatory disease or disorder is lupus, scleroderma, Sjögren syndrome, ANCA-induced vasculitis, anti-phospholipid syndrome, or myasthenia gravis.

9. The method of claim 1, wherein the immune-related or inflammatory disease or disorder is scleroderma.

10. The method of claim 1, wherein the immune-related or inflammatory disease or disorder is systemic lupus erythematosus (SLE), cutaneous lupus erythematosus (CLE), discoid lupus erythematosus (DLE), or drug-induced lupus.

11. The method of claim 10, wherein the immune-related or inflammatory disease or disorder is systemic lupus erythematosus (SLE).

12. The method of claim 10, wherein the immune-related or inflammatory disease or disorder is cutaneous lupus erythematosus (CLE).

13. The method of claim 1, wherein the cancer is multiple myeloma.

14. The method of claim 1, wherein the lupus is systemic lupus erythematosus (SLE), cutaneous lupus erythematosus (CLE), discoid lupus erythematosus (DLE), or drug-induced lupus.

* * * * *